United States Patent
Zhang et al.

(10) Patent No.: US 10,533,173 B2
(45) Date of Patent: Jan. 14, 2020

(54) PRECURSOR MIRNA AND APPLICATIONS IN TUMOR THERAPY THEREOF

(71) Applicant: JIANGSU MICROMEDMARK BIOTECH CO., LTD., Jiangsu (CN)

(72) Inventors: Chenyu Zhang, Jiangsu (CN); Ke Zeng, Jiangsu (CN); Xi Chen, Jiangsu (CN); Junfeng Zhang, Jiangsu (CN); Hongwei Liang, Jiangsu (CN)

(73) Assignee: JIANGSU MICROMEDMARK BIOTECH CO., LTD., Jiangsu (CN)

( * ) Notice: Subject to any disclaimer, the term of this patent is extended or adjusted under 35 U.S.C. 154(b) by 0 days.

(21) Appl. No.: 15/571,587

(22) PCT Filed: May 5, 2016

(86) PCT No.: PCT/CN2016/081195
§ 371 (c)(1),
(2) Date: Nov. 3, 2017

(87) PCT Pub. No.: WO2016/177343
PCT Pub. Date: Nov. 10, 2016

(65) Prior Publication Data
US 2018/0223277 A1    Aug. 9, 2018

(30) Foreign Application Priority Data
May 5, 2015  (CN) .......................... 2015 1 0224944

(51) Int. Cl.
| A61K 48/00 | (2006.01) |
| C07H 21/02 | (2006.01) |
| C07H 21/04 | (2006.01) |
| C12N 15/113 | (2010.01) |
| A61P 35/00 | (2006.01) |

(52) U.S. Cl.
CPC ............ *C12N 15/113* (2013.01); *A61P 35/00* (2018.01); *C12N 2310/141* (2013.01); *C12N 2330/51* (2013.01)

(58) Field of Classification Search
CPC .. C12N 15/113; C12N 15/115; C12N 2310/14
See application file for complete search history.

(56) References Cited

U.S. PATENT DOCUMENTS

| 8,603,744 B2* | 12/2013 | Croce ................. C12N 15/111 |
| | | 435/6.1 |
| 8,735,074 B2 | 5/2014 | Mambo et al. |
| 2005/0182005 A1* | 8/2005 | Tuschl .................. C07H 21/02 |
| | | 514/44 R |
| 2011/0021607 A1 | 1/2011 | Clarke et al. |
| 2011/0053158 A1 | 3/2011 | Mambo et al. |
| 2014/0274791 A1 | 9/2014 | Mambo et al. |

FOREIGN PATENT DOCUMENTS

| CN | 101899443 A | 12/2010 |
| CN | 101981206 A | 2/2011 |
| CN | 102335189 A | 2/2012 |
| CN | 102725632 A | 10/2012 |

OTHER PUBLICATIONS

International Search Report dated Aug. 8, 2016 issued in corresponding PCT/CN2016/081195 application (2 pages).
English Abstract of CN 101899443 A published Dec. 1, 2010.
English Abstract of CN 102335189 A published Feb. 1, 2012.

* cited by examiner

*Primary Examiner* — Amy H Bowman
(74) *Attorney, Agent, or Firm* — Millen White Zelano and Branigan, PC; Csaba Henter

(57) ABSTRACT

Provided are a new precursor miRNA and the applications in tumor therapy thereof. The precursor miRNA, from 5'- to 3'-end thereof, has the structure represented by formula (I). B1 is an anti-miRNA and/or siRNA to be expressed; B2 is a sequence substantially or completely complementary to B1, and B2 is not complementary to C; C is a sequence with stem-loop structure; A1 and A2 are independently hydrogen or optionally a RNA sequence consisting of 4 to 5 bases. The precursor miRNA can be processed to form an anti-miRNA and/or siRNA in hosts.

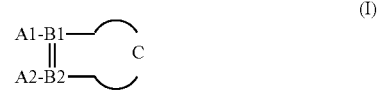

(I)

20 Claims, 31 Drawing Sheets
Specification includes a Sequence Listing.

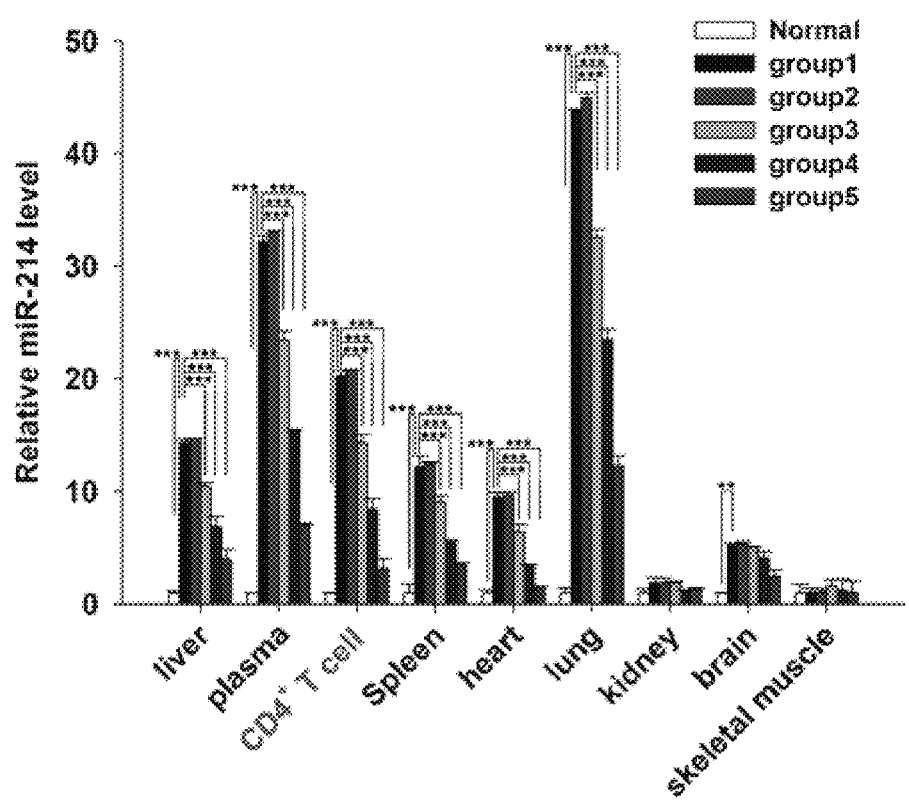
Fig. 16
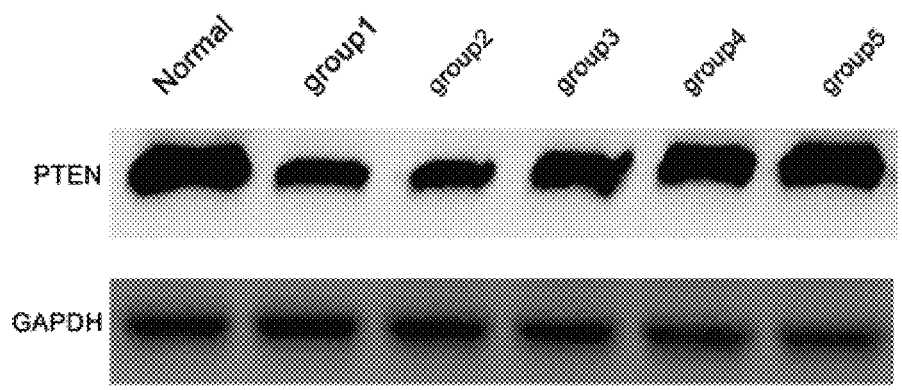

SEQUENCE LISTING

<160> NUMBER OF SEQ ID NOS: 930

<210> SEQ ID NO 1
<211> LENGTH: 19
<212> TYPE: RNA
<213> ORGANISM: Artificial Sequence
<220> FEATURE:
<223> OTHER INFORMATION: miRNA/siRNA

```
<400> SEQUENCE: 1
guuuuggcca cugacugac                                               19

<210> SEQ ID NO 2
<211> LENGTH: 23
<212> TYPE: RNA
<213> ORGANISM: Artificial Sequence
<220> FEATURE:
<223> OTHER INFORMATION: miRNA/siRNA

<400> SEQUENCE: 2
acugccuguc ugugccugcc ugu                                          23

<210> SEQ ID NO 3
<211> LENGTH: 21
<212> TYPE: RNA
<213> ORGANISM: Artificial Sequence
<220> FEATURE:
<223> OTHER INFORMATION: miRNA/siRNA

<400> SEQUENCE: 3
acaggcaggc agacaggcag u                                            21

<210> SEQ ID NO 4
<211> LENGTH: 62
<212> TYPE: DNA
<213> ORGANISM: Artificial Sequence
<220> FEATURE:
<223> OTHER INFORMATION: miRNA/siRNA

<400> SEQUENCE: 4
tgctgactgc ctgtctgtgc ctgcctgtgt tttggccact gaccaaagta tcatctttgt  60
ag                                                                 62

<210> SEQ ID NO 5
<211> LENGTH: 60
<212> TYPE: DNA
<213> ORGANISM: Artificial Sequence
<220> FEATURE:
<223> OTHER INFORMATION: miRNA/siRNA

<400> SEQUENCE: 5
cctgctacaa agatgatact ttggtcagtg gccaaaacac aggcaggcag acaggcagtc  60

<210> SEQ ID NO 6
<211> LENGTH: 64
<212> TYPE: DNA
<213> ORGANISM: Artificial Sequence
<220> FEATURE:
<223> OTHER INFORMATION: miRNA/siRNA

<400> SEQUENCE: 6
tgctgaaatg tactgcgcgt ggagacgttt tggccactga ctgacgtctc cacgcagtac  60
attt                                                               64

<210> SEQ ID NO 7
<211> LENGTH: 64
<212> TYPE: DNA
<213> ORGANISM: Artificial Sequence
<220> FEATURE:
<223> OTHER INFORMATION: miRNA/siRNA

<400> SEQUENCE: 7
cctgaaatgt actgcgtgga gacgtcagtc agtggccaaa acgtctccac gcgcagtaca  60
``` tttc                                                              64

<210> SEQ ID NO 8
<211> LENGTH: 24
<212> TYPE: DNA
<213> ORGANISM: Artificial Sequence
<220> FEATURE:
<223> OTHER INFORMATION: miRNA/siRNA

<400> SEQUENCE: 8
tgctggtttt ggccactgac tgac                                        24

<210> SEQ ID NO 9
<211> LENGTH: 24
<212> TYPE: DNA
<213> ORGANISM: Artificial Sequence
<220> FEATURE:
<223> OTHER INFORMATION: miRNA/siRNA

<400> SEQUENCE: 9
cctggtcagt cagtggccaa aacc                                        24

<210> SEQ ID NO 10
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 10
ggccaguuau agcuuauua                                              19

<210> SEQ ID NO 11
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 11
gguccuagua ggaaauaaa                                              19

<210> SEQ ID NO 12
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 12
gcagcagcaa cauuaauaa                                              19

<210> SEQ ID NO 13
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 13
ggcagaccca guaugaaau                                              19

<210> SEQ ID NO 14
<211> LENGTH: 19
<212> TYPE: RNA

-continued

```
<213> ORGANISM: Artificial Sequence
<220> FEATURE:
<223> OTHER INFORMATION: miRNA/siRNA

<400> SEQUENCE: 14
ggugugccaa gacauuaau                                               19

<210> SEQ ID NO 15
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 15
ggacucuucu uccauauua                                               19

<210> SEQ ID NO 16
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 16
ggcaauggaa acuauuaua                                               19

<210> SEQ ID NO 17
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 17
gcaguugauu acuucuuau                                               19

<210> SEQ ID NO 18
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 18
ggacuuagca agaaguuau                                               19

<210> SEQ ID NO 19
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 19
gcucagcaca aucuguaaa                                               19

<210> SEQ ID NO 20
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 20
cuccuuucca cugcuauua                                               19
```

-continued

<210> SEQ ID NO 21
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 21
gcuguggaua uuauguaaa                                                  19

<210> SEQ ID NO 22
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 22
cucagcacaa ucuguaaau                                                  19

<210> SEQ ID NO 23
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 23
guugguguga aacaaauua                                                  19

<210> SEQ ID NO 24
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 24
gggcauguua aguuacagu                                                  19

<210> SEQ ID NO 25
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 25
gugccaauuu cuuacuagu                                                  19

<210> SEQ ID NO 26
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 26
cacacugcau aggaauuua                                                  19

<210> SEQ ID NO 27
<211> LENGTH: 19
<212> TYPE: RNA
<213> ORGANISM: Artificial Sequence
<220> FEATURE:

<223> OTHER INFORMATION: miRNA/siRNA

<400> SEQUENCE: 27
gcucuuucau aguauaacu                                                    19

<210> SEQ ID NO 28
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 28
ccugguaaca guauacau                                                     19

<210> SEQ ID NO 29
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 29
gcucaggacu uagcaagaa                                                    19

<210> SEQ ID NO 30
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 30
gacuaugagu guguauuua                                                    19

<210> SEQ ID NO 31
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 31
gccauagaca cuauaguau                                                    19

<210> SEQ ID NO 32
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 32
ggcacugggu auauggau                                                     19

<210> SEQ ID NO 33
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 33
gacccagaga uaacacgau                                                    19

```
<210> SEQ ID NO 34
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 34
gaggaguaca gugcaauga                                                  19

<210> SEQ ID NO 35
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 35
gguagcagca gcaacauua                                                  19

<210> SEQ ID NO 36
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 36
cucugugcca gcucuauaa                                                  19

<210> SEQ ID NO 37
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 37
gugcuagugu ggucuguaa                                                  19

<210> SEQ ID NO 38
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 38
cuguacuacu ccuaauuau                                                  19

<210> SEQ ID NO 39
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 39
cuaguguggu cuguaauau                                                  19

<210> SEQ ID NO 40
<211> LENGTH: 19
<212> TYPE: RNA
<213> ORGANISM: Artificial Sequence
<220> FEATURE:
<223> OTHER INFORMATION: miRNA/siRNA
```

```
<400> SEQUENCE: 40
gcagacguau auuguauca                                               19

<210> SEQ ID NO 41
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 41
gggcuauauu uacaugcua                                               19

<210> SEQ ID NO 42
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 42
gugcugugaa gugaucuaa                                               19

<210> SEQ ID NO 43
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 43
ccugucucuu ggauauucu                                               19

<210> SEQ ID NO 44
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 44
gugcugugga uauuaugua                                               19

<210> SEQ ID NO 45
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 45
ggagggcuuu cuuugugua                                               19

<210> SEQ ID NO 46
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 46
cuaggaaugu uggucauau                                               19

<210> SEQ ID NO 47
<211> LENGTH: 19
```

```
<212> TYPE: RNA
<213> ORGANISM: Artificial Sequence
<220> FEATURE:
<223> OTHER INFORMATION: miRNA/siRNA

<400> SEQUENCE: 47
cguguuugcu uaaacuuaa                                              19

<210> SEQ ID NO 48
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 48
gcugaugcuu ugaacaucu                                              19

<210> SEQ ID NO 49
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 49
ggucuguaau aucuuacua                                              19

<210> SEQ ID NO 50
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 50
ccuugacgau acagcuaau                                              19

<210> SEQ ID NO 51
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 51
guggauaucu ccaugaagu                                              19

<210> SEQ ID NO 52
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 52
caccauuaua gagaacaaa                                              19

<210> SEQ ID NO 53
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 53
```
gcuuccugau gaugauucu                                        19

<210> SEQ ID NO 54
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 54
caucccugau gaauguaaa                                        19

<210> SEQ ID NO 55
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 55
gaagcaagua guaauugau                                        19

<210> SEQ ID NO 56
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 56
ggacgaauau gauccaaca                                        19

<210> SEQ ID NO 57
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 57
guucccaagu aggcauucu                                        19

<210> SEQ ID NO 58
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 58
ccugaccuca agugauuca                                        19

<210> SEQ ID NO 59
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 59
gaacuguacu acuccuaau                                        19

<210> SEQ ID NO 60
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 60
guccuuaggu agugcuagu                                               19

<210> SEQ ID NO 61
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 61
ggcuauuuca aggucagaa                                               19

<210> SEQ ID NO 62
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 62
ccugaugaau guaaaguua                                               19

<210> SEQ ID NO 63
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 63
gugucagacu gcucuuuca                                               19

<210> SEQ ID NO 64
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 64
ccgaaaugga uaggaaua                                                19

<210> SEQ ID NO 65
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 65
gacugcucuu ucauaguau                                               19

<210> SEQ ID NO 66
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 66
caagucugau ccauauuua                                               19

```
<210> SEQ ID NO 67
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 67
gaugagcaaa gaugguaaa                                                   19

<210> SEQ ID NO 68
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 68
caagagguga aguuuauau                                                   19

<210> SEQ ID NO 69
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 69
gguagggugu uaagacuua                                                   19

<210> SEQ ID NO 70
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 70
cuaggcauca uguccuaua                                                   19

<210> SEQ ID NO 71
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 71
gagugaaugu ucccaagua                                                   19

<210> SEQ ID NO 72
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 72
ccuaguagga aauaaaugu                                                   19

<210> SEQ ID NO 73
<211> LENGTH: 19
<212> TYPE: RNA
<213> ORGANISM: Artificial Sequence
<220> FEATURE:
<223> OTHER INFORMATION: miRNA/siRNA
```

<400> SEQUENCE: 73
ggaagcaagu aguaauuga                                                   19

<210> SEQ ID NO 74
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 74
gcuguggaua ucuccauga                                                   19

<210> SEQ ID NO 75
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 75
ccagaaaucu ucaugcaau                                                   19

<210> SEQ ID NO 76
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 76
gccugaacua guucacaga                                                   19

<210> SEQ ID NO 77
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 77
cagacguaua uuguaucau                                                   19

<210> SEQ ID NO 78
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 78
guguauguca gauauucau                                                   19

<210> SEQ ID NO 79
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 79
ggcuaguucu cuuaacacu                                                   19

<210> SEQ ID NO 80

```
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 80
gaaggugacu uagguucua                                              19

<210> SEQ ID NO 81
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 81
gaaccuuuga gcuucaua                                               19

<210> SEQ ID NO 82
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 82
gccuugacga uacagcuaa                                              19

<210> SEQ ID NO 83
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 83
gagugccaau uucuuacua                                              19

<210> SEQ ID NO 84
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 84
cagacaagga aacuucuau                                              19

<210> SEQ ID NO 85
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 85
cuucgaucaa gcuacuuua                                              19

<210> SEQ ID NO 86
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 86
```
gcugacaaau caagagcau                                                19

<210> SEQ ID NO 87
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 87
gucaucucaa acucuuagu                                                19

<210> SEQ ID NO 88
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 88
guugucacca uugcacaau                                                19

<210> SEQ ID NO 89
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 89
gaugaugccu ucuauacau                                                19

<210> SEQ ID NO 90
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 90
cugguaugaa uagacagaa                                                19

<210> SEQ ID NO 91
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 91
cacugaguca caucagaaa                                                19

<210> SEQ ID NO 92
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 92
gucaagcuca gcacaaucu                                                19

<210> SEQ ID NO 93
<211> LENGTH: 19
<212> TYPE: RNA

```
<213> ORGANISM: Artificial Sequence
<220> FEATURE:
<223> OTHER INFORMATION: miRNA/siRNA

<400> SEQUENCE: 93
ggacucugaa gauguaccu                                                19

<210> SEQ ID NO 94
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 94
gggauuauua uagcaacca                                                19

<210> SEQ ID NO 95
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 95
cuaggaagaa ggugacuua                                                19

<210> SEQ ID NO 96
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 96
cuguggauau cuccaugaa                                                19

<210> SEQ ID NO 97
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 97
guggacgaau augauccaa                                                19

<210> SEQ ID NO 98
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 98
caugaguucu ugaagaaua                                                19

<210> SEQ ID NO 99
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 99
cugaguagcu gggauuaca                                                19
```

```
<210> SEQ ID NO 100
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 100
gugaaccuuu gagcuuuca                                                    19

<210> SEQ ID NO 101
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 101
gacaaggaaa cuucuaugu                                                    19

<210> SEQ ID NO 102
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 102
caguaauaca uuccauugu                                                    19

<210> SEQ ID NO 103
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 103
ccugguauga auagacaga                                                    19

<210> SEQ ID NO 104
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 104
gaauauagca gacguauau                                                    19

<210> SEQ ID NO 105
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 105
cgaucaagcu acuuuaugu                                                    19

<210> SEQ ID NO 106
<211> LENGTH: 19
<212> TYPE: RNA
<213> ORGANISM: Artificial Sequence
<220> FEATURE:
```

```
<223> OTHER INFORMATION: miRNA/siRNA

<400> SEQUENCE: 106
ggacaucacu uacuaucca                                                   19

<210> SEQ ID NO 107
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 107
gaagguaauu gauacacaa                                                   19

<210> SEQ ID NO 108
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 108
caaggaaacu ucuauguaa                                                   19

<210> SEQ ID NO 109
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 109
gaacccagca guuaccuua                                                   19

<210> SEQ ID NO 110
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 110
cagcaggcua uuucaaggu                                                   19

<210> SEQ ID NO 111
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 111
cugaauaccu aagauuucu                                                   19

<210> SEQ ID NO 112
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 112
gaucaagcua cuuuaugua                                                   19
```

```
<210> SEQ ID NO 113
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 113
gcucuauuua acugaguca                                                19

<210> SEQ ID NO 114
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 114
cuagaacagu agacacaaa                                                19

<210> SEQ ID NO 115
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 115
gauacagcua auucagaau                                                19

<210> SEQ ID NO 116
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 116
gcaggcuauu ucaagguca                                                19

<210> SEQ ID NO 117
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 117
ccuuagguaa ucuauaacu                                                19

<210> SEQ ID NO 118
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 118
ccuaaccaua agauuuacu                                                19

<210> SEQ ID NO 119
<211> LENGTH: 19
<212> TYPE: RNA
<213> ORGANISM: Artificial Sequence
<220> FEATURE:
<223> OTHER INFORMATION: miRNA/siRNA
```

```
<400> SEQUENCE: 119
ccuacaggaa gcaaguagu                                                  19

<210> SEQ ID NO 120
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 120
guguugauga ugccuucua                                                  19

<210> SEQ ID NO 121
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 121 gcaugugaa acuacagau                                                   19

<210> SEQ ID NO 122
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 122
gaaguaauga cuccauaca                                                  19

<210> SEQ ID NO 123
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 123
caucagaaau gcccuacau                                                  19

<210> SEQ ID NO 124
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 124
cugcugugga uaucuccau                                                  19

<210> SEQ ID NO 125
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 125
cucguuucua cacagagaa                                                  19

<210> SEQ ID NO 126
<211> LENGTH: 19
```

```
<212> TYPE: RNA
<213> ORGANISM: Artificial Sequence
<220> FEATURE:
<223> OTHER INFORMATION: miRNA/siRNA

<400> SEQUENCE: 126
cacaugaguu cuugaagaa                                                    19

<210> SEQ ID NO 127
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 127 gguuggcua guucucuua                                                     19

<210> SEQ ID NO 128
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 128
gcuauauuua caugcuacu                                                    19

<210> SEQ ID NO 129
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 129
cgaauaugau ccaacaaua                                                    19

<210> SEQ ID NO 130
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 130
ccucguuucu acacagaga                                                    19

<210> SEQ ID NO 131
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 131 ccuuccacu gcuauuagu                                                     19

<210> SEQ ID NO 132
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 132
```

-continued gacuuaggca uuaacaugu                                                    19

<210> SEQ ID NO 133
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 133
cucauuugua uuccauuga                                                    19

<210> SEQ ID NO 134
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 134
gaaacugaau accuaagau                                                    19

<210> SEQ ID NO 135
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 135
gugaggugaa aguaucacu                                                    19

<210> SEQ ID NO 136
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 136
caaagacaaa guguguaau                                                    19

<210> SEQ ID NO 137
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 137
gagucacacu gcauaggaa                                                    19

<210> SEQ ID NO 138
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 138
gauggagaaa ccugucucu                                                    19

<210> SEQ ID NO 139
<211> LENGTH: 19
<212> TYPE: RNA
<213> ORGANISM: Artificial Sequence

```
<220> FEATURE:
<223> OTHER INFORMATION: miRNA/siRNA

<400> SEQUENCE: 139
gaaaugcccu acaucuuau                                                    19

<210> SEQ ID NO 140
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 140
ggauacacuu auuugucaa                                                    19

<210> SEQ ID NO 141
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 141
cagcaacauu aauaaugga                                                    19

<210> SEQ ID NO 142
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 142
gaauguuggu gugaaacaa                                                    19

<210> SEQ ID NO 143
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 143
cuguuuaggu aggguguua                                                    19

<210> SEQ ID NO 144
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 144
gaauguuggu cauaucaaa                                                    19

<210> SEQ ID NO 145
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 145
ggaagaaggu gacuuaggu                                                    19
```

```
<210> SEQ ID NO 146
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 146
cacagagcua acuggguua                                              19

<210> SEQ ID NO 147
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 147
gagaguuuca cagcaugga                                              19

<210> SEQ ID NO 148
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 148
gauagcucaa caagauaca                                              19

<210> SEQ ID NO 149
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 149
gcauaggaau uuagaaccu                                              19

<210> SEQ ID NO 150
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 150
cacugaaacu cuucgauca                                              19

<210> SEQ ID NO 151
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 151
ccauuuacau aaggauaca                                              19

<210> SEQ ID NO 152
<211> LENGTH: 19
<212> TYPE: RNA
<213> ORGANISM: Artificial Sequence
<220> FEATURE:
<223> OTHER INFORMATION: miRNA/siRNA
```

<400> SEQUENCE: 152
cagugacuau gagugugua                                          19

<210> SEQ ID NO 153
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 153
gacuagggca guuuggaua                                          19

<210> SEQ ID NO 154
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 154
cuuuguguau uugccauaa                                          19

<210> SEQ ID NO 155
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 155
gaguuaagga cucugaaga                                          19

<210> SEQ ID NO 156
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 156
gucucuugga uauucucga                                          19

<210> SEQ ID NO 157
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 157
ggaagaauau agcagacgu                                          19

<210> SEQ ID NO 158
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 158
gaccuaggaa uguugguca                                          19

<210> SEQ ID NO 159

```
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 159
gacuacuccu gguaacagu                                              19

<210> SEQ ID NO 160
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 160
gcaguuaccu uaaagcuga                                              19

<210> SEQ ID NO 161
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 161
guucucuuaa cacugguua                                              19

<210> SEQ ID NO 162
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 162
gucaaagaca aagugugua                                              19

<210> SEQ ID NO 163
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 163
gcaaguagua auugaugga                                              19

<210> SEQ ID NO 164
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 164
cacugcuauu agucauggu                                              19

<210> SEQ ID NO 165
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 165
```

```
ccgaaaguuu ccaauucca                                                  19

<210> SEQ ID NO 166
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 166
guguugaaga gaccaaggu                                                  19

<210> SEQ ID NO 167
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 167
cauccagugu ugucaugca                                                  19

<210> SEQ ID NO 168
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 168
gacaucacuu acuauccau                                                  19

<210> SEQ ID NO 169
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 169
gaagaauaua gcagacgua                                                  19

<210> SEQ ID NO 170
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 170
caguuuggau agcucaaca                                                  19

<210> SEQ ID NO 171
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 171
ggauuauuau agcaaccau                                                  19

<210> SEQ ID NO 172
<211> LENGTH: 19
<212> TYPE: RNA
```

```
<213> ORGANISM: Artificial Sequence
<220> FEATURE:
<223> OTHER INFORMATION: miRNA/siRNA

<400> SEQUENCE: 172
ccaauuucuu acuaguacu                                                        19

<210> SEQ ID NO 173
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 173
ccuaauuauu acagccuua                                                        19

<210> SEQ ID NO 174
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 174
cuguacacau uaaggugua                                                        19

<210> SEQ ID NO 175
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 175
cugaaacauu gagggaaca                                                        19

<210> SEQ ID NO 176
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 176
cuaggcucua uuuaacuga                                                        19

<210> SEQ ID NO 177
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 177
caguuaccuu aaagcugaa                                                        19

<210> SEQ ID NO 178
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 178
caaugaggga ccaguacau                                                        19
```

<210> SEQ ID NO 179
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 179
cuauaguaua ccagugaau                                              19

<210> SEQ ID NO 180
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 180
ccuucuagaa caguagaca                                              19

<210> SEQ ID NO 181
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 181
gaaacugaau agcugucau                                              19

<210> SEQ ID NO 182
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 182
gacuuacaca guaccucgu                                              19

<210> SEQ ID NO 183
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 183
cagaaguaau gacuccaua                                              19

<210> SEQ ID NO 184
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 184
caacuugagu cuuugaaga                                              19

<210> SEQ ID NO 185
<211> LENGTH: 19
<212> TYPE: RNA
<213> ORGANISM: Artificial Sequence
<220> FEATURE:

```
<223> OTHER INFORMATION: miRNA/siRNA

<400> SEQUENCE: 185
gaagagacca agguugcaa                                                    19

<210> SEQ ID NO 186
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 186
cuuggauauu cucgacaca                                                    19

<210> SEQ ID NO 187
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 187
gaaauggaua uggaauacu                                                    19

<210> SEQ ID NO 188
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 188
gaacucauuu auucagcaa                                                    19

<210> SEQ ID NO 189
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 189
cgauacagcu aauucagaa                                                    19

<210> SEQ ID NO 190
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 190
gucaugcauu gguuaguca                                                    19

<210> SEQ ID NO 191
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 191
gucagaagua augacucca                                                    19
```

```
<210> SEQ ID NO 192
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 192
gauuucugaa uugcuaugu                                                   19

<210> SEQ ID NO 193
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 193
gaaucugaca gauaccaua                                                   19

<210> SEQ ID NO 194
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 194
gagaaucuga cagauacca                                                   19

<210> SEQ ID NO 195
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 195
gaacuagcaa ugccuguga                                                   19

<210> SEQ ID NO 196
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 196
gaaaucuuca ugcaaugaa                                                   19

<210> SEQ ID NO 197
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 197
cuucuauaca uuaguucga                                                   19

<210> SEQ ID NO 198
<211> LENGTH: 19
<212> TYPE: RNA
<213> ORGANISM: Artificial Sequence
<220> FEATURE:
<223> OTHER INFORMATION: miRNA/siRNA
```

```
<400> SEQUENCE: 198
caucucauuu guauuccau                                                19

<210> SEQ ID NO 199
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 199
gauagcauga auucugcau                                                19

<210> SEQ ID NO 200
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 200
gcauacuagu acaaguggu                                                19

<210> SEQ ID NO 201
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 201
cugaagaugu accuauggu                                                19

<210> SEQ ID NO 202
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 202
caaaccuggu augaauaga                                                19

<210> SEQ ID NO 203
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 203
caagauacaa ucucacucu                                                19

<210> SEQ ID NO 204
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 204
gaauugcuau gugaaacua                                                19

<210> SEQ ID NO 205
<211> LENGTH: 19
```

```
<212> TYPE: RNA
<213> ORGANISM: Artificial Sequence
<220> FEATURE:
<223> OTHER INFORMATION: miRNA/siRNA

<400> SEQUENCE: 205
gauuugaccu aaucacuaa                                                    19

<210> SEQ ID NO 206
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 206
ccaauccauu agcgacagu                                                    19

<210> SEQ ID NO 207
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 207
cagagaaaga aauggccau                                                    19

<210> SEQ ID NO 208
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 208
cuuggccuca uaaaccugu                                                    19

<210> SEQ ID NO 209
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 209
cuaguucaca gacaaggaa                                                    19

<210> SEQ ID NO 210
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 210
ccauuagcga caguaggau                                                    19

<210> SEQ ID NO 211
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 211
```
ccuacaucuu auuccuca                                         19

<210> SEQ ID NO 212
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 212
cuaugguccu aguaggaaa                                        19

<210> SEQ ID NO 213
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 213
cugaaagaau uccuuaggu                                        19

<210> SEQ ID NO 214
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 214
cuauguuaca ccaucuuca                                        19

<210> SEQ ID NO 215
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 215
gaauuccuua gguaaucua                                        19

<210> SEQ ID NO 216
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 216
cacuauagua uaccaguga                                        19

<210> SEQ ID NO 217
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 217
caucagcaaa gacaagaca                                        19

<210> SEQ ID NO 218
<211> LENGTH: 19
<212> TYPE: RNA
<213> ORGANISM: Artificial Sequence

```
<220> FEATURE:
<223> OTHER INFORMATION: miRNA/siRNA

<400> SEQUENCE: 218
caagaggagu acagugcaa                                                  19

<210> SEQ ID NO 219
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 219
ggaauacuuu auaagccau                                                  19

<210> SEQ ID NO 220
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 220
caugaauucu gcauugaga                                                  19

<210> SEQ ID NO 221
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 221
guuuccaauu ccacugucu                                                  19

<210> SEQ ID NO 222
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 222
cauguccuau aguuuguca                                                  19

<210> SEQ ID NO 223
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 223
gugaaaguau cacuggacu                                                  19

<210> SEQ ID NO 224
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 224
gaguuucaca gcauggacu                                                  19
```

```
<210> SEQ ID NO 225
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 225
guaacauguu uaccuggaa                                              19

<210> SEQ ID NO 226
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 226
cugaacuagu ucacagaca                                              19

<210> SEQ ID NO 227
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 227
cucaagagaa ucugacaga                                              19

<210> SEQ ID NO 228
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 228
guaacaguaa uacauucca                                              19

<210> SEQ ID NO 229
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 229
caauccauua gcgacagua                                              19

<210> SEQ ID NO 230
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 230
gaaagauacu cacaugagu                                              19

<210> SEQ ID NO 231
<211> LENGTH: 19
<212> TYPE: RNA
<213> ORGANISM: Artificial Sequence
<220> FEATURE:
<223> OTHER INFORMATION: miRNA/siRNA
```

<400> SEQUENCE: 231
ccaaaugugu aauauucca                                                    19

<210> SEQ ID NO 232
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 232
guuugggaua augauaggu                                                    19

<210> SEQ ID NO 233
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 233
caacaauaga ggauccua                                                     19

<210> SEQ ID NO 234
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 234
caugaacugu acuacuccu                                                    19

<210> SEQ ID NO 235
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 235
gaaacauuga gggaacaca                                                    19

<210> SEQ ID NO 236
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 236
cucuuggaua uucucgaca                                                    19

<210> SEQ ID NO 237
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 237
gcauuaacau guuugugga                                                    19

<210> SEQ ID NO 238

```
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 238
cugaauauaa acuguggu                                                    19

<210> SEQ ID NO 239
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 239
guaaaggcgu guuugcuua                                                   19

<210> SEQ ID NO 240
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 240
cuuugaacau cucuuugcu                                                   19

<210> SEQ ID NO 241
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 241
ccauacuuca ggaacugca                                                   19

<210> SEQ ID NO 242
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 242
cuauacauua guucgagaa                                                   19

<210> SEQ ID NO 243
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 243
cuucuaggca ucauguccu                                                   19

<210> SEQ ID NO 244
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 244
```
gaauaccuaa gauuucugu                    19

<210> SEQ ID NO 245
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 245
cauacuagua caaguggua                    19

<210> SEQ ID NO 246
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 246
cauaggaauu uagaaccua                    19

<210> SEQ ID NO 247
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 247
gaaacuauua uaaggccau                    19

<210> SEQ ID NO 248
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 248
cuuagcaaga aguuaugga                    19

<210> SEQ ID NO 249
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 249
cuucuguguu aauacugga                    19

<210> SEQ ID NO 250
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 250
cuuaaggcau acuaguaca                    19

<210> SEQ ID NO 251
<211> LENGTH: 19
<212> TYPE: RNA

```
<213> ORGANISM: Artificial Sequence
<220> FEATURE:
<223> OTHER INFORMATION: miRNA/siRNA

<400> SEQUENCE: 251
ccuauaguuu gucaucccu                                                   19

<210> SEQ ID NO 252
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 252
cuuugagcuu ucauagaga                                                   19

<210> SEQ ID NO 253
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 253
caaguaggca uucuaggcu                                                   19

<210> SEQ ID NO 254
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 254
caagagacau aaucccggu                                                   19

<210> SEQ ID NO 255
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 255
caauuccacu gucuugugu                                                   19

<210> SEQ ID NO 256
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 256
guuauagcuu auuaggugu                                                   19

<210> SEQ ID NO 257
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 257
gauauucaua uugacccaa                                                   19
```

<210> SEQ ID NO 258
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 258
cauagagagu uucacagca                                                 19

<210> SEQ ID NO 259
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 259
guaaucuaua acuaggacu                                                 19

<210> SEQ ID NO 260
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 260
gaacacaaau uuaugggcu                                                 19

<210> SEQ ID NO 261
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 261
guuuauagga guaugugcu                                                 19

<210> SEQ ID NO 262
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 262
cauaaaggga uuugaccua                                                 19

<210> SEQ ID NO 263
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 263
cauaagauuu acugcugcu                                                 19

<210> SEQ ID NO 264
<211> LENGTH: 19
<212> TYPE: RNA
<213> ORGANISM: Artificial Sequence
<220> FEATURE:

<223> OTHER INFORMATION: miRNA/siRNA

<400> SEQUENCE: 264
cuuugguaua cgacccaga                                                    19

<210> SEQ ID NO 265
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 265
guaaacugaa acaugcaca                                                    19

<210> SEQ ID NO 266
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 266
ggaaacuauu auaaggcca                                                    19

<210> SEQ ID NO 267
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 267
caauugugaa uguuggugu                                                    19

<210> SEQ ID NO 268
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 268
cuaagugcca guauuccca                                                    19

<210> SEQ ID NO 269
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 269
cauuugaaga uauucacca                                                    19

<210> SEQ ID NO 270
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 270
cuuauuuccu cagggcuca                                                    19

<210> SEQ ID NO 271
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 271
caaauaaaca ggugccuga                                              19

<210> SEQ ID NO 272
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 272
ggugacuuag guucuagau                                              19

<210> SEQ ID NO 273
<211> LENGTH: 66
<212> TYPE: DNA
<213> ORGANISM: Artificial Sequence
<220> FEATURE:
<223> OTHER INFORMATION: miRNA/siRNA

<400> SEQUENCE: 273
tgctgaattc ggtgacttag gttctagatg ttttggccac tgactgacat ctagaataag    60
tcacca                                                               66

<210> SEQ ID NO 274
<211> LENGTH: 66
<212> TYPE: DNA
<213> ORGANISM: Artificial Sequence
<220> FEATURE:
<223> OTHER INFORMATION: miRNA/siRNA

<400> SEQUENCE: 274
tgctgaattc ggtgacttag guucuagaug ttttggccac tgactgacat ctagaataag    60
tcacca                                                               66

<210> SEQ ID NO 275
<211> LENGTH: 65
<212> TYPE: DNA
<213> ORGANISM: Artificial Sequence
<220> FEATURE:
<223> OTHER INFORMATION: miRNA/siRNA

<400> SEQUENCE: 275
cctgaccggt ggtgacttat tctagatgtc agtcagtggc caaaacatct agaacctaag    60
tcacc                                                                65

<210> SEQ ID NO 276
<211> LENGTH: 64
<212> TYPE: DNA
<213> ORGANISM: Artificial Sequence
<220> FEATURE:
<223> OTHER INFORMATION: miRNA/siRNA

<400> SEQUENCE: 276
tgctgaaatg tactgcgcgt ggagacgttt tggccactga ctgacgtctc cacgcagtac    60
attt                                                                 64

-continued

<210> SEQ ID NO 277
<211> LENGTH: 64
<212> TYPE: DNA
<213> ORGANISM: Artificial Sequence
<220> FEATURE:
<223> OTHER INFORMATION: miRNA/siRNA

<400> SEQUENCE: 277
cctgaaatgt actgcgtgga gacgtcagtc agtggccaaa acgtctccac gcgcagtaca    60
tttc    64

<210> SEQ ID NO 278
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 278
gucgcuauca aggaauuaa    19

<210> SEQ ID NO 279
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 279
gggaacacaa agacaauau    19

<210> SEQ ID NO 280
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 280
gaggaugaca caucaaaua    19

<210> SEQ ID NO 281
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 281
ggcagguaca guaggauaa    19

<210> SEQ ID NO 282
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 282
cgggaacaca aagacaaua    19

<210> SEQ ID NO 283
<211> LENGTH: 19
<212> TYPE: RNA
<213> ORGANISM: Artificial Sequence

```
<220> FEATURE:
<223> OTHER INFORMATION: miRNA/siRNA

<400> SEQUENCE: 283
ggcuugcauu gauagaaau                                                19

<210> SEQ ID NO 284
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 284
ccacaaagca gugaauuua                                                19

<210> SEQ ID NO 285
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 285
ggaugacaca ucaaauaau                                                19

<210> SEQ ID NO 286
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 286
guggaauuca gguaguaaa                                                19

<210> SEQ ID NO 287
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 287
gaggcaaagu gccuaucaa                                                19

<210> SEQ ID NO 288
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 288
gugcggaaga gaaagaaua                                                19

<210> SEQ ID NO 289
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 289
cagcccacau uggauucau                                                19
```

<210> SEQ ID NO 290
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 290
gugcuaugca aauacaaua                                               19

<210> SEQ ID NO 291
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 291
guggcuugca uugauagaa                                               19

<210> SEQ ID NO 292
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 292
gugauggaga ugugauaau                                               19

<210> SEQ ID NO 293
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 293
gggcauagau cagaagacu                                               19

<210> SEQ ID NO 294
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 294
cuccagagga uguucaaua                                               19

<210> SEQ ID NO 295
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 295
gcgaaugaca guagcauua                                               19

<210> SEQ ID NO 296
<211> LENGTH: 19
<212> TYPE: RNA
<213> ORGANISM: Artificial Sequence
<220> FEATURE:
<223> OTHER INFORMATION: miRNA/siRNA

```
<400> SEQUENCE: 296
cagugccuga auacauaaa                                                    19

<210> SEQ ID NO 297
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 297
cuugggaauu uggaaauua                                                    19

<210> SEQ ID NO 298
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 298
guggauggca uuggaauca                                                    19

<210> SEQ ID NO 299
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 299
gccuuugaga accagaaaa                                                    19

<210> SEQ ID NO 300
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 300
cagcugagaa uguggaaua                                                    19

<210> SEQ ID NO 301
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 301
gagcguuaga cugacuugu                                                    19

<210> SEQ ID NO 302
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 302
cccagugccu gaauacaua                                                    19

<210> SEQ ID NO 303
```

```
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 303
ggugacuccu ucacacaua                                                    19

<210> SEQ ID NO 304
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 304
gauccaagaa ggccuucau                                                    19

<210> SEQ ID NO 305
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 305
cugccagaaa cugaccaaa                                                    19

<210> SEQ ID NO 306
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 306
guccgcaagu guaagaagu                                                    19

<210> SEQ ID NO 307
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 307
gugacuuucu cagcaacau                                                    19

<210> SEQ ID NO 308
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 308
cuccauaaau gcuacgaau                                                    19

<210> SEQ ID NO 309
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 309
```
ggaaguugca uuccuuugu                                                19

<210> SEQ ID NO 310
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 310
caggaacgua cuggugaaa                                                19

<210> SEQ ID NO 311
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 311
gucagccuga acauaacau                                                19

<210> SEQ ID NO 312
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 312
ccuaugugca gaggaauua                                                19

<210> SEQ ID NO 313
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 313
cagcaguccu uuguaaaca                                                19

<210> SEQ ID NO 314
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 314
ccuuugagca gaaauuuau                                                19

<210> SEQ ID NO 315
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 315
gaucccagaa ggugagaaa                                                19

<210> SEQ ID NO 316
<211> LENGTH: 19
<212> TYPE: RNA

```
<213> ORGANISM: Artificial Sequence
<220> FEATURE:
<223> OTHER INFORMATION: miRNA/siRNA

<400> SEQUENCE: 316
guaccaucga ugucuacau                                              19

<210> SEQ ID NO 317
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 317
ggauggcauu ggaaucaau                                              19

<210> SEQ ID NO 318
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 318
cagaucauca gaggaaaua                                              19

<210> SEQ ID NO 319
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 319
cccuacagca uuguuaaga                                              19

<210> SEQ ID NO 320
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 320
gagaggauga cacaucaaa                                              19

<210> SEQ ID NO 321
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 321
ggagauaagu gauggagau                                              19

<210> SEQ ID NO 322
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 322
ggagcgaauu ccuuuggaa                                              19
```

```
<210> SEQ ID NO 323
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 323
ggaacuggau auucugaaa                                              19

<210> SEQ ID NO 324
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 324
cagcauuguu aagaaagua                                              19

<210> SEQ ID NO 325
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 325
gggauggaau ucuuccuua                                              19

<210> SEQ ID NO 326
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 326
cccugaugga ugaagaaga                                              19

<210> SEQ ID NO 327
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 327
gcucucuuga ggaucuuga                                              19

<210> SEQ ID NO 328
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 328
gaggcucaga ugaaaugca                                              19

<210> SEQ ID NO 329
<211> LENGTH: 19
<212> TYPE: RNA
<213> ORGANISM: Artificial Sequence
<220> FEATURE:
```

<223> OTHER INFORMATION: miRNA/siRNA

<400> SEQUENCE: 329
guccuuggga auuuggaaa                              19

<210> SEQ ID NO 330
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 330
gcucagauga aaugcauca                              19

<210> SEQ ID NO 331
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 331
gaaggaaacu gaauucaaa                              19

<210> SEQ ID NO 332
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 332
cauccagcaa gaauauugu                              19

<210> SEQ ID NO 333
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 333
cgugaguuga ucaucgaau                              19

<210> SEQ ID NO 334
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 334
gcucuuccaa caaggaaga                              19

<210> SEQ ID NO 335
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 335
cuggaugaua gacgcagau                              19

```
<210> SEQ ID NO 336
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 336
ccuacagcau uguuaagaa                                                    19

<210> SEQ ID NO 337
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 337
cggaucggua cuguaucaa                                                    19

<210> SEQ ID NO 338
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 338
ggagaacucu gagugcaua                                                    19

<210> SEQ ID NO 339
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 339
ccaucgaugu cuacaugau                                                    19

<210> SEQ ID NO 340
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 340
cagaggaugu ucaauaacu                                                    19

<210> SEQ ID NO 341
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 341
cacaggaacu ggauauucu                                                    19

<210> SEQ ID NO 342
<211> LENGTH: 19
<212> TYPE: RNA
<213> ORGANISM: Artificial Sequence
<220> FEATURE:
<223> OTHER INFORMATION: miRNA/siRNA
```

```
<400> SEQUENCE: 342
gugcgaauga caguagcau                                              19

<210> SEQ ID NO 343
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 343
cugucuugcu gucaugaaa                                              19

<210> SEQ ID NO 344
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 344
ccuuugagaa ccuagaaau                                              19

<210> SEQ ID NO 345
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 345
gccuacaguu auguucagu                                              19

<210> SEQ ID NO 346
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 346
guguggaauu cagguagua                                              19

<210> SEQ ID NO 347
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 347
gaggaaauau guacuacga                                              19

<210> SEQ ID NO 348
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 348
gugauaauuu caggaaaca                                              19

<210> SEQ ID NO 349
<211> LENGTH: 19
```

```
<212> TYPE: RNA
<213> ORGANISM: Artificial Sequence
<220> FEATURE:
<223> OTHER INFORMATION: miRNA/siRNA

<400> SEQUENCE: 349
cagucacaca cacauacaa                                               19

<210> SEQ ID NO 350
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 350
gaguugauca ucgaauucu                                               19

<210> SEQ ID NO 351
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 351
ggaauaggua uuggugaau                                               19

<210> SEQ ID NO 352
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 352
gcaguccuuu guaaacagu                                               19

<210> SEQ ID NO 353
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 353
gaucuuuccu ucuuaaaga                                               19

<210> SEQ ID NO 354
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 354
ccuugaguca ucuauucaa                                               19

<210> SEQ ID NO 355
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 355
```

```
cccucaagga gauaaguga                                               19

<210> SEQ ID NO 356
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 356
cagaagguga gaaaguuaa                                               19

<210> SEQ ID NO 357
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 357
ccuacagacu ccaacuucu                                               19

<210> SEQ ID NO 358
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 358
gcauuccuuu gucuucaaa                                               19

<210> SEQ ID NO 359
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 359
cuugccgcaa aguguguaa                                               19

<210> SEQ ID NO 360
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 360
cgguacugua ucaagucau                                               19

<210> SEQ ID NO 361
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 361
gaucgguacu guaucaagu                                               19

<210> SEQ ID NO 362
<211> LENGTH: 19
<212> TYPE: RNA
<213> ORGANISM: Artificial Sequence
```

```
<220> FEATURE:
<223> OTHER INFORMATION: miRNA/siRNA

<400> SEQUENCE: 362
ggacuucuuu cccaaggaa                                                19

<210> SEQ ID NO 363
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 363
ccuguaaccu gacugguua                                                19

<210> SEQ ID NO 364
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 364
gcagugacuu ucucagcaa                                                19

<210> SEQ ID NO 365
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 365
gcugucauga aaucagcaa                                                19

<210> SEQ ID NO 366
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 366
cgaaagccaa caaggaaau                                                19

<210> SEQ ID NO 367
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 367
ccgaguaucu caacacugu                                                19

<210> SEQ ID NO 368
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 368
gaccagacaa cuguaucca                                                19
```

```
<210> SEQ ID NO 369
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 369
guuagacuga cuuguuugu                                                      19

<210> SEQ ID NO 370
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 370
ggaaauaugu acuacgaaa                                                      19

<210> SEQ ID NO 371
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 371
gcuacgaaua uuaaacacu                                                      19

<210> SEQ ID NO 372
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 372
cuacagcauu guuaagaaa                                                      19

<210> SEQ ID NO 373
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 373
guagcauuau gaguagugu                                                      19

<210> SEQ ID NO 374
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 374
caucuccgaa agccaacaa                                                      19

<210> SEQ ID NO 375
<211> LENGTH: 19
<212> TYPE: RNA
<213> ORGANISM: Artificial Sequence
<220> FEATURE:
<223> OTHER INFORMATION: miRNA/siRNA
```

-continued

<400> SEQUENCE: 375
gaggaugcuu gauuccagu                                                19

<210> SEQ ID NO 376
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 376
gacaguagca uuaugagua                                                19

<210> SEQ ID NO 377
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 377
ccgaaagcca acaaggaaa                                                19

<210> SEQ ID NO 378
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 378
gcaacguuua caccgacua                                                19

<210> SEQ ID NO 379
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 379
ccaagccaua ugacggaau                                                19

<210> SEQ ID NO 380
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 380
gaucaucgaa uucuccaaa                                                19

<210> SEQ ID NO 381
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 381
cggaauaggu auuggugaa                                                19

<210> SEQ ID NO 382

```
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 382
guguuacuua uggaagaua                                                      19

<210> SEQ ID NO 383
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 383
caagcucucu ugaggaucu                                                      19

<210> SEQ ID NO 384
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 384
cugcagauca ucagaggaa                                                      19

<210> SEQ ID NO 385
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 385
gacuuucuca gcaacaugu                                                      19

<210> SEQ ID NO 386
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 386
cugugaagca uuuacagaa                                                      19

<210> SEQ ID NO 387
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 387
ggaagagaaa gaauaccau                                                      19

<210> SEQ ID NO 388
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 388
```
ggaucuugaa ggaaacuga                                              19

<210> SEQ ID NO 389
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 389
ccuuagcagu cuuaucuaa                                              19

<210> SEQ ID NO 390
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 390
gcuaugagau ggaggaaga                                              19

<210> SEQ ID NO 391
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 391
gcaaagggca ugaacuacu                                              19

<210> SEQ ID NO 392
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 392
ggaauuaaga gaagcaaca                                              19

<210> SEQ ID NO 393
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 393
caucagcauu uggaccaau                                              19

<210> SEQ ID NO 394
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 394
gcaaccagca acaauucca                                              19

<210> SEQ ID NO 395
<211> LENGTH: 19
<212> TYPE: RNA

```
<213> ORGANISM: Artificial Sequence
<220> FEATURE:
<223> OTHER INFORMATION: miRNA/siRNA

<400> SEQUENCE: 395
gaggauagua ugagcccua                                                    19

<210> SEQ ID NO 396
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 396
caagggaguu uguggagaa                                                    19

<210> SEQ ID NO 397
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 397
cguaccagau ggaugugaa                                                    19

<210> SEQ ID NO 398
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 398
ccugaauaca uaaaccagu                                                    19

<210> SEQ ID NO 399
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 399
ccagacaacu guauccagu                                                    19

<210> SEQ ID NO 400
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 400
cucuccauaa augcuacga                                                    19

<210> SEQ ID NO 401
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 401
ggauguucaa uaacuguga                                                    19
```

```
<210> SEQ ID NO 402
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 402
cuccuucaca cauacuccu                                            19

<210> SEQ ID NO 403
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 403
cugugcagaa uccugucua                                            19

<210> SEQ ID NO 404
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 404
ccuaauuuga ggcucagau                                            19

<210> SEQ ID NO 405
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 405
caguagcauu augaguagu                                            19

<210> SEQ ID NO 406
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 406
gcauuugcca aguccuaca                                            19

<210> SEQ ID NO 407
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 407
caaagugugu aacggaaua                                            19

<210> SEQ ID NO 408
<211> LENGTH: 19
<212> TYPE: RNA
<213> ORGANISM: Artificial Sequence
<220> FEATURE:
```

-continued

```
<223> OTHER INFORMATION: miRNA/siRNA

<400> SEQUENCE: 408
gauaaugcuu ucacaacau                                              19

<210> SEQ ID NO 409
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 409
ccguaauuau guggugaca                                              19

<210> SEQ ID NO 410
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 410
gaugcuugau uccaguggu                                              19

<210> SEQ ID NO 411
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 411
guuaacagca guccuuugu                                              19

<210> SEQ ID NO 412
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 412
cugacuuguu ugucuucca                                              19

<210> SEQ ID NO 413
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 413
cauccaauuu aucaaggaa                                              19

<210> SEQ ID NO 414
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 414
ccauccaauu uaucaagga                                              19
```

```
<210> SEQ ID NO 415
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 415
cugagaaugu ggaauaccu                                                 19

<210> SEQ ID NO 416
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 416
gacauaguca gcagugacu                                                 19

<210> SEQ ID NO 417
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 417
cucuccuagu caauaucca                                                 19

<210> SEQ ID NO 418
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 418
cggaagagaa agaauacca                                                 19

<210> SEQ ID NO 419
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 419
cgcaaagugu guaacggaa                                                 19

<210> SEQ ID NO 420
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 420
gaguugauga ccuuuggau                                                 19

<210> SEQ ID NO 421
<211> LENGTH: 19
<212> TYPE: RNA
<213> ORGANISM: Artificial Sequence
<220> FEATURE:
<223> OTHER INFORMATION: miRNA/siRNA
```

<400> SEQUENCE: 421
caaggaauua agagaagca					19

<210> SEQ ID NO 422
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 422
cuaugccuua gcagucuua					19

<210> SEQ ID NO 423
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 423
gugaauuuaa agacucacu					19

<210> SEQ ID NO 424
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 424
ccuucuuaaa gaccaucca					19

<210> SEQ ID NO 425
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 425
gaugugauaa uuucaggaa					19

<210> SEQ ID NO 426
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 426
caccaaauua gccuggaca					19

<210> SEQ ID NO 427
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 427
caacaaggaa auccucgau					19

<210> SEQ ID NO 428
<211> LENGTH: 19

-continued

<210> SEQ ID NO 428 (continued)
<212> TYPE: RNA
<213> ORGANISM: Artificial Sequence
<220> FEATURE:
<223> OTHER INFORMATION: miRNA/siRNA

<400> SEQUENCE: 428
ccaugccuuu gagaaccua                                              19

<210> SEQ ID NO 429
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 429
ggauucauca gcauuugga                                              19

<210> SEQ ID NO 430
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 430
caaggagaua agugaugga                                              19

<210> SEQ ID NO 431
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 431
caguaggaua agccacucu                                              19

<210> SEQ ID NO 432
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 432
guagugugga auucaggua                                              19

<210> SEQ ID NO 433
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 433
cugacugguu aacagcagu                                              19

<210> SEQ ID NO 434
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 434
caugagcguu agacugacu                                                19

<210> SEQ ID NO 435
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 435
ccaacaagga aauccucga                                                19

<210> SEQ ID NO 436
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 436
ggaauaccua aggauagca                                                19

<210> SEQ ID NO 437
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 437
ggaauuugga aauuaccua                                                19

<210> SEQ ID NO 438
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 438
cagcaagaau auugcccu                                                 19

<210> SEQ ID NO 439
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 439
gcaugaacua cuuggagga                                                19

<210> SEQ ID NO 440
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 440
cuuacgcuuu gucacacaa                                                19

<210> SEQ ID NO 441
<211> LENGTH: 19
<212> TYPE: RNA
<213> ORGANISM: Artificial Sequence

```
<220> FEATURE:
<223> OTHER INFORMATION: miRNA/siRNA

<400> SEQUENCE: 441
gucaacagca cauucgaca                                               19

<210> SEQ ID NO 442
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 442
cacaagucuu ccagaggau                                               19

<210> SEQ ID NO 443
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 443
caugagaaau uuacaggaa                                               19

<210> SEQ ID NO 444
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 444
cuacaguuau guucaguca                                               19

<210> SEQ ID NO 445
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 445
gcaaguguaa gaagugcga                                               19

<210> SEQ ID NO 446
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 446
ccuuacgcuu ugucacaca                                               19

<210> SEQ ID NO 447
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 447
ccaugagaaa uuuacagga                                               19
```

```
<210> SEQ ID NO 448
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 448
gucuacauga ucaugguca                                              19

<210> SEQ ID NO 449
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 449
cagugaauuu auuggagca                                              19

<210> SEQ ID NO 450
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 450
cagaugaaau gcaucaggu                                              19

<210> SEQ ID NO 451
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 451
ccuaucaagu ggauggcau                                              19

<210> SEQ ID NO 452
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 452
gcaaauacaa uaaacugga                                              19

<210> SEQ ID NO 453
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 453
guuuguguua cuuauggaa                                              19

<210> SEQ ID NO 454
<211> LENGTH: 19
<212> TYPE: RNA
<213> ORGANISM: Artificial Sequence
<220> FEATURE:
<223> OTHER INFORMATION: miRNA/siRNA
```

-continued

```
<400> SEQUENCE: 454
cuucacacau acuccuccu                                              19

<210> SEQ ID NO 455
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 455
cuaucaagga auuaagaga                                              19

<210> SEQ ID NO 456
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 456
cagacucuuu cgauaccca                                              19

<210> SEQ ID NO 457
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 457
cacauuggau ucaucagca                                              19

<210> SEQ ID NO 458
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 458
gaaaucagca agagaggau                                              19

<210> SEQ ID NO 459
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 459
cuauauucau uuccacucu                                              19

<210> SEQ ID NO 460
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 460
gaaauuuaca ggaaauccu                                              19

<210> SEQ ID NO 461
```

```
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 461
guuugggagu ugaugaccu                                        19

<210> SEQ ID NO 462
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 462
caucaaauaa uaacucgga                                        19

<210> SEQ ID NO 463
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 463
guaauuaugu ggugacaga                                        19

<210> SEQ ID NO 464
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 464
gaacauaaca uccuuggga                                        19

<210> SEQ ID NO 465
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 465
cacaaagaca auauuggcu                                        19

<210> SEQ ID NO 466
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 466
cauuaugagu aguguggaa                                        19

<210> SEQ ID NO 467
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 467
```

-continued cuagaaauca uacgcggca                                    19

<210> SEQ ID NO 468
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 468 cuuccuucu uaaagacca                                     19

<210> SEQ ID NO 469
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 469
gaaauuaccu augugcaga                                    19

<210> SEQ ID NO 470
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 470
caaagaguau auguuccu                                     19

<210> SEQ ID NO 471
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 471
guaaauauga aacuagggu                                    19

<210> SEQ ID NO 472
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 472
guaaaggaaa ucacagggu                                    19

<210> SEQ ID NO 473
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 473
guuauguccu cauugcccu                                    19

<210> SEQ ID NO 474
<211> LENGTH: 21
<212> TYPE: RNA

```
<213> ORGANISM: Artificial Sequence
<220> FEATURE:
<223> OTHER INFORMATION: miRNA/siRNA

<400> SEQUENCE: 474
aggaauuaag agaagcaaca u                                              21

<210> SEQ ID NO 475
<211> LENGTH: 74
<212> TYPE: DNA
<213> ORGANISM: Artificial Sequence
<220> FEATURE:
<223> OTHER INFORMATION: miRNA/siRNA

<400> SEQUENCE: 475
tgctgaattc gaggaattaa gagaagcaac atgttttggc cactgactga catgttgctt    60
ctcttaattc ctca                                                      74

<210> SEQ ID NO 476
<211> LENGTH: 72
<212> TYPE: DNA
<213> ORGANISM: Artificial Sequence
<220> FEATURE:
<223> OTHER INFORMATION: miRNA/siRNA

<400> SEQUENCE: 476
cctgaccggt gaggaattaa gagaagcaac atgtcagtca gtggccaaaa catgttgctt    60
ctcttaattc ct                                                        72

<210> SEQ ID NO 477
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 477
gccgacuaca agcgaauua                                                 19

<210> SEQ ID NO 478
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 478
cugggagcca ucuuauuau                                                 19

<210> SEQ ID NO 479
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 479
gaggaagcaa acagauuaa                                                 19

<210> SEQ ID NO 480
<211> LENGTH: 19
<212> TYPE: RNA
<213> ORGANISM: Artificial Sequence
<220> FEATURE:
<223> OTHER INFORMATION: miRNA/siRNA
```

<400> SEQUENCE: 480
cggguugaga aucccuaau                                                19

<210> SEQ ID NO 481
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 481
gaccuugaua cuuucaaau                                                19

<210> SEQ ID NO 482
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 482
ggaggaaaua ggccaaugu                                                19

<210> SEQ ID NO 483
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 483
caggcaaugu gggacuuaa                                                19

<210> SEQ ID NO 484
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 484
gagccuccaa gcaaaucau                                                19

<210> SEQ ID NO 485
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 485
gacgguugga uauacuuaa                                                19

<210> SEQ ID NO 486
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 486
guggcaucca agauacaaa                                                19

<210> SEQ ID NO 487

```
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 487
ggagcucaua guauaauga                                                19

<210> SEQ ID NO 488
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 488
ggaggagaau gaagaaaga                                                19

<210> SEQ ID NO 489
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 489
ggcugcacua auugucuau                                                19

<210> SEQ ID NO 490
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 490
ggcacauccu ccaaaugaa                                                19

<210> SEQ ID NO 491
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 491
ggacagaguu uggauuugu                                                19

<210> SEQ ID NO 492
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 492
cgggacagua uuuauguau                                                19

<210> SEQ ID NO 493
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 493
```

```
ggugcacuga gucaaucua                                                19

<210> SEQ ID NO 494
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 494
gggcauucca gaaagauga                                                19

<210> SEQ ID NO 495
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 495
cuugcccaaa ccaguaaau                                                19

<210> SEQ ID NO 496
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 496
gugccaggca uugaaucua                                                19

<210> SEQ ID NO 497
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 497
cugccuuuca uucauaugu                                                19

<210> SEQ ID NO 498
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 498
gugguuguga augauuucu                                                19

<210> SEQ ID NO 499
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 499
guugccaaga ggaggaaau                                                19

<210> SEQ ID NO 500
<211> LENGTH: 19
<212> TYPE: RNA
```

```
<213> ORGANISM: Artificial Sequence
<220> FEATURE:
<223> OTHER INFORMATION: miRNA/siRNA

<400> SEQUENCE: 500
ggacucacuu gguaauucu                                                    19

<210> SEQ ID NO 501
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 501
gccauauucu ggugucaau                                                    19

<210> SEQ ID NO 502
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 502
ccagcacacu gagaaucaa                                                    19

<210> SEQ ID NO 503
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 503
gaggaggaga augaagaaa                                                    19

<210> SEQ ID NO 504
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 504
gcagauggaa ugaauuuga                                                    19

<210> SEQ ID NO 505
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 505
gagucaaucu aguccuaaa                                                    19

<210> SEQ ID NO 506
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 506
gggaaaugga ggauaagaa                                                    19
```

```
<210> SEQ ID NO 507
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 507
cuccacucaa ugccucaau                                                    19

<210> SEQ ID NO 508
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 508
caguaucugu uccauuuaa                                                    19

<210> SEQ ID NO 509
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 509
ggacaguauu uauguauga                                                    19

<210> SEQ ID NO 510
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 510
gccaggcauu gaaucuaca                                                    19

<210> SEQ ID NO 511
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 511
gaggaggaaa uaggccaau                                                    19

<210> SEQ ID NO 512
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 512
gcuacugccu uucauucau                                                    19

<210> SEQ ID NO 513
<211> LENGTH: 19
<212> TYPE: RNA
<213> ORGANISM: Artificial Sequence
<220> FEATURE:
```

<223> OTHER INFORMATION: miRNA/siRNA

<400> SEQUENCE: 513
ggcauaggca gagaugaua                                                19

<210> SEQ ID NO 514
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 514
gugguagccu acacacaua                                                19

<210> SEQ ID NO 515
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 515
ccugaagguu cagcauagu                                                19

<210> SEQ ID NO 516
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 516
gugugacagu guucuuugu                                                19

<210> SEQ ID NO 517
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 517
guugugauaa ccacuauua                                                19

<210> SEQ ID NO 518
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 518
gccuuugcca uauaaucua                                                19

<210> SEQ ID NO 519
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 519
gagguuucga gauucagau                                                19

```
<210> SEQ ID NO 520
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 520
gagaccuuga uacuuucaa                                                  19

<210> SEQ ID NO 521
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 521
cuggagguuu cgagauuca                                                  19

<210> SEQ ID NO 522
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 522
ggcacauagu cuacucagu                                                  19

<210> SEQ ID NO 523
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 523
guagcaauau gacaauuga                                                  19

<210> SEQ ID NO 524
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 524
ggcugaagaa acagugucu                                                  19

<210> SEQ ID NO 525
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 525
gacagggaga aaggauacu                                                  19

<210> SEQ ID NO 526
<211> LENGTH: 19
<212> TYPE: RNA
<213> ORGANISM: Artificial Sequence
<220> FEATURE:
<223> OTHER INFORMATION: miRNA/siRNA
```

```
<400> SEQUENCE: 526
gagugugguu gugaaugau                                                19

<210> SEQ ID NO 527
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 527
gucuccucua uaacuacaa                                                19

<210> SEQ ID NO 528
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 528
ggagaaugau ggaugugaa                                                19

<210> SEQ ID NO 529
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 529
ggauuuguaa ggcacuuua                                                19

<210> SEQ ID NO 530
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 530
gguuggauau acuuaaaca                                                19

<210> SEQ ID NO 531
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 531
cuccucuaua acuacaagu                                                19

<210> SEQ ID NO 532
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 532
cauaggaugu caccuuuau                                                19

<210> SEQ ID NO 533
<211> LENGTH: 19
```

```
<212> TYPE: RNA
<213> ORGANISM: Artificial Sequence
<220> FEATURE:
<223> OTHER INFORMATION: miRNA/siRNA

<400> SEQUENCE: 533
gaagcaaaca gauuaagua                                                      19

<210> SEQ ID NO 534
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 534
gucucauguu ucaucguaa                                                      19

<210> SEQ ID NO 535
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 535
ccuuguguua ucuguuugu                                                      19

<210> SEQ ID NO 536
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 536
ggucuccucu auaacuaca                                                      19

<210> SEQ ID NO 537
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 537
gcugucuuua uauucauga                                                      19

<210> SEQ ID NO 538
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 538
gaugugagca agacaaagu                                                      19

<210> SEQ ID NO 539
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 539
```

```
gggagaauga uggauguga                                              19

<210> SEQ ID NO 540
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 540
cagcauugga acuucugau                                              19

<210> SEQ ID NO 541
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 541
gagcaaggca cauagucua                                              19

<210> SEQ ID NO 542
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 542
guagcacuga cauucaucu                                              19

<210> SEQ ID NO 543
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 543
guguagcacu gacauucau                                              19

<210> SEQ ID NO 544
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 544
caguguucuu ugugugaau                                              19

<210> SEQ ID NO 545
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 545
cauccuccaa gccauucaa                                              19

<210> SEQ ID NO 546
<211> LENGTH: 19
<212> TYPE: RNA
<213> ORGANISM: Artificial Sequence
```

```
<220> FEATURE:
<223> OTHER INFORMATION: miRNA/siRNA

<400> SEQUENCE: 546
cugagaauca acacaacaa                                                    19

<210> SEQ ID NO 547
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 547
caaccaccau uuguuaagu                                                    19

<210> SEQ ID NO 548
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 548
cucuguauga cagaaucau                                                    19

<210> SEQ ID NO 549
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 549
gguagaguau gguagcaau                                                    19

<210> SEQ ID NO 550
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 550
cacacauaau cucauuuca                                                    19

<210> SEQ ID NO 551
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 551
ccucauucgu ugugcuuga                                                    19

<210> SEQ ID NO 552
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 552
gauggaauga auuugaagu                                                    19
```

```
<210> SEQ ID NO 553
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 553
gaagcaaagu gauacacau                                                19

<210> SEQ ID NO 554
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 554
cugcugugua cuuugcuau                                                19

<210> SEQ ID NO 555
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 555
caagcgaauu acugugaaa                                                19

<210> SEQ ID NO 556
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 556
gucauagcau aaggaugau                                                19

<210> SEQ ID NO 557
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 557
guugaccuaa ucuuauucu                                                19

<210> SEQ ID NO 558
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 558
gugaauuaca ggcaagaau                                                19

<210> SEQ ID NO 559
<211> LENGTH: 19
<212> TYPE: RNA
<213> ORGANISM: Artificial Sequence
<220> FEATURE:
<223> OTHER INFORMATION: miRNA/siRNA
```

<400> SEQUENCE: 559
ccuccaagca aaucaucca                    19

<210> SEQ ID NO 560
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 560
caggcauuga aucuacaga                    19

<210> SEQ ID NO 561
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 561
gaagaaagau ggagucaaa                    19

<210> SEQ ID NO 562
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 562
caugccuucu uuguuucua                    19

<210> SEQ ID NO 563
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 563
cgugacaaga ggaaggaau                    19

<210> SEQ ID NO 564
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 564
gcaaggcaca uagucuacu                    19

<210> SEQ ID NO 565
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 565
ccuguuguga uaaccacua                    19

<210> SEQ ID NO 566

```
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 566
gcaaacagau uaaguaacu                                                  19

<210> SEQ ID NO 567
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 567
ccuacacaca uaaucucau                                                  19

<210> SEQ ID NO 568
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 568
gugugaauua caggcaaga                                                  19

<210> SEQ ID NO 569
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 569
gucuacauuu ggaaaugua                                                  19

<210> SEQ ID NO 570
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 570
gaguauggua gcaauauga                                                  19

<210> SEQ ID NO 571
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 571
ggagaaagga uacuucuga                                                  19

<210> SEQ ID NO 572
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 572
```

```
cuuguggugu uggauuugu                                          19

<210> SEQ ID NO 573
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 573
gacaagcagu gaccaucaa                                          19

<210> SEQ ID NO 574
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 574
caagcaguga ccaucaagu                                          19

<210> SEQ ID NO 575
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 575
gugguagagu augguagca                                          19

<210> SEQ ID NO 576
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 576
gugucaauga caaggagua                                          19

<210> SEQ ID NO 577
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 577
gugacaggga gaaaggaua                                          19

<210> SEQ ID NO 578
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 578
cuccaagcaa aucauccau                                          19

<210> SEQ ID NO 579
<211> LENGTH: 19
<212> TYPE: RNA
```

```
<213> ORGANISM: Artificial Sequence
<220> FEATURE:
<223> OTHER INFORMATION: miRNA/siRNA

<400> SEQUENCE: 579
ccuacuggca uuugcugaa                                                 19

<210> SEQ ID NO 580
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 580
gguauuguuu aacaguucu                                                 19

<210> SEQ ID NO 581
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 581
gugacagugu ucuuugugu                                                 19

<210> SEQ ID NO 582
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 582
cugucaagua uaaacuuca                                                 19

<210> SEQ ID NO 583
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 583
cagauggaau gaauuugaa                                                 19

<210> SEQ ID NO 584
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 584
cucauucguu gugcuugaa                                                 19

<210> SEQ ID NO 585
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 585
gagccaucuu auuaugccu                                                 19
```

```
<210> SEQ ID NO 586
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 586
cuuucccucu uggccauau                                                19

<210> SEQ ID NO 587
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 587
cuguugugau aaccacuau                                                19

<210> SEQ ID NO 588
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 588
caagauacaa acucaaaga                                                19

<210> SEQ ID NO 589
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 589
caugggagau gguuggaaa                                                19

<210> SEQ ID NO 590
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 590
guacagcuga ggaagcaaa                                                19

<210> SEQ ID NO 591
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 591
cuggugucaa ugacaagga                                                19

<210> SEQ ID NO 592
<211> LENGTH: 19
<212> TYPE: RNA
<213> ORGANISM: Artificial Sequence
<220> FEATURE:
```

<223> OTHER INFORMATION: miRNA/siRNA

<400> SEQUENCE: 592
cagcugucau cacuacaca                                                    19

<210> SEQ ID NO 593
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 593
gauuugccuu ugccauaua                                                    19

<210> SEQ ID NO 594
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 594
cuccaaauga aaggacuca                                                    19

<210> SEQ ID NO 595
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 595
gucuauuccu aaguccuaa                                                    19

<210> SEQ ID NO 596
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 596
gagagucuca guguuggaa                                                    19

<210> SEQ ID NO 597
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 597
cagaggagga gaaugaaga                                                    19

<210> SEQ ID NO 598
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 598
cugcacuuca gaucacaga                                                    19

```
<210> SEQ ID NO 599
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 599
cuacugccuu ucauucaua                                                   19

<210> SEQ ID NO 600
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 600
gacagaauca ugucuggaa                                                   19

<210> SEQ ID NO 601
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 601
caccaccaau uccaagaga                                                   19

<210> SEQ ID NO 602
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 602
gagaaaggau acuucugaa                                                   19

<210> SEQ ID NO 603
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 603
cuuguguuau cuguuugua                                                   19

<210> SEQ ID NO 604
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 604
gcuuguuuau auagugucu                                                   19

<210> SEQ ID NO 605
<211> LENGTH: 19
<212> TYPE: RNA
<213> ORGANISM: Artificial Sequence
<220> FEATURE:
<223> OTHER INFORMATION: miRNA/siRNA
```

```
<400> SEQUENCE: 605
cauuugcuga acgcauuua                                                    19

<210> SEQ ID NO 606
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 606
cuguaugaca gaaucaugu                                                    19

<210> SEQ ID NO 607
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 607
caaguccuga gugguaaga                                                    19

<210> SEQ ID NO 608
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 608
ggagauuaga uccugagga                                                    19

<210> SEQ ID NO 609
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 609
gcucauagua uaaugagga                                                    19

<210> SEQ ID NO 610
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 610
cauggaguau uuguaaggu                                                    19

<210> SEQ ID NO 611
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 611
ccuuugccau auaaucuaa                                                    19

<210> SEQ ID NO 612
<211> LENGTH: 19
```

```
<212> TYPE: RNA
<213> ORGANISM: Artificial Sequence
<220> FEATURE:
<223> OTHER INFORMATION: miRNA/siRNA

<400> SEQUENCE: 612
guucagcaua guagcuaca                                                19

<210> SEQ ID NO 613
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 613
cauccuccaa augaaagga                                                19

<210> SEQ ID NO 614
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 614
ggauuuguuu auguuugcu                                                19

<210> SEQ ID NO 615
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 615
cacuucagau cacagaugu                                                19

<210> SEQ ID NO 616
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 616
ggauacuucu gaacaagga                                                19

<210> SEQ ID NO 617
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 617
cacacugaga aucaacaca                                                19

<210> SEQ ID NO 618
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 618
```

-continued

```
guucuucuaa agauagucu                                               19

<210> SEQ ID NO 619
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 619
cauccaagau acaaacuca                                               19

<210> SEQ ID NO 620
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 620
gagauuagau ccugaggaa                                               19

<210> SEQ ID NO 621
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 621
gucaaguaua aacuucacu                                               19

<210> SEQ ID NO 622
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 622
cacaugucaa ggcugaaga                                               19

<210> SEQ ID NO 623
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 623
gucuucuugu caugugagu                                               19

<210> SEQ ID NO 624
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 624
cagugucaua gcauaagga                                               19

<210> SEQ ID NO 625
<211> LENGTH: 19
<212> TYPE: RNA
<213> ORGANISM: Artificial Sequence
```

```
<220> FEATURE:
<223> OTHER INFORMATION: miRNA/siRNA

<400> SEQUENCE: 625
cugugcagua ucuguucca                                                   19

<210> SEQ ID NO 626
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 626
caugugcauu uguacagua                                                   19

<210> SEQ ID NO 627
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 627
cucugaacau gaacugaca                                                   19

<210> SEQ ID NO 628
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 628
gaagucaucu ggacaagca                                                   19

<210> SEQ ID NO 629
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 629
caguguaccu ugacugcua                                                   19

<210> SEQ ID NO 630
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 630
caucuuauua ugccuuggu                                                   19

<210> SEQ ID NO 631
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 631
gcuuaaugau uugcucaca                                                   19
```

<210> SEQ ID NO 632
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 632
cugagucaau cuaguccua                                                      19

<210> SEQ ID NO 633
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 633
cuucuaaaga uagucuaca                                                      19

<210> SEQ ID NO 634
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 634
caaggaccua uauguggua                                                      19

<210> SEQ ID NO 635
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 635
cacauagucu acucagucu                                                      19

<210> SEQ ID NO 636
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 636
cacauuugga ggagacgua                                                      19

<210> SEQ ID NO 637
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 637
cuauuccuaa guccuaacu                                                      19

<210> SEQ ID NO 638
<211> LENGTH: 19
<212> TYPE: RNA
<213> ORGANISM: Artificial Sequence
<220> FEATURE:
<223> OTHER INFORMATION: miRNA/siRNA

```
<400> SEQUENCE: 638
cauaguauaa ugaggagau                                                19

<210> SEQ ID NO 639
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 639
cucuaggaca gaguuugga                                                19

<210> SEQ ID NO 640
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 640
cuucuuguca ugugagugu                                                19

<210> SEQ ID NO 641
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 641
cuacaaguau acauuggaa                                                19

<210> SEQ ID NO 642
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 642
cuuggccaua uucggugu                                                 19

<210> SEQ ID NO 643
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 643
guaugacaga aucaugucu                                                19

<210> SEQ ID NO 644
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 644
guuaucuguu uguacaugu                                                19

<210> SEQ ID NO 645
```

```
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 645
gcuuuacaau uauguggua                                                     19

<210> SEQ ID NO 646
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 646
ccaaggaccu auauguggu                                                     19

<210> SEQ ID NO 647
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 647
caaguauaca uuggaagca                                                     19

<210> SEQ ID NO 648
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 648
ccaaaugaaa ggacucacu                                                     19

<210> SEQ ID NO 649
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 649
gauuugcuca caucuagua                                                     19

<210> SEQ ID NO 650
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 650
ccauugcuca uccuaggaa                                                     19

<210> SEQ ID NO 651
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 651
```
gaugauaccu aauucugca                                             19

<210> SEQ ID NO 652
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 652
gucuuuauau ucaugaccu                                             19

<210> SEQ ID NO 653
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 653
cuucagauca cagauguga                                             19

<210> SEQ ID NO 654
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 654
ccuugcaaua ucaaucgcu                                             19

<210> SEQ ID NO 655
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 655
cugaacgcau uuacuguca                                             19

<210> SEQ ID NO 656
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 656
gucaccuuua uuuaaccca                                             19

<210> SEQ ID NO 657
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 657
gugauacaca uuuggagga                                             19

<210> SEQ ID NO 658
<211> LENGTH: 19
<212> TYPE: RNA

```
<213> ORGANISM: Artificial Sequence
<220> FEATURE:
<223> OTHER INFORMATION: miRNA/siRNA

<400> SEQUENCE: 658
cacauuguau gucugcugu                                                    19

<210> SEQ ID NO 659
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 659
gaauuacugu gaaagucaa                                                    19

<210> SEQ ID NO 660
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 660
cucuuggcca uauucuggu                                                    19

<210> SEQ ID NO 661
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 661
cuuaaugauu ugcucacau                                                    19

<210> SEQ ID NO 662
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 662
cuugucaugu gaguguggu                                                    19

<210> SEQ ID NO 663
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 663
guguuucuua uauagcaga                                                    19

<210> SEQ ID NO 664
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 664
cugaucuuca agcagggau                                                    19
```

```
<210> SEQ ID NO 665
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 665
cauuguaugu cugcugugu                                               19

<210> SEQ ID NO 666
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 666
ccaaacuaaa cuugcugcu                                               19

<210> SEQ ID NO 667
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 667
cauucaaguu uccuuucca                                               19

<210> SEQ ID NO 668
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 668
cuaauugucu auugggaaa                                               19

<210> SEQ ID NO 669
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 669
gauacuuuca aaugccuga                                               19

<210> SEQ ID NO 670
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 670
cauaguagcu acagacaga                                               19

<210> SEQ ID NO 671
<211> LENGTH: 19
<212> TYPE: RNA
<213> ORGANISM: Artificial Sequence
<220> FEATURE:
```

<223> OTHER INFORMATION: miRNA/siRNA

<400> SEQUENCE: 671
cagaugugaa auugcagga					19

<210> SEQ ID NO 672
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 672
cugaauuggu caucccaga					19

<210> SEQ ID NO 673
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 673
guuucaucgu aaauggcau					19

<210> SEQ ID NO 674
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 674
gaaugaagaa agauggagu					19

<210> SEQ ID NO 675
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 675
gauacacauu uggaggaga					19

<210> SEQ ID NO 676
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 676
guuacuuggu acaccagca					19

<210> SEQ ID NO 677
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 677
caagaauugu ggcugagca					19

```
<210> SEQ ID NO 678
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 678
cuuugaugcu guacuugca                                            19

<210> SEQ ID NO 679
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 679
ccaauuccaa gagagagga                                            19

<210> SEQ ID NO 680
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 680
guguuggauu uguaaggca                                            19

<210> SEQ ID NO 681
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 681
guaaauagca gaccucaga                                            19

<210> SEQ ID NO 682
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 682
cuuuccagaa gcaacugcu                                            19

<210> SEQ ID NO 683
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 683
cauuuguaca guaauuggu                                            19

<210> SEQ ID NO 684
<211> LENGTH: 19
<212> TYPE: RNA
<213> ORGANISM: Artificial Sequence
<220> FEATURE:
<223> OTHER INFORMATION: miRNA/siRNA
```

<400> SEQUENCE: 684
cuauugggaa auggaggau					19

<210> SEQ ID NO 685
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 685
cuaaguccua acuccuccu					19

<210> SEQ ID NO 686
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 686
gaaucccuaa uuugagggu					19

<210> SEQ ID NO 687
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 687
cacuaauugu cuauuggga					19

<210> SEQ ID NO 688
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 688
gauuaaguaa cuugcccaa					19

<210> SEQ ID NO 689
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 689
cuugaacccu ugaaugcca					19

<210> SEQ ID NO 690
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 690
cauuccagaa agaugagga					19

<210> SEQ ID NO 691
<211> LENGTH: 19

```
<212> TYPE: RNA
<213> ORGANISM: Artificial Sequence
<220> FEATURE:
<223> OTHER INFORMATION: miRNA/siRNA

<400> SEQUENCE: 691
caaaccagua aauagcaga                                              19

<210> SEQ ID NO 692
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 692
cuuucuggaa auuccggca                                              19

<210> SEQ ID NO 693
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 693
cccugugguu cuauuauau                                              19

<210> SEQ ID NO 694
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 694
caggccuaga gaaguuuca                                              19

<210> SEQ ID NO 695
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 695
ccaggauggu ucuuagacu                                              19

<210> SEQ ID NO 696
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 696
gcuucgugcu aaacuggua                                              19

<210> SEQ ID NO 697
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 697
```
gaguaugcca ccauugucu                                              19

<210> SEQ ID NO 698
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 698
guuucaggga aggucagaa                                              19

<210> SEQ ID NO 699
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 699
cuagagaagu uucagggaa                                              19

<210> SEQ ID NO 700
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 700
cuaaacuggu accgcauga                                              19

<210> SEQ ID NO 701
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 701 cauuccuca ggagaagca                                               19

<210> SEQ ID NO 702
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 702
cauugucuuu ccuagcgga                                              19

<210> SEQ ID NO 703
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 703
ggccuguaua ccggauaau                                              19

<210> SEQ ID NO 704
<211> LENGTH: 19
<212> TYPE: RNA
<213> ORGANISM: Artificial Sequence

```
<220> FEATURE:
<223> OTHER INFORMATION: miRNA/siRNA

<400> SEQUENCE: 704
gcccugauca ucagcaaau                                                    19

<210> SEQ ID NO 705
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 705
gagccaccua cguauuuaa                                                    19

<210> SEQ ID NO 706
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 706
ggagccaccu acguauuua                                                    19

<210> SEQ ID NO 707
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 707
gggcgagcua cuauagaaa                                                    19

<210> SEQ ID NO 708
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 708
ggagagggaa cggaaauaa                                                    19

<210> SEQ ID NO 709
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 709
ccaguacaaa ccaguuaau                                                    19

<210> SEQ ID NO 710
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 710
cccaguacaa accaguuaa                                                    19
```

<210> SEQ ID NO 711
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 711
gguggcugga augauaaca                                                    19

<210> SEQ ID NO 712
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 712
ccaccuacgu auuuaagau                                                    19

<210> SEQ ID NO 713
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 713
gcugcuucua uguuucaua                                                    19

<210> SEQ ID NO 714
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 714
gagugcugcu augggaaau                                                    19

<210> SEQ ID NO 715
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 715
ccggcaucau gauugugua                                                    19

<210> SEQ ID NO 716
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 716
gugcugcuau gggaaaucu                                                    19

<210> SEQ ID NO 717
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 717
cagagagacu ggagaauaa                                              19

<210> SEQ ID NO 718
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 718
guggacauga gccauuuga                                              19

<210> SEQ ID NO 719
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 719
gcuccuuucu ccuucucaa                                              19

<210> SEQ ID NO 720
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 720
gcuccugguu uacagagaa                                              19

<210> SEQ ID NO 721
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 721
ccucccuuca accauagua                                              19

<210> SEQ ID NO 722
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 722
cugcauugga gagaacaau                                              19

<210> SEQ ID NO 723
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 723
cuccugguuu acagagaaa                                              19

<210> SEQ ID NO 724

```
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 724
gcuggucauu acgaggaua                                              19

<210> SEQ ID NO 725
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 725
ggucauagcu ccuuggaau                                              19

<210> SEQ ID NO 726
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 726
gcuucaaugu agucagaau                                              19

<210> SEQ ID NO 727
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 727
cagcacccaa aucaagaaa                                              19

<210> SEQ ID NO 728
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 728
gcagaauaca gcacccaaa                                              19

<210> SEQ ID NO 729
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 729
gcuuccaggu cuguuucau                                              19

<210> SEQ ID NO 730
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 730
```
gagcaugggu ucauccuau                                              19

<210> SEQ ID NO 731
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 731 cuuguggaa ugucaauua                                               19

<210> SEQ ID NO 732
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 732
gccuuguuga uguggacau                                              19

<210> SEQ ID NO 733
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 733
guggcuguca guauuugga                                              19

<210> SEQ ID NO 734
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 734
caggucuguu ucauuuaga                                              19

<210> SEQ ID NO 735
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 735
ccuuaugcuu cuuucaaau                                              19

<210> SEQ ID NO 736
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 736
cacgugaaua uggcauucu                                              19

<210> SEQ ID NO 737
<211> LENGTH: 19
<212> TYPE: RNA

```
<213> ORGANISM: Artificial Sequence
<220> FEATURE:
<223> OTHER INFORMATION: miRNA/siRNA

<400> SEQUENCE: 737
cuccuucacu uguuggaau                                                    19

<210> SEQ ID NO 738
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 738
cauggguuca uccuauucu                                                    19

<210> SEQ ID NO 739
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 739
cugugaggua gacgaaugu                                                    19

<210> SEQ ID NO 740
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 740
gagagaacaa ugugauaga                                                    19

<210> SEQ ID NO 741
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 741
gaaggaauau ucacuucua                                                    19

<210> SEQ ID NO 742
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 742
gucagaauua gcugcuucu                                                    19

<210> SEQ ID NO 743
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 743
cuccuuggaa ucaccaaca                                                    19
```

```
<210> SEQ ID NO 744
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 744
ccuacguauu uaagaugaa                                                    19

<210> SEQ ID NO 745
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 745
ggaaggaaua uucacuucu                                                    19

<210> SEQ ID NO 746
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 746
gcauuggaga gaacaaugu                                                    19

<210> SEQ ID NO 747
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 747
ggaguuauuu guaaugacu                                                    19

<210> SEQ ID NO 748
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 748
gccgauagaa uauggucca                                                    19

<210> SEQ ID NO 749
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 749
gggaagugaa uauuaagca                                                    19

<210> SEQ ID NO 750
<211> LENGTH: 19
<212> TYPE: RNA
<213> ORGANISM: Artificial Sequence
<220> FEATURE:
```

<223> OTHER INFORMATION: miRNA/siRNA

<400> SEQUENCE: 750
gcaucuucaa ccuggagaa                                                19

<210> SEQ ID NO 751
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 751
cugccaauau gaaggaggu                                                19

<210> SEQ ID NO 752
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 752
ggacacguga auauggcau                                                19

<210> SEQ ID NO 753
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 753
gagaagauga gagccagau                                                19

<210> SEQ ID NO 754
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 754
cugaucauca gcaaauuca                                                19

<210> SEQ ID NO 755
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 755
ggaagugaau auuaagcau                                                19

<210> SEQ ID NO 756
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 756
gaagaugaga gccagaugu                                                19

```
<210> SEQ ID NO 757
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 757
cgcuucugaa agugcuaca                                                   19

<210> SEQ ID NO 758
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 758
gaggauauau aggcggcaa                                                   19

<210> SEQ ID NO 759
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 759
caugcucuau ugcucagua                                                   19

<210> SEQ ID NO 760
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 760
cuccuucaca aaccagaga                                                   19

<210> SEQ ID NO 761
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 761
cugcuccagu ucaaucuca                                                   19

<210> SEQ ID NO 762
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 762
cugcuucaau guagucaga                                                   19

<210> SEQ ID NO 763
<211> LENGTH: 19
<212> TYPE: RNA
<213> ORGANISM: Artificial Sequence
<220> FEATURE:
<223> OTHER INFORMATION: miRNA/siRNA
```

```
<400> SEQUENCE: 763
guaccaagga cguucaga                                                19

<210> SEQ ID NO 764
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 764
gaaaccuguu ugagagaaa                                               19

<210> SEQ ID NO 765
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 765
gugagguaga cgaauguca                                               19

<210> SEQ ID NO 766
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 766
gaacugcagu gaaggaaca                                               19

<210> SEQ ID NO 767
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 767
ccaucuuuga cccuacagu                                               19

<210> SEQ ID NO 768
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 768
cacacucacu ucucuuccu                                               19

<210> SEQ ID NO 769
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 769
cacaagguca ucugcuucu                                               19

<210> SEQ ID NO 770
<211> LENGTH: 19
```

```
<212> TYPE: RNA
<213> ORGANISM: Artificial Sequence
<220> FEATURE:
<223> OTHER INFORMATION: miRNA/siRNA

<400> SEQUENCE: 770 gcaaaucaa ccaccagaa                                              19

<210> SEQ ID NO 771
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 771
cccaaaucaa gaaaccugu                                             19

<210> SEQ ID NO 772
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 772
caagagagau ccuccugau                                             19

<210> SEQ ID NO 773
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 773
gcugucagua uuuggagga                                             19

<210> SEQ ID NO 774
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 774
cauggaaucu caccuggau                                             19

<210> SEQ ID NO 775
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 775
cauggaagga auauucacu                                             19

<210> SEQ ID NO 776
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 776
```
ccaugcucua uugcucagu                                                19

<210> SEQ ID NO 777
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 777
cugaaagcca caaggucau                                                19

<210> SEQ ID NO 778
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 778
guucauccua uucuuucga                                                19

<210> SEQ ID NO 779
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 779
cugucaguau uuggaggaa                                                19

<210> SEQ ID NO 780
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 780
cagagaccaa augucacgu                                                19

<210> SEQ ID NO 781
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 781
gucauuacga ggauaccau                                                19

<210> SEQ ID NO 782
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 782
cugaaaggca uccagaucu                                                19

<210> SEQ ID NO 783
<211> LENGTH: 19
<212> TYPE: RNA
<213> ORGANISM: Artificial Sequence

```
<220> FEATURE:
<223> OTHER INFORMATION: miRNA/siRNA

<400> SEQUENCE: 783
cuuugacccu acaguucau                                                    19

<210> SEQ ID NO 784
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 784
cugaguacaa gcugagcaa                                                    19

<210> SEQ ID NO 785
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 785
caccagaaca uuguucgcu                                                    19

<210> SEQ ID NO 786
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 786
ccauaguagu uccucugua                                                    19

<210> SEQ ID NO 787
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 787
ggaacggaaa uaaaggagu                                                    19

<210> SEQ ID NO 788
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 788
caaugugaua gaagaagaa                                                    19

<210> SEQ ID NO 789
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 789
gggaauguca auuacggcu                                                    19
```

```
<210> SEQ ID NO 790
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 790
gaaagccaca aggucaucu                                                     19

<210> SEQ ID NO 791
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 791
gaauacagca cccaaauca                                                     19

<210> SEQ ID NO 792
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 792
cggauaauga cucagugcu                                                     19

<210> SEQ ID NO 793
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 793
cucugcuuca auguaguca                                                     19

<210> SEQ ID NO 794
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 794
cacuugugga agaggaaga                                                     19

<210> SEQ ID NO 795
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 795
guacaaacca guuaaucca                                                     19

<210> SEQ ID NO 796
<211> LENGTH: 19
<212> TYPE: RNA
<213> ORGANISM: Artificial Sequence
<220> FEATURE:
<223> OTHER INFORMATION: miRNA/siRNA
```

```
<400> SEQUENCE: 796
cucuuggaua uaugccaua                                        19

<210> SEQ ID NO 797
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 797
gagcuacuau agaaaggga                                        19

<210> SEQ ID NO 798
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 798
gaagaagaaa uccguguga                                        19

<210> SEQ ID NO 799
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 799
guagucagaa uuagcugcu                                        19

<210> SEQ ID NO 800
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 800
caaccauagu aguccucu                                         19

<210> SEQ ID NO 801
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 801
cuuguuggaa ugggacagu                                        19

<210> SEQ ID NO 802
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 802
cuucuuucaa auugugugu                                        19

<210> SEQ ID NO 803
```

```
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 803
cauuggcugu ucaccacau                                                    19

<210> SEQ ID NO 804
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 804
gcauuaucua aacugcagu                                                    19

<210> SEQ ID NO 805
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 805
caaaccaguu aauccagaa                                                    19

<210> SEQ ID NO 806
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 806
cuugccuugu ugaugugga                                                    19

<210> SEQ ID NO 807
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 807
guucuggagu uugucacca                                                    19

<210> SEQ ID NO 808
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 808
ggaaugucaa uuacggcua                                                    19

<210> SEQ ID NO 809
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 809
``` cguuucauu uagacuccu                                                    19

<210> SEQ ID NO 810
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 810
cgauagaaua ugguccacu                                                   19

<210> SEQ ID NO 811
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 811
cacuucucuu ccuugggau                                                   19

<210> SEQ ID NO 812
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 812
gauagaagaa gaaauccgu                                                   19

<210> SEQ ID NO 813
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 813
cuguuugaga gaaacccaa                                                   19

<210> SEQ ID NO 814
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 814
cuuugaagau ggcuucugu                                                   19

<210> SEQ ID NO 815
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 815
gaaacccaaa caaggagcu                                                   19

<210> SEQ ID NO 816
<211> LENGTH: 19
<212> TYPE: RNA

```
<213> ORGANISM: Artificial Sequence
<220> FEATURE:
<223> OTHER INFORMATION: miRNA/siRNA

<400> SEQUENCE: 816
gaauacaucu ccaguggaa                                                      19

<210> SEQ ID NO 817
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 817
ggauugaaua cugcaccca                                                      19

<210> SEQ ID NO 818
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 818
cuuucaaauu gugugugcu                                                      19

<210> SEQ ID NO 819
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 819
gaaagugcua cagugacca                                                      19

<210> SEQ ID NO 820
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 820
gauaacacuu ccuugcucu                                                      19

<210> SEQ ID NO 821
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 821
gauaaauaca aggcccaga                                                      19

<210> SEQ ID NO 822
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 822
gugauaaaua caaggccca                                                      19
```

```
<210> SEQ ID NO 823
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 823
cauagauguu uccuugccu                                                       19

<210> SEQ ID NO 824
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 824
ggagcuacca ucugcaaau                                                       19

<210> SEQ ID NO 825
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 825
guggcagcaa cuauuauaa                                                       19

<210> SEQ ID NO 826
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 826
gugcucauua gagucaaau                                                       19

<210> SEQ ID NO 827
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 827
gcagcaacua uuauaagau                                                       19

<210> SEQ ID NO 828
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 828
gaggcacuga uuuaaugaa                                                       19

<210> SEQ ID NO 829
<211> LENGTH: 19
<212> TYPE: RNA
<213> ORGANISM: Artificial Sequence
<220> FEATURE:
```

```
<223> OTHER INFORMATION: miRNA/siRNA

<400> SEQUENCE: 829
caggacauga gaagauaua                                                    19

<210> SEQ ID NO 830
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 830
cccugacuua ugagaacau                                                    19

<210> SEQ ID NO 831
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 831
ggcagcaacu auuauaaga                                                    19

<210> SEQ ID NO 832
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 832
gagccacaaa cuaauacua                                                    19

<210> SEQ ID NO 833
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 833
gcgucuuuca gugcuuuga                                                    19

<210> SEQ ID NO 834
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 834
cuccuggaca aucaguaaa                                                    19

<210> SEQ ID NO 835
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 835
ccuggacaau caguaaaga                                                    19
```

```
<210> SEQ ID NO 836
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 836
gaggagcaga cuacaagaa                                                    19

<210> SEQ ID NO 837
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 837
caguguucuu cgcauauau                                                    19

<210> SEQ ID NO 838
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 838
ggcaaugcaa augcaagaa                                                    19

<210> SEQ ID NO 839
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 839
cagcagccaa aggagaaua                                                    19

<210> SEQ ID NO 840
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 840
cuccaggaca ugagaagau                                                    19

<210> SEQ ID NO 841
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 841
ccgugaguuu guccuuuca                                                    19

<210> SEQ ID NO 842
<211> LENGTH: 19
<212> TYPE: RNA
<213> ORGANISM: Artificial Sequence
<220> FEATURE:
<223> OTHER INFORMATION: miRNA/siRNA
```

```
<400> SEQUENCE: 842
gacugugucu uggcaaacu                                              19

<210> SEQ ID NO 843
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 843
ccucugaaga cccuucaaa                                              19

<210> SEQ ID NO 844
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 844
gcuguuggaa auagcuucu                                              19

<210> SEQ ID NO 845
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 845
gacugcagua aaggauucu                                              19

<210> SEQ ID NO 846
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 846
guaccauauu gaugaagaa                                              19

<210> SEQ ID NO 847
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 847
gcaucaccau ggcauaugu                                              19

<210> SEQ ID NO 848
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 848
ggauguucau ugcuaaaca                                              19

<210> SEQ ID NO 849
<211> LENGTH: 19
```

```
<212> TYPE: RNA
<213> ORGANISM: Artificial Sequence
<220> FEATURE:
<223> OTHER INFORMATION: miRNA/siRNA

<400> SEQUENCE: 849 ccugcauua cccauugua                                          19

<210> SEQ ID NO 850
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 850
gugaguuugu ccuucaaa                                          19

<210> SEQ ID NO 851
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 851
gagaccaucu uggcuaaca                                         19

<210> SEQ ID NO 852
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 852
gugcauuucu uguaggaaa                                         19

<210> SEQ ID NO 853
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 853
gcuucugcaa ucaaaguaa                                         19

<210> SEQ ID NO 854
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 854
ccugaagacu guaagaagu                                         19

<210> SEQ ID NO 855
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 855
```

-continued

| | |
|---|---|
| guucuucgca uauauuugu | 19 |

<210> SEQ ID NO 856
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 856

| | |
|---|---|
| gauguucauu gcuaaacau | 19 |

<210> SEQ ID NO 857
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 857

| | |
|---|---|
| gacuguaaga aguacaacu | 19 |

<210> SEQ ID NO 858
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 858

| | |
|---|---|
| ggagacugca guaaaggau | 19 |

<210> SEQ ID NO 859
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 859

| | |
|---|---|
| gaguugagaa guuaaacau | 19 |

<210> SEQ ID NO 860
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 860

| | |
|---|---|
| cuucugcaau caaaguaau | 19 |

<210> SEQ ID NO 861
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 861

| | |
|---|---|
| gguuaaugua acccaacaa | 19 |

<210> SEQ ID NO 862
<211> LENGTH: 19
<212> TYPE: RNA
<213> ORGANISM: Artificial Sequence

```
<220> FEATURE:
<223> OTHER INFORMATION: miRNA/siRNA

<400> SEQUENCE: 862
cuuggagaaa gcccuucaa                                                    19

<210> SEQ ID NO 863
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 863
gucucucuau ugguggaaa                                                    19

<210> SEQ ID NO 864
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 864
gcuaccaucu gcaaaucgu                                                    19

<210> SEQ ID NO 865
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 865
gcagagacau cuguaugca                                                    19

<210> SEQ ID NO 866
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 866
ggucucucua uugguggaa                                                    19

<210> SEQ ID NO 867
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 867
gugauggaga cugcaguaa                                                    19

<210> SEQ ID NO 868
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 868
gucauggaga uguccguaa                                                    19
```

```
<210> SEQ ID NO 869
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 869
cagacugugu cuuggcaaa                                                19

<210> SEQ ID NO 870
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 870
cccugugaua aacuguggu                                                19

<210> SEQ ID NO 871
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 871
guuccuuacu gccaacucu                                                19

<210> SEQ ID NO 872
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 872
ggaaauagca gcugcuucu                                                19

<210> SEQ ID NO 873
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 873
gcaacuauua uaagaugcu                                                19

<210> SEQ ID NO 874
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 874
cugugcucau uagagucaa                                                19

<210> SEQ ID NO 875
<211> LENGTH: 19
<212> TYPE: RNA
<213> ORGANISM: Artificial Sequence
<220> FEATURE:
<223> OTHER INFORMATION: miRNA/siRNA
```

```
<400> SEQUENCE: 875
ccugugcuca uuagaguca                                              19

<210> SEQ ID NO 876
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 876
cagcauugau caucucaca                                              19

<210> SEQ ID NO 877
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 877
guaaggucuu gccaagaaa                                              19

<210> SEQ ID NO 878
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 878
gcaaggguca uggagaugu                                              19

<210> SEQ ID NO 879
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 879
gaacgggaca cuuugcuaa                                              19

<210> SEQ ID NO 880
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 880
cguaaggucu ugccaagaa                                              19

<210> SEQ ID NO 881
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 881
cuacuguauu caaggcaau                                              19

<210> SEQ ID NO 882
```

```
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 882
ccaucugcaa aucgugacu                                                19

<210> SEQ ID NO 883
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 883
gucuuggcaa acuggaaga                                                19

<210> SEQ ID NO 884
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 884 cguuccuua cugccaacu                                                 19

<210> SEQ ID NO 885
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 885
cuugccaaga aauauugcu                                                19

<210> SEQ ID NO 886
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 886
cuguaugcau uccugucau                                                19

<210> SEQ ID NO 887
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 887
gacuggaugu ucauugcua                                                19

<210> SEQ ID NO 888
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 888
```
gucuaguucu gggaugcau                                             19

<210> SEQ ID NO 889
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 889
gaagacugua agaaguaca                                             19

<210> SEQ ID NO 890
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 890
cuucaagugu uucaccaaa                                             19

<210> SEQ ID NO 891
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 891
gacaucugua ugcauuccu                                             19

<210> SEQ ID NO 892
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 892
gugauaaacu guggucacu                                             19

<210> SEQ ID NO 893
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 893
cccuucaagu guuucacca                                             19

<210> SEQ ID NO 894
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 894
gugacuaagu acauccuga                                             19

<210> SEQ ID NO 895
<211> LENGTH: 19
<212> TYPE: RNA

```
<213> ORGANISM: Artificial Sequence
<220> FEATURE:
<223> OTHER INFORMATION: miRNA/siRNA

<400> SEQUENCE: 895
gcagacuaca agaauggca                                          19

<210> SEQ ID NO 896
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 896
guaauuccua cuguauuca                                          19

<210> SEQ ID NO 897
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 897
guuucaccaa auccacgau                                          19

<210> SEQ ID NO 898
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 898
caucugcaaa ucgugacua                                          19

<210> SEQ ID NO 899
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 899
gaagguuaau guaacccaa                                          19

<210> SEQ ID NO 900
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 900
guaaagagua ccauauuga                                          19

<210> SEQ ID NO 901
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 901
cugugcauuu cuuguagga                                          19
```

<210> SEQ ID NO 902
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 902
guucucauuu cgugaugga                                              19

<210> SEQ ID NO 903
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 903
gcauugauca ucucacaga                                              19

<210> SEQ ID NO 904
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 904
cuguaucuua ucauuggaa                                              19

<210> SEQ ID NO 905
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 905
ccuacuguau ucaaggcaa                                              19

<210> SEQ ID NO 906
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 906
cuguauucaa ggcaaugca                                              19

<210> SEQ ID NO 907
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 907
gauucuuccu ggucucucu                                              19

<210> SEQ ID NO 908
<211> LENGTH: 19
<212> TYPE: RNA
<213> ORGANISM: Artificial Sequence
<220> FEATURE:

-continued

<223> OTHER INFORMATION: miRNA/siRNA

<400> SEQUENCE: 908
cuucgagaaa gaguugaga                                               19

<210> SEQ ID NO 909
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 909
cauuguaaca gagccacaa                                               19

<210> SEQ ID NO 910
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 910
gaucaucuca cagaccaca                                               19

<210> SEQ ID NO 911
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 911
cacaaacuaa uacuaugca                                               19

<210> SEQ ID NO 912
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 912
cgcauauauu ugucuggcu                                               19

<210> SEQ ID NO 913
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 913
gagaagauau augccacca                                               19

<210> SEQ ID NO 914
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 914
cugugauaaa cugugguca                                               19

```
<210> SEQ ID NO 915
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 915
ggaagguuaa uguaaccca                                              19

<210> SEQ ID NO 916
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 916
gagaaguuaa acaugcuca                                              19

<210> SEQ ID NO 917
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 917
caaaguaauu ccuacugua                                              19

<210> SEQ ID NO 918
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 918
guaagaagua caacugaga                                              19

<210> SEQ ID NO 919
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 919
guacaacuga gaaaucccu                                              19

<210> SEQ ID NO 920
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 920
cuuacugcca acucuccaa                                              19

<210> SEQ ID NO 921
<211> LENGTH: 19
<212> TYPE: RNA
<213> ORGANISM: Artificial Sequence
<220> FEATURE:
<223> OTHER INFORMATION: miRNA/siRNA
```

```
<400> SEQUENCE: 921
cuaaacaucu gccugaucu                                                19

<210> SEQ ID NO 922
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 922
ccaaaggaga auaagaccu                                                19

<210> SEQ ID NO 923
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 923
caaucaguaa agaguacca                                                19

<210> SEQ ID NO 924
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 924 gcauccugu cauuaccca                                                 19

<210> SEQ ID NO 925
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 925
caaaucguga cuaaguaca                                                19

<210> SEQ ID NO 926
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 926
caugagaaga uauaugcca                                                19

<210> SEQ ID NO 927
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 927
guaaaggauu cuuccuggu                                                19

<210> SEQ ID NO 928
<211> LENGTH: 19
```

```
<212> TYPE: RNA
<213> ORGANISM: Artificial Sequence
<220> FEATURE:
<223> OTHER INFORMATION: miRNA/siRNA

<400> SEQUENCE: 928
cuuaugagaa cauggacgu                                         19

<210> SEQ ID NO 929
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 929
cauuacccau uguaacaga                                         19

<210> SEQ ID NO 930
<211> LENGTH: 19
<212> TYPE: RNA
<213> ORGANISM: Artificial Sequence
<220> FEATURE:
<223> OTHER INFORMATION: miRNA/siRNA

<400> SEQUENCE: 930
cauugcuaaa caucugccu                                         19
```

PRECURSOR MIRNA AND APPLICATIONS IN TUMOR THERAPY THEREOF

TECHNICAL FIELD

The present invention relates to the tumor treatment field, and particularly to new precursor miRNAs and a method and use thereof for inhibiting tumor growth.

BACKGROUND ART

MicroRNAs are derived from long chain RNA primary transcripts (pri-miRNAs) with a length of about 1000 bp which are cleaved in the cell nucleus by enzyme Drosha into miRNA precursors having a stem-loop structure with a length of about 60-80 nt. The precursor miRNAs are further cleaved into double-strand miRNAs with a length of about 18-26 nt after being transported to the cytoplasm. After the double-strand miRNAs are unwound, the mature miRNAs enter into RNA-induced silencing complexes (RISC), which are completely or not completely paired with the complementary mRNAs, so that the target mRNAs are degraded or the expression thereof is repressed.

MicroRNAs account for a small proportion of the total cellular RNA; however, miRNAs participate in a series of important processes in the life process, including early embryonic development, cell proliferation and cell death, apoptosis and fat metabolism, cell differentiation. Considering their role in gene expression regulation, and that abnormal cell proliferation, apoptosis and the like often occur in tumors, it is therefore presumed that abnormal deletion, mutation or over-expression of miRNAs will lead to the occurrence of human diseases.

Recently, increasing amounts of evidence shows that miRNAs play a very important role in inhibiting tumor cell growth, proliferation and differentiation. In the art, there is an urgent need to understand the roles of various different miRNAs to develop new medicaments for treating tumors.

RNA interference (RNAi) is a powerful experimental tool in the laboratory that uses homologous double-stranded RNAs (dsRNAs) to induce the silencing of sequence-specific target genes and rapidly block gene activity. siRNAs play a central role in an RNA silencing pathway and are guiding elements for degradation of specific messenger RNAs (mRNAs). siRNAs are intermediates in the RNAi pathway and are necessary factors for RNAi to exert its effect. The formation of siRNAs is mainly completed by regulation of Dicer and Rde-1. The dsRNAs appear in the cell due to RNA virus invasion, transcription of transposon, transcription of reverse repeats in the genome and other facotrs. The protein encoded by Rde-1 (RNAi defective gene-1) recognizes exogenous dsRNAs, and when dsRNAs reach a certain amount, Rde-1 directs dsRNAs binding to Dicer (Dicer is an endonuclease with RNaseIII activity, and has four domains: PAZ domain of the Argonaute family, type III RNase active region, dsRNAs binding region, and DEAH/DEXH RNA helicase active region) encoded by Rde-1 to form an enzyme-dsRNA complex. After cleavage of Dicer, siRNAs form, and then with the participation of ATP, key steps in RNAi interference by RNA-induced silencing complexes present in cells are assembly of RISCs and synthesis of siRNA proteins that mediate specific responses. The siRNAs are incorporated into RISCs and then fully paired with the target gene coding regions or UTR regions to degrade the target genes, and thus it can be said that siRNAs only degrade mRNAs that are complementary to their sequences. The mechanism of the above-mentioned regulation is silencing the expression of corresponding target genes through complementary pairing, and thus it is a typical negative regulatory mechanism. The recognition of target sequences by siRNAs is highly specific. Since the degradation occurs first at a central position relative to the siRNAs, these base sites at the central position are of paramount importance, and the RNAi effect would be severely inhibited once mismatches occur. As an emerging therapeutic technology, siRNA has also entered the clinical trial stage at an unprecedented speed.

K-RAS is a member of the RAS gene family and encodes K-RAS protein, and is related to the formation, proliferation, migration, spread and angiogenesis of tumors.

K-RAS protein has GTPase activity, which is activated when it binds to GTP, and inactivated when it binds to GDP. After PKC phosphorylates K-RAS mainly located on the cell membrane, such phosphorylation process renders the binding of K-RAS to the cell membrane weakened, so that its position is changed and moved to the endoplasmic reticulum, Golgi apparatus, mitochondrion and other positions. K-RAS plays a role of a molecular switch and plays an important role in many signaling pathways.

Studies have shown that about 30% of human malignancies are associated with mutations in the RAS gene, and the product generated from mutated RAS can remain activated. In leukemia, lung cancer, rectal cancer and pancreatic cancer, K-RAS mutations are common, with 30% to 35% of patients with rectal cancer having such mutations. The mutations are related to the survival, proliferation, migration, spread and angiogenesis of tumor cells. K-RAS gene is divided into mutant type and wild type. The common mutation sites are codons 12 and 13 of exon 2 and codon 61 of exon 3 in the K-RAS gene, of which there are 7 mutation hotspots: G12C, G12R, G12S, G12V, G12D, G12A, and G13V/D, and these seven kinds of mutations account for not less than 90%.

Currently EGFR-targeted drugs on the market are: gefitinib (Iressa), erlotinib (Tarceva), cetuximab (ERBITUX), and panitumumab (Vectibix). However, EGFR-targeted drugs have a poor therapeutic effect on K-RAS mutant patients, that is because K-RAS is also activated to deliver signals downstream even in the absence of EGFR signaling; therefore, the K-RAS gene status should be first detected and then medication is selected in personalized medication. If K-RAS is a mutant, use of EGFR-targeted drugs is not recommended.

Therefore, considering that if both EGFR and K-RAS pathways can be targeted at the same time, then the upstream and downstream of pathways can be simultaneously inhibited, so that EGFR-targeted drugs produce a better therapeutic effect on K-RAS mutant patients. Therefore, there is an urgent need for a targeting therapy for K-RAS gene suppression and relevant drugs, so as to address the current problems such as there had not been drugs specific for K-RAS mutation and the K-RAS mutation renders EGFR-targeted drugs ineffective.

SUMMARY OF THE INVENTION

The present invention provides new precursor miRNAs expressing anti-miRNA-214, and the use thereof in treating tumors.

The first aspect of the present invention provides a pharmaceutical preparation comprising:
(a) an expression vector for expressing anti-miRNAs and/or siRNAs; and
(b) a pharmaceutically acceptable carrier.

In another preferred example, with regard to the precursor as shown in formula I-1 expressed by the expression vector,

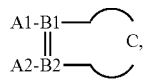

formula I

B1 is a first ribonucleic acid sequence as desired, and comprises an anti-miRNA sequence form or a siRNA sequence form;

B2 is a sequence substantially or completely complementary to B1, and B2 is not complementary to C;

C is a stem-loop structure sequence; and

A1 and A2 are null or are optionally RNA sequences consisting of 4-5 bases respectively;

Wherein, the said precursor can express (or produce or enrich) the said first ribonucleic acid sequence in a host, but cannot express (or produce or enrich) a second ribonucleic acid sequence complementary to the said first ribonucleic acid sequence.

In another preferred example, the said first ribonucleic acid sequence is in the form of 5p, and the second ribonucleic acid sequence in the form of 3p.

In another preferred example, the said first ribonucleic acid sequence is in the form of 3p, and the second ribonucleic acid sequence in the form of 5p.

In another preferred example, the said first ribonucleic acid sequence is anti-miRNAs and/or siRNAs.

In another preferred example, the said B1 is miRNAs or siRNAs against tumors.

In another preferred example, the said B1 is anti-miRNA-214-5p.

In another preferred example, the first ribonucleic acid sequence is anti-miRNA-214-5p, and the second ribonucleic acid sequence is anti-miRNA-214-3p.

In another preferred example, the said preparation is in a liquid dosage form.

In another preferred example, the said preparation is an injection.

In another preferred example, the said expression vector comprises a plasmid.

In another preferred example, the said expression vector or plasmid contains a promoter, a replication origin and a marker gene.

In another preferred example, the expression vector or plasmid contains a pCMV promoter, spectinomycin and a pUC promoter.

In another preferred example, the said expression vector contains an expression cassette expressing anti-miRNAs and/or siRNAs.

In another preferred example, the said expression cassette (i.e. a polynucleotide) is double-stranded and has the following structure:

a promoter-attB1-an optional tag protein (such as GFP or emGFP)-a 5'miR flanking region sequence-the sequence as shown in formula I-a 5'miR flanking region sequence-attB2-an optional TKPA element.

In another preferred example, the said preparation is a liposome preparation.

In another preferred example, the anti-miRNA and/or siRNA is a RNA selected from the group consisting of anti-miRNA-214, K-RAS siRNA, EGFR siRNA, PDL1 siRNA, PDCD1 siRNA, ALK siRNA and IDO1 siRNA;

preferably, the anti-miRNA-214 has a sequence shown as SEQ ID NO: 2;

the K-RAS siRNA has a sequence selected from the group consisting of SEQ ID NO: 12, SEQ ID NO: 35, SEQ ID NO: 50, SEQ ID NO: 56, SEQ ID NO: 61, SEQ ID NO: 82, SEQ ID NO: 97, SEQ ID NO: 107, SEQ ID NO: 110 and SEQ ID NO: 115 (or sequence numbers 3, 26, 41, 47, 52, 73, 88, 98, 101 and 106 in Table 11);

the EGFR siRNA has a sequence selected from the group consisting of SEQ ID NO: 294, SEQ ID NO: 297, SEQ ID NO: 312, SEQ ID NO: 319, SEQ ID NO: 324, SEQ ID NO: 329, SEQ ID NO: 336, SEQ ID NO: 340, SEQ ID NO: 345 and SEQ ID NO: 349 (or sequence numbers 17, 20, 35, 42, 47, 52, 59, 63, 68 and 72 in Table 14);

the PDL1 siRNA has a sequence selected from the group consisting of SEQ ID NO: 693, SEQ ID NO: 694, SEQ ID NO: 695, SEQ ID NO: 696, SEQ ID NO: 697, SEQ ID NO: 698, SEQ ID NO: 699, SEQ ID NO: 700, SEQ ID NO: 701 and SEQ ID NO: 702 (or sequence numbers 1, 2, 3, 4, 5, 6, 7, 8, 9 and 10 in Table 15);

the PDCD1 siRNA has a sequence selected from the group consisting of SEQ ID NO: 494, SEQ ID NO: 513, SEQ ID NO: 529, SEQ ID NO: 534, SEQ ID NO: 537, SEQ ID NO: 572, SEQ ID NO: 575, SEQ ID NO: 579, SEQ ID NO: 605 and SEQ ID NO: 634 (or sequence numbers 18, 37, 53, 58, 61, 96, 99, 103, 129 and 158 in Table 16);

the ALK siRNA has a sequence selected from the group consisting of SEQ ID NO: 708, SEQ ID NO: 713, SEQ ID NO: 718, SEQ ID NO: 721, SEQ ID NO: 725, SEQ ID NO: 729, SEQ ID NO: 732, SEQ ID NO: 734, SEQ ID NO: 742 and SEQ ID NO: 743 (or sequence numbers 6, 11, 16, 19, 23, 27, 30, 32, 40 and 41 in Table 17); and the IDO1 siRNA has a sequence selected from the group consisting of SEQ ID NO: 825, SEQ ID NO: 827, SEQ ID NO: 831, SEQ ID NO: 832, SEQ ID NO: 834, SEQ ID NO: 836, SEQ ID NO: 849, SEQ ID NO: 851, SEQ ID NO: 852 and SEQ ID NO: 870 (or sequence numbers 2, 4, 8, 9, 11, 13, 26, 28, 29 and 47 in Table 18)

The second aspect of the present invention provides a method for administering a medicament, comprising the step of:

To administer the said pharmaceutical preparation of the first aspect of the present invention at a first body site of a mammal, so that the expression vector is processed in vivo to form microvesicles, which are transported to a second body site of the mammal where the anti-miRNAs and/or siRNAs are expressed.

In another preferred example, the said mammal includes human and non-human mammals.

In another preferred example, the said first site includes a subcutaneous, intravenous or gastrointestinal tract site.

In another preferred example, the said second site includes the liver, lung, and kidney.

In another preferred example, the said administering includes oral intake, subcutaneous injection, intramuscular injection and intravenous injection.

The third aspect of the present invention provides a precursor sequence having a structure from the 5' terminus to the 3' terminus as shown in formula I:

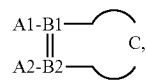

formula I

Wherein, B1 is a first ribonucleic acid sequence as desired and comprises an anti-miRNA sequence form or a siRNA sequence form;

B2 is a sequence substantially or completely complementary to B1, and B2 is not complementary to C;

C is a stem-loop structure sequence; and

A1 and A2 are null, or are optionally RNA sequences consisting of 4-5 bases respectively;

Wherein, the said precursor can express (or produce or enrich) the said first ribonucleic acid sequence in a host, but cannot express (or produce or enrich) a second ribonucleic acid sequence that is complementary to the said first ribonucleic acid sequence.

The fourth aspect of the present invention provides a precursor sequence having a structure from the 5' terminus to the 3' terminus as shown in formula I:

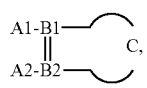
formula I

Wherein, B1 is anti-miRNA-214-5p;

B2 is a sequence substantially or completely complementary to B1, and B2 is not complementary to C;

C is a stem-loop structure sequence, preferably a sequence shown as SEQ ID NO.: 1 (GUUUUGGCCA-CUGACUGAC); and A1 and A2 are null, or are optionally RNA sequences consisting of 4-5 bases respectively;

Wherein, the precursor sequence as shown can be processed in the host into anti-miRNA-214, and only anti-miRNA-214-5p, rather than anti-miRNA-214-3p, in the said anti-miRNA-214 is expressed.

In another preferred example, the wording "only anti-miRNA-214-5p, rather than anti-miRNA-214-3p, is expressed" means that the ratio of F5/F3 is ≥5, preferably ≥10, more preferably ≥20, and most preferably ≥50, wherein F5 is the expression amount of anti-miRNA-214-5p and F3 is the expression amount of anti-miRNA-214-3p. In another preferred example, the said anti-miRNA-214-5p is shown as SEQ ID NO.: 2 (ACUGCCUGUCUGUGCCUGCCUGU).

In another preferred example, the said anti-miRNA-214-3p is shown as SEQ ID NO.: 3 (ACAGGCAGGC AGACA-GGCAGU).

In another preferred example, there are 2-8 non-complementary bases between the said B2 and B1, preferably, 3-5 non-complementary bases between the said B2 and B1.

In another preferred example, 1-2 bases are added or deleted in the said B2 as compared with B1.

In another preferred example, 1-2 bases, preferably 2 bases, are deleted in the said B2 as compared with B1.

In another preferred example, the deleted 1-2 bases are in the middle of B1, i.e., 1-2 bases at positions 9-14, such as positions 9-10, 10-11, 11-12, 12-13 or 13-14.

In another preferred example, the said A1 is UGCUG; and/or
the said A2 is CAGG or CAGGA.

In another preferred example, A2 is preferably CAGG.

In another preferred example, the precursor sequence has a structure from the 5' terminus to the 3' terminus as shown in formula I:

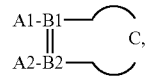
formula I wherein B1 is K-RAS siRNA;

B2 is a sequence substantially or completely complementary to B1, and B2 is not complementary to C;

C is a stem-loop structure sequence, preferably a sequence shown as SEQ ID NO.: 1; and A1 and A2 are null or are optionally RNA sequences consisting of 4-5 bases respectively;

wherein the precursor sequence as shown can be processed in the host to form the K-RAS siRNA; and wherein the nucleotide sequence of the sense strand of the K-RAS siRNA is selected from sequences shown as SEQ ID NO: 12, SEQ ID NO: 35, SEQ ID NO: 50, SEQ ID NO: 56, SEQ ID NO: 61, SEQ ID NO: 82, SEQ ID NO: 97, SEQ ID NO: 107, SEQ ID NO: 110 and SEQ ID NO: 115 in the sequence listing (or sequence numbers 3, 26, 41, 47, 52, 73, 88, 98, 101 and 106 in Table 11).

In another preferred example, the precursor sequence has a structure from the 5' terminus to the 3' terminus as shown in formula I:

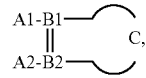
formula I

B1 is EGFR siRNA;

B2 is a sequence substantially or completely complementary to B1, and B2 is not complementary to C;

C is a stem-loop structure sequence, preferably a sequence shown as SEQ ID NO.: 1; and A1 and A2 are null or are optionally RNA sequences consisting of 4-5 bases respectively;

wherein the precursor sequence as shown can be processed in the host to form the EGFR siRNA; and wherein the nucleotide sequence of the sense strand of the EGFR siRNA is selected from sequences shown as SEQ ID NO: 294, SEQ ID NO: 297, SEQ ID NO: 312, SEQ ID NO: 319, SEQ ID NO: 324, SEQ ID NO: 329, SEQ ID NO: 336, SEQ ID NO: 340, SEQ ID NO: 345 and SEQ ID NO: 349 in the sequence listing (or sequence numbers 17, 20, 35, 42, 47, 52, 59, 63, 68 and 72 in Table 14).

In another preferred example, the B1 is PDL1 siRNA, wherein the nucleotide sequence of the sense strand of the PDL1 siRNA is selected from sequences shown as SEQ ID NO: 693, SEQ ID NO: 694, SEQ ID NO: 695, SEQ ID NO: 696, SEQ ID NO: 697, SEQ ID NO: 698, SEQ ID NO: 699, SEQ ID NO: 700, SEQ ID NO: 701 and SEQ ID NO: 702 in the sequence listing (or sequence numbers 1, 2, 3, 4, 5, 6, 7, 8, 9 and 10 in Table 15).

In another preferred example, the B1 is PDCD1 siRNA, wherein the nucleotide sequence of the sense strand of the PDL1 siRNA is selected from sequences shown as SEQ ID NO: 494, SEQ ID NO: 513, SEQ ID NO: 529, SEQ ID NO: 534, SEQ ID NO: 537, SEQ ID NO: 572, SEQ ID NO: 575, SEQ ID NO: 579, SEQ ID NO: 605 and SEQ ID NO: 634 in the sequence listing (or sequence numbers 18, 37, 53, 58, 61, 96, 99, 103, 129 and 158 in Table 16).

In another preferred example, the B1 is ALK siRNA, wherein the nucleotide sequence of the sense strand of the ALK siRNA is selected from sequences shown as SEQ ID NO: 708, SEQ ID NO: 713, SEQ ID NO: 718, SEQ ID NO: 721, SEQ ID NO: 725, SEQ ID NO: 729, SEQ ID NO: 732, SEQ ID NO: 734, SEQ ID NO: 742 and SEQ ID NO: 743 in the sequence listing (or sequence numbers 6, 11, 16, 19, 23, 27, 30, 32, 40 and 41 in Table 17).

In another preferred example, the B1 is IDO1 siRNA, wherein the nucleotide sequence of the sense strand of the IDO1 siRNA is selected from sequences shown as SEQ ID NO: 825, SEQ ID NO: 827, SEQ ID NO: 831, SEQ ID NO: 832, SEQ ID NO: 834, SEQ ID NO: 836, SEQ ID NO: 849, SEQ ID NO: 851, SEQ ID NO: 852 and SEQ ID NO: 870 in the sequence listing (or sequence numbers 2, 4, 8, 9, 11, 13, 26, 28, 29 and 47 in Table 18).

The fifth aspect of the present invention provides a polynucleotide, which can be transcribed by a host to form the precursor sequence as said in the fourth aspect of the present invention.

In another preferred example, the said polynucleotide is double-stranded and has the following structure:

attB1-an optional tag protein (such as GFP or emGFP)-a 5'miR flanking sequence-the sequence as shown in formula I-a 5'miR flanking sequence-attB2.

The sixth aspect of the present invention provides an expression vector containing the precursor sequence as said in the fourth aspect of the present invention or the polynucleotide as said in the fifth aspect of the present invention.

In another preferred example, the said expression vector includes viral vector and non-viral vector.

In another preferred example, the said expression vector is a plasmid.

In another preferred example, the strain from which the expression vector is derived includes *E. coli* DH5a, XL10-GOLD, BB4, DE3, BM25.5, BMH71-18mutS, BW313, C-1a, C600, DH1, DH5, DP50supF, ED8654, ED8767, ER1647, HB101, HMS174, JM83, JM101, JM105, JM106, JM107, JM108, JM109, JM110, K802, K803, LE392, MC1061, MV1184, MV1193, NovaBlue, RR1, TAP90, TG1, TG2, XL1-Blue, x1776, Y-1088, Y-1089 and Y-1090.

In another preferred example, the strain from which the expression vector is derived includes *E. coli* DH5a and XL10-GOLD.

In another preferred example, the strain from which the expression vector is derived includes *E. coli* DH5a.

In another preferred example, the upstream of the polynucleotide as said in the fifth aspect of the present invention is a promoter, and the downstream thereof is a TKPA element.

The seventh aspect of the present invention provides a pharmaceutical composition comprising the precursor sequence as said in the fourth aspect of the present invention or the expression vector as said in the sixth aspect of the present invention, and a pharmaceutically acceptable carrier.

In another preferred example, the said pharmaceutical composition comprises the anti-miR-214 plasmid.

In another preferred example, the said pharmaceutical composition is the expression vector of the sixth aspect as said in the present invention, and preferably, a plasmid containing the precursor sequence as said in the fourth aspect of the present invention.

In another preferred example, the dosage form of the said pharmaceutical composition includes:

a tablet, a capsule, a powder, a pill, a granule, a syrup, a solution, a suspension liquid, an emulsion, a suspension, an injection solution, or an injectable powder.

In another preferred example, the dosage form of the said pharmaceutical composition also comprises a spray, an aerosol, a powder spray, a volatile liquid, a topical solution, a lotion, a pour-on agent, a liniment, a cataplasma, a medicinal paste, a rubber paste, an ointment, a plaster, a paste, an eye drop, a nasal drop, an ophthalmic ointment, a mouth wash, a sublingual tablet, or a suppository.

In another preferred example, the said dosage form is an injection, preferably an intravenous injection or an intraperitoneal injection.

The eighth aspect of the present invention provides the use of the precursor sequence as said in the fourth aspect of the present invention or the expression vector as said in the sixth aspect of the present invention, including (i) for preparing an inhibitor of miRNA-214; and/or (ii) for preparing a pharmaceutical composition against malignant tumors with high expression of miRNA-214.

In another preferred example, the said malignant tumors include liver cancer, lung cancer, stomach cancer, oesophageal cancer, ovarian cancer, colorectal cancer, cervical cancer, pancreatic cancer, prostatic cancer, leukaemia or breast cancer.

The ninth aspect of the present invention provides a method for inhibiting the growth of malignant tumor cells with high expression of miRNA-214 in a non-therapeutic manner in vitro, comprising the step of:

Culturing the malignant tumor cells with high expression of miRNA-214 in the presence of the pharmaceutical composition as said in the seventh aspect of the present invention, so as to inhibit the growth of malignant tumor cells with high expression of miRNA-214.

The tenth aspect of the present invention provides a method for treating malignant tumors with high expression of miRNA-214, which involves administering a safe and effective amount of the expression vector as said in the sixth aspect of the present invention or the pharmaceutical composition as said in the seventh aspect of the present invention to a subject in need, so as to treat malignant tumors with high expression of miRNA-214.

In another preferred example, the dosage of the said administering is 0.05-10 mg/kg, preferably 0.1-5 mg/kg.

In another preferred example, the manners of the said administering include oral, respiratory tract, injection, transdermal, mucosal, or cavity administration.

In another preferred example, the said administering comprises a plasmid injection.

The eleventh aspect of the present invention provides a method for treating malignant tumors with high expression of miRNA-214, characterised in that the method involves administering the anti-miR-214 plasmid containing the precursor sequence as said in the fourth aspect of the present invention by intravenous injection to a subject in need, so as to treat malignant tumors with high expression of miRNA-214.

It should be understood that all of the various technical features described above and specifically described hereinafter (such as in the examples) can be combined with one another within the scope of the present invention, so as to form new or preferred technical solutions. Due to space limitations, these are no longer tired out one by one.

BRIEF DESCRIPTION OF THE DRAWINGS

FIG. 16 shows the expression level of the miR-214.

PARTICULAR EMBODIMENTS

Figure 1:
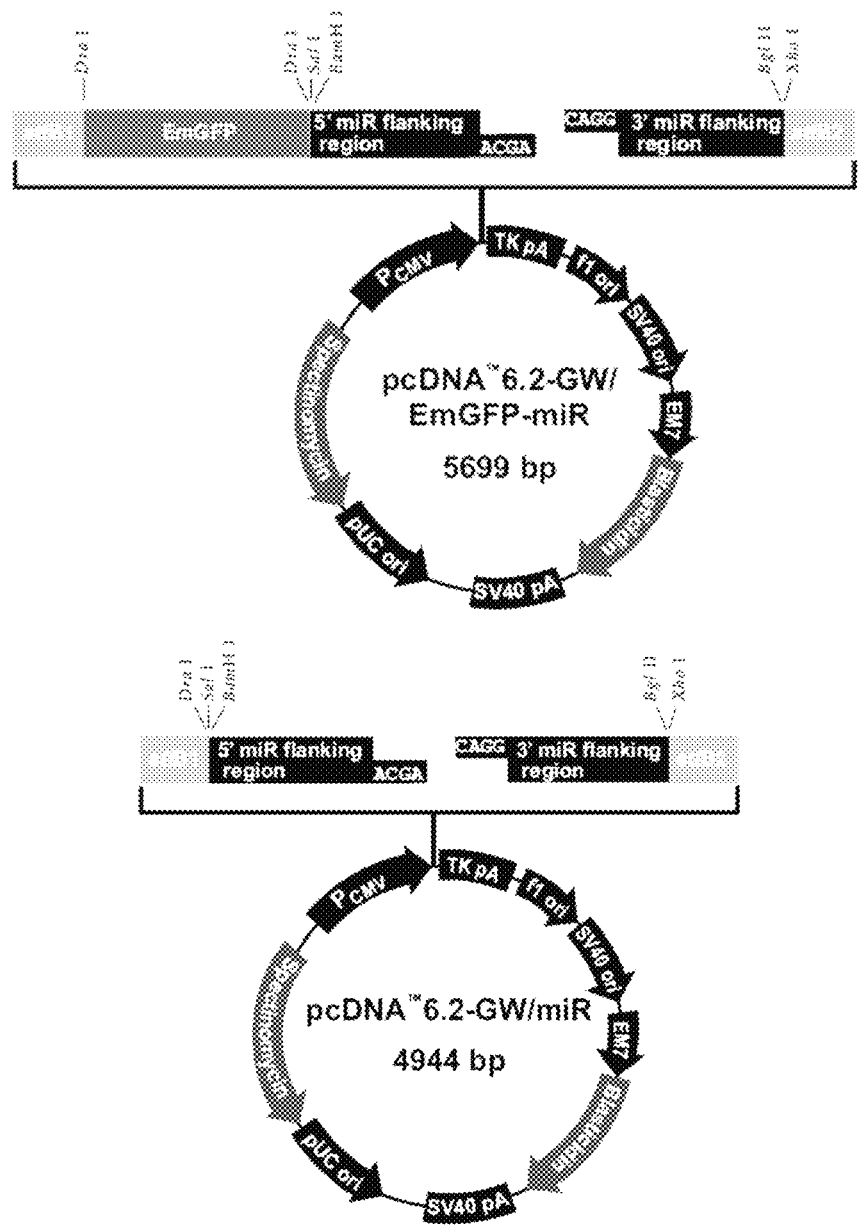
FIG. 1 shows a representative plasmid profile of the present invention, wherein the "flanking region" represents a flanking region (sequence).

The inventors firstly designed and prepared miRNA precursors capable of efficiently expressing anti-miRNA-214 by extensive and deep studies. The precursor miRNAs of the present invention, after having been processed by a host cell, can efficiently express anti-miRNA-214-5p, without producing or substantially producing anti-miRNA-214-3p, so as to effectively avoid the interference effect of the reverse complementary sequence of a target sequence on the functioning of the target sequence. The experiment demonstrated that the precursor miRNAs of the present invention can efficiently express the anti-miRNA-214-5p sequence, and has a more effective therapeutic effect on various malignant tumors. The present invention is accomplished on this basis.

MiRNAs and their Precursors

As used herein, the "miRNAs" refer to a class of RNA molecules, which are originated from miRNA precursors that are products of transcript procession. The mature miRNAs generally have 18-26 nucleotides (nt) (more specifically, about 19-22 nt), not excluding miRNA molecules having other numbers of nucleotides. MiRNA can generally be detected by Northern blotting.

The miRNAs derived from humans can be isolated from human cells. As used herein, "isolated" means that the substance is isolated from its original environment (if it is a natural substance, the original environment is the natural environment). For example, polynucleotides and polypeptides in the natural environment of living cells are not isolated and purified, but when the same polynucleotides or polypeptides are isolated from other substances coexisting in the natural environment, they are isolated and purified.

MiRNAs can be obtained by processing the precursor miRNAs (pre-miRNAs), and the precursor miRNAs can be folded into a stable stem-loop (hairpin) structure having a general length of 50-100 bp. The precursor miRNAs can be folded into a stable stem-loop structure, and two sides of the stem of the stem-loop structure contain two sequences substantially complementary to each other.

In the present invention, the precursor miRNAs are artificially synthesised precursor miRNAs, and the precursor miRNAs have the structure as shown in formula I:

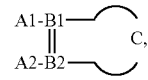

formula I

Wherein, as a representative example, B1 is anti-miRNA-214-5p;

B2 is a sequence complementary (comprising substantially and completely complementary) to B1;

C is a sequence shown as SEQ ID NO.: 1 (GUUUUG-GCCACUGACUGAC);

A1 and A2 are null or are optionally nucleotide sequences consisting of 4-5 bases respectively;

Wherein, the precursor miRNAs as shown can be processed in the host to form anti-miRNA-214, and only the anti-miRNA-214-5p, rather than the anti-miRNA-214-3p, of the anti-miRNA-214 is expressed.

In the present invention, the precursor miRNAs forming the anti-miRNA-214-5p can be cleaved to generate miRNAs antagonistic to miRNA-214, i.e. anti-miRNA-214-5p (SEQ ID NO.: 2).

In formula I, B2 and B1 are substantially complementary to each other. As used herein, "substantially complementary" means that the nucleotide sequence is sufficiently complementary and that same can act upon each other in a predictable manner, e.g., forming a secondary structure (such as a stem-loop structure). Generally, at least 70% of nucleotides in two "substantially complementary" nucleotide sequences are complementary; preferably, at least 80% of nucleotides are complementary; and more preferably, at least 90% of nucleotides are complementary. Generally, there are at most 8 non-matched nucleotides, preferably 1, 2, 3, 4 and 5 non-matched nucleotides, between two sufficiently complementary molecules.

As used in the present application, the "stem-loop" structure, also known as the "hairpin" structure, refers to a nucleotide molecule which can form a secondary structure comprising a double-stranded region (stem) formed of two regions (on a same molecule) of this nucleotide molecule, the two regions being at two sides of the double-stranded portion; and the structure further comprises at least one "loop" structure, including non-complementary nucleotide molecules, i.e., a single-stranded region. Even if the two regions of the nucleotide molecule are not completely complementary, the double-stranded part of the nucleotide can also maintain the double-stranded form. For example, insertion, deletion, substitution or the like may lead to a non-complementary small region or make the small region itself form a stem-loop structure or another form of secondary structure. However, the two regions can still be substantially complementary to each other and act upon each other in a predictable manner to form a double-stranded region of the stem-loop structure. The stem-loop structure is well known to a person skilled in the art, who can generally determine, when given a nucleic acid having a nucleotide sequence of the primary structure, whether the nucleic acid can form a stem-loop structure.

In the present invention, a "stem-loop structure" can be present at the end of the precursor miRNAs as shown in formula I, for example, after B1 and B2 form a substantially complementary structure, C will form a stable stem-loop structure at the end thereof; the "stem-loop structure" can also be present in the interior of the precursor miRNAs as shown in formula I, for example, since B1 and B2 are not completely complementary, the bases of B1 or B2 which do not bind with the others in a complementary manner will form an internal loop.

The miRNA-214 of the present invention refers to the microRNA-214 (miRNA-214) family comprising miRNA-214 or modified miRNA-214 derivatives which function identically or substantially identically to miRNA-214.

Referring to the miRNA sequences provided in the present invention, polynucleotide constructs, which can, after introduction, be processed into miRNAs capable of affecting the expression of the corresponding mRNAs, can be designed, i.e., the polynucleotide constructs can up-regulate the level of the corresponding anti-miRNA-214-5p in vivo so as to decrease the level of miRNA-214. Therefore, the present invention provides an isolated polynucleotide (construct), and the polynucleotide (construct) can be transcribed by human cells into precursor miRNAs which can be cleaved and expressed as the miRNAs in human cells.

Polynucleotide Constructs

As a preferred mode of the present invention, the polynucleotide construct contains a structure from the 5' terminus to the 3' terminus as shown in formula II:

formula II in formula II, b1 is a nucleotide sequence which can be expressed as the anti-miRNA-214-5p in a cell, b2 is a nucleotide sequence substantially or completely complementary to b1; c is a spacer sequence between b1 and b2, and the spacer sequence is not complementary to B1 and B2;

a1 and a2 are null or are optionally nucleotide sequences consisting of 4-5 bases respectively;

and after being introduced into the cell, the structure as shown in formula II forms a secondary structure as shown in formula I:

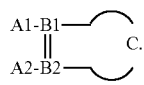

formula I

Generally, the polynucleotide constructs are located on the expression vector. Therefore, the present invention further comprises a vector containing the miRNAs or the polynucleotide constructs. The expression vector typically further contains a promoter, an origin of replication and/or a marker gene, etc. Methods well known to a person skilled in the art can be used to construct the expression vector required by the present invention. These methods include in vitro recombinant DNA technology, DNA synthesis technology, in vivo recombination technology, etc. The expression vector preferably contains one or more selectable marker genes to provide a phenotypic trait for the selection of transformed host cells, such as kanamycin, gentamicin, hygromycin or ampicillin resistance.

In the present invention, there is no special limitation on the expression vector, comprising commercially available or conventionally prepared expression vectors. Representative examples include (but are not limited to): pcDNATM6.2-GW/miR, pcDNA3, pMIR-REPORT miRNA, pAdTrack-CMV, pCAMBIA3101+pUC-35S, pCMVp-NEO-BAN, pBI121, pBin438, pCAMBIA1301, pSV2, a CMV4 expression vector, pmiR-RB-Report™, pshOK-basic, mmu-mir 300-399 miRNASelect™, pshRNA-copGFP Lentivector, GV317, GV309, GV253, GV250, GV249, GV234, GV233, GV232, GV201, GV159 or other expression vectors of the GV series.

In another preferred example, in the said expression vector, the promoter operably linked to the polynucleotide expressing the precursor miRNAs comprises a constitutive promoter or a tissue-specific promoter, preferably a promoter specifically performing initiation in liver tissues. In other words, these promoters are used to drive the expression of the precursor miRNAs.

Representative promoters include (but are not limited to): a Pcmv promoter, U6, H1, a CD43 promoter, a CD45 (LCA) promoter, a CD68 promoter, an Endoglin (CD105) promoter, a Fibronectin promoter, a Flt-1 (VEGFR-1) promoter, a GFAP promoter, a GPIIb (Integrin αIIb) promoter, an ICAM-2 (CD102) promoter, a MB (Myoglobin) promoter, a NphsI (Nephrin) promoter, a SPB promoter, a SV40/hAlb promoter, a SYN1 promoter, a WASP promoter or a combination thereof.

Pharmaceutical Composition and Administration Methods

As used herein, the term "effective amount" or "effective dose" refers to the amount which can induce a function or activity in humans and/or animals and can also be acceptable to humans and/or animals.

As used herein, the term "pharmaceutically acceptable" component is applicable to humans and/or mammals without excessive adverse side effects (such as toxicity, irritation and allergic responses), i.e., a substance with a reasonable benefit/risk ratio. The term "pharmaceutically acceptable carrier" refers to a carrier for the administration of a therapeutic agent, including various excipients and diluents.

The pharmaceutical composition of the present invention contains a safe and effective amount of the active component of the present invention and a pharmaceutically acceptable carrier. Such carrier includes, but is not limited to, saline, a buffer, glucose, water, glycerol, ethanol, and a combination thereof. Generally, a pharmaceutical preparation shall match the administration mode, and the dosage form of the pharmaceutical composition of the present invention can be an injection, an oral preparation (a tablet, a capsule, or an oral liquid), a transdermal agent, or a slow release agent. For example, preparation thereof is performed by a conventional method using physiological saline or an aqueous solution containing glucose and other adjuvants. The pharmaceutical composition is preferably produced under sterile conditions.

The effective amount of the active component of the present invention may vary depending on the administration mode and the severity of the disease to be treated. A person skilled in the art could determine the selection of the preferred effective amount depending on various factors (e.g., by clinical trials). The factors include, but are not limited to, the pharmacokinetic parameters of said active component, e.g., the bioavailability, metabolism, half-life, etc.; and the severity of the patient's disease to be treated, the patient's weight, the patient's immune state, the administration route, etc. Generally, when the active component of the present invention is administered at a dose of about 0.00001-50 mg/kg body weight (preferably 0.0001-10 mg/kg body weight) per day, satisfactory results can be achieved. For example, due to the urgent requirements of the treatment status, several separate doses can be administered daily, or the dosage is reduced proportionally.

The pharmaceutically acceptable carrier of the present invention includes (but is not limited to): water, saline, liposomes, lipids, micro particles, micro vesicles, exosomes, shedding vesicles, nanocapsules/nanoparticles, β-cyclodextrin capsule (β-cyclodextriniclusion compound) proteins, protein-antibody conjugates, peptides, cellulose, nanogels, or a combination thereof. The choice of carriers should match the administration mode, which would be well known to a person skilled in the art.

In the present invention, the expression vector can be directly administered to a subject, and the expression vector can also be administered by preparing same into a pharmaceutical composition with a pharmaceutically acceptable carrier. The administration comprises an intravenous injection.

Therapeutic Method

The present invention further provides a method for treating malignant tumors highly expressing miRNA-214, i.e., administering a safe and effective amount of the expression vector or the pharmaceutical composition of the present invention to a subject in need, so as to treat malignant tumors highly expressing miRNA-214. Generally, "malignant tumors highly expressing miRNA-214" means that the expression amount E1 of miRNA-214 in the tumors is significantly different from the amount E0 of miRNA-214 in para-carcinoma tissues or normal tissues, and preferably, the wording "highly expressing" means that $E1 \geq 1.5\ E0$, more preferably $E1 \geq 2\ E0$. In tumor tissues, whether miRNA-214 is highly expressed can be detected through conventional methods. Generally, the malignant tumors highly expressing miRNA-214 include (but are not limited to) liver cancer, lung cancer, stomach cancer, oesophageal cancer, ovarian cancer, colorectal cancer, cervical cancer, pancreatic cancer, prostatic cancer, leukaemia or breast cancer.

Beneficial Effects of the Present Invention

The precursor miRNAs of the present invention can effectively avoid the over-expression of a target sequence and also the over-expression of the reverse complementary sequence of the target sequence at the same time, so as to effectively avoid the interference effect of the reverse complementary sequence of a target sequence on the functioning of the target sequence.

The precursor miRNAs of the present invention can effectively express the anti-miRNA-214-5p sequence in vivo, and have an effective therapeutic effect on various malignant tumors, so that the precursor miRNAs can be used for developing new medicaments for treating tumors.

Example 1: The Construction of Anti-miR-214 Over-Expression Vector

MicroRNA vectors can rapidly, efficiently and sustainably express pre-miRNAs using the CMV promoter in the cell of various mammals, the pre-miRNAs form small hairpin pre-miRNAs (about 70 nt) by the action of Drosha (RNaseIII), which form mature microRNAs (about 22 nt) by the action of Dicer, and the mature microRNAs act on target mRNAs and function to regulate the expression. By using optimised vectors, the expression module of anti-miR-214 is simulated, thereby effectively avoiding the problem that -3p and -5p are produced when some endogenous miRNAs are expressed.

1. Anti-miR-214-5p Sequence
>anti-miR-214-5p (SEQ ID NO.: 2)
5'-ACUGCCUGUCUGUGCCUGCCUGU-3'

2. Anti-miR-214 Vector
2.1. Design and Synthesis of Oligo DNAs

According to the gene sequences, 2 pairs of complementary oligo DNAs were designed and synthesised (for the oligo design method and framework, reference can be made to point 6 of the product instructions), and for the sequences, reference can be made to Table 1.

The designed and synthesised oligo structures are as follows:

TABLE 1

The oligo DNA sequences and their corresponding precursor miRNA elements

Oligo name  Oligo DNA sequence 5'-3'

Mature sequence of >anti-miR-214-5p: 5'-ACUGCCUGUCUGUGCCUGCCUGU-3' (SEQ ID NO.: 2)

13MR0041-1F  TGCTGACTGCCTGTGTGTGCCTGCCTGTGTTTTGGCCACTGACcaaagtatcatctttgtag
             |A1|        B1        |    C    |       B2         |
             (SEQ ID NO.: 4, TGCTGACTGCCTGTCTGTGCCTGCCTGTGTTTTGGCCACTGACcaaagtatcatctttgtag)

13MR0041-1R  CCTGctacaaagatgatactttgGTCAGTGGCCAAAACACAGGCAGGCAGACAGGCAGTC
             |A2|      B2            |    C    |      B1         |
             (SEQ ID NO.: 5, CCTGctacaaagatgatactttgGTCAGTGGCCAAAACACAGGCAGGCAGACAGGCAGTC)

Negative control sequence

Negative-F   tgctgAAATGTACTGCGCGTGGAGACGTTTTGGCCACTGACTGACGTCTCCACGCAGTACATTT
             |A1 | multiple cloning site |    C    | multiple cloning site |
             (SEQ ID NO.: 6,
             tgctgAAATGTACTGCGCGTGGAGACGTTTTGGCCACTGACTGACGTCTCCACGCAGTACATTT)

TABLE 1-continued

The oligo DNA sequences and their corresponding precursor miRNA elements

| Oligo name | Oligo DNA sequence 5'-3' |
|---|---|
| Negative-R | cctgAAATGTACTGCGTGGAGACGTCAGTCAGTGGCCAAAACGTCTCCACGCGCAGTACATTTc<br>\|A2\|multiple cloning site\|         C         \| multiple cloning site \|<br>(SEQ ID NO.: 7,<br>    cctgAAATGTACTGCGTGGAGACGTCAGTCAGTGGCCAAAACGTCTCCACGCGCAGTACATTTc) |

2.2 the Construction and Validation of the miRNA Vector 2.2.1 Materials

BLOCK-iT™ Pol II miR RNAi expression vector cassette containing EmGFP (purchased from Life)

Oligo DNA (purchased from Life)

Competent cell DH5α (purchased from Life)

2.2.2 Methods (1) Annealing

The synthesised 2 pairs of oligo single-stranded DNAs were dissolved in ddH$_2$O to 100 μM, and 5 μl of each of the complementary single strands were taken and mixed pairwise, and annealed in the system given in Table 2. 2 portions of the oligo mixture were heated at 95° C. for 5 minutes, and then placed at room temperature for 20 minutes to form double-stranded DNAs.

TABLE 2

Oligo DNA annealing system

| | |
|---|---|
| 100 μM top strand oligo | 5 μl |
| 100 μM bottom strand oligo | 5 μl |
| 10× oligo annealing buffer | 2 μl |
| ddH$_2$O | 8 μl |
| Total volume | 20 μl |

(2) Ligation

The annealed double-stranded DNAs were then diluted to a concentration of 10 nM, and ligated at room temperature in the system given in Table 3 for 30 minutes.

TABLE 3

Enzyme ligation system

| | |
|---|---|
| 5× ligation buffer | 4 μl |
| pcDNA6.2-GW/EmGFP-miR<br>Or pcDNA6.2-GW/miR | 2 μl |
| ds oligo (10 nM) | 4 μl |
| T4 DNA ligase(1 U/μl) | 1 μl |
| ddH$_2$O | 9 μl |
| Total volume | 20 μl |

Note:
the structures of pcDNA6.2-GW/EmGFP-miR and pcDNA6.2-GW/miR are as shown in FIG. 1.

(3) Transformation

100 μl competent cells of DH5a were transformed with 10 μl of ligated product, followed by spreading on LB plates (containing 50 μg/ml spectinomycin) and incubating at 37° C.

(4) Sequencing and Validation 3 clones were respectively picked from each transformation plate, followed by shaking same and extracting plasmids therefrom, and sequencing to validate whether the inserted fragment sequence in the recombinant clones was consistent with the designed oligo single-stranded DNA sequence or not.

Example 2: Cell Experiment for Validating the Efficiency of the Over-Expression of Anti-miR-214

A549 cells (purchased from Cell Resource Centre, Shanghai Institute for Biological Sciences of the Chinese Academy of Sciences) were transfected with the anti-miR-214 plasmids, the total RNAs were collected, and then the levels of anti-miR-214-5p, anti-miR-214-3p and miR-214 were detected by Real-time-PCR using primers for anti-miR-214-5p, anti-miR-214-3p and miR-214 respectively, customised from ABI Corporation. The results were presented as Ct values, which represent the cycle number undergone when the fluorescence signal in each reaction tube reached a set threshold, wherein there was a linear relationship between the Ct value of each template and the logarithm of the initial copy number of the template, i.e., the larger the initial copy number, the less the Ct value, and the less the initial copy number, the larger the Ct value. Table 4 shows the assay for the expression levels of anti-miRNA and miRNA using Real-time PCR.

TABLE 4

The expression levels of anti-miR-214-5p, anti-miR-214-3p, and miR-214

| (Ct) | anti-miR-214-5p |
|---|---|
| Blank plasmid | 39.63 ± 0.2928 |
| anti-miR-214 plasmid | 24.55 ± 0.5052 |
| (Ct) | anti-miR-214-3p |
| Blank plasmid | 30.45 ± 0.7865 |
| anti-miR-214 plasmid | 33.87 ± 0.5683 |
| (Ct) | miR-214 |
| Blank plasmid | 20.55 ± 0.6822 |
| anti-miR-214 plasmid | 23.63 ± 0.5119 |

Conclusion: after the A549 cells were transfected with the anti-miR-214 plasmids, a sharp increase in the anti-miR-214-5p can be detected (p<0.01), the anti-miR-214-3p cannot be substantially detected (p>0.05), and a rise in miR-214 could not be caused, and on the contrary, a decrease in miR-214 was caused (p<0.05). Based on the difference of the Ct values, it can be determined that the ratio of F5 to F3 is much more than 50/1.

Example 3: In Vivo Experiment for Validating the Efficiency of the Over-Expression of Anti-miR-214

The C57/BL6 mice were administered with the anti-miR-214 plasmids by intravenous tail injection, and perfused after 24 h, followed by taking blood, heart, liver, spleen, lung, kidney, brain and muscle tissues, collecting the total RNAs, and then performing q-PCR for detecting the levels of the anti-miR-214-5p, anti-miR-214-3p and miR-214. The results can be seen in Table 5.

TABLE 5

The expression levels of anti-miR-214-5p and anti-miR-214-3p

| (Ct) | anti-miR-214-5p | anti-miR-214-3p |
|---|---|---|
| Blank mouse blood | 38.80 ± 0.4171 | 30.80 ± 0.8066 |
| 0.1 mg plasmids, in mouse blood | 24.11 ± 0.4588 | 30.74 ± 0.1667 |
| 0.01 mg plasmids, in mouse blood | 28.09 ± 0.9880 | 30.50 ± 0.1404 |
| Blank mouse liver | 39.37 ± 0.8329 | 30.61 ± 0.1288 |
| 0.1 mg plasmids, in mouse liver | 20.52 ± 0.3156 | 30.67 ± 0.1311 |
| 0.01 mg plasmids, in mouse liver | 25.30 ± 0.1404 | 33.70 ± 0.1351 |
| Blank mouse lung | 39.25 ± 0.5662 | 33.12 ± 0.1290 |
| 0.1 mg plasmids, in mouse lung | 26.37 ± 0.3754 | 30.08 ± 0.1283 |
| 0.01 mg plasmids, in mouse lung | 30.76 ± 0.1895 | 33.58 ± 0.1387 |

The experimental results suggested that:

it can be seen from the experimental results that after injecting with 0.1 mg plasmids, the levels of anti-miR-214-5p in mouse whole blood, liver, and lung have been significantly increased ($p<0.05$), and a change in anti-miR-214-3p cannot be detected ($p<0.05$).

Figure 2:
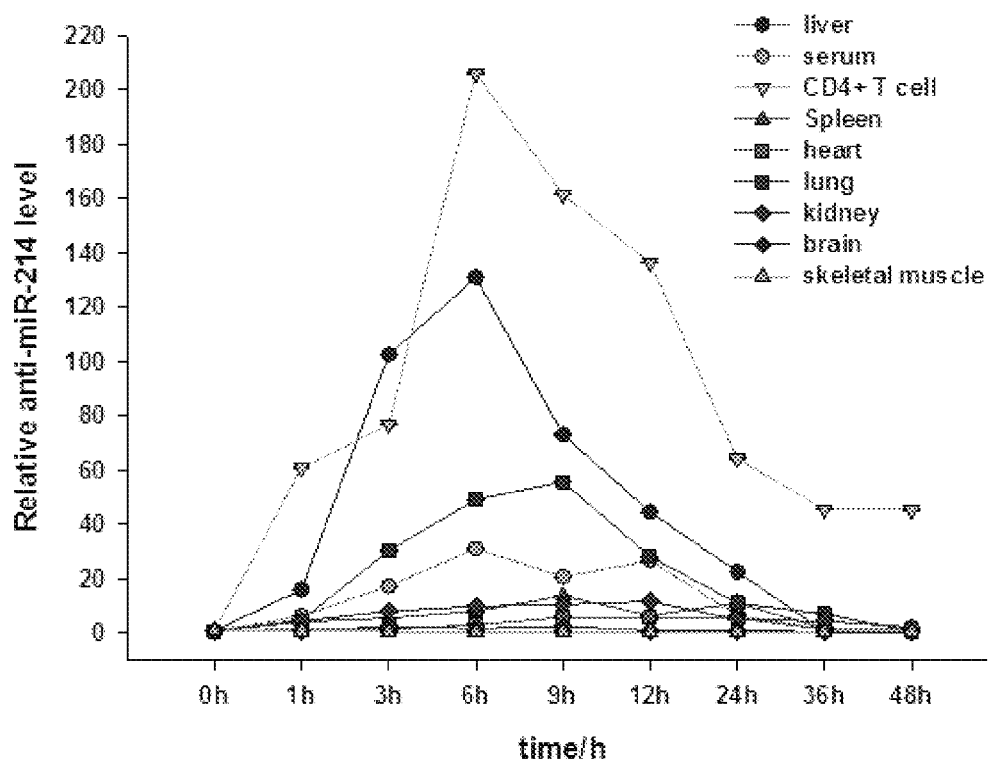
FIG. 2 shows the siRNA amounts in various tissues or visceral organs of mice detected at time points of 1 h, 3 h, 6 h, 24 h and the like after the anti-miR-214 overexpressing-plasmids are administered by intravenous tail injection.

Example 4: In Vivo Experiment for Validating the Metabolism Kinetics of the Over-Expressed siRNAs The mice were administered with the anti-miR-214 overexpression plasmid by intravenous tail injection (in the following experiments, the anti-miR-214 always refers to anti-miR-214-5p), the siRNA amounts in the plasma, heart, liver, spleen, lung, kidney, brain, skeletal muscle and CD4+ T cells were detected after 1 h, 3 h, 6 h, 9 h, 12 h, 24 h, 36 h and 48 h, and the detailed results are shown in FIG. 2. It can be seen from FIG. 2 that siRNAs can actually enter the lung and reach a peak concentration after 6 h, and can be detected within 24 h.

Example 5: Experiment in Tumor-Bearing Mice

A lung cancer metastasis model was constructed by injecting LLC cells from the tail-vein of mice, and after the model was successfully constructed, the anti-miR-214 overexpression plasmid was administered by intravenous tail injection, and the therapeutic effect was observed. After the mice were sacrificed, various tissues of the mice were taken for detecting the distribution of anti-miR-214 in various tissues by Real-time PCR, and tissue sections were made for detecting and observing the therapeutic effect.

(1) The Change in the Quantity of CD25+ and Foxp3+ T Cells

Figure 3:
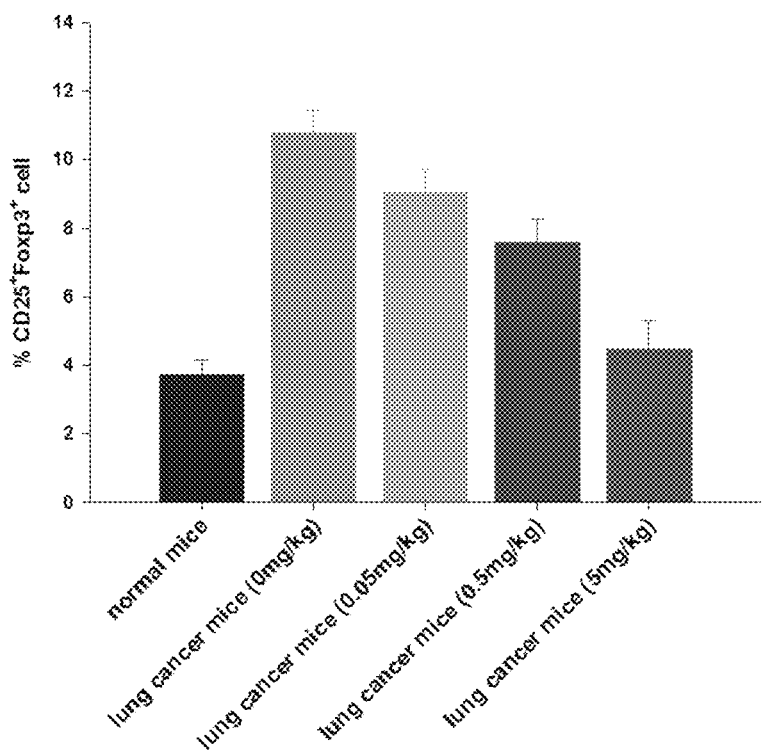
FIG. 3 shows the CD4+ T cell count changes.

The detailed results are shown in FIG. 3. It can be seen from FIG. 3 that the anti-miR-214 plasmid can effectively inhibit the quantity of new T cells CD25+ and Foxp3+ T cells (Treg) in the tumor-bearing mice in a dose-dependent manner, and as the concentration of the injected plasmids increases, the quantity of CD25+ and Foxp3+ T cells (Treg) decreases.

(2) The Amounts of Anti-miR-214 in Various Tissues

Figure 4:
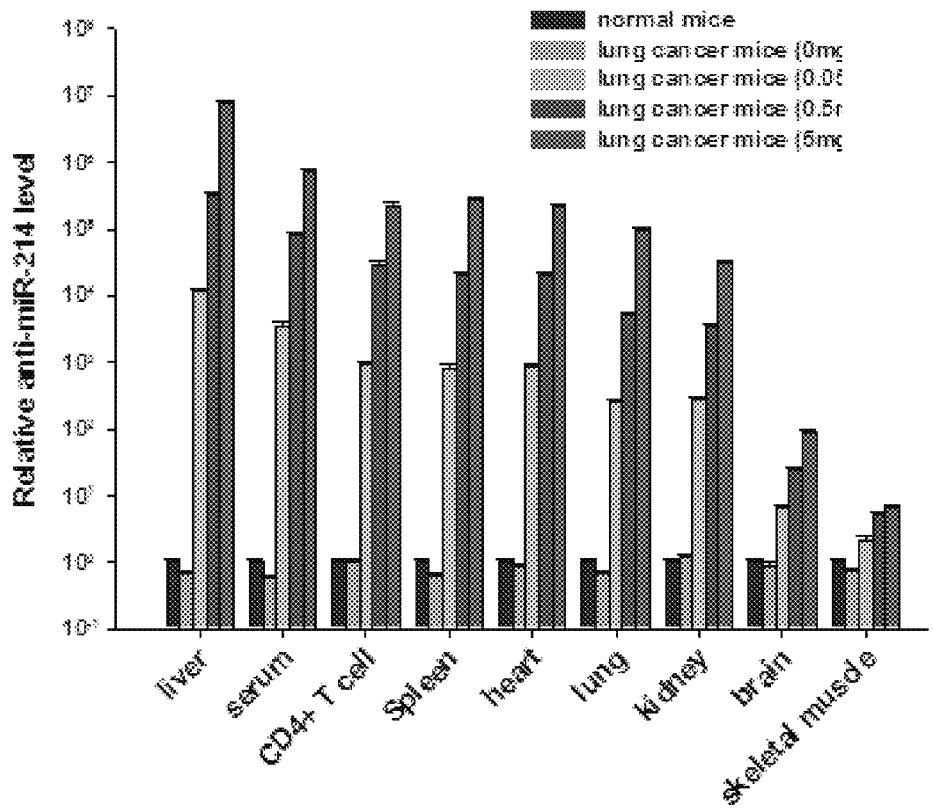
FIG. 4 shows the amounts of anti-miR-214 in various tissues.

The detailed results are as shown in FIG. 4. It can be seen from FIG. 4 that after injecting with the anti-miR-214 plasmid, anti-miR-214 can be delivered by the liver to various tissues, resulting in a sharp increase in the level of anti-miR-214 in various tissues.

Example 6: Cell Experiment Verifies that Liver Cells can Overexpress Anti-miR-214 and are Able to Transport the Anti-miR-214 to CD4+ T Cells Using Exosomes Experimental Process 1) The anti-miR-214 plasmid was transfected into HepG2 cells using liposome. After 6 h, the medium was changed. After 24 h, the cells were collected, and RNA was extracted to detect the expression level of the anti-miR-214.

2) The anti-miR-214 plasmid was transfected into HepG2 cells using liposome. After 6 h, the medium was changed. After 24 h, the cell culture medium was collected, exosomes were isolated, and RNA was extracted to detect the expression level of the anti-miR-214.

3) The anti-miR-214 plasmid was transfected into HepG2 cells using liposome. After 6 h, the medium was changed. After 24 h, the cell culture medium was collected, exosomes were isolated and added into the cultured CD4+ T cells, and RNA was extracted to detect the expression levels of the anti-miR-214, the miR-214 and PTEN.

Experimental Results

Figure 5:
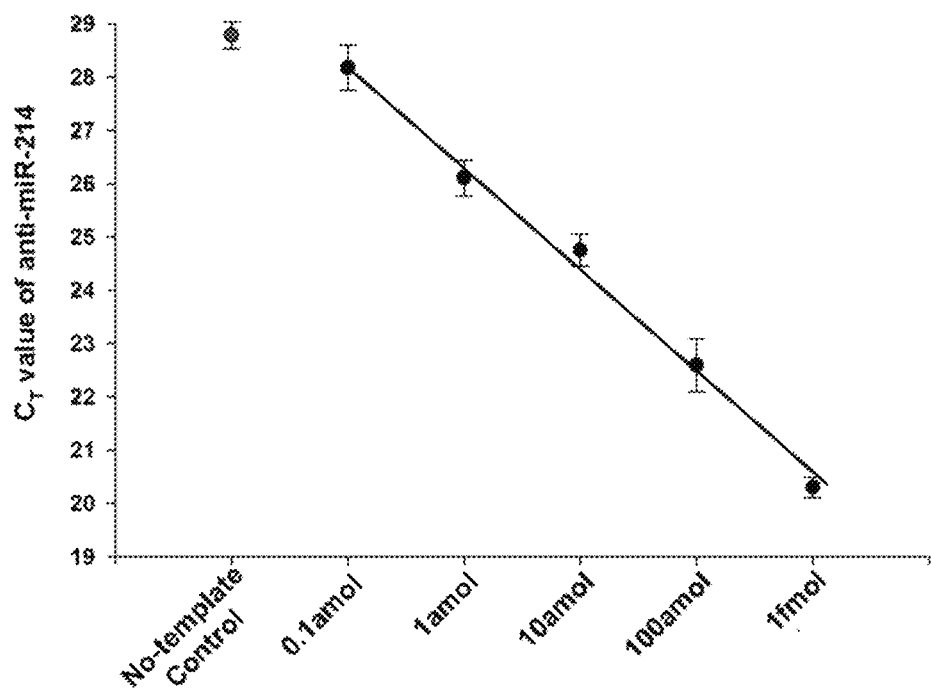
FIG. 5 shows the $C_T$ value of the anti-miR-214.

The linear detection range of an anti-miR-214 probe was detected by q-PCR technology using synthesized single-stranded anti-miR-214. The specific results are shown in FIG. 5. NO-template control: Water was used alone without RNA during reverse transcription, i.e., water background. FIG. 5 shows the $C_T$ value of the anti-miR-214. It was found from the experimental results that the anti-miR-214 probe can detect a minimum of 0.1 amol, and the $C_T$ value of the water background was 28.5.

Figure 6:
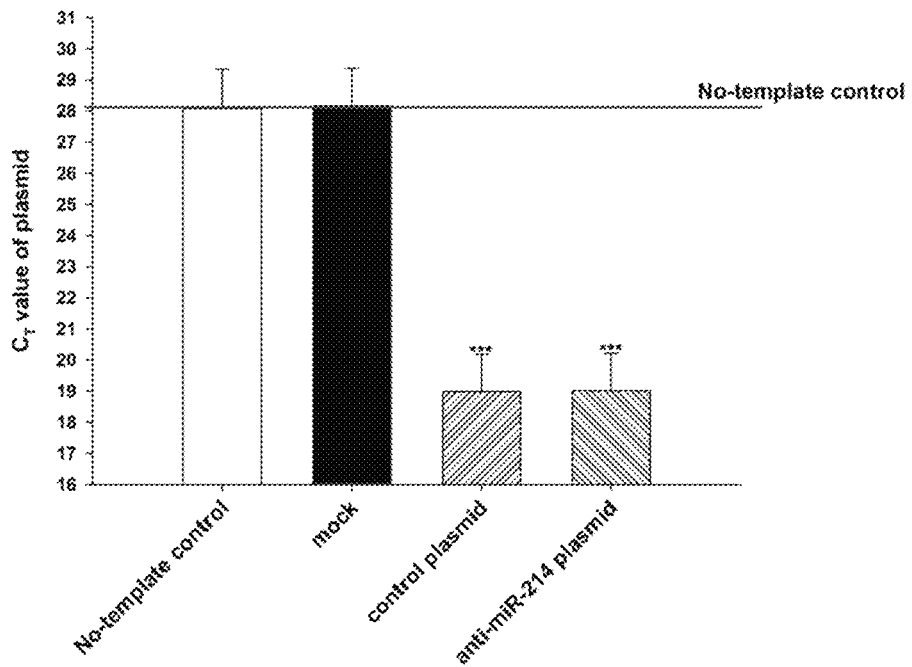
FIG. 6 shows the $C_T$ value of the plasmid.

The anti-miR-214 plasmid was then transfected into HepG2 cells using liposome, and the level of the anti-miR-214 plasmid was detected first, wherein the plasmid was detected using q-PCR, and the primer sequences were as follows: forward primer: 5'-GGCATGGACGAGCTGTA-CAA-3'; and reverse primer: 5'-CTCTAGATCAAC-CACTTTGT-3'. The specific results are shown in FIG. 6. FIG. 6 shows the $C_T$ value of the plasmid. NO-template control: Water was used alone without RNA during reverse transcription, i.e., water background; Mock: HepG2 cells were used without any treatment, i.e., blank control; and Control plasmid: pcDNA6.2 blank backbone expressing no microRNA sequence was used as a control. It can be seen from the results that the anti-miR-214 plasmid can be efficiently transfected into HepG2 cells.

Figure 7:
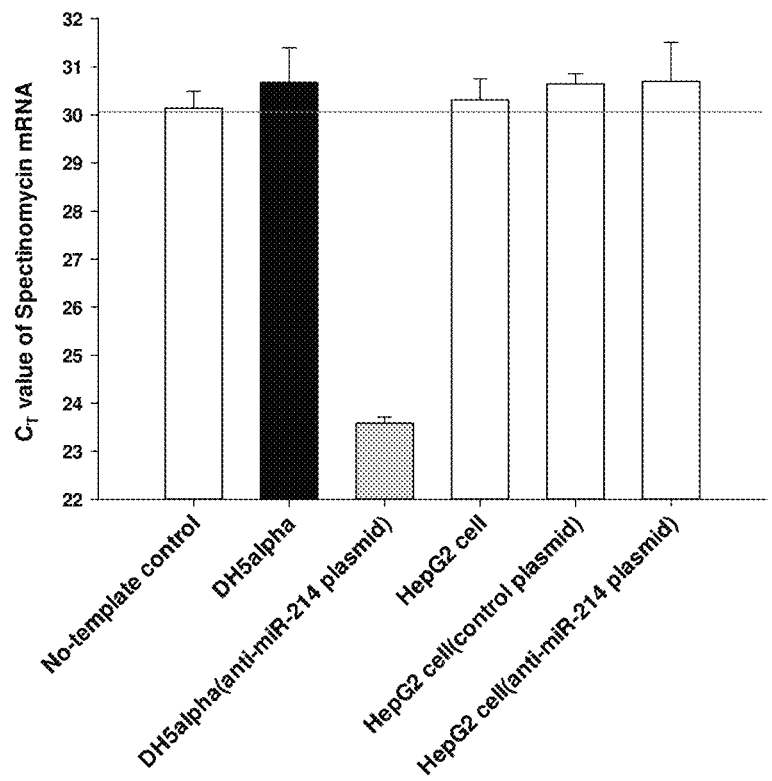
FIG. 7 shows the $C_T$ value of the spectinomycin mRNA.

The expression situation of spectinomycin was detected, wherein spectinomycin was detected using q-PCR, and the primer sequences were as follows: forward primer: 5'-TGAGGCGCTAAATGAAACCT-3'; and reverse primer: 5'-ATTTGCCGACTACCTTGGTG-3'. The specific results are shown in FIG. 7. FIG. 7 shows the $C_T$ value of the spectinomycin mRNA. DH5alpha: blank competent bacteria; DH5alpha (anti-miR-214 plasmid): competent bacteria transformed with the anti-miR-214 plasmid; HepG2 cell: HepG2 cells without any treatment; HepG2 cell (Control plasmid): HepG2 cells transfected with the blank plasmid; and HepG2 cell (anti-miR-214 plasmid): HepG2 cells transfected with the anti-miR-214 plasmid. It can be seen from the results that spectinomycin was not expressed in eukaryotic HepG2 cells. The aim of this experiment was to ensure that the antibiotic screening gene expressed by the plasmid in prokaryotic bacteria was not expressed in eukaryotic cells.

Figure 8:
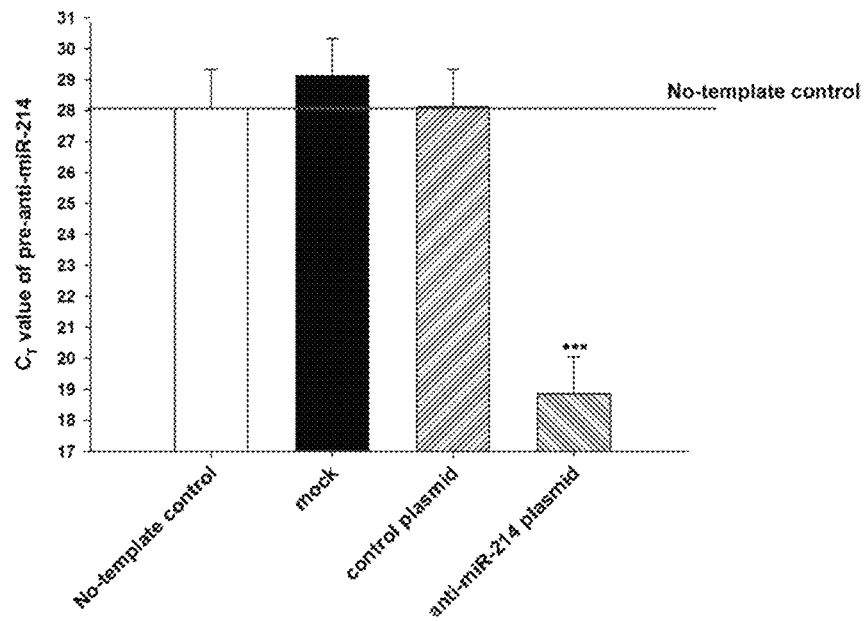
FIG. 8 shows the $C_T$ value of the pre-anti-miR-214.

The expression situation of the anti-pre-miR-214 was detected, wherein the detection was performed using qRT-PCR, and the primer sequences were as follows: RT primer: 5'-CTGTCTGTGTGCTGTGTCAGTC-3'; forward primer:

5'-GGCACAGACAGGCAGTCAGCA-3'; and reverse primer: 5'-CTGTCTGTGTGCTGTGTCAGTC-3'. The specific results are shown in FIG. 8. FIG. 8 shows the $C_T$ value of the pre-anti-miR-214. It can be seen from the results that the anti-miR-214 plasmid was expressed in HepG2 cells.

Figure 9:
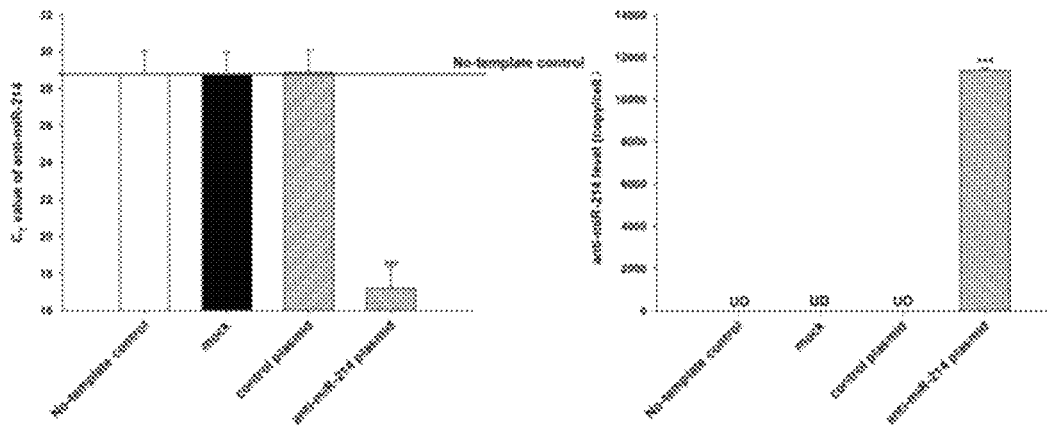
FIG. 9 shows the $C_T$ value and expression level of the anti-miR-214. The first graph shows the $C_T$ value of the anti-miR-214, and the second graph shows the expression level of the anti-miR-214.

The expression situation of the anti-miR-214 was detected using a QIAGEN Tailing kit, wherein the reverse transcription primer was the same as the reverse primer for qRT-PCR, and the forward primer was as follows: 5'-ACACTCCA-GCTGGGACTGCCTGTCTGTGCC-3'. The specific results are shown in FIG. 9. FIG. 9 shows the $C_T$ value and expression level of the anti-miR-214. The first graph shows the $C_T$ value of the anti-miR-214, and the second graph shows the expression level of anti-miR-214. It can be seen from the results that the anti-miR-214 plasmid was expressed in HepG2 cells.

Figure 10:
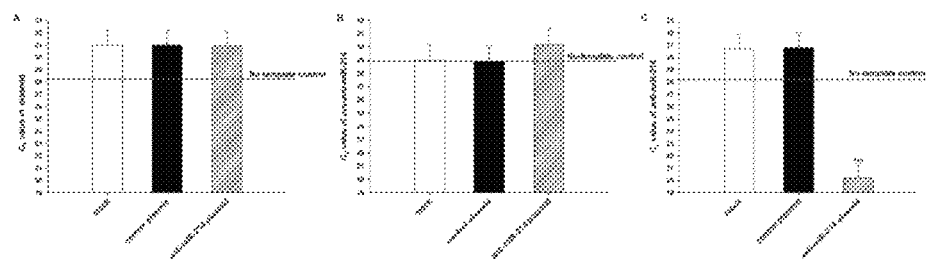
FIG. 10 shows the $C_T$ values of the plasmid, pre-anti-miR-214 and anti-miR-214 in exosomes. The first graph labeled A shows the $C_T$ value of the plasmid; the second graph labeled B shows the $C_T$ value of the pre-anti-miR-214; and the third graph labeled C shows the $C_T$ value of the anti-miR-214.

The exosomes were isolated from the culture supernatant of the cultured HepG2 cells by ultra-high speed centrifugation. Then, DNA was isolated from part of the extracted exosomes to detect the content of the anti-miR-214 plasmid, and RNA was extracted from the other part to detect the contents of the pre-miR-214 and the mature miR-214. The specific results are shown in FIG. 10. FIG. 10 shows the $C_T$ values of the plasmid, pre-anti-miR-214 and anti-miR-214 in exosomes. The first graph labeled A shows the $C_T$ value of the plasmid; the second graph labeled B shows the $C_T$ value of the pre-anti-miR-214; and the third graph labeled C shows the $C_T$ value of the anti-miR-214. It was found from the results that as shown in the first graph labeled A, the exosomes did not contain the plasmid; as shown in the second graph labeled B, the exosomes did not contain the pre-miR-214; and as shown in the third graph labeled C, the exosomes contained the anti-miR-214 at a high level.

Figure 11:
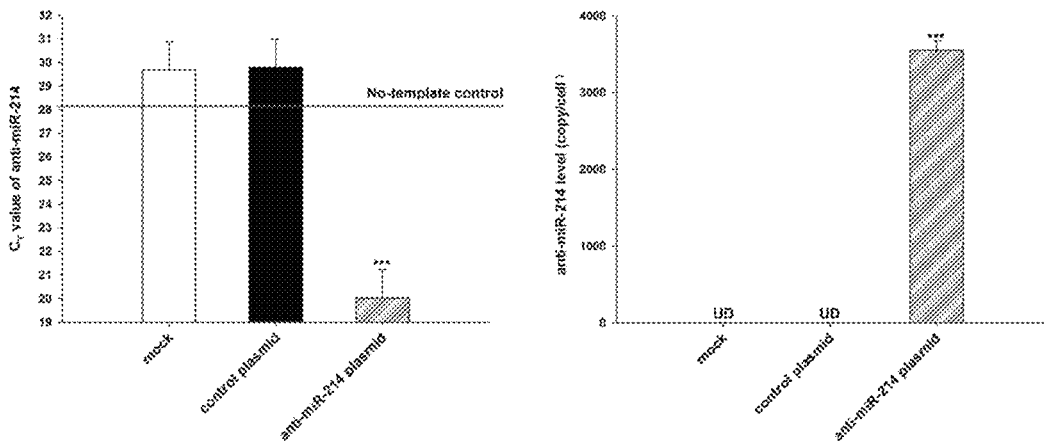
FIG. 11 shows the $C_T$ value and expression level of the anti-miR-214 in CD4+ T cells. The first graph shows the $C_T$ value of the anti-miR-214; and the second graph shows the expression level of the anti-miR-214.

CD4$^+$ T cells were isolated from mice using a CD4$^+$ T cell Isolation Kit (Miltenyi Biotec, Inc.) and cultured in cell culture dishes, followed by the addition of exosomes isolated from the culture supernatant of HepG2 cells, and the anti-miR-214 content was then detected in CD4$^+$ T cells. The specific results are shown in FIG. 11. FIG. 11 shows the $C_T$ value and expression level of the anti-miR-214 in CD4$^+$ T cells. The first graph shows the $C_T$ value of the anti-miR-214; and the second graph shows the expression level of the anti-miR-214. It was found from the results that exosomes can effectively carry the anti-miR-214 into CD4$^+$ T cells.

Figure 12:
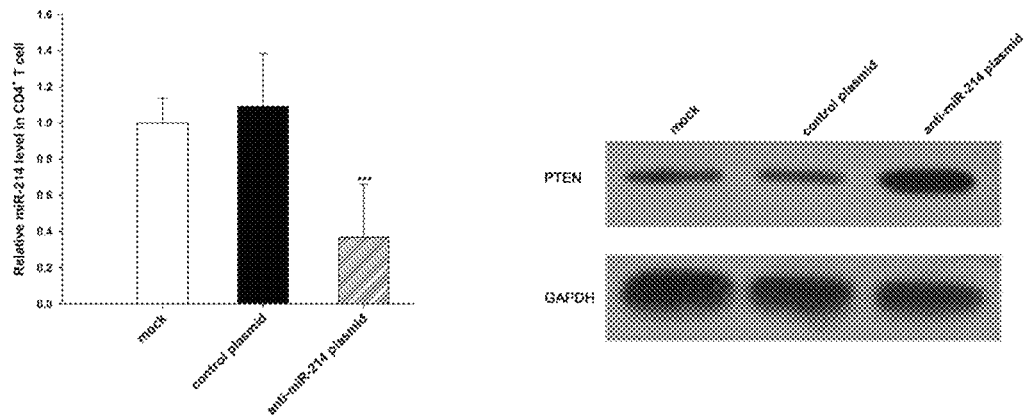
FIG. 12 shows the relative expression level of the miR-214 and the protein level of PTEN in CD4+ T cells. The graph shows the relative expression level of the miR-214 in CD4+ T cells; and the images show the protein level of PTEN.

The miR-214 content was then determined in CD4$^+$ T cells. The specific results are shown in FIG. 12. FIG. 12 shows the relative expression level of the miR-214 and the protein level of PTEN in CD4$^+$ T cells. The graph shows the relative expression level of the miR-214 in CD4$^+$ T cells; and the images show shows the protein level of PTEN. It was found from the results that the miR-214 content in CD4$^+$ T cells with anti-miR-214-containing exosomes added was significantly decreased, and the protein content of the miR-214 target gene, PTEN, was increased.

Figure 13:
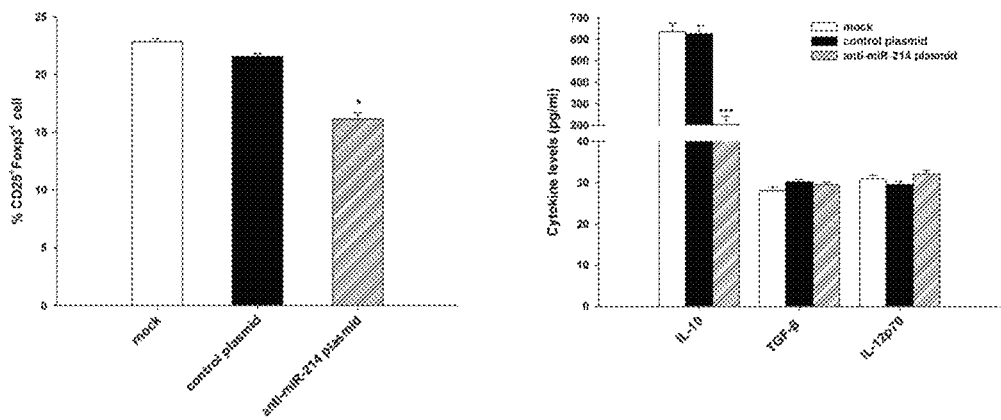
FIG. 13 shows the ratio of Treg and the expression level of cytokines. The first graph shows the ratio of Treg; and the second graph shows the expression level of cytokines.

The ratio of Treg induced by CD4$^+$ T cells was then detected using a flow cytometer. The specific results are shown in FIG. 13. FIG. 13 shows the ratio of Treg and the expression level of cytokines. The first graph shows the ratio of Treg; and the second graph shows the expression level of cytokines. The results showed that the induction rate of Treg in CD4$^+$ T cells with anti-miR-214-containing exosomes added was significantly decreased, and IL-10 released from Treg was also significantly decreased.

Example 7: The Study of the Therapeutic Effect of Anti-miR-214 on the Mouse Lewis Lung Cancer 1.2 Experimental Methods In the experiments, healthy C57BL/6 mice were taken, and injected at 0.2 ml/mouse through the tail-vein slowly, and after the injection was finished, all the modeled mice were classified into Group 1: mice injected with PBS through the tail-vein slowly (negative control group); Group 2: mice injected with the control plasmid (5 mg/kg) through the tail-vein slowly; Group 3: mice injected with the anti-miR-214 plasmid (5 mg/kg) through the tail-vein slowly; Group 4: mice injected with the anti-miR-214 plasmid (0.5 mg/kg) through the tail-vein slowly; and Group 5: mice injected with the anti-miR-214 plasmid (0.05 mg/kg) through the tail-vein slowly. In addition, another group of normal mice was taken and used as a normal control (Normal). During model construction, the spirit, dietary status, defecation, body weight, activity and other conditions of C57BL/6 mice were observed periodically. Starting from day 14, the mice were administered at 0.1 ml/10 g body weight by intravenous tail injection, and the control group was administered with the corresponding amount of normal saline. During administration, the mice were administered with same once every 3 days, 7 times in total. On day 3 after the last administration, the mice were anaesthetized with diethyl ether, followed by taking the blood, lung and liver. The lung and liver were placed in 10% formalin, pathological sections were made, and the lung cancer model construction situation and the treatment situation of the anti-miR-214 on the lung cancer were observed.

Figure 14:
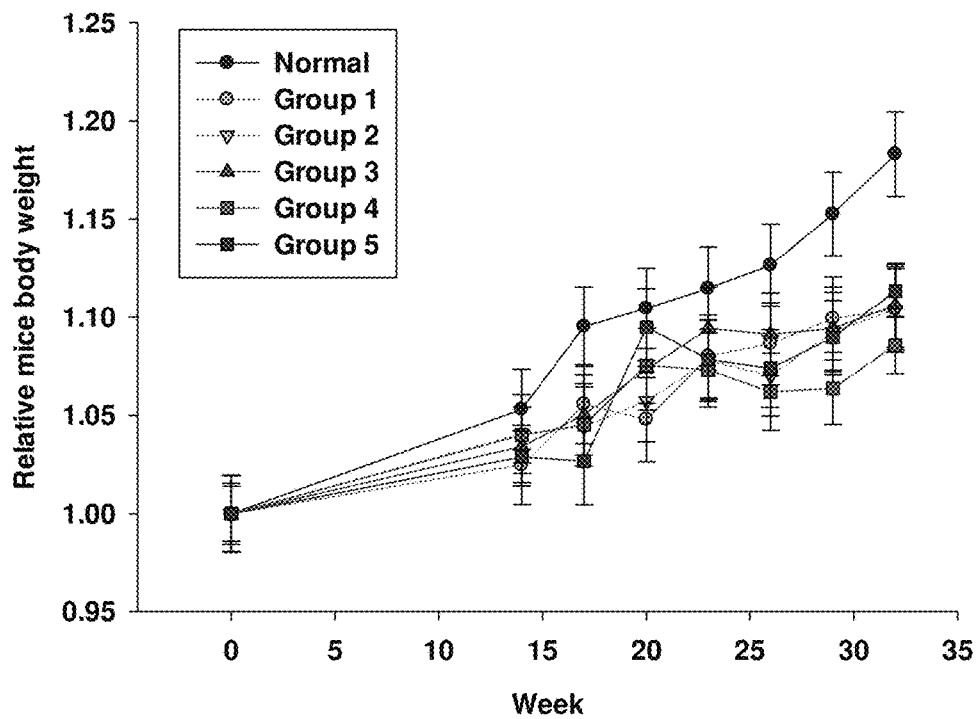
FIG. 14 shows the effect of the anti-miR-214 plasmid on the weight of tumour-bearing mice.

2. Results 2.1 Observation of General Situations of Animals During Model Construction and Administration The results are shown in FIG. 14 below. FIG. 14 shows the effect of the anti-miR-214 plasmid on the body weight of tumour-bearing mice. It can be seen from the results that during administration, the body weight of all animals increased in varying degrees.

Figure 15:
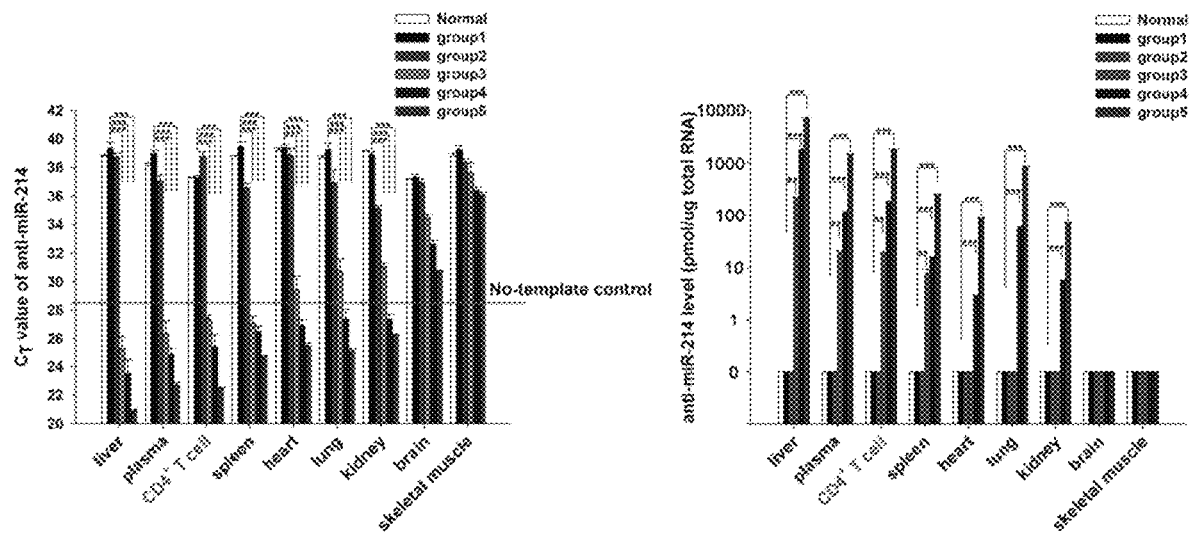
FIG. 15 shows the $C_T$ value and expression level of the anti-miR-214. The first graph shows the $C_T$ value of the anti-miR-214; and the second graph shows the expression level of the anti-miR-214.

2.2 the Therapeutic Effect of the Anti-miR-214 Plasmid on the Mouse Lewis Lung Cancer 2 weeks after the C57BL/6 mice were used for Lewis lung cancer model construction, the anti-miR-214 plasmid was administered by intravenous injection for treatment; during administration, the mice were administered with same once every 3 days; and, the animals were sacrificed on day 3 after the final administration, for taking the blood, lung, liver and various tissues and organs. The anti-miR-214 content in various tissues and organs was detected by qRT-PCR. The specific results are shown in FIG. 15. FIG. 15 shows the $C_T$ value and expression level of the anti-miR-214. The first graph shows the $C_T$ value of the anti-miR-214; and the second graph shows the expression level of the anti-miR-214. As can be seen from the determination results, in addition to the brain and skeletal muscle, the anti-miR-214 entered into other tissues and organs, such as the liver and lung, in particular, it can be transported into CD4$^+$ T cells.

The expression level of miRNA in various tissues and organs was then detected. The specific results are shown in FIG. 16. FIG. 16 shows the expression level of the miR-214. The experimental results suggested that the anti-miR-214 significantly reduced the miR-214 level in the liver, lung and other tissues and organs, especially it significantly reduced the miR-214 level in CD4$^+$ T cells.

Figure 17:
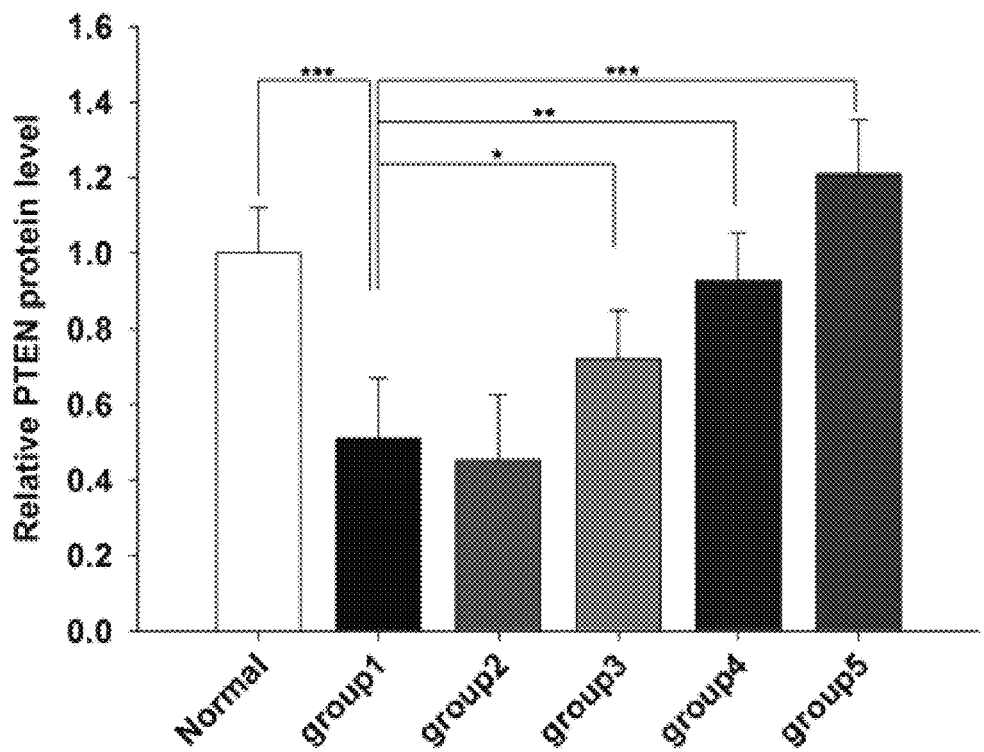
FIG. 17 shows the expression level of the PTEN protein in each group of CD4+ T cells. The images show the western blotting results of the PTEN protein in each group of CD4+ T cells; and the graph shows the expression level of the PTEN protein in each group of CD4+ T cells corresponding to the images.

CD4$^+$ T cells were isolated from mice using a CD4$^+$ T cell Isolation Kit (Miltenyi Biotec, Inc.), proteins were then extracted, and the expression level of the PTEN protein in each group of CD4$^+$ T cells was detected using a western blotting experiment. The specific results are shown in FIG. 17. FIG. 17 shows the expression level of the PTEN protein in each group of CD4$^+$ T cells. The images show the western blotting results of the PTEN protein in each group of CD4$^+$ T cells; and the graph shows the expression level of the PTEN protein in each group of CD4+ T cells corresponding to the images. It was found from the experimental results that the anti-miR-214 plasmid can significantly increase the PTEN protein in CD4+ T cells in a dose-dependent manner.

Figure 18:
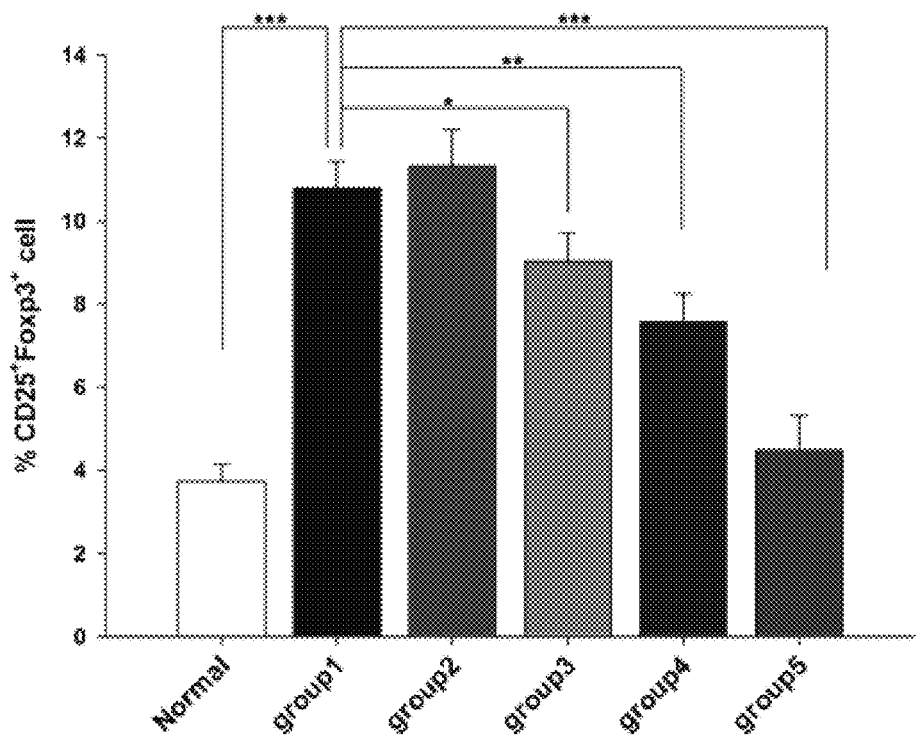
FIG. 18 shows the Treg content in the blood of each group of mice.

The Treg content in the blood of each group of mice was determined using a flow cytometer. The specific results are shown in FIG. 18. FIG. 18 shows the Treg content in the blood of each group of mice. It was found from the results that Treg was significantly increased in the mice of the untreated lung cancer groups (Group 1 and Group 2), whereas Treg was significantly decreased in the mice of the lung cancer groups (Group 3, Group 4 and Group 5) administered with the anti-miR-214 plasmid for treatment, wherein the Treg level in Group 5 even returned to the normal level.

Figure 19:
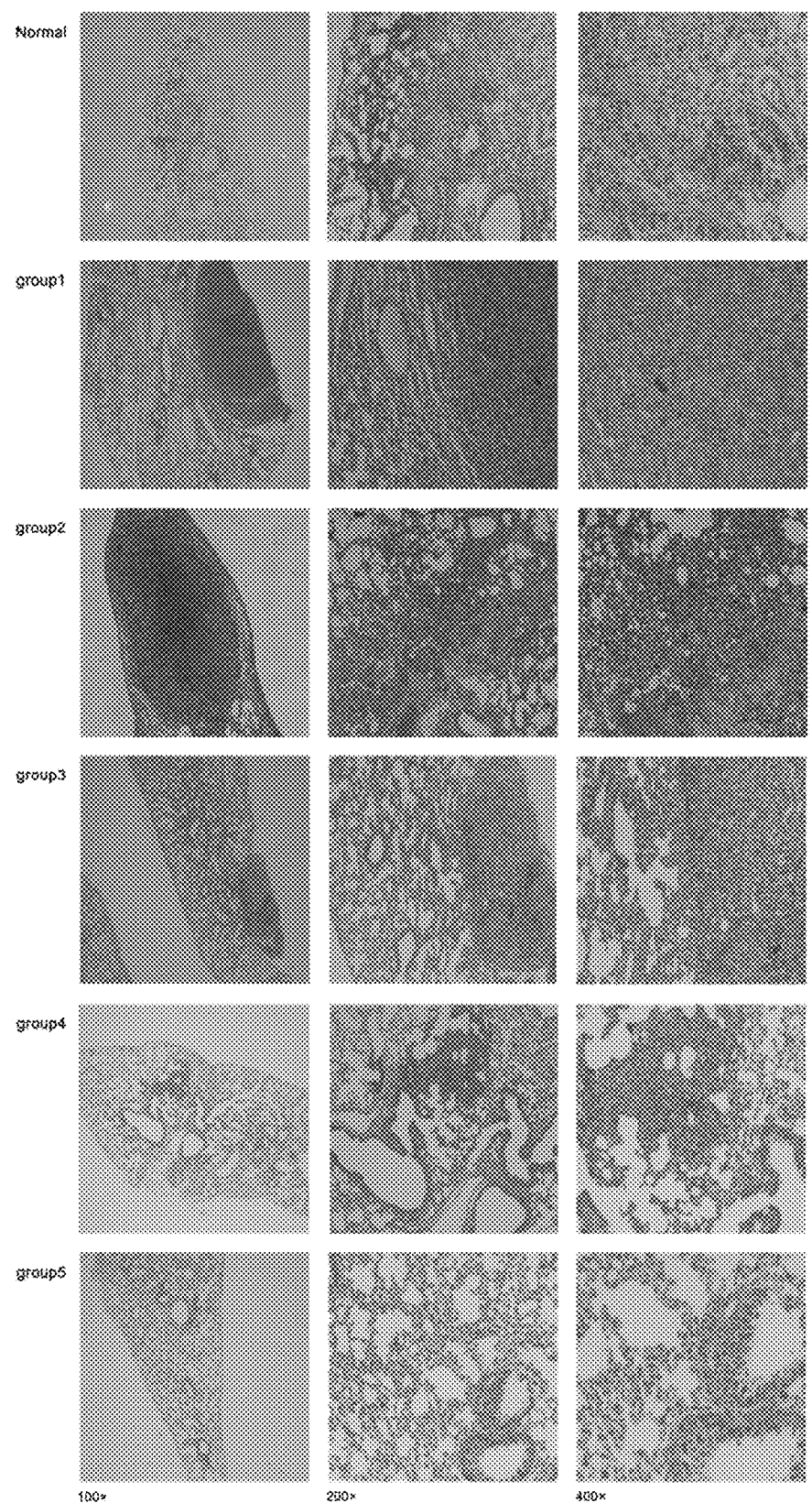
FIG. 19 shows tumour tissue section images showing the therapeutic effect of the anti-miR-214 on the mouse Lewis lung cancer, wherein A: ×40; B: ×100; and C: ×400.

In addition to those for the detection of molecular indicators, the rest of the lung and liver were fixed with formalin, and pathological tissue sections were made for examining the tumour situations of the organs. The specific results are shown in FIG. 19. FIG. 19 shows the results of pathological sections in each group of tumour tissues. The results showed that tumour lesions were not seen in all the liver sections in each group. In the lung, tumour cell foci with a flake-shaped nucleus being stained largely and deeply to different extents can be seen in each treatment group.

Figure 20:
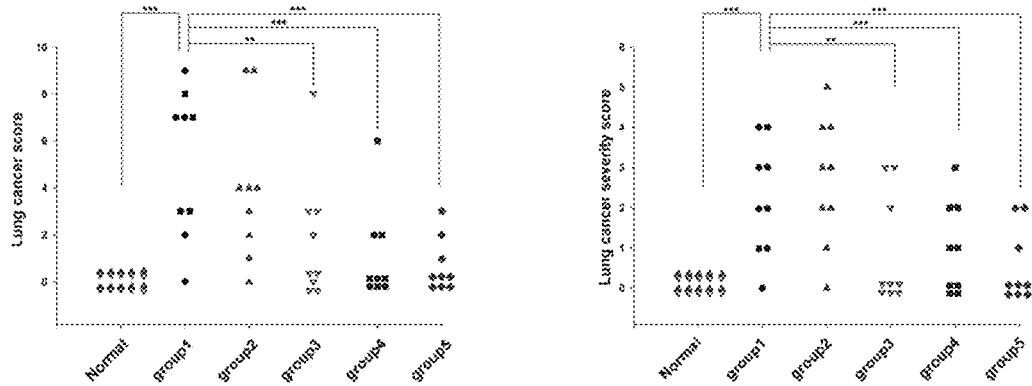
FIG. 20 shows the results of the therapeutic effect of the Lewis lung cancer in each administration group. The first graph shows the lung cancer score; and the second graph shows the lung cancer sensitivity score.

In each administration group, a high dose (i.e., Group 5) had a good therapeutic effect on the in vivo Lewis lung cancer, wherein the score and severity thereof were less than those of the control group and the number of mouse individuals where tumour lesions were not seen under a light microscope was also more than that of the control group; and the medium dose group (i.e., Group 4) and the low dose group (i.e., Group 3) also had a certain therapeutic effect on the in situ Lewis lung cancer. The results are shown in FIG. 20 below. FIG. 20 shows the results of the therapeutic effect of the Lewis lung cancer in each administration group. The first graph shows the lung cancer score; and the second graph shows the lung cancer severity score. The lung cancer score refers to the comprehensive score of lung cancer, including tumour size, distribution, etc.; and the lung cancer severity score refers specifically to the degree of lung cancer in the lung, that is, a score reflecting the effect of lung cancer on the degree of lung respiratory function in mice.

Example 8. Clinical Trials

Volunteers with end-stage breast cancer metastasis were injected with the anti-miR-214 plasmid, with an infusion twice per week of 1 mg each time. Each indicator was detected in the volunteers after medication for one month.

(1) Detection of Anti-miR-214

Figure 21:
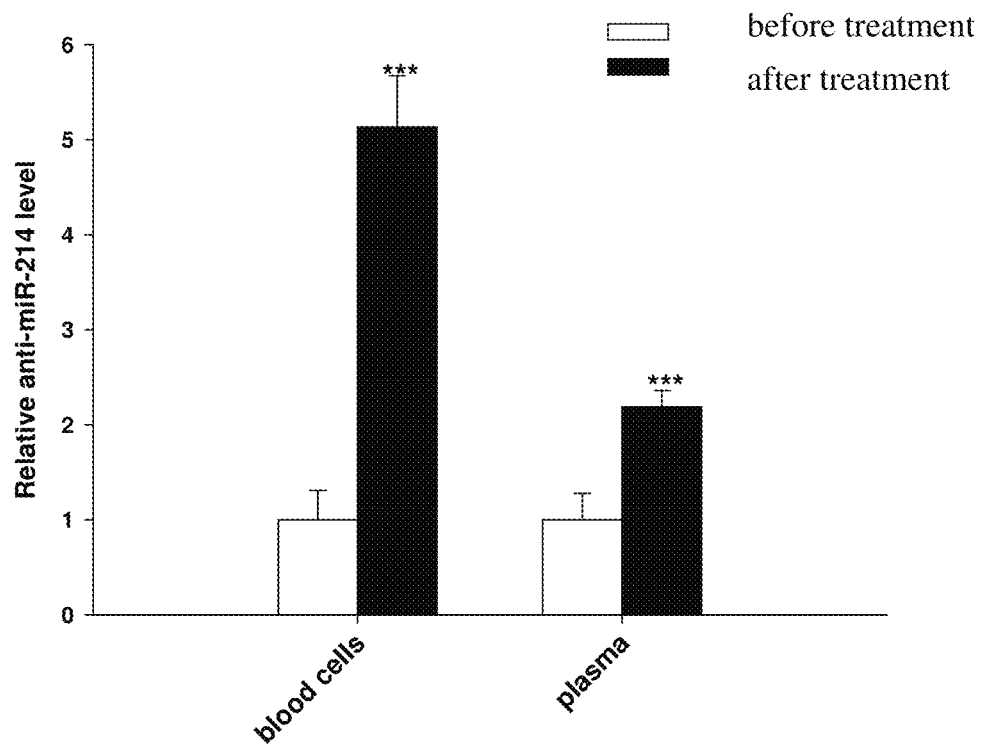
FIG. 21 shows the anti-miR-214 contents in blood cells and plasma before and after volunteers with end-stage tumours are injected with the plasmid.

The detailed results are shown in FIG. 21. It can be seen from FIG. 21 that after the volunteers with end-stage tumors were injected with the plasmid (after treatment), high contents of anti-miR-214 can be detected in both the blood cells and the plasma in the volunteers with end-stage tumors, which sufficiently suggested that the intravenous injection of the anti-miR-214 plasmid can actually result in high expression of anti-miR-214 in vivo.

(2) Results of miR-214 in the Serum

Figure 22:
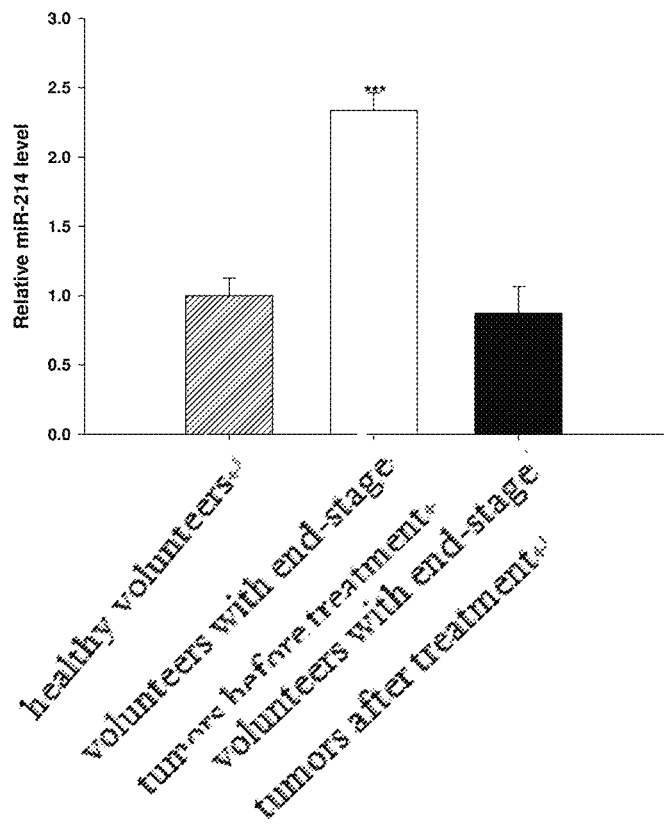
FIG. 22 shows the expression level of the miR-214 in the serum.

FIG. 22 shows the expression level of miR-214 in the serum. It can be seen from FIG. 22 that after injecting with the plasmid, the miR-214 in the sera of the volunteer patients was significantly decreased compared with that before the treatment, and almost decreased to a comparable level as that in a normal human, which suggests that the anti-miR-214 plasmid injected was not only expressed in vivo, but also functioned to adsorb the miR-214 in vivo so as to significantly decrease its expression level.

(3) Changing Situations of Tumors

After injecting with the anti-miR-214 plasmid, the conditions of the volunteers with end-stage breast cancer metastasis were improved to some extent, but the tumor size and volume were not changed, and tumor metastasis did not occur; it can be seen therefrom that the miR-214 inhibitor had an inhibitory effect on tumor growth, and the miR-214 inhibitor can be used in tumor treatment.

Example 9 Precursor miRNAs Adapted for Other Over-Expression Vectors

Figure 23:
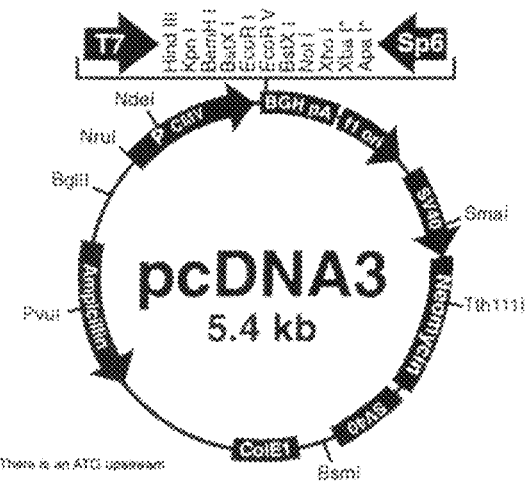
FIG. 23 shows the profile structure of the pcDNA3 plasmid.

The expression module constructed by inserting the precursor miRNA structure into the expression vector pcDNA3 likewise effectively avoids the problem that -3p and -5p are produced when some endogenous miRNAs are expressed. The profile structure of pcDNA3 was as shown in FIG. 23.

1. Anti-miR-214-5p Sequence
>anti-miR-214-5p (SEQ ID NO.: 2)
5'-ACUGCCUGUCUGUGCCUGCCUGU-3'

2. Anti-miR-214 Vector 2.1. Design and Synthesis of Oligo DNAs

According to anti-miR-214, 2 pairs of complementary oligo DNAs, i.e. the structures of the precursor miRNAs, were designed and synthesised as described in point 2.1 of Example 1.

2.2 the Construction and Validation of the miRNA Vector

The particular operating procedures are as described in point 2.2 of Example 1. The method for validating the efficiency of the over-expression of anti-miR-214 was the same as that in Example 2. Table 6 shows the assay for the expression levels of anti-miRNA and miRNA using Real-time PCR.

TABLE 6

The expression levels of anti-miR-214-5p, anti-miR-214-3p, and miR-214

| (Ct) | anti-miR-214-5p |
|---|---|
| Blank plasmid | 38.25 ± 0.2564 |
| anti-miR-214 plasmid | 25.43 ± 0.5123 |
| (Ct) | anti-miR-214-3p |
| Blank plasmid | 31.25 ± 0.4585 |
| anti-miR-214 plasmid | 32.89 ± 0.6245 |
| (Ct) | miR-214 |
| Blank plasmid | 21.03 ± 0.5874 |
| anti-miR-214 plasmid | 24.08 ± 0.1254 |

Conclusion: after the A549 cells were transfected with other over-expression vector plasmids constructed using the precursor miRNAs, a sharp increase in the anti-miR-214-5p can be detected (p<0.01), the anti-miR-214-3p cannot be detected, and a rise in miR-214 could not be caused, and on the contrary, a decrease in miR-214 was caused (p<0.05). Inserting the precursor miRNA structure into other expression vectors likewise effectively avoids the problem that -3p and -5p are produced when some endogenous miRNAs are expressed.

Comparative Example 1

The precursor miRNAs which are different from those in the present invention were constructed using anti-miR-214, and the constructed precursor miRNAs were inserted into the vector pcDNA™ 6.2 identical to that in the present invention. A549 cells were transfected with the anti-miR-214 plasmids, the total RNAs were collected, and then the levels of anti-miR-214-5p, anti-miR-214-3p and miR-214 were detected by q-PCR using primers for anti-miR-214-5p, anti-miR-214-3p and miR-214 respectively, customised from ABI Corporation.

1. Anti-miR-214-5p Sequence
>anti-miR-214-5p (SEQ ID NO.: 2)
5'-ACUGCCUGUCUGUGCCUGCCUGU-3'

2. Anti-miR-214 Vector
2.1. Design and Synthesis of Oligo DNAs

According to the gene sequences, 2 pairs of complementary oligo DNAs were designed and synthesised, and for the sequences, reference can be made to Table 7.

The oligo structures designed and synthesised are as follows:

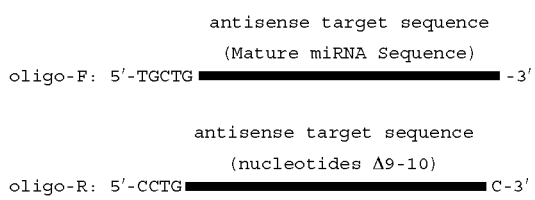

TABLE 7

The oligo DNA sequences and their corresponding precursor miRNA elements

| Oligo name | Oligo DNA sequence 5'-3' |
|---|---|
| | Mature sequence of >anti-miR-214-5p: 5'-ACUGCCUGUCUGUGCCUGCCUGU-3' (SEQ ID NO.: 2) |
| 13MR0041-1F | TGCTGGTTTTGGCCACTGACTGAC (SEQ ID NO.: 8) |
| 13MR0041-1R | CCTGGTCAGTCAGTGGCCAAAACC (SEQ ID NO.: 9) |
| | Negative control sequence |
| Negative-F | (SEQ ID NO.: 6, tgctgAAATGTACTGCGCGTGGAGACGTTTTGGCCACTGACTGACGTCTCCACGCAGTACATTT) |
| Negative-R | (SEQ ID NO.: 7, cctgAAATGTACTGCGTGGAGACGTCAGTCAGTGGCCAAAACGTCTCCACGCGCAGTACATTTc) |

2.2 the Construction and Validation of the miRNA Vector

The particular operating procedures are as described in point 2.2 of Example 1. The results can be seen in Table 8.

TABLE 8

The expression levels of anti-miR-214-5p, anti-miR-214-3p, and miR-214

| (Ct) | anti-miR-214-5p |
|---|---|
| Blank plasmid | 35.92 ± 0.1545 |
| anti-miR-214 plasmid | 26.45 ± 0.1535 |
| (Ct) | anti-miR-214-3p |
| Blank plasmid | 32.12 ± 0.1657 |
| anti-miR-214 plasmid | 25.48 ± 0.1456 |
| (Ct) | miR-214 |
| Blank plasmid | 21.26 ± 0.5652 |
| anti-miR-214 plasmid | 21.43 ± 0.4586 |

It can be seen from Table 8 that after A549 cells were transfected with precursor miRNA plasmids which are different from those in the present invention, a sharp increase in anti-miR-214-5p can be detected ($p<0.05$); however, the expression level of anti-miR-214-3p was also very high ($p<0.05$), and the level of miR-214 was not significantly changed. This is because the precursor miRNA plasmid which is different to that in the present invention can not only express anti-miR-214-5p, but can also express anti-miR-214-3p, and due to competitive binding, the mass anti-miR-214-5p was adsorbed by anti-miR-214-3p, so that the expression level of miR-214 cannot be decreased.

Example 10

Examples 1 and 2 were repeated, except for that the structure of A2 was changed from CAGG to CAGGA.

The results indicated that the change in the structure of A2 from CAGG to CAGGA resulted in a further increase of the ratio of F5 to F3 by about 50%. This suggested that the use of CAGGA were more helpful for improving the ratio of F5 to F3.

Figure 24:
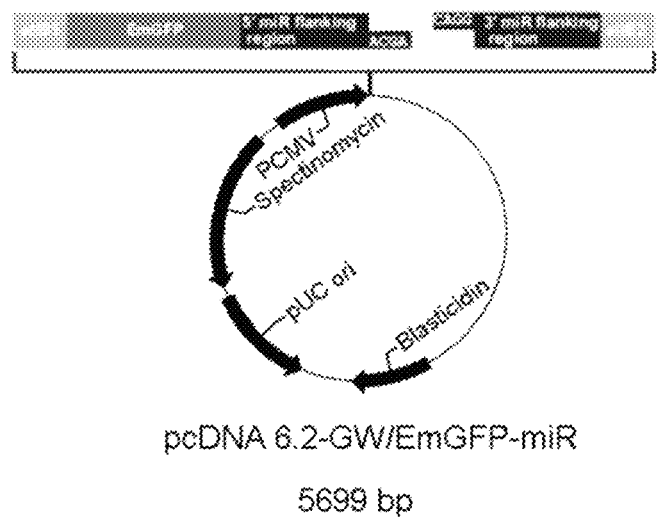
FIG. 24 is a schematic of the plasmid before modification.

Example 11: KRAS siRNAs were Effectively Expressed by Preezusnc Sequence and had a Therapeutic Effect on Cancer 1. Construction of Expression Vector According to the biosafety reasons, the plasmid was first modified. Biologically toxic elements, such as EmGFP and Blasticidin, were cut with DNA restriction endonucleases. FIG. 24 shows the plasmid before modification, which is the same as the post-modified plasmid in Example 1 after cutting EmGFP and Blasticidin.

pCMV represents an eukaryotic promoter, pUC ori represents the replication origin of the plasmid in prokaryotic cells which does not express an insertion sequence, and Spectinomycin represents the spectinomycin resistance gene for plasmid screening.

The construction process of the expression vector was the same as that in Example 1, except that the complementary oligo DNA was designed and synthesized according to the K-RAS gene sequence. The K-RAS siRNA sequence was as follows: 5'-GGTGACTTAGGTTCTAGAT-3', and the sequences are shown in Table 9.

TABLE 9

The oligo DNA sequences and their corresponding precursor siRNA elements

| Oligo name | Oligo DNA sequence 5'-3' |
|---|---|
| | > Mature K-RAS siRNA sequence: 5'-GGUGACUUAGGUUCUAGAU-3' |
| 13MR0041-1F | TGCTGAATTC<u>GGTGACTTAGGTTCTAGAT</u>GTTTTGGCCACTGACTGAC<u>ATCTAG</u><br><u>AATAAGTCACCA</u><br>      \| A1    \|    B1    \|  C    \|      B2<br>\| TGCTGAATTCGGUGACUUAGGUUCUAGAUGTTTTGGCCACTGACTGACATC<br>TAGAATAAGTCACCA) |
| 13MR0041- | CCTGACCGGTGGTGACTTATTCTAGATGTCAGTCAGTGGCCAAAACATCTAGA<br>ACCTAAGTCACC<br>      \| A2    \|    B2    \|  C    \|      B1<br>\| CCTGACCGGTGGTGACTTATTCTAGATGTCAGTCAGTGGCCAAAACATCTAG<br>AACCTAAGTCACC) |
| | Negative control sequence |
| Negative-F |         tgctgAAATGTACTGCGCGTGGAGACGTTTTGGCCACTGACTGACGTCTCCACGCAGTACATTT<br>        \|A1 \|multiple cloning site\|    C    \| multiple cloning site \|<br>        tgctgAAATGTACTGCGCGTGGAGACGTTTTGGCCACTGACTGACGTCTCCACGC<br>        AGTACATTT) |
| Negative-R |         cctgAAATGTACTGCGTGGAGACGTCAGTCAGTGGCCAAAACGTCTCCACGCGCAGTACATTTc<br>        \|A2\| multiple cloning site \|    C    \|multiple cloning site\|<br>        cctgAAATGTACTGCGTGGAGACGTCAGTCAGTGGCCAAAACGTCTCCACGCGC<br>        AGTACATTTc) |

2. The Therapeutic Effect of K-RAS siRNA on the Mouse Lewis Lung Cancer

For the specific experimental materials and methods, please refer to Example 2, except that the test compound was K-RAS siRNA plasmid provided by the College of Life Sciences, Nanjing University.

Figure 25:
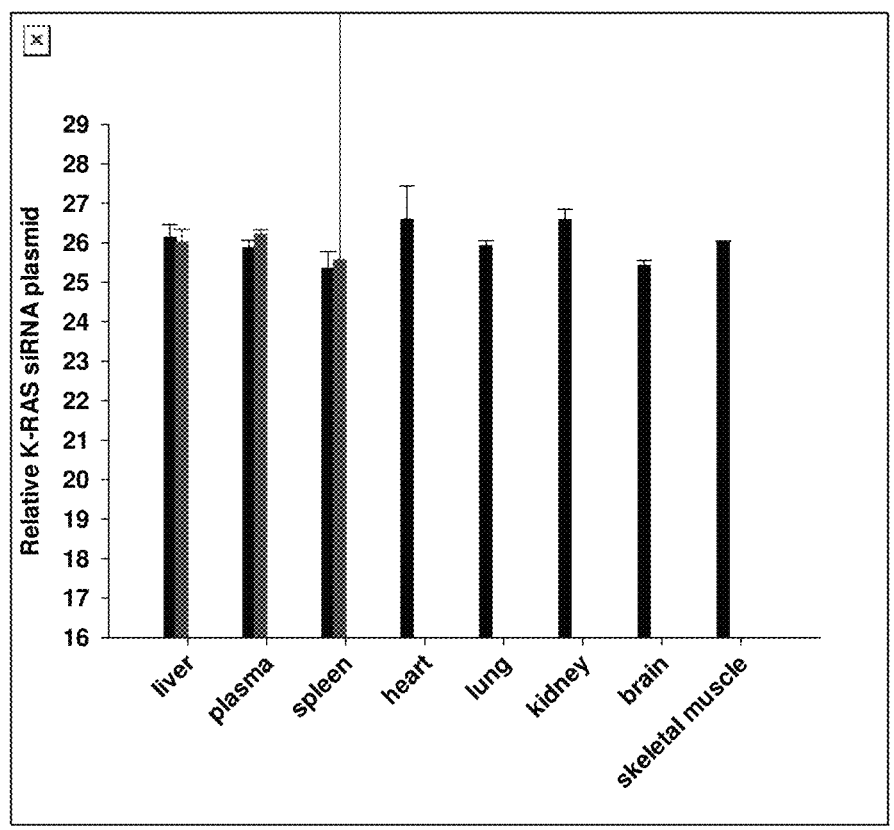
FIG. 25 is a schematic showing the $C_T$ value of the K-RAS siRNA content in various tissues and organs.

Two weeks after the C57BL/6 mice were used for Lewis lung cancer model construction, the K-RAS siRNA plasmid was administered by intravenous injection for treatment; during administration, the mice were administered with same once every 3 days; and, the animals were sacrificed on day 3 after the final administration, for taking the blood, lung, liver and various tissues and organs. The K-RAS siRNA content in various tissues and organs was detected by qRT-PCR. FIG. 25 shows the $C_T$ value of the K-RAS siRNA content in various tissues and organs. In FIG. 25, each set of histograms from left to right were Normal, PBS, the control plasmid and the EGFR siRNA plasmid. As can be seen from the determination results, in addition to the brain and skeletal muscle, the K-RAS siRNA entered into other tissues and organs, such as the liver and lung.

Figure 26:
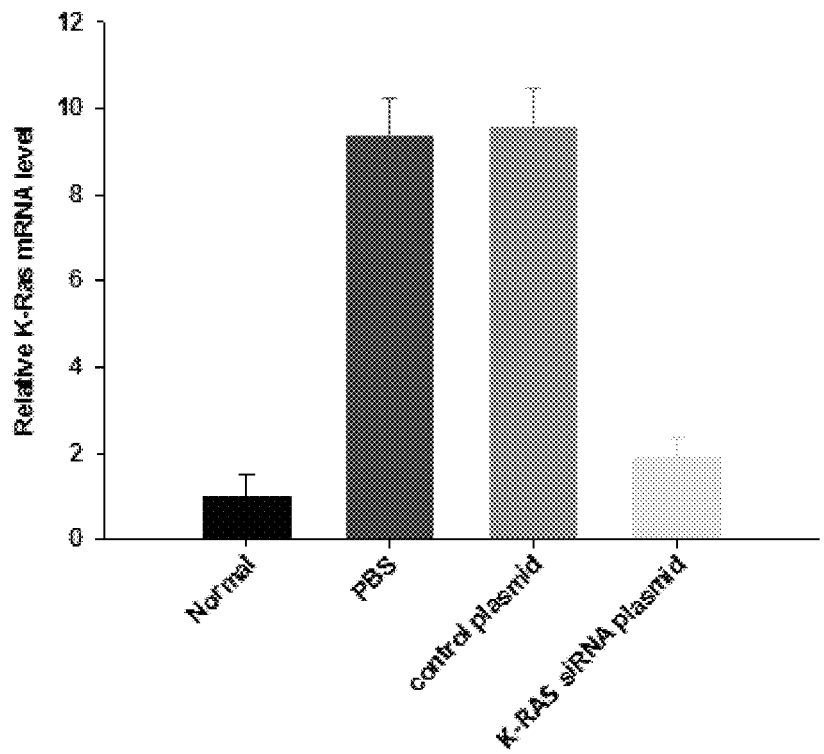
FIG. 26 is a schematic showing the expression level of the K-RAS mRNA in the lung.

FIG. 26 shows the expression level of the K-RAS mRNA in the lung, and the results showed that the K-RAS siRNA significantly reduced the K-RAS mRNA level in the lung tissues and organs.

Figure 27:
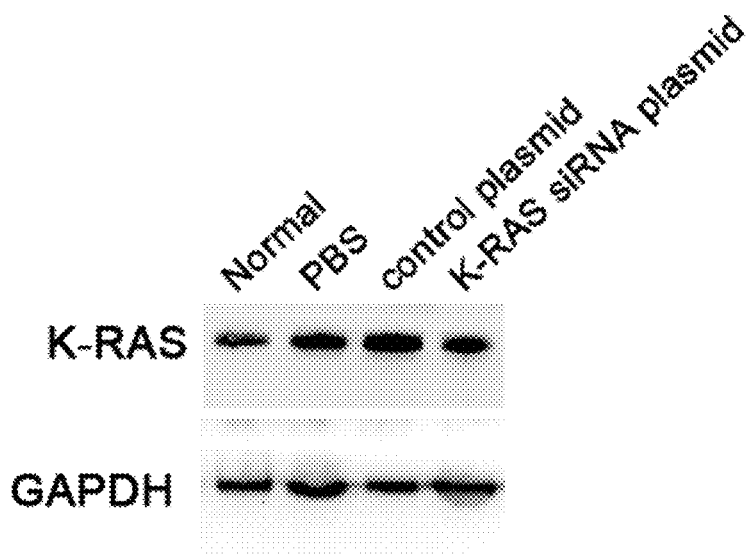
FIG. 27 is an electrophoretogram showing the expression level of the K-RAS protein in the lung.
Figure 28:
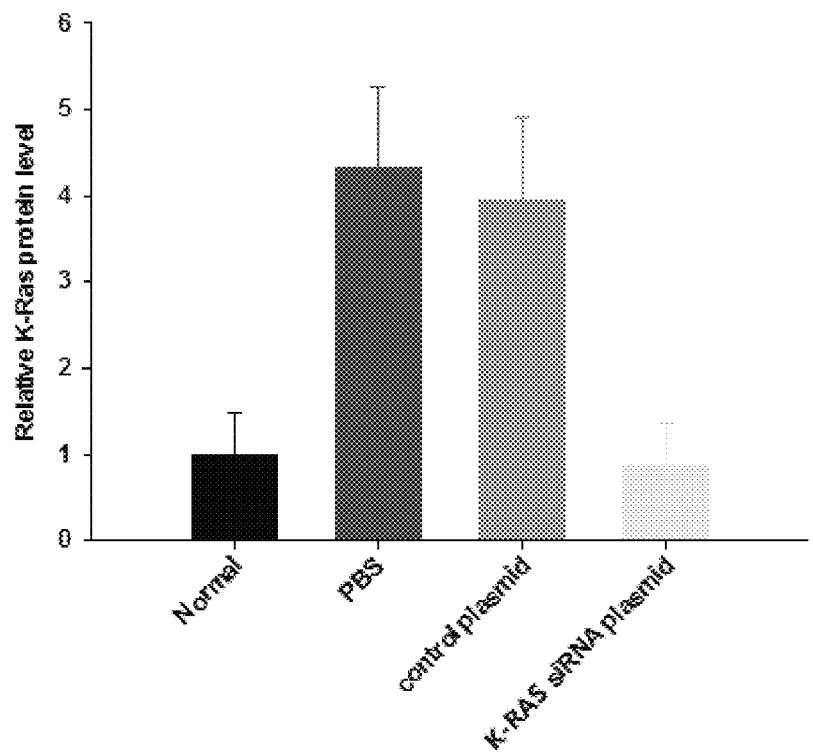
FIG. 28 is a schematic showing the expression level of the K-RAS protein in the lung.

FIG. 27 and FIG. 28 show the expression level of the K-RAS protein in the lung tissues detected using a western blotting experiment after the lung tissue proteins were extracted.

Figure 29:
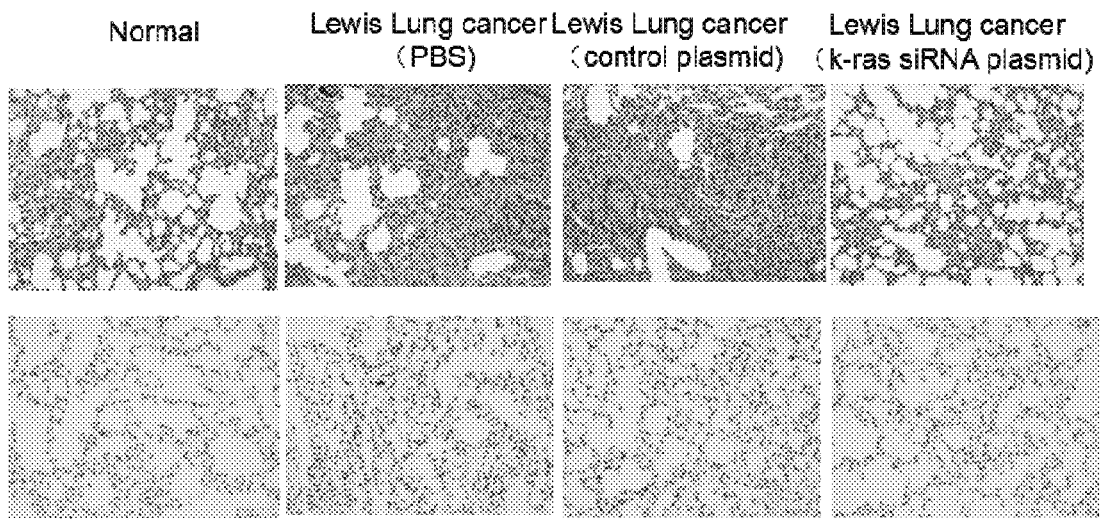
FIG. 29 is a schematic showing the results of pathological sections in the liver and lungs of mice.

In addition to those for the detection of molecular indicators, the rest of the lung and liver were fixed with formalin, and pathological tissue sections were made for examining the tumour situations of the organs. The results of the pathological sections are shown in FIG. 29, wherein tumour lesions were not seen in all the liver sections in each group. In the lung, tumour cell foci with a flake-shaped nucleus being stained largely and deeply to different extents can be seen in each treatment group.

The results above showed that the K-RAS siRNA plasmid can significantly reduce the expression level of the K-RAS protein in the lung tumour tissues.

3. The Therapeutic Effect of the K-RAS siRNA Plasmid on the Mouse Colon Cancer

Colon cancer cell line: mouse colon cancer cell line CT-26 (derived from BALB/c, H-2Kd) provided by the College of Life Sciences, Nanjing University.

Experimental animals for model construction: 6-7 week-old female BALB/c mice provided by the Model Animal Institute, Nanjing University.

Animal model establishment: BALB/c mice were the same species of animals as the CT-26 tumour cell line. The recovered CT-26 was subcultured. When the cells were grown to a certain amount, cells in logarithmic growth phase were taken and 0.9% normal saline was added to adjust the cell concentration to $5 \times 10^6$/ml, the tumour cells were inoculated on the right axilla of the mice subcutaneously at a dose of 0.2 ml/mouse ($1 \times 10^6$ cells/mouse), and the mice were fed with a normal diet after inoculation.

1 week later, tumour growth was seen in the axilla of all 15 tumour-bearing BALB/c mice, that is, the model construction was successful. 15 mice were selected and randomly classified into:

Group 1: mice injected with PBS on the left axilla subcutaneously (negative control group);

Group 2: mice injected with the control plasmid (5 mg/kg) on the left axilla subcutaneously; and Group 3: mice injected with the K-RAS siRNA plasmid (5 mg/kg) on the left axilla subcutaneously.

In addition, another group of normal mice was taken and used as a normal control (Normal).

During model construction, the existing condition, tumour size and appearance of the tumour-bearing BALB/c mice were observed periodically. Starting from day 8, the mice were administered with 0.1 ml/10 g body weight by intravenous tail injection, and the control group was administered with the corresponding amount of normal saline. During administration, the mice were administered with same once every 3 days, 7 times in total. On day 3 after the final administration, all the mice were sacrificed by spinal dislocation, the skin was incised quickly at the site of tumour growth, and the tumour was completely excised.

The therapeutic effect of the K-RAS siRNA plasmid on the mouse colon cancer was then verified.

The effect of the K-RAS siRNA plasmid on the volume of mouse colon cancer subcutaneous transplanted tumours The long diameter (a) and short diameter (b) of tumours were measured with a vernier caliper, and the tumour volume V (mm$^3$) was calculated as $\frac{1}{6}\pi ab^2$. After the measurement, the tumours were fixed in 10% formaldehyde.

The tumour inhibition rate was calculated: tumour inhibition rate (%)=(V in control group−V in experimental group)/V in control group×100%.

Compared with the tumour volume in Group 1 and Group 2, the volume in Group 3 was significantly smaller (P<0.05), as shown in Table 10 below.

TABLE 10

Tumour volumes and tumour inhibition rates in different groups of experimental mice

| Group n | Tumour average volume (V/mm$^3$) | Tumour inhibition rate (%) |
|---|---|---|
| Group 1 | 3768.15 ± 696.13 | 0 |
| Group 2 | 3659.73 ± 951.13 | 0 |
| Group 3 | 2392.75 ± 559.21 | 34.6%*, 36.5%# |

*Relative to Group 2,
relative to Group 1

The K-RAS siRNA content in the transplanted tumours was detected by qRT-PCR, and the results showed that the K-RAS siRNA entered into the transplanted tumours.

Figure 30:
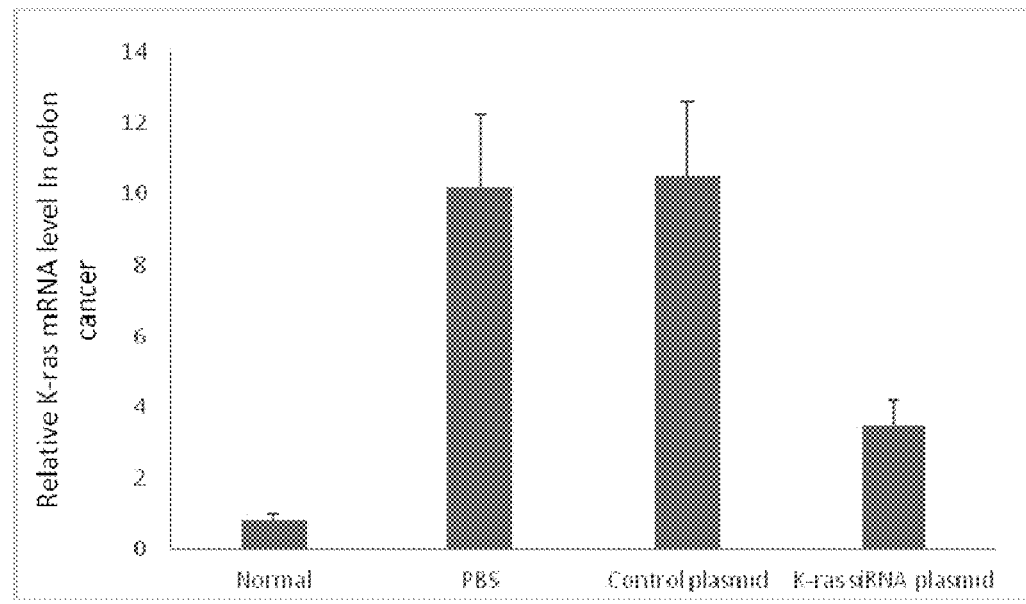
FIG. 30 is a schematic showing the expression level of the K-RAS mRNA in colon cancer transplanted tumours.

The expression level of the K-RAS mRNA in individual transplanted tumours was then detected, and the experimental results (FIG. 30) showed that the K-RAS siRNA plasmid significantly reduced the K-RAS mRNA level in the transplanted tumours.

Figure 31:
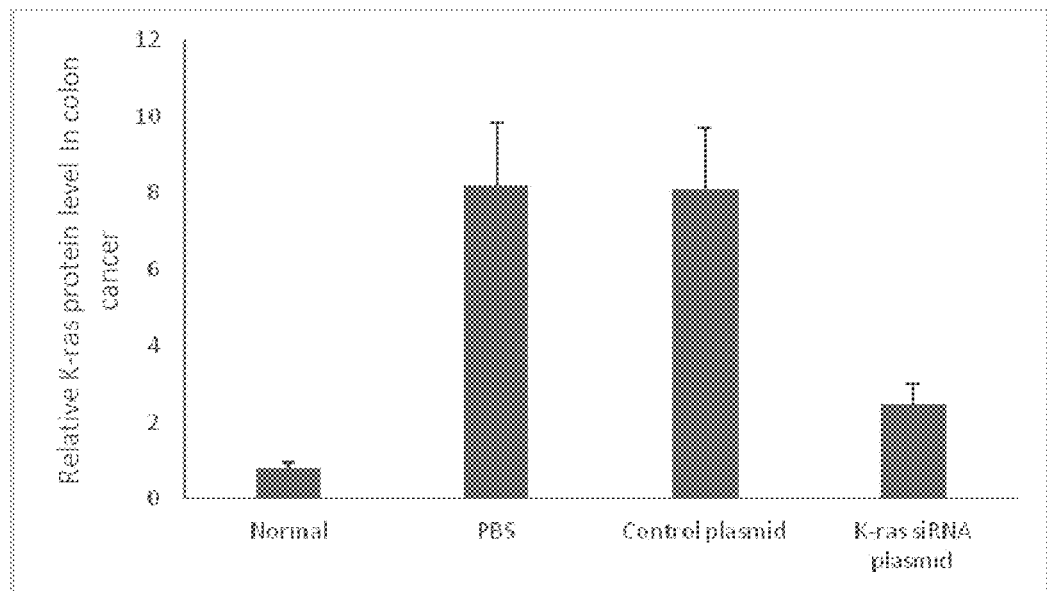
FIG. 31 is a schematic showing the expression level of the K-RAS protein in colon cancer transplanted tumours.

The tumour tissue proteins were extracted, and the expression level of the K-RAS protein in tumour tissues was detected using a western blotting experiment. It was found from the experimental results (see FIG. 31) that the K-RAS siRNA plasmid can significantly reduce the K-RAS protein in the transplanted tumour tissues.

The K-RAS siRNA plasmid had a therapeutic effect on the in vivo colon cancer, and the abnormal responses related with the medication were not seen during administration.

4. The Therapeutic Effect of the K-RAS siRNA Plasmid on the Mouse Pancreatic Cancer PATU8988, a human pancreatic cancer cell line, was provided by ATCC.

RPMI-1640 complete medium and fetal bovine serum were provided by GIBCO. In experiments, the human pancreatic cancer cell line was placed in 10% RPMI-1640 complete medium and cultured in an incubator at 37° C., 5% $CO_2$; the medium was changed once every 2 days; and on day 2-3, the cells were digested with 0.25% trypsin and subcultured at a ratio of 1:3.

The experimental animals were 15 half-male and half-female 6-week-old nude BALB/c (nu/nu) mice provided by Beijing Weitong Lihua Laboratory Animal Technology Co., Ltd.

When the human pancreatic cancer cells were filled with the bottom of the bottle, the single cell suspension was collected, and the mice were injected with 0.2 ml at 5×10$^6$ tumour cells/mouse into the pancreas in situ to establish a tumour model.

The pancreatic cancer mice were randomly classified into three groups:

Group 1: mice injected with PBS through the tail-vein slowly (negative control group);

Group 2: mice injected with the control plasmid (5 mg/kg) through the tail-vein slowly; and Group 3: mice injected with the K-RAS siRNA1 plasmid (5 mg/kg) through the tail-vein slowly.

In addition, another group of normal mice was taken and used as a normal control. During model construction, the spirit, dietary status, defecation, body weight, activity and other conditions of the nude BALB/c (nu/nu) mice were observed periodically. Starting from day 14, the mice were administered at 0.1 ml/10 g body weight by intravenous tail injection, and the control group was administered with the corresponding amount of normal saline. During administration, the mice were administered with same once every 3 days, 7 times in total. On day 3 after the last administration, the mice were anaesthetized with diethyl ether, followed by taking the blood, pancreas and liver. The pancreas and liver were placed in 10% formalin, pathological sections were made, and the pancreatic cancer model construction situation and the treatment situation of the K-RAS siRNA plasmid on the pancreatic cancer were observed.

Two weeks after the BALB/c (nu/nu) mice were used for human pancreatic cancer model construction, the K-RAS siRNA plasmid was administered by intravenous injection for treatment; during administration, the mice were administered with same once every 3 days; and, the animals were sacrificed on day 3 after the final administration, for taking the blood, pancreas and liver.

Figure 32:
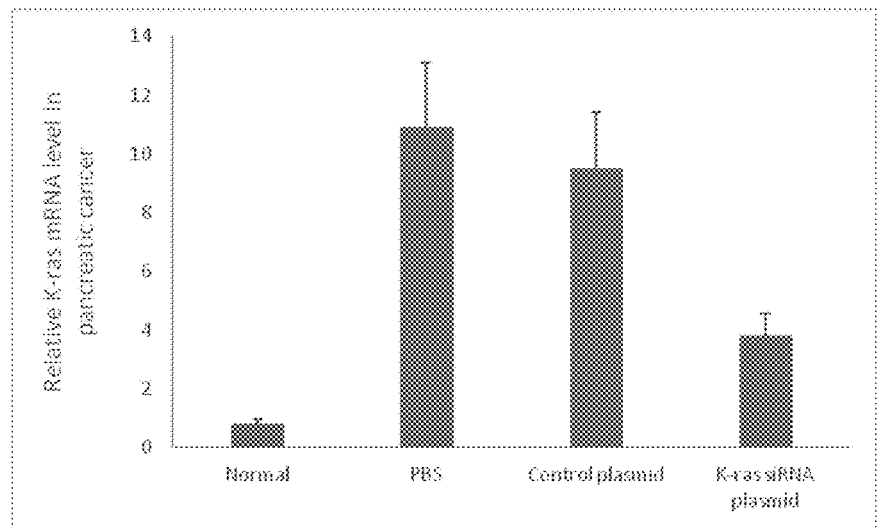
FIG. 32 is a schematic showing the expression level of the K-RAS mRNA in the pancreas.

The expression level of the K-RAS mRNA in the transplanted tumours was then detected, and the experimental results (FIG. 32) showed that the K-RAS siRNA plasmid significantly reduced the K-RAS mRNA level in the transplanted tumours.

Figure 33:
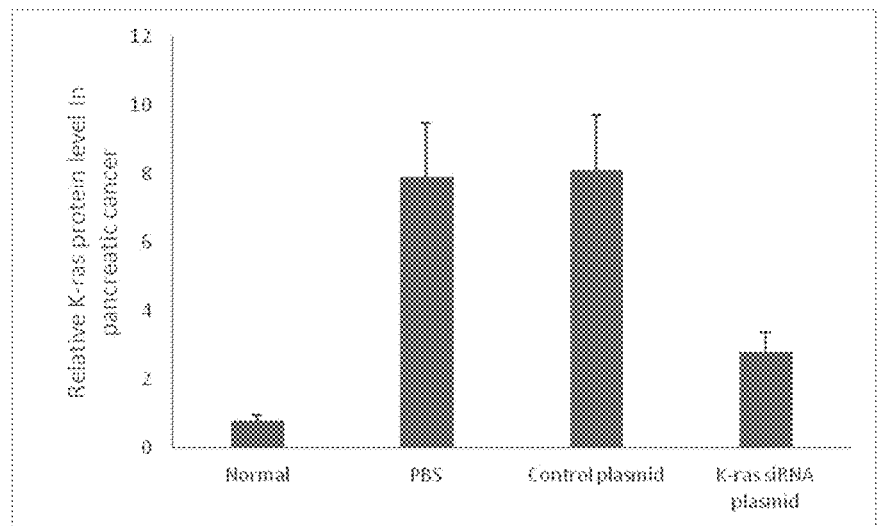
FIG. 33 is a schematic showing the expression level of the K-RAS protein in the pancreas.
Figure 34:
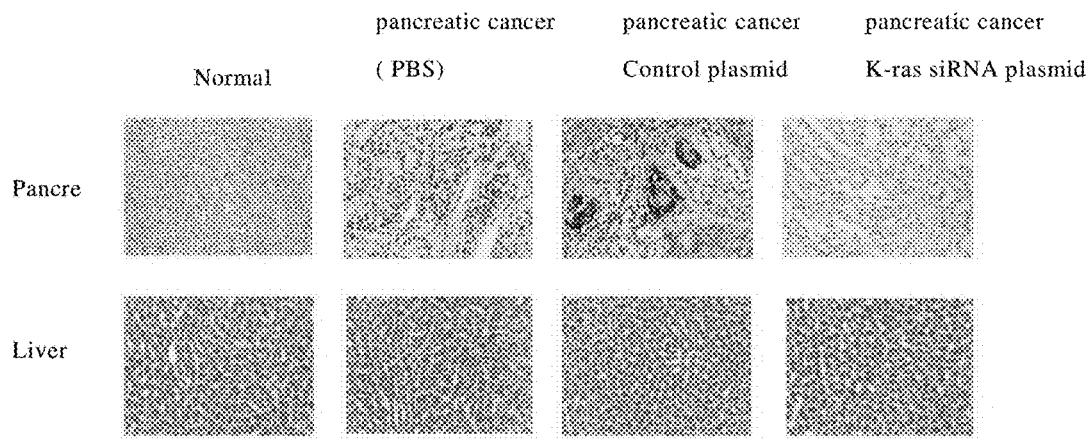
FIG. 34 is a schematic showing the results of pathological sections in the liver and pancreas of mice.

The tumour tissue proteins were extracted, and the expression level of the K-RAS protein in tumour tissues was detected using a western blotting experiment. It was found from the experimental results (see FIG. 33) that the K-RAS siRNA plasmid can significantly reduce the K-RAS protein in the transplanted tumour tissues. The results of the pathological sections are shown in FIG. 34, wherein tumour lesions were not seen in all the liver sections in each group. In the pancreas, tumour cell foci with a flake-shaped nucleus being stained largely and deeply to different extents can be seen in each treatment group.

5. Design and Verification of More K-RAS siRNA Sequences

Up to 260 possible siRNA sequences for multiple sites of the K-RAS gene were further designed in this example, see Table 11 for details. Ten siRNA sequences with excellent stability and evident specific inhibitory effects were further screened from the siRNA sequences above for the expression verification. The sequence numbers of the ten siRNAs in Table 11 were 3, 26, 41, 47, 52, 73, 88, 98, 101 and 106, respectively.

The expression levels of the K-RAS mRNA and proteins were verified using the expression vector construction method in Example 1 and the verification method in Example 2, respectively.

Figure 35:
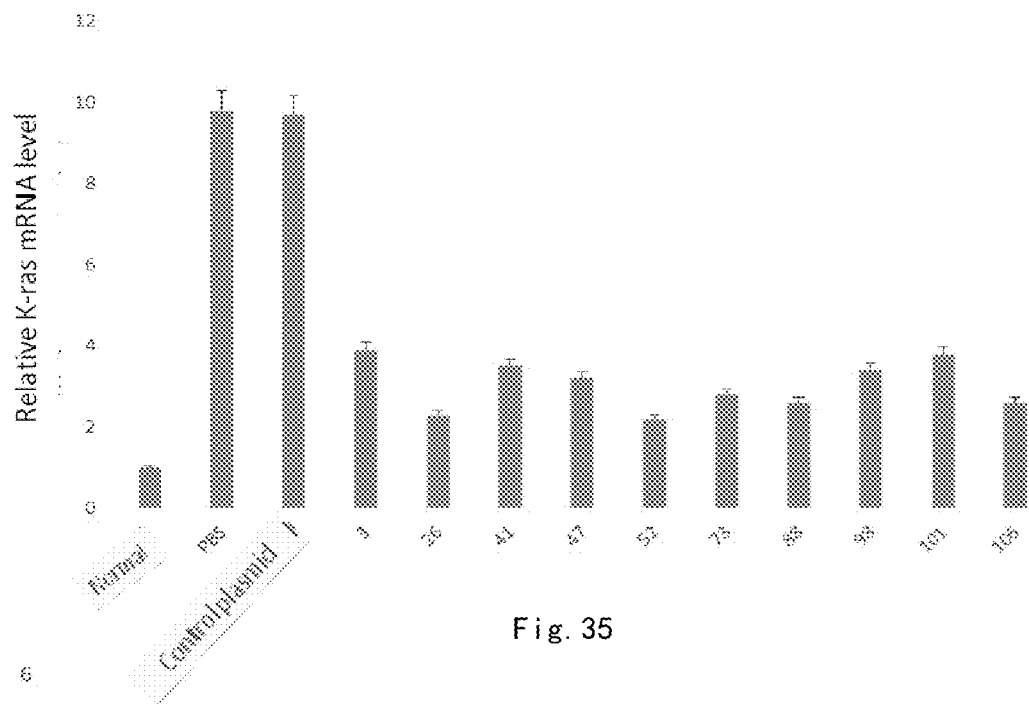
FIG. 35 is a schematic showing the expression level of the K-RAS mRNA in the lung after ten K-RAS siRNAs are introduced.

FIG. 35 shows the expression level of the K-RAS mRNA in the lung, and the results showed that all the plasmids constructed using the screened ten K-RAS siRNAs reduced the K-RAS mRNA level in the lung tissues and organs.

Figure 36:
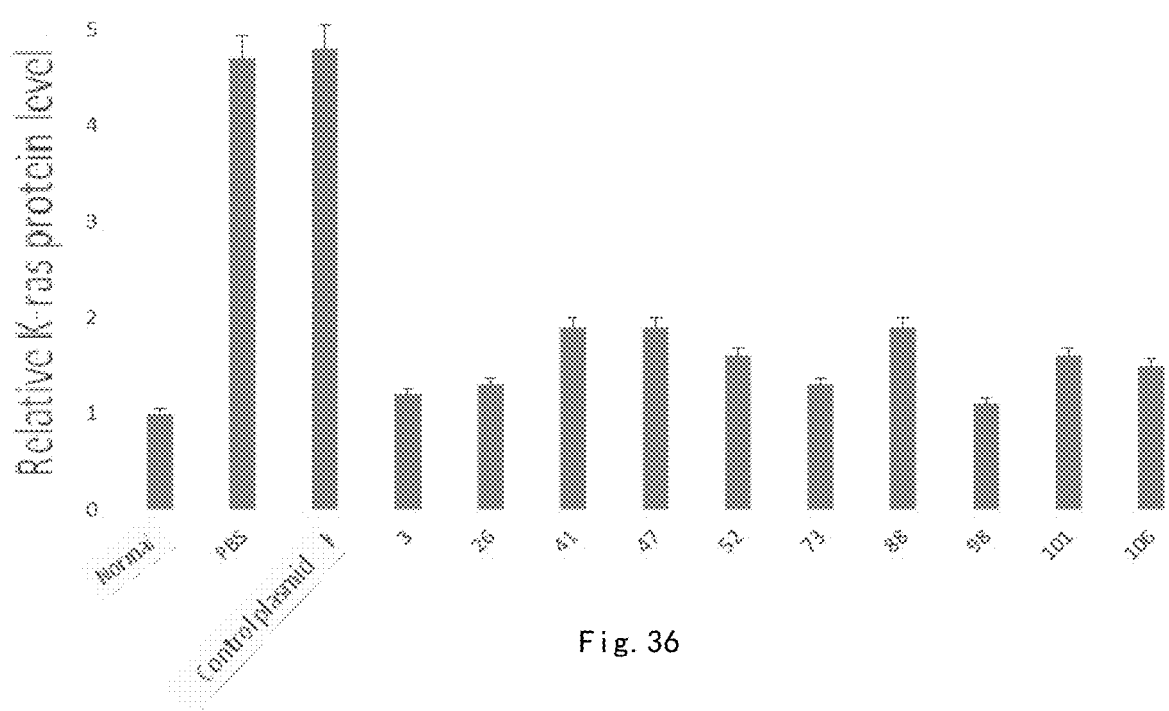
FIG. 36 is a schematic showing the expression level of the K-RAS protein in the lung after ten K-RAS siRNAs are introduced.

FIG. 36 shows the expression level of the K-RAS protein in the lung tissues detected using a western blotting experiment after the lung tissue proteins were extracted.

The results above showed that the plasmids constructed using the screened ten K-RAS siRNAs can significantly reduce the expression level of the K-RAS protein in the lung tumour tissues.

TABLE 11

| Sense strand sequences of K-RAS siRNAs | | |
|---|---|---|
| Seq. No. | siRNA sense strand | |
| 1 | 5' GGCCAGUUAUAGCUUAUUA | 3' |
| 2 | 5' GGUCCUAGUAGGAAAUAAA | 3' |
| 3 | 5' GCAGCAGCAACAUUAAUAA | 3' |
| 4 | 5' GGCAGACCCAGUAUGAAAU | 3' |
| 5 | 5' GGUGUGCCAAGACAUUAAU | 3' |
| 6 | 5' GGACUCUUCUUCCAUAUUA | 3' |
| 7 | 5' GGCAAUGGAAACUAUUAUA | 3' |
| 8 | 5' GCAGUUGAUUACUUCUUAU | 3' |
| 9 | 5' GGACUUAGCAAGAAGUUAU | 3' |
| 10 | 5' GCUCAGCACAAUCUGUAAA | 3' |
| 11 | 5' CUCCUUUCCACUGCUAUUA | 3' |
| 12 | 5' GCUGUGGAUAUUAUGUAAA | 3' |
| 13 | 5' CUCAGCACAAUCUGUAAAU | 3' |
| 14 | 5' GUUGGUGUGAAACAAAUUA | 3' |
| 15 | 5' GGGCAUGUUAAGUUACAGU | 3' |
| 16 | 5' GUGCCAAUUUCUUACUAGU | 3' |
| 17 | 5' CACACUGCAUAGGAAUUUA | 3' |
| 18 | 5' GCUCUUUCAUAGUAUAACU | 3' |
| 19 | 5' CCUGGUAACAGUAAUACAU | 3' |
| 20 | 5' GCUCAGGACUUAGCAAGAA | 3' |
| 21 | 5' GACUAUGAGUGUGUAUUUA | 3' |
| 22 | 5' GCCAUAGACACUAUAGUAU | 3' |
| 23 | 5' GGCACUGGGUAUAUGGUAU | 3' |
| 24 | 5' GACCCAGAGAUAACACGAU | 3' |
| 25 | 5' GAGGAGUACAGUGCAAUGA | 3' |
| 26 | 5' GGUAGCAGCAGCAACAUUA | 3' |
| 27 | 5' CUCUGUGCCAGCUCUAUAA | 3' |
| 28 | 5' GUGCUAGUGUGGUCUGUAA | 3' |
| 29 | 5' CUGUACUACUCCUAAUUAU | 3' |
| 30 | 5' CUAGUGUGGUCUGUAAUAU | 3' |
| 31 | 5' GCAGACGUAUAUUGUAUCA | 3' |
| 32 | 5' GGGCUAUAUUUACAUGCUA | 3' |

TABLE 11-continued

| Sense strand sequences of K-RAS siRNAs | | |
|---|---|---|
| Seq. No. | siRNA sense strand | |
| 33 | 5' GUGCUGUGAAGUGAUCUAA | 3' |
| 34 | 5' CCUGUCUCUUGGAUAUUCU | 3' |
| 35 | 5' GUGCUGUGGAUAUUAUGUA | 3' |
| 36 | 5' GGAGGGCUUUCUUUGUGUA | 3' |
| 37 | 5' CUAGGAAUGUUGGUCAUAU | 3' |
| 38 | 5' CGUGUUUGCUUAAACUUAA | 3' |
| 39 | 5' GCUGAUGCUUUGAACAUCU | 3' |
| 40 | 5' GGUCUGUAAUAUCUUACUA | 3' |
| 41 | 5' CCUUGACGAUACAGCUAAU | 3' |
| 42 | 5' GUGGAUAUCUCCAUGAAGU | 3' |
| 43 | 5' CACCAUUAUAGAGAACAAA | 3' |
| 44 | 5' GCUUCCUGAUGAUGAUUCU | 3' |
| 45 | 5' CAUCCCUGAUGAAUGUAAA | 3' |
| 46 | 5' GAAGCAAGUAGUAAUUGAU | 3' |
| 47 | 5' GGACGAAUAUGAUCCAACA | 3' |
| 48 | 5' GUUCCCAAGUAGGCAUUCU | 3' |
| 49 | 5' CCUGACCUCAAGUGAUUCA | 3' |
| 50 | 5' GAACUGUACUACUCCUAAU | 3' |
| 51 | 5' GUCCUUAGGUAGUGCUAGU | 3' |
| 52 | 5' GGCUAUUUCAAGGUCAGAA | 3' |
| 53 | 5' CCUGAUGAAUGUAAAGUUA | 3' |
| 54 | 5' GUGUCAGACUGCUCUUUCA | 3' |
| 55 | 5' CCGAAAUGGAUAUGGAAUA | 3' |
| 56 | 5' GACUGCUCUUUCAUAGUAU | 3' |
| 57 | 5' CAAGUCUGAUCCAUAUUUA | 3' |
| 58 | 5' GAUGAGCAAAGAUGGUAAA | 3' |
| 59 | 5' CAAGAGGUGAAGUUUAUAU | 3' |
| 60 | 5' GGUAGGGUGUUAAGACUUA | 3' |
| 61 | 5' CUAGGCAUCAUGUCCUAUA | 3' |
| 62 | 5' GAGUGAAUGUUCCCAAGUA | 3' |
| 63 | 5' CCUAGUAGGAAAUAAAUGU | 3' |
| 64 | 5' GGAAGCAAGUAGUAAUUGA | 3' |
| 65 | 5' GCUGUGGAUAUCUCCAUGA | 3' |
| 66 | 5' CCAGAAAUCUUCAUGCAAU | 3' |
| 67 | 5' GCCUGAACUAGUUCACAGA | 3' |
| 68 | 5' CAGACGUAUAUUGUAUCAU | 3' |
| 69 | 5' GUGUAUGUCAGAUAUUCAU | 3' |

TABLE 11-continued

Sense strand sequences of K-RAS siRNAs

| Seq. No. | siRNA sense strand |
|---|---|
| 70 | 5' GGCUAGUUCUCUUAACACU 3' |
| 71 | 5' GAAGGUGACUUAGGUUCUA 3' |
| 72 | 5' GAACCUUUGAGCUUUCAUA 3' |
| 73 | 5' GCCUUGACGAUACAGCUAA 3' |
| 74 | 5' GAGUGCCAAUUUCUUACUA 3' |
| 75 | 5' CAGACAAGGAAACUUCUAU 3' |
| 76 | 5' CUUCGAUCAAGCUACUUUA 3' |
| 77 | 5' GCUGACAAAUCAAGAGCAU 3' |
| 78 | 5' GUCAUCUCAAACUCUUAGU 3' |
| 79 | 5' GUUGUCACCAUUGCACAAU 3' |
| 80 | 5' GAUGAUGCCUUCUAUACAU 3' |
| 81 | 5' CUGGUAUGAAUAGACAGAA 3' |
| 82 | 5' CACUGAGUCACAUCAGAAA 3' |
| 83 | 5' GUCAAGCUCAGCACAAUCU 3' |
| 84 | 5' GGACUCUGAAGAUGUACCU 3' |
| 85 | 5' GGGAUUAUUAUAGCAACCA 3' |
| 86 | 5' CUAGGAAGAAGGUGACUUA 3' |
| 87 | 5' CUGUGGAUAUCUCCAUGAA 3' |
| 88 | 5' GUGGACGAAUAUGAUCCAA 3' |
| 89 | 5' CAUGAGUUCUUGAAGAAUA 3' |
| 90 | 5' CUGAGUAGCUGGGAUUACA 3' |
| 91 | 5' GUGAACCUUUGAGCUUUCA 3' |
| 92 | 5' GACAAGGAAACUUCUAUGU 3' |
| 93 | 5' CAGUAAUACAUUCCAUUGU 3' |
| 94 | 5' CCUGGUAUGAAUAGACAGA 3' |
| 95 | 5' GAAUAUAGCAGACGUAUAU 3' |
| 96 | 5' CGAUCAAGCUACUUUAUGU 3' |
| 97 | 5' GGACAUCACUUACUAUCCA 3' |
| 98 | 5' GAAGGUAAUUGAUACACAA 3' |
| 99 | 5' CAAGGAAACUUCUAUGUAA 3' |
| 100 | 5' GAACCCAGCAGUUACCUUA 3' |
| 101 | 5' CAGCAGGCUAUUUCAAGGU 3' |
| 102 | 5' CUGAAUACCUAAGAUUUCU 3' |
| 103 | 5' GAUCAAGCUACUUUAUGUA 3' |
| 104 | 5' GCUCUAUUUAACUGAGUCA 3' |
| 105 | 5' CUAGAACAGUAGACACAAA 3' |
| 106 | 5' GAUACAGCUAAUUCAGAAU 3' |
| 107 | 5' GCAGGCUAUUUCAAGGUCA 3' |
| 108 | 5' CCUUAGGUAAUCUAUAACU 3' |
| 109 | 5' CCUAACCAUAAGAUUUACU 3' |
| 110 | 5' CCUACAGGAAGCAAGUAGU 3' |
| 111 | 5' GUGUUGAUGAUGCCUUCUA 3' |
| 112 | 5' GCUAUGUGAAACUACAGAU 3' |
| 113 | 5' GAAGUAAUGACUCCAUACA 3' |
| 114 | 5' CAUCAGAAAUGCCCUACAU 3' |
| 115 | 5' CUGCUGUGGAUAUCUCCAU 3' |
| 116 | 5' CUCGUUUCUACACAGAGAA 3' |
| 117 | 5' CACAUGAGUUCUUGAAGAA 3' |
| 118 | 5' GGUUUGGCUAGUUCUCUUA 3' |
| 119 | 5' GCUAUAUUUACAUGCUACU 3' |
| 120 | 5' CGAAUAUGAUCCAACAAUA 3' |
| 121 | 5' CCUCGUUUCUACACAGAGA 3' |
| 122 | 5' CCUUUCCACUGCUAUUAGU 3' |
| 123 | 5' GACUUAGGCAUUAACAUGU 3' |
| 124 | 5' CUCAUUUGUAUUCCAUUGA 3' |
| 125 | 5' GAAACUGAAUACCUAAGAU 3' |
| 126 | 5' GUGAGGUGAAAGUAUCACU 3' |
| 127 | 5' CAAAGACAAAGUGUGUAAU 3' |
| 128 | 5' GAGUCACACUGCAUAGGAA 3' |
| 129 | 5' GAUGGAGAAACCUGUCUCU 3' |
| 130 | 5' GAAAUGCCCUACAUCUUAU 3' |
| 131 | 5' GGAUACACUUAUUUGUCAA 3' |
| 132 | 5' CAGCAACAUUAAUAAUGGA 3' |
| 133 | 5' GAAUGUUGGUGUGAAACAA 3' |
| 134 | 5' CUGUUUAGGUAGGGUGUUA 3' |
| 135 | 5' GAAUGUUGUCAUAUCAAA 3' |
| 136 | 5' GGAAGAAGGUGACUUAGGU 3' |
| 137 | 5' CACAGAGCUAACGGGUUA 3' |
| 138 | 5' GAGAGUUUCACAGCAUGGA 3' |
| 139 | 5' GAUAGCUCAACAAGAUACA 3' |
| 140 | 5' GCAUAGGAAUUUAGAACCU 3' |
| 141 | 5' CACUGAAACUCUUCGAUCA 3' |
| 142 | 5' CCAUUUACAUAAGGAUACA 3' |
| 143 | 5' CAGUGACUAUGAGUGUGUA 3' |
| 144 | 5' GACUAGGGCAGUUUGGAUA 3' |

TABLE 11-continued

Sense strand sequences of K-RAS siRNAs

| Seq. No. | siRNA sense strand |
|---|---|
| 145 | 5' CUUUGUGUAUUUGCCAUAA 3' |
| 146 | 5' GAGUUAAGGACUCUGAAGA 3' |
| 147 | 5' GUCUCUUGGAUAUUCUCGA 3' |
| 148 | 5' GGAAGAAUAUAGCAGACGU 3' |
| 149 | 5' GACCUAGGAAUGUUGGUCA 3' |
| 150 | 5' GACUACUCCUGGUAACAGU 3' |
| 151 | 5' GCAGUUACCUUAAAGCUGA 3' |
| 152 | 5' GUUCUCUUAACACUGGUUA 3' |
| 153 | 5' GUCAAAGACAAAGUGUGUA 3' |
| 154 | 5' GCAAGUAGUAAUUGAUGGA 3' |
| 155 | 5' CACUGCUAUUAGUCAUGGU 3' |
| 156 | 5' CCGAAAGUUUCCAAUUCCA 3' |
| 157 | 5' GUGUUGAAGAGACCAAGGU 3' |
| 158 | 5' CAUCCAGUGUUGUCAUGCA 3' |
| 159 | 5' GACAUCACUUACUAUCCAU 3' |
| 160 | 5' GAAGAAUAUAGCAGACGUA 3' |
| 161 | 5' CAGUUUGGAUAGCUCAACA 3' |
| 162 | 5' GGAUUAUUAUAGCAACCAU 3' |
| 163 | 5' CCAAUUUCUUACUAGUACU 3' |
| 164 | 5' CCUAAUUAUUACAGCCUUA 3' |
| 165 | 5' CUGUACACAUUAAGGUGUA 3' |
| 166 | 5' CUGAAACAUUGAGGGAACA 3' |
| 167 | 5' CUAGGCUCUAUUUAACUGA 3' |
| 168 | 5' CAGUUACCUUAAAGCUGAA 3' |
| 169 | 5' CAAUGAGGGACCAGUACAU 3' |
| 170 | 5' CUAUAGUAUACCAGUGAAU 3' |
| 171 | 5' CCUUCUAGAACAGUAGACA 3' |
| 172 | 5' GAAACUGAAUAGCUGUCAU 3' |
| 173 | 5' GACUUACACAGUACCUCGU 3' |
| 174 | 5' CAGAAGUAAUGACUCCAUA 3' |
| 175 | 5' CAACUUGAGUCUUUGAAGA 3' |
| 176 | 5' GAAGAGACCAAGGUUGCAA 3' |
| 177 | 5' CUUGGAUAUUCUCGACACA 3' |
| 178 | 5' GAAAUGGAUAUGGAAUACU 3' |
| 179 | 5' GAACUCAUUUAUUCAGCAA 3' |
| 180 | 5' CGAUACAGCUAAUUCAGAA 3' |
| 181 | 5' GUCAUGCAUUGGGUUAGUCA 3' |
| 182 | 5' GUCAGAAGUAAUGACUCCA 3' |
| 183 | 5' GAUUUCUGAAUUGCUAUGU 3' |
| 184 | 5' GAAUCUGACAGAUACCAUA 3' |
| 185 | 5' GAGAAUCUGACAGAUACCA 3' |
| 186 | 5' GAACUAGCAAUGCCUGUGA 3' |
| 187 | 5' GAAAUCUUCAUGCAAUGAA 3' |
| 188 | 5' CUUCUAUACAUUAGUUCGA 3' |
| 189 | 5' CAUCUCAUUUGUAUUCCAU 3' |
| 190 | 5' GAUAGCAUGAAUUCUGCAU 3' |
| 191 | 5' GCAUACUAGUACAAGUGGU 3' |
| 192 | 5' CUGAAGAUGUACCUAUGGU 3' |
| 193 | 5' CAAACCUGGUAUGAAUAGA 3' |
| 194 | 5' CAAGAUACAAUCUCACUCU 3' |
| 195 | 5' GAAUUGCUAUGUGAAACUA 3' |
| 196 | 5' GAUUUGACCUAAUCACUAA 3' |
| 197 | 5' CCAAUCCAUUAGCGACAGU 3' |
| 198 | 5' CAGAGAAAGAAAUGGCCAU 3' |
| 199 | 5' CUUGGCCUCAUAAACCUGU 3' |
| 200 | 5' CUAGUUCACAGACAAGGAA 3' |
| 201 | 5' CCAUUAGCGACAGUAGGAU 3' |
| 202 | 5' CCUACAUCUUAUUUCCUCA 3' |
| 203 | 5' CUAUGGUCCUAGUAGGAAA 3' |
| 204 | 5' CUGAAAGAAUUCCUUAGGU 3' |
| 205 | 5' CUAUGUUACACCAUCUUCA 3' |
| 206 | 5' GAAUUCCUUAGGUAAUCUA 3' |
| 207 | 5' CACUAUAGUAUACCAGUGA 3' |
| 208 | 5' CAUCAGCAAAGACAAGACA 3' |
| 209 | 5' CAAGAGGAGUACAGUGCAA 3' |
| 210 | 5' GGAAUACUUUAUAAGCCAU 3' |
| 211 | 5' CAUGAAUUCUGCAUUGAGA 3' |
| 212 | 5' GUUCCAAUUCCACUGUCU 3' |
| 213 | 5' CAUGUCCUAUAGUUUGUCA 3' |
| 214 | 5' GUGAAAGUAUACUGGACU 3' |
| 215 | 5' GAGUUUCACAGCAUGGACU 3' |
| 216 | 5' GUAACAUGUUUACCUGGAA 3' |
| 217 | 5' CUGAACUAGUUCACAGACA 3' |
| 218 | 5' CUCAAGAGAAUCUGACAGA 3' |
| 219 | 5' GUAACAGUAAUACAUUCCA 3' |

TABLE 11-continued

Sense strand sequences of K-RAS siRNAs

| Seq. No. | siRNA sense strand | |  |
|---|---|---|---|
| 220 | 5' | CAAUCCAUUAGCGACAGUA | 3' |
| 221 | 5' | GAAAGAUACUCACAUGAGU | 3' |
| 222 | 5' | CCAAAUGUGUAAUAUUCCA | 3' |
| 223 | 5' | GUUUGGGAUAAUGAUAGGU | 3' |
| 224 | 5' | CAACAAUAGAGGAUUCCUA | 3' |
| 225 | 5' | CAUGAACUGUACUACUCCU | 3' |
| 226 | 5' | GAAACAUUGAGGGAACACA | 3' |
| 227 | 5' | CUCUUGGAUAUUCUCGACA | 3' |
| 228 | 5' | GCAUUAACAUGUUUGUGGA | 3' |
| 229 | 5' | CUGAAUAUAAACUUGUGGU | 3' |
| 230 | 5' | GUAAAGGCGUGUUUGCUUA | 3' |
| 231 | 5' | CUUUGAACAUCUCUUUGCU | 3' |
| 232 | 5' | CCAUACUUCAGGAACUGCA | 3' |
| 233 | 5' | CUAUACAUUAGUUCGAGAA | 3' |
| 234 | 5' | CUUCUAGGCAUCAUGUCCU | 3' |
| 235 | 5' | GAAUACCUAAGAUUUCUGU | 3' |
| 236 | 5' | CAUACUAGUACAAGUGGUA | 3' |
| 237 | 5' | CAUAGGAAUUUAGAACCUA | 3' |
| 238 | 5' | GAAACUAUUAUAAGGCCAU | 3' |
| 239 | 5' | CUUAGCAAGAAGUUAUGGA | 3' |
| 240 | 5' | CUUCUGUGUUAAUACUGGA | 3' |
| 241 | 5' | CUUAAGGCAUACUAGUACA | 3' |
| 242 | 5' | CCUAUAGUUUGUCAUCCCU | 3' |
| 243 | 5' | CUUUGAGCUUUCAUAGAGA | 3' |
| 244 | 5' | CAAGUAGGCAUUCUAGGCU | 3' |
| 245 | 5' | CAAGAGACAUAAUCCCGGU | 3' |
| 246 | 5' | CAAUUCCACUGUCUUGUGU | 3' |
| 247 | 5' | GUUAUAGCUUAUUAGGUGU | 3' |
| 248 | 5' | GAUAUUCAUAUUGACCCAA | 3' |
| 249 | 5' | CAUAGAGAGUUUCACAGCA | 3' |
| 250 | 5' | GUAAUCUAUAACUAGGACU | 3' |
| 251 | 5' | GAACACAAAUUUAUGGGCU | 3' |
| 252 | 5' | GUUUAUAGGAGUAUGUGCU | 3' |
| 253 | 5' | CAUAAAGGGAUUUGACCUA | 3' |
| 254 | 5' | CAUAAGAUUUACUGCUGCU | 3' |
| 255 | 5' | CUUUGGUAUACGACCCAGA | 3' |
| 256 | 5' | GUAAACUGAAACAUGCACA | 3' |
| 257 | 5' | GGAAACUAUUAUAAGGCCA | 3' |
| 258 | 5' | CAAUUGUGAAUGUUGGUGU | 3' |
| 259 | 5' | CUAAGUGCCAGUAUUCCCA | 3' |
| 260 | 5' | CAUUUGAAGAUAUUCACCA | 3' |
| 261 | 5' | CUUAUUUCCUCAGGGCUCA | 3' |
| 262 | 5' | CAAAUAAACAGGUGCCUGA | 3' |
| 263 | 5' | GGUGACUUAGGUUCUAGAU | 3' |
|  |  |  | 3' |

Comparative Example 2

Two siRNAs (designated siRNA I and siRNA II) that inhibit the K-RAS expression in U.S. Pat. No. 8,008,474 B2 were selected.

```
siRNA I:
sense strand: 5'-CGAAUAUGAUCCAACAAUA-3';
and antisense strand: 5'-UAUUGUUGGAUCAUAUUCG-3'.

siRNA II:
sense strand: 5'-GAUGAUGCCUUCUAUACAU-3';
and antisense strand: 5'-AUGUAUAGAAGGCAUCAUG-3'.
```

Figure 37:
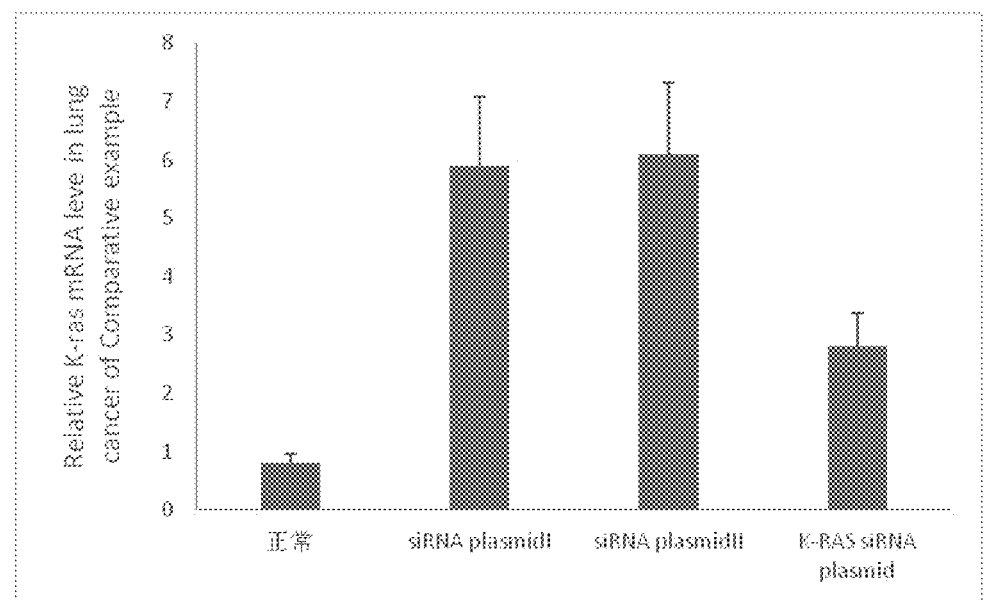
FIG. 37 shows the expression level of the K-RAS mRNA in the lung under the action of siRNA I, siRNA II and the siRNA of the present application.

Plasmid vectors were constructed in the same manner as in Example 1, designated siRNA I plasmid and siRNA II plasmid, respectively. The method in Example 2 was applied to the mouse Lewis lung cancer model, and the expression level of the K-RAS mRNA in individual lungs was then detected. The experimental results (FIG. 37) showed that as compared with the siRNA I plasmid and siRNA II plasmid, the K-RAS siRNA plasmid of the present application significantly reduced the K-RAS mRNA level in the lung tissues and organs, indicating that the inhibitory effect thereof was superior to that of the siRNA sequences that inhibit K-RAS in the prior art.

Example 12: EGFR siRNAs were Effectively Expressed by Sequence and had a Therapeutic Effect on Cancer 1. Construction of EGFR siRNA Overexpression Vector The construction process of the expression vector was the same as that in Example 1, except that 2 pairs of complementary oligo DNAs were designed and synthesized according to the EGFR gene sequence, and the sequences are shown in Table 12.

TABLE 12

The oligo DNA sequences and their corresponding precursor siRNA elements

| Oligo name | Oligo DNA sequence 5'-3' |
|---|---|
| > Mature EGFR siRNA sense strand sequence: 5'-AGGAAUUAAGAGAAGCAACAU-3' (SEQ ID NO.: 474) | |
| 13MR0041-1F | TGCTGAATTCGAGGAATTAAGAGAAGCAACATGTTTTGGCCACTGACTGACATGTTGCTTCTCTTAATTCCTCA<br>☐A1      ☐    B1     ☐    C    ☐    B2<br>☐TGCTGAATTCGAGGAATTAAGAGAAGCAACATGTTTTGGCCACTGACTGACATGTTGCTTCTCTTAATTCCTCA) |
| 13MR0041-1R | CCTGACCGGTGAGGAATTAAGAGAAGCAACATGTCAGTCAGTGGCCAAAACATGTTGCTTCTCTTAATTCCT<br>☐A2     ☐     B2          ☐     C     ☐     B1<br>(CCTGACCGGTGAGGAATTAAGAGAAGCAACATGTCAGTCAGTGGCCAAAACATGTTGCTTCTCTTAATTCCT) |
| Negative control sequence | |
| Negative-F | tgctgAAATGTACTGCGCGTGGAGACGTTTTGGCCACTGACTGACGTCTCCACGCAGTACATTT<br>\|A1 \|multiple cloning site\|       C        \| multiple cloning site\|<br>(SEQ ID NO.: 276,<br>tgctgAAATGTACTGCGCGTGGAGACGTTTTGGCCACTGACTGACGTCTCCACGCAGTACATTT) |
| Negative-R | ctgAAATGTACTGCGTGGAGACGTCAGTCAGTGGCCAAAACGTCTCCACGCGCAGTACATTTc<br>\|A2\|multiple cloning site\|        C         \|multiple cloning site\|<br>(SEQ ID NO.: 277,<br>cctgAAATGTACTGCGTGGAGACGTCAGTCAGTGGCCAAAACGTCTCCACGCGCAGTACATTTc) |

2. The Therapeutic Effect of the EGFR siRNA Plasmid on the Mouse Lewis Lung Cancer For the specific experimental materials and methods, please refer to Example 2, except that the test compound was EGFR siRNA plasmid provided by the College of Life Sciences, Nanjing University.

Figure 38:
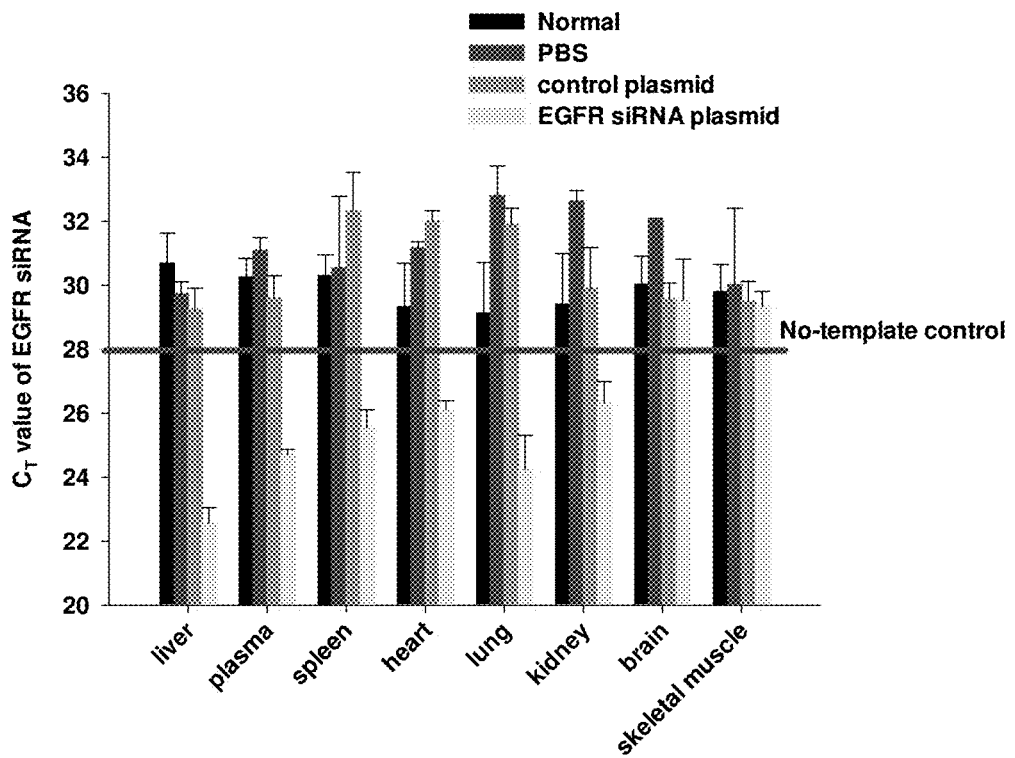
FIG. 38 shows the EGFR siRNA content in various tissues and organs.

2 weeks after the C57BL/6 mice were used for Lewis lung cancer model construction, the EGFR siRNA plasmid was administered by intravenous injection for treatment; during administration, the mice were administered with same once every 3 days; and, the animals were sacrificed on day 3 after the final administration, for taking the blood, lung, liver and various tissues and organs. The EGFR siRNA content in various tissues and organs was detected by qRT-PCR. As can be seen from the determination results (as shown in FIG. 38, each set of histograms from left to right were Normal, PBS, the control plasmid and the EGFR siRNA plasmid successively in FIG. 38), in addition to the brain and skeletal muscle, the EGFR siRNA entered into other tissues and organs, such as the liver and lung.

Figure 39:
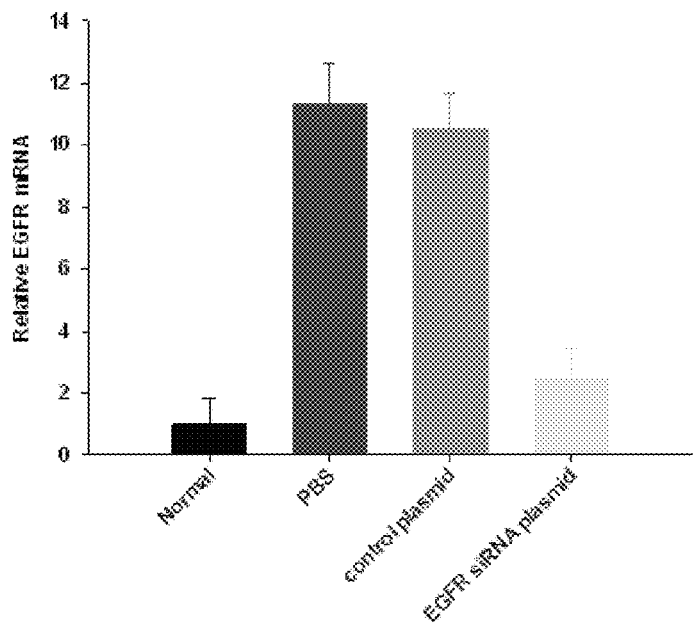
FIG. 39 is a schematic showing the expression level of the EGFR mRNA in the lung.

The expression level of the EGFR mRNA in the lung was then detected, and the experimental results (FIG. 39) showed that the EGFR siRNA plasmid significantly reduced the EGFR mRNA level in the lung tissues and organs.

Figure 40:
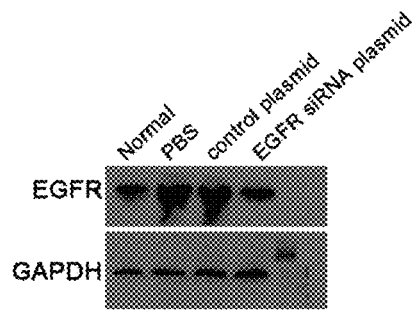
FIG. 40 shows the western blotting results of the expression level of the EGFR protein in the lung.
Figure 41:
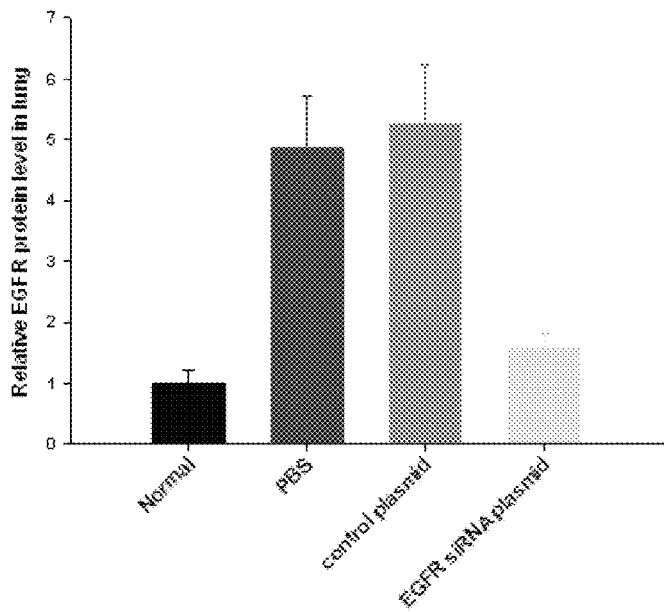
FIG. 41 is a schematic showing the expression level of the EGFR protein in the lung.

The lung tissue proteins were extracted, and the expression level of the EGFR protein in the lung tissues was detected using a western blotting experiment. It was found from the experimental results (FIG. 40 and FIG. 41) that the EGFR siRNA plasmid can significantly reduce the EGFR protein in the lung tumour tissues.

Figure 42:
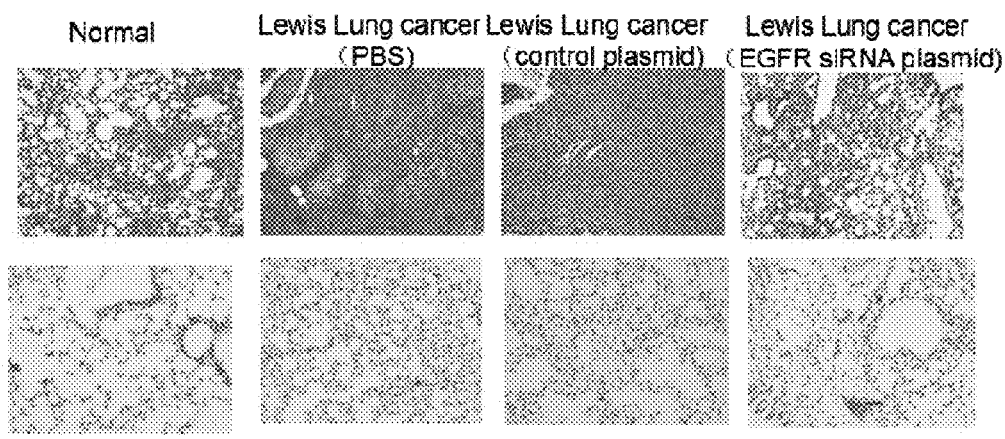
FIG. 42 is a schematic showing the results of pathological sections in the lung of mice.

In addition to those for the detection of molecular indicators, the rest of the lung and liver were fixed with formalin, and pathological tissue sections were made for examining the tumour situations of the organs. The results of the pathological sections showed that tumour lesions were not seen in all the liver sections in each group. In the lung, tumour cell foci with a flake-shaped nucleus being stained largely and deeply to different extents can be seen in each treatment group (the results were shown as in FIG. 42).

The EGFR siRNA plasmid had a therapeutic effect on the in vivo mouse Lewis lung cancer, and the abnormal responses related with the medication were not seen during administration.

3. The Therapeutic Effect of the EGFR siRNA Plasmid on the Mouse Colon Cancer

For the specific experimental materials and methods, please refer to Example 11, except that the test compound was EGFR siRNA plasmid provided by the College of Life Sciences, Nanjing University.

The effect of the EGFR siRNA plasmid on the volume of mouse colon cancer subcutaneous transplanted tumours The long diameter (a) and short diameter (b) of tumours were measured with a vernier caliper, and the tumour volume V (mm$^3$) was calculated as $1/6\pi ab^2$. After the measurement, the tumours were fixed in 10% formaldehyde.

The tumour inhibition rate was calculated: tumour inhibition rate (%)=(V in control group−V in experimental group)/V in control group×100%.

Compared with the tumour volume in Group 1 and Group 2, the volume in Group 3 was significantly smaller (P<0.05).

As shown in Table 13 below

TABLE 13

Tumour volumes and tumour inhibition rates in different groups of experimental mice

| Group n | Tumour average volume (V/mm$^3$) | Tumour inhibition rate (%) |
|---|---|---|
| Group 1 | 3902.34 ± 824.32 | 0 |
| Group 2 | 3929.14 ± 956.80 | 0 |
| Group 3 | 2686.29 ± 1021.20 | 31.6%*, 31.2%# |

*Relative to Group 2,
relative to Group 1

The EGFR siRNA content in the transplanted tumours was detected by qRT-PCR, and the results showed that the EGFR siRNA entered into the transplanted tumours.

Figure 43:
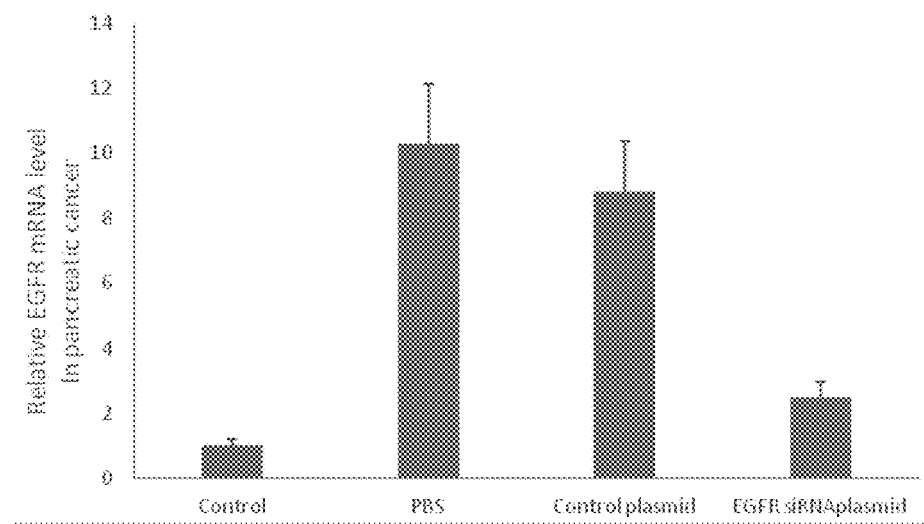
FIG. 43 is a schematic showing the expression level of the EGFR mRNA in colon cancer transplanted tumours.

The expression level of the EGFR mRNA in individual transplanted tumours was then detected, and the experimental results (FIG. 43) showed that the EGFR siRNA plasmid significantly reduced the EGFR mRNA level in the transplanted tumours.

Figure 44:
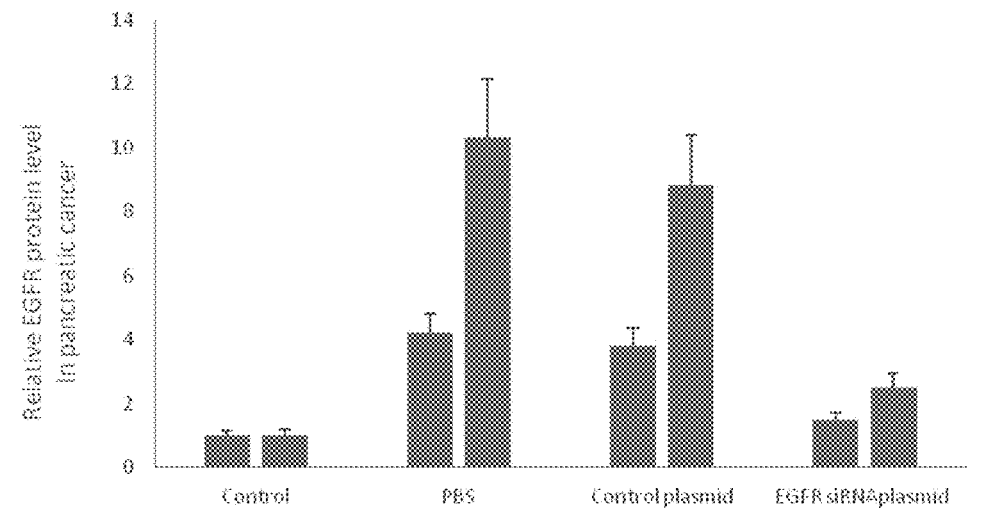
FIG. 44 is a schematic showing the expression level of the EGFR protein in colon cancer transplanted tumours.

The transplanted tumour tissue proteins were extracted, and the expression level of the EGFR protein in the transplanted tumour tissues was detected using a western blotting experiment. It was found from the experimental results (see FIG. 44) that the EGFR siRNA plasmid can significantly reduce the EGFR protein in the transplanted tumour tissues.

The EGFR siRNA plasmid had a therapeutic effect on the colon cancer, and the abnormal responses related with the medication were not seen during administration.

4. The Therapeutic Effect of the EGFR siRNA Plasmid on the Mouse Pancreatic Cancer For the specific experimental materials and methods, please refer to Example 11, except that the test compound was EGFR siRNA plasmid provided by the College of Life Sciences, Nanjing University.

Two weeks after the BALB/c mice were used for pancreatic cancer model construction, the EGFR siRNA plasmid was administered by intravenous injection for treatment; during administration, the mice were administered with same once every 3 days; and, the animals were sacrificed on day 3 after the final administration, for taking the pancreas. The EGFR siRNA content in the pancrease was detected by qRT-PCR, and the results showed that the EGFR siRNA entered into the pancreas.

Figure 45:
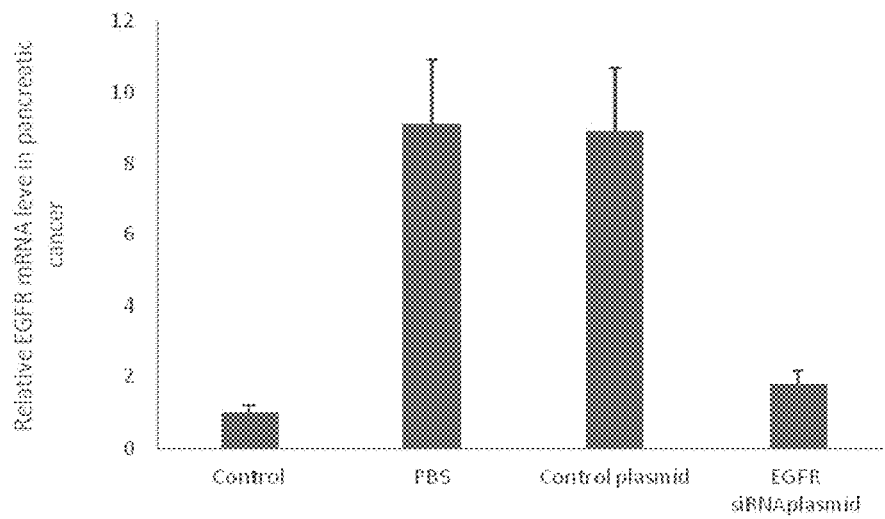
FIG. 45 is a schematic showing the expression level of the EGFR mRNA in the pancreas.

FIG. 45 shows the expression level of EGFR mRNAs in the pancreas, and the results showed that the EGFR siRNA significantly reduced the EGFR mRNA level in the pancreatic tissues and organs.

Figure 46:
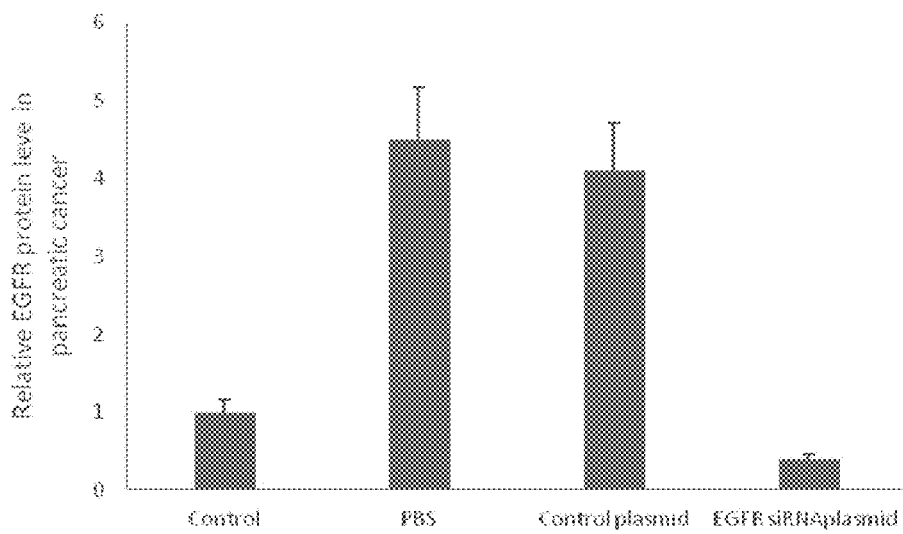
FIG. 46 is a schematic showing the expression level of the EGFR protein in the pancreas.

FIG. 46 shows the expression level of the EGFR protein in the pancreatic tissues detected using a western blotting experiment after the pancreatic tumour tissue proteins were extracted.

The results above showed that the EGFR siRNA plasmid can significantly reduce the expression level of the EGFR protein in the pancreatic tumour tissues.

5. Design and Verification of More EGFR siRNA Sequences

This example further provided 196 siRNA sequences for the EGFR gene, see Table 14 for details. Ten siRNA sequences with excellent stability and evident specific inhibitory effects were further screened from the siRNA sequences above for the expression verification. The sequence numbers of the ten siRNAs in Table 14 were 17, 20, 35, 42, 47, 52, 59, 63, 68 and 72, respectively.

The expression levels of the EGFR mRNA and proteins were verified using the expression vector construction method in Example 1 and the verification method in Example 2, respectively.

Figure 47:
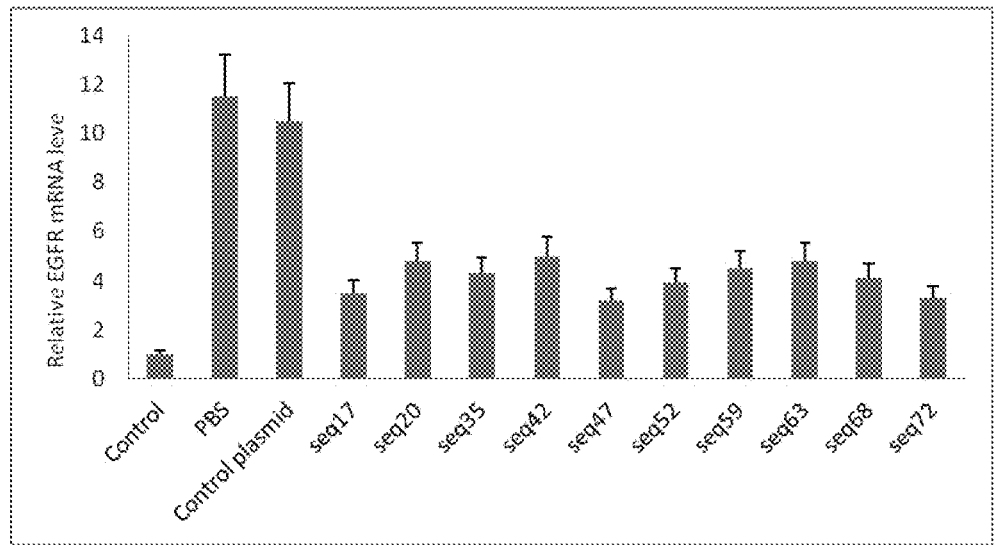
FIG. 47 shows the expression level of the EGFR mRNA in the lung after siRNAs are introduced.

FIG. 47 shows the expression level of the EGFR mRNA in the lung, and the results showed that all the plasmids constructed using the screened ten EGFR siRNAs reduced the EGFR mRNA level in the lung tissues and organs.

Figure 48:
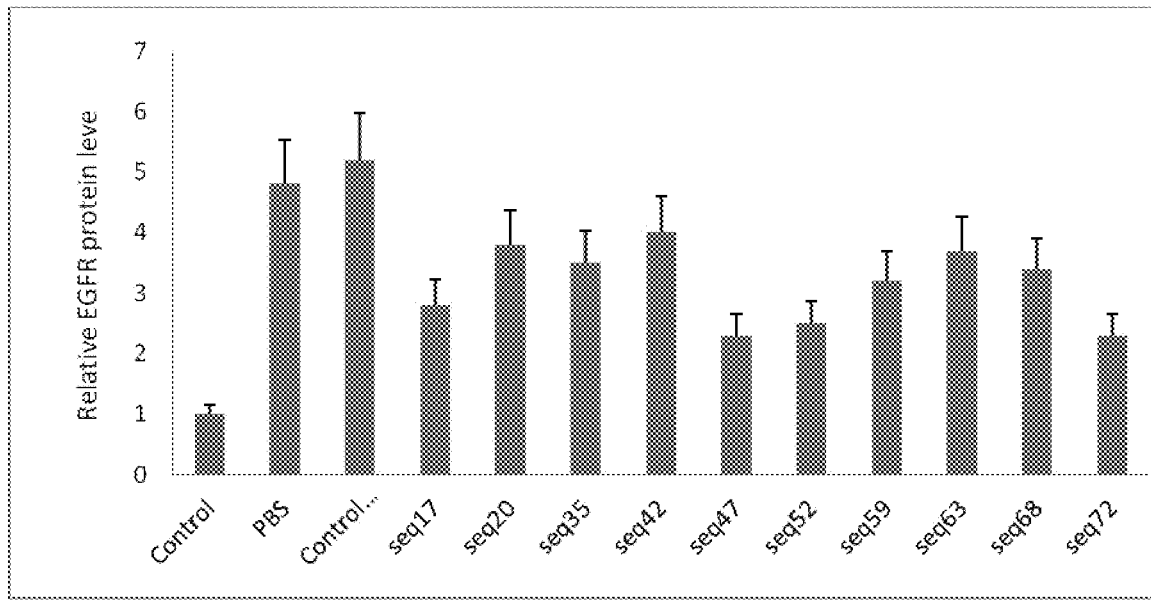
FIG. 48 shows the expression level of the EGFR protein in the lung after siRNAs are introduced.

FIG. 48 shows the expression level of the EGFR protein in the lung tissues detected using a western blotting experiment after the lung tissue proteins were extracted.

The results above showed that the plasmids constructed using the screened ten EGFR siRNAs can significantly reduce the expression level of the EGFR protein in the lung tumour tissues.

TABLE 14

Sense strand sequences of EGFR siRNAs

| Sequence number | siRNA sense strand |
|---|---|
| 1 | 5'   GUCGCUAUCAAGGAAUUAA   3' |
| 2 | 5'   GGGAACACAAAGACAAUAU   3' |
| 3 | 5'   GAGGAUGACACAUCAAAUA   3' |
| 4 | 5'   GGCAGGUACAGUAGGAUAA   3' |
| 5 | 5'   CGGGAACACAAAGACAAUA   3' |
| 6 | 5'   GGCUUGCAUUGAUAGAAAU   3' |
| 7 | 5'   CCACAAAGCAGUGAAUUUA   3' |
| 8 | 5'   GGAUGACACAUCAAAUAAU   3' |
| 9 | 5'   GUGGAAUUCAGGUAGUAAA   3' |
| 10 | 5'   GAGGCAAAGUGCCUAUCAA   3' |
| 11 | 5'   GUGCGGAAGAGAAAGAAUA   3' |
| 12 | 5'   CAGCCCACAUUGGAUUCAU   3' |
| 13 | 5'   GUGCUAUGCAAAUACAAUA   3' |
| 14 | 5'   GUGGCUUGCAUUGAUAGAA   3' |
| 15 | 5'   GUGAUGGAGAUGUGAUAAU   3' |
| 16 | 5'   GGGCAUAGAUCAGAAGACU   3' |
| 17 | 5'   CUCCAGAGGAUGUUCAAUA   3' |
| 18 | 5'   GCGAAUGACAGUAGCAUUA   3' |
| 19 | 5'   CAGUGCCUGAAUACAUAAA   3' |
| 20 | 5'   CUUGGGAAUUUGGAAAUUA   3' |
| 21 | 5'   GUGGAUGGCAUUGGAAUCA   3' |
| 22 | 5'   GCCUUUGAGAACCUAGAAA   3' |
| 23 | 5'   CAGCUGAGAAUGUGGAAUA   3' |
| 24 | 5'   GAGCGUUAGACUGACUUGU   3' |
| 25 | 5'   CCCAGUGCCUGAAUACAUA   3' |
| 26 | 5'   GGUGACUCCUUCACACAUA   3' |
| 27 | 5'   GAUCCAAGAAGGCCUUCAU   3' |
| 28 | 5'   CUGCCAGAAACUGACCAAA   3' |
| 29 | 5'   GUCCGCAAGUGUAAGAAGU   3' |
| 30 | 5'   GUGACUUUCUCAGCAACAU   3' |
| 31 | 5'   CUCCAUAAAUGCUACGAAU   3' |
| 32 | 5'   GGAAGUUGCAUUCCUUUGU   3' |
| 33 | 5'   CAGGAACGUACUGGUGAAA   3' |
| 34 | 5'   GUCAGCCUGAACAUAACAU   3' |
| 35 | 5'   CCUAUGUGCAGAGGAAUUA   3' |
| 36 | 5'   CAGCAGUCCUUUGUAAACA   3' |
| 37 | 5'   CCUUUGAGCAGAAAUUUAU   3' |
| 38 | 5'   GAUCCCAGAAGGUGAGAAA   3' |
| 39 | 5'   GUACCAUCGAUGUCUACAU   3' |
| 40 | 5'   GGAUGGCAUUGGAAUCAAU   3' |

TABLE 14-continued

Sense strand sequences of EGFR siRNAs

| Sequence number | siRNA sense strand | | |
|---|---|---|---|
| 41 | 5' | CAGAUCAUCAGAGGAAAUA | 3' |
| 42 | 5' | CCCUACAGCAUUGUUAAGA | 3' |
| 43 | 5' | GAGAGGAUGACACAUCAAA | 3' |
| 44 | 5' | GGAGAUAAGUGAUGGAGAU | 3' |
| 45 | 5' | GGAGCGAAUUCCUUUGGAA | 3' |
| 46 | 5' | GGAACUGGAUAUUCUGAAA | 3' |
| 47 | 5' | CAGCAUUGUUAAGAAAGUA | 3' |
| 48 | 5' | GGGAUGGAAUUCUUCCUUA | 3' |
| 49 | 5' | CCCUGAUGGAUGAAGAAGA | 3' |
| 50 | 5' | GCUCUCUUGAGGAUCUUGA | 3' |
| 51 | 5' | GAGGCUCAGAUGAAAUGCA | 3' |
| 52 | 5' | GUCCUUGGGAAUUUGGAAA | 3' |
| 53 | 5' | GCUCAGAUGAAAUGCAUCA | 3' |
| 54 | 5' | GAAGGAAACUGAAUUCAAA | 3' |
| 55 | 5' | CAUCCAGCAAGAAUAUUGU | 3' |
| 56 | 5' | CGUGAGUUGAUCAUCGAAU | 3' |
| 57 | 5' | GCUCUUCCAACAAGGAAGA | 3' |
| 58 | 5' | CUGGAUGAUAGACGCAGAU | 3' |
| 59 | 5' | CCUACAGCAUUGUUAAGAA | 3' |
| 60 | 5' | CGGAUCGUACUGUAUCAA | 3' |
| 61 | 5' | GGAGAACUCUGAGUGCAUA | 3' |
| 62 | 5' | CCAUCGAUGUCUACAUGAU | 3' |
| 63 | 5' | CAGAGGAUGUUCAAUAACU | 3' |
| 64 | 5' | CACAGGAACUGGAUAUUCU | 3' |
| 65 | 5' | GUGCGAAUGACAGUAGCAU | 3' |
| 66 | 5' | CUGUCUUGCUGUCAUGAAA | 3' |
| 67 | 5' | CCUUUGAGAACCUAGAAAU | 3' |
| 68 | 5' | GCCUACAGUUAUGUUCAGU | 3' |
| 69 | 5' | GUGUGGAAUUCAGGUAGUA | 3' |
| 70 | 5' | GAGGAAAUAUGUACUACGA | 3' |
| 71 | 5' | GUGAUAAUUUCAGGAAACA | 3' |
| 72 | 5' | CAGUCACACACAUACAA | 3' |
| 73 | 5' | GAGUUGAUCAUCGAAUUCU | 3' |
| 74 | 5' | GGAAUAGGUAUUGGUGAAU | 3' |
| 75 | 5' | GCAGUCCUUUGUAAACAGU | 3' |
| 76 | 5' | GAUCUUCCUUCUUAAAGA | 3' |
| 77 | 5' | CCUUGAGUCAUCUAUUCAA | 3' |
| 78 | 5' | CCCUCAAGGAGAUAAGUGA | 3' |

TABLE 14-continued

Sense strand sequences of EGFR siRNAs

| Sequence number | siRNA sense strand | | |
|---|---|---|---|
| 79 | 5' | CAGAAGGUGAGAAAGUUAA | 3' |
| 80 | 5' | CCUACAGACUCCAACUUCU | 3' |
| 81 | 5' | GCAUUCCUUUGUCUUCAAA | 3' |
| 82 | 5' | CUUGCCGCAAAGUGUGUAA | 3' |
| 83 | 5' | CGGUACUGUAUCAAGUCAU | 3' |
| 84 | 5' | GAUCGGUACUGUAUCAAGU | 3' |
| 85 | 5' | GGACUUCUUUCCCAAGGAA | 3' |
| 86 | 5' | CCUGUAACCUGACUGGUUA | 3' |
| 87 | 5' | GCAGUGACUUUCUCAGCAA | 3' |
| 88 | 5' | GCUGUCAUGAAAUCAGCAA | 3' |
| 89 | 5' | CGAAAGCCAACAAGGAAAU | 3' |
| 90 | 5' | CCGAGUAUCUCAACACUGU | 3' |
| 91 | 5' | GACCAGACAACUGUAUCCA | 3' |
| 92 | 5' | GUUAGACUGACUUGUUUGU | 3' |
| 93 | 5' | GGAAAUAUGUACUACGAAA | 3' |
| 94 | 5' | GCUACGAAUAUUAAACACU | 3' |
| 95 | 5' | CUACAGCAUUGUUAAGAAA | 3' |
| 96 | 5' | GUAGCAUUAUGAGUAGUGU | 3' |
| 97 | 5' | CAUCUCCGAAAGCCAACAA | 3' |
| 98 | 5' | GAGGAUGCUUGAUUCCAGU | 3' |
| 99 | 5' | GACAGUAGCAUUAUGAGUA | 3' |
| 100 | 5' | CCGAAAGCCAACAAGGAAA | 3' |
| 101 | 5' | GCAACGUUUACACCGACUA | 3' |
| 102 | 5' | CCAAGCCAUAUGACGGAAU | 3' |
| 103 | 5' | GAUCAUCGAAUUCUCCAAA | 3' |
| 104 | 5' | CGGAAUAGGUAUUGGUGAA | 3' |
| 105 | 5' | GUGUUACUUAUGGAAGAUA | 3' |
| 106 | 5' | CAAGCUCUCUUGAGGAUCU | 3' |
| 107 | 5' | CUGCAGAUCAUCAGAGGAA | 3' |
| 108 | 5' | GACUUUCUCAGCAACAUGU | 3' |
| 109 | 5' | CUGUGAAGCAUUUACAGAA | 3' |
| 110 | 5' | GGAAGAGAAAGAAUACCAU | 3' |
| 111 | 5' | GGAUCUUGAAGGAAACUGA | 3' |
| 112 | 5' | CCUUAGCAGUCUUAUCUAA | 3' |
| 113 | 5' | GCUAUGAGAUGGAGGAAGA | 3' |
| 114 | 5' | GCAAAGGGCAUGAACUACU | 3' |
| 115 | 5' | GGAAUUAAGAGAAGCAACA | 3' |

TABLE 14-continued

Sense strand sequences of EGFR siRNAs

| Sequence number | siRNA sense strand | |  |
|---|---|---|---|
| 116 | 5' | CAUCAGCAUUUGGACCAAU | 3' |
| 117 | 5' | GCAACCAGCAACAAUUCCA | 3' |
| 118 | 5' | GAGGAUAGUAUGAGCCCUA | 3' |
| 119 | 5' | CAAGGGAGUUUGUGGAGAA | 3' |
| 120 | 5' | CGUACCAGAUGGAUGUGAA | 3' |
| 121 | 5' | CCUGAAUACAUAAACCAGU | 3' |
| 122 | 5' | CCAGACAACUGUAUCCAGU | 3' |
| 123 | 5' | CUCUCCAUAAAUGCUACGA | 3' |
| 124 | 5' | GGAUGUUCAAUAACUGUGA | 3' |
| 125 | 5' | CUCCUUCACACAUACUCCU | 3' |
| 126 | 5' | CUGUGCAGAAUCCUGUCUA | 3' |
| 127 | 5' | CCUAAUUUGAGGCUCAGAU | 3' |
| 128 | 5' | CAGUAGCAUUAUGAGUAGU | 3' |
| 129 | 5' | GCAUUUGCCAAGUCCUACA | 3' |
| 130 | 5' | CAAAGUGUGUAACGGAAUA | 3' |
| 131 | 5' | GAUAAUGCUUUCACAACAU | 3' |
| 132 | 5' | CCGUAAUUAUGUGGUGACA | 3' |
| 133 | 5' | GAUGCUUGAUUCCAGUGGU | 3' |
| 134 | 5' | GUUAACAGCAGUCCUUUGU | 3' |
| 135 | 5' | CUGACUUGUUUGUCUUCCA | 3' |
| 136 | 5' | CAUCCAAUUUAUCAAGGAA | 3' |
| 137 | 5' | CCAUCCAAUUUAUCAAGGA | 3' |
| 138 | 5' | CUGAGAAUGUGGAAUACCU | 3' |
| 139 | 5' | GACAUAGUCAGCAGUGACU | 3' |
| 140 | 5' | CUCUCCUAGUCAAUAUCCA | 3' |
| 141 | 5' | CGGAAGAGAAAGAAUACCA | 3' |
| 142 | 5' | CGCAAAGUGUGUAACGGAA | 3' |
| 143 | 5' | GAGUUGAUGACCUUUGGAU | 3' |
| 144 | 5' | CAAGGAAUUAAGAGAAGCA | 3' |
| 145 | 5' | CUAUGCCUUAGCAGUCUUA | 3' |
| 146 | 5' | GUGAAUUUAAAGACUCACU | 3' |
| 147 | 5' | CCUUCUUAAAGACCAUCCA | 3' |
| 148 | 5' | GAUGUGAUAAUUUCAGGAA | 3' |
| 149 | 5' | CACCAAAUUAGCCUGGACA | 3' |
| 150 | 5' | CAACAAGGAAAUCCUCGAU | 3' |
| 151 | 5' | CCAUGCCUUUGAGAACCUA | 3' |
| 152 | 5' | GGAUUCAUCAGCAUUUGGA | 3' |
| 153 | 5' | CAAGGAGAUAAGUGAUGGA | 3' |
| 154 | 5' | CAGUAGGAUAAGCCACUCU | 3' |
| 155 | 5' | GUAGUGUGGAAUUCAGGUA | 3' |
| 156 | 5' | CUGACUGGUUAACAGCAGU | 3' |
| 157 | 5' | CAUGAGCGUUAGACUGACU | 3' |
| 158 | 5' | CCAACAAGGAAAUCCUCGA | 3' |
| 159 | 5' | GGAAUACCUAAGGAUAGCA | 3' |
| 160 | 5' | GGAAUUUGGAAAUUACCUA | 3' |
| 161 | 5' | CAGCAAGAAUAUUGUCCCU | 3' |
| 162 | 5' | GCAUGAACUACUUGGAGGA | 3' |
| 163 | 5' | CUUACGCUUUGUCACACAA | 3' |
| 164 | 5' | GUCAACAGCACAUUCGACA | 3' |
| 165 | 5' | CACAAGUCUUCCAGAGGAU | 3' |
| 166 | 5' | CAUGAGAAAUUUACAGGAA | 3' |
| 167 | 5' | CUACAGUUAUGUUCAGUCA | 3' |
| 168 | 5' | GCAAGUGUAAGAAGUGCGA | 3' |
| 169 | 5' | CCUUACGCUUUGUCACACA | 3' |
| 170 | 5' | CCAUGAGAAAUUUACAGGA | 3' |
| 171 | 5' | GUCUACAUGAUCAUGGUCA | 3' |
| 172 | 5' | CAGUGAAUUUAUUGGAGCA | 3' |
| 173 | 5' | CAGAUGAAAUGCAUCAGGU | 3' |
| 174 | 5' | CCUAUCAAGUGGAUGGCAU | 3' |
| 175 | 5' | GCAAAUACAAUAAACUGGA | 3' |
| 176 | 5' | GUUUGUGUUACUUAUGGAA | 3' |
| 177 | 5' | CUUCACACAUACUCCUCCU | 3' |
| 178 | 5' | CUAUCAAGGAAUUAAGAGA | 3' |
| 179 | 5' | CAGACUCUUUCGAUACCCA | 3' |
| 180 | 5' | CACAUUGGAUUCAUCAGCA | 3' |
| 181 | 5' | GAAAUCAGCAAGAGAGGAU | 3' |
| 182 | 5' | CUAUAUUCAUUUCCACUCU | 3' |
| 183 | 5' | GAAAUUUACAGGAAAUCCU | 3' |
| 184 | 5' | GUUUGGGAGUUGAUGACCU | 3' |
| 185 | 5' | CAUCAAAUAAUAACUCGGA | 3' |
| 186 | 5' | GUAAUUAUGUGGUGACAGA | 3' |
| 187 | 5' | GAACAUAACAUCCUUGGGA | 3' |
| 188 | 5' | CACAAAGACAAUAUUGGCU | 3' |
| 189 | 5' | CAUUAUGAGUAGUGUGGAA | 3' |
| 190 | 5' | CUAGAAAUCAUACGCGGCA | 3' |

TABLE 14-continued

Sense strand sequences of EGFR siRNAs

| Sequence number | | siRNA sense strand | |
|---|---|---|---|
| 191 | 5' | CUUUCCUUCUUAAAGACCA | 3' |
| 192 | 5' | GAAAUUACCUAUGUGCAGA | 3' |
| 193 | 5' | CAAAGAGUAUAUGUUCCCU | 3' |
| 194 | 5' | GUAAAUAUGAAACUAGGGU | 3' |
| 195 | 5' | GUAAAGGAAAUCACAGGGU | 3' |
| 196 | 5' | GUUAUGUCCUCAUUGCCCU | 3' |
| 197 | 5' | AGGAAUUAAGAGAAGCAACAU | 3' |

Comparative Example 3

The siRNA (designated siRNA I) that inhibits the expression of EGFR in Chinese patent literature CN 101353656 and siRNA (designated siRNA II) that inhibits the expression of EGFR in CN 104232743 A

Figure 49:
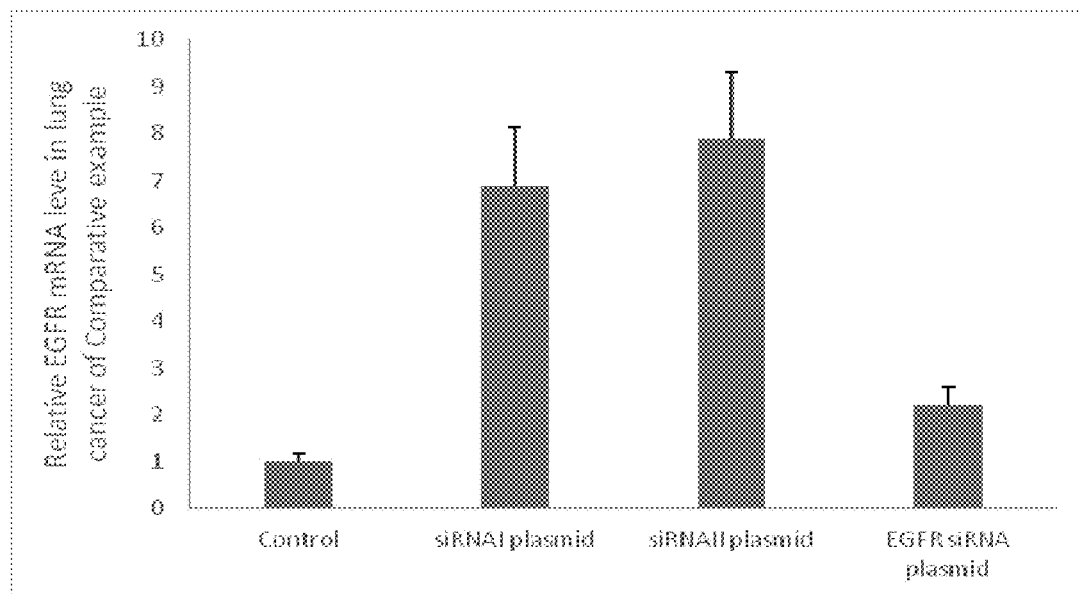
FIG. 49 shows the expression level of the EGFR mRNA in the lung of mice under the action of siRNA I, siRNA II and the siRNA of the present application.

```
siRNA I:
sense strand: 5'-GGCUGGUUAUGUCCUCAUU-3';
and antisense strand: 5'-AAUGAGGACAUAACCAGCC-3'.

siRNA II:
sense strand: 5'-CCAUAAAUGCUACGAAUAU-3';
and antisense strand: 5'-AUAUUCGUAGCAUUUAUGG-3'.
``` were used for constructing plasmid vectors in the same manner as in Example 1, designated siRNA I plasmid and siRNA II plasmid, respectively. The method in Example 2 was applied to the mouse Lewis lung cancer model, and the expression level of the EGFR mRNA in individual lungs was then detected. The experimental results (FIG. 49) showed that as compared with the siRNA I plasmid and siRNA II plasmid, the EGFR siRNA plasmid of the present application significantly reduced the EGFR mRNA level in lung tissues and organs.

Example 13: PDCD1 siRNAs or PDL1 siRNAs were Effectively Expressed by a Precursor Sequence and had a Therapeutic Effect on Cancer A first ribonucleic acid sequence of a precursor sequence includes the siRNA sequence form, apart from effectively expressing KRAS siRNAs or EGFR siRNAs, effectively expressing PDCD1 siRNAs and PDL1 siRNAs, which have a therapeutic effect on cancer.

Ten possible siRNA sequences were designed for the PDCD1 gene locus in this example, and please refer to Table 15 for the sequences. The expression vector construction method in Example 1 was repeated to construct a PDCD1 siRNA expression vector.

TABLE 15

Sense strand sequences of PDCD1 siRNAs

| Sequence number | | siRNA sense strand | |
|---|---|---|---|
| 1 | 5' | CCCUGUGGUUCUAUUAUAU | 3' |
| 2 | 5' | CAGGCCUAGAGAAGUUUCA | 3' |
| 3 | 5' | CCAGGAUGGUUCUUAGACU | 3' |
| 4 | 5' | GCUUCGUGCUAAACUGGUA | 3' |
| 5 | 5' | GAGUAUGCCACCAUUGUCU | 3' |
| 6 | 5' | GUUUCAGGGAAGGUCAGAA | 3' |
| 7 | 5' | CUAGAGAAGUUUCAGGGAA | 3' |
| 8 | 5' | CUAAACUGGUACCGCAUGA | 3' |
| 9 | 5' | CAUUUCCUCAGGAGAAGCA | 3' |
| 10 | 5' | CAUUGUCUUUCCUAGCGGA | 3' |

216 possible siRNA sequences were designed for the PDL1 gene locus in this example, and please refer to Table 16 for the sequences. Ten siRNA sequences with excellent stability and evident specific inhibitory effects were further screened from the siRNA sequences above for the expression verification. The sequence numbers of the ten siRNAs in Table 16 were 18, 37, 53, 58, 61, 96, 99, 103, 129 and 158, respectively.

TABLE 16

Sense strand sequences of PDL1 siRNAs

| Sequence number | | siRNA sense strand | |
|---|---|---|---|
| 1 | 5' | GCCGACUACAAGCGAAUUA | 3' |
| 2 | 5' | CUGGGAGCCAUCUUAUUAU | 3' |
| 3 | 5' | GAGGAAGCAAACAGAUUAA | 3' |
| 4 | 5' | CGGGUUGAGAAUCCCUAAU | 3' |
| 5 | 5' | GACCUUGAUACUUUCAAAU | 3' |
| 6 | 5' | GGAGGAAAUAGGCCAAUGU | 3' |
| 7 | 5' | CAGGCAAUGUGGGACUUAA | 3' |
| 8 | 5' | GAGCCUCCAAGCAAAUCAU | 3' |
| 9 | 5' | GACGGUUGGAUAUACUUAA | 3' |
| 10 | 5' | GUGGCAUCCAAGAUACAAA | 3' |
| 11 | 5' | GGAGCUCAUAGUAUAAUGA | 3' |
| 12 | 5' | GGAGGAGAAUGAAGAAAGA | 3' |
| 13 | 5' | GGCUGCACUAAUUGUCUAU | 3' |
| 14 | 5' | GGCACAUCCUCCAAAUGAA | 3' |
| 15 | 5' | GGACAGAGUUUGGAUUUGU | 3' |
| 16 | 5' | CGGGACAGUAUUUAUGUAU | 3' |
| 17 | 5' | GGUGCACUGAGUCAAUCUA | 3' |
| 18 | 5' | GGGCAUUCCAGAAAGAUGA | 3' |

TABLE 16-continued

Sense strand sequences of PDL1 siRNAs

| Sequence number | siRNA sense strand |  |  |
|---|---|---|---|
| 19 | 5' | CUUGCCCAAACCAGUAAAU | 3' |
| 20 | 5' | GUGCCAGGCAUUGAAUCUA | 3' |
| 21 | 5' | CUGCCUUUCAUUCAUAUGU | 3' |
| 22 | 5' | GUGGUUGUGAAUGAUUUCU | 3' |
| 23 | 5' | GUUGCCAAGAGGAGGAAAU | 3' |
| 24 | 5' | GGACUCACUUGGUAAUUCU | 3' |
| 25 | 5' | GCCAUAUUCUGGUGUCAAU | 3' |
| 26 | 5' | CCAGCACACUGAGAAUCAA | 3' |
| 27 | 5' | GAGGAGGAGAAUGAAGAAA | 3' |
| 28 | 5' | GCAGAUGGAAUGAAUUUGA | 3' |
| 29 | 5' | GAGUCAAUCUAGUCCUAAA | 3' |
| 30 | 5' | GGGAAAUGGAGGAUAAGAA | 3' |
| 31 | 5' | CUCCACUCAAUGCCUCAAU | 3' |
| 32 | 5' | CAGUAUCUGUUCCAUUUAA | 3' |
| 33 | 5' | GGACAGUAUUUAUGUAUGA | 3' |
| 34 | 5' | GCCAGGCAUUGAAUCUACA | 3' |
| 35 | 5' | GAGGAGGAAAUAGGCCAAU | 3' |
| 36 | 5' | GCUACUGCCUUUCAUUCAU | 3' |
| 37 | 5' | GGCAUAGGCAGAGAUGAUA | 3' |
| 38 | 5' | GUGGUAGCCUACACACAUA | 3' |
| 39 | 5' | CCUGAAGGUUCAGCAUAGU | 3' |
| 40 | 5' | GUGUGACAGUGUUCUUUGU | 3' |
| 41 | 5' | GUUGUGAUAACCACUAUUA | 3' |
| 42 | 5' | GCCUUUGCCAUAUAAUCUA | 3' |
| 43 | 5' | GAGGUUUCGAGAUUCAGAU | 3' |
| 44 | 5' | GAGACCUUGAUACUUUCAA | 3' |
| 45 | 5' | CUGGAGGUUUCGAGAUUCA | 3' |
| 46 | 5' | GGCACAUAGUCUACUCAGU | 3' |
| 47 | 5' | GUAGCAAUAUGACAAUUGA | 3' |
| 48 | 5' | GGCUGAAGAAACAGUGUCU | 3' |
| 49 | 5' | GACAGGGAGAAAGGAUACU | 3' |
| 50 | 5' | GAGUGUGGUUGUGAAUGAU | 3' |
| 51 | 5' | GUCUCCUCUAUAACUACAA | 3' |
| 52 | 5' | GGAGAAUGAUGGAUGUGAA | 3' |
| 53 | 5' | GGAUUUGUAAGGCACUUUA | 3' |
| 54 | 5' | GGUUGGAUAUACUUAAACA | 3' |
| 55 | 5' | CUCCUCUAUAACUACAAGU | 3' |
| 56 | 5' | CAUAGGAUGUCACCUUUAU | 3' |
| 57 | 5' | GAAGCAAACAGAUUAAGUA | 3' |
| 58 | 5' | GUCUCAUGUUUCAUCGUAA | 3' |
| 59 | 5' | CCUUGUGUUAUCUGUUUGU | 3' |
| 60 | 5' | GGUCUCCUCUAUAACUACA | 3' |
| 61 | 5' | GCUGUCUUUAUAUUCAUGA | 3' |
| 62 | 5' | GAUGUGAGCAAGACAAAGU | 3' |
| 63 | 5' | GGGAGAAUGAUGGAUGUGA | 3' |
| 64 | 5' | CAGCAUUGGAACUUCUGAU | 3' |
| 65 | 5' | GAGCAAGGCACAUAGUCUA | 3' |
| 66 | 5' | GUAGCACUGACAUUCAUCU | 3' |
| 67 | 5' | GUGUAGCACUGACAUUCAU | 3' |
| 68 | 5' | CAGUGUUCUUUGUGUGAAU | 3' |
| 69 | 5' | CAUCCUCCAAGCCAUUCAA | 3' |
| 70 | 5' | CUGAGAAUCAACACAACAA | 3' |
| 71 | 5' | CAACCACCAUUUGUUAAGU | 3' |
| 72 | 5' | CUCUGUAUGACAGAAUCAU | 3' |
| 73 | 5' | GGUAGAGUAUGGUAGCAAU | 3' |
| 74 | 5' | CACACAUAAUCUCAUUUCA | 3' |
| 75 | 5' | CCUCAUUCGUUGUGCUUGA | 3' |
| 76 | 5' | GAUGGAAUGAAUUUGAAGU | 3' |
| 77 | 5' | GAAGCAAAGUGAUACACAU | 3' |
| 78 | 5' | CUGCUGUGUACUUUGCUAU | 3' |
| 79 | 5' | CAAGCGAAUUACUGUGAAA | 3' |
| 80 | 5' | GUCAUAGCAUAAGGAUGAU | 3' |
| 81 | 5' | GUUGACCUAAUCUUAUUCU | 3' |
| 82 | 5' | GUGAAUUACAGGCAAGAAU | 3' |
| 83 | 5' | CCUCCAAGCAAAUCAUCCA | 3' |
| 84 | 5' | CAGGCAUUGAAUCUACAGA | 3' |
| 85 | 5' | GAAGAAAGAUGGAGUCAAA | 3' |
| 86 | 5' | CAUGCCUUCUUUGUUUCUA | 3' |
| 87 | 5' | CGUGACAAGAGGAAGGAAU | 3' |
| 88 | 5' | GCAAGGCACAUAGUCUACU | 3' |
| 89 | 5' | CCUGUUGUGAUAACCACUA | 3' |
| 90 | 5' | GCAAACAGAUUAAGUAACU | 3' |
| 91 | 5' | CCUACACACAUAAUCUCAU | 3' |
| 92 | 5' | GUGUGAAUUACAGGCAAGA | 3' |
| 93 | 5' | GUCUACAUUUGGAAAUGUA | 3' |

TABLE 16-continued

Sense strand sequences of PDL1 siRNAs

| Sequence number | siRNA sense strand | |  |
|---|---|---|---|
| 94 | 5' | GAGUAUGGUAGCAAUAUGA | 3' |
| 95 | 5' | GGAGAAAGGAUACUUCUGA | 3' |
| 96 | 5' | CUUGUGGUGUUUGGAUUUGU | 3' |
| 97 | 5' | GACAAGCAGUGACCAUCAA | 3' |
| 98 | 5' | CAAGCAGUGACCAUCAAGU | 3' |
| 99 | 5' | GUGGUAGAGUAUGGUAGCA | 3' |
| 100 | 5' | GUGUCAAUGACAAGGAGUA | 3' |
| 101 | 5' | GUGACAGGGAGAAAGGAUA | 3' |
| 102 | 5' | CUCCAAGCAAAUCAUCCAU | 3' |
| 103 | 5' | CCUACUGGCAUUUGCUGAA | 3' |
| 104 | 5' | GGUAUUGUUUAACAGUUCU | 3' |
| 105 | 5' | GUGACAGUGUUCUUUGUGU | 3' |
| 106 | 5' | CUGUCAAGUAUAAACUUCA | 3' |
| 107 | 5' | CAGAUGGAAUGAAUUUGAA | 3' |
| 108 | 5' | CUCAUUCGUUGUGCUUGAA | 3' |
| 109 | 5' | GAGCCAUCUUAUUAUGCCU | 3' |
| 110 | 5' | CUUUCCCUCUUGGCCAUAU | 3' |
| 111 | 5' | CUGUUGUGAUAACCACUAU | 3' |
| 112 | 5' | CAAGAUACAAACUCAAAGA | 3' |
| 113 | 5' | CAUGGGAGAUGGUUGGAAA | 3' |
| 114 | 5' | GUACAGCUGAGGAAGCAAA | 3' |
| 115 | 5' | CUGGGUGUCAAUGACAAGGA | 3' |
| 116 | 5' | CAGCUGUCAUCACUACACA | 3' |
| 117 | 5' | GAUUUGCCUUUGCCAUAUA | 3' |
| 118 | 5' | CUCCAAAUGAAAGGACUCA | 3' |
| 119 | 5' | GUCUAUUCCUAAGUCCUAA | 3' |
| 120 | 5' | GAGAGUCUCAGUGUUGGAA | 3' |
| 121 | 5' | CAGAGGAGGAGAAUGAAGA | 3' |
| 122 | 5' | CUGCACUUCAGAUCACAGA | 3' |
| 123 | 5' | CUACUGCCUUUCAUUCAUA | 3' |
| 124 | 5' | GACAGAAUCAUGUCUGGAA | 3' |
| 125 | 5' | CACCACCAAUUCCAAGAGA | 3' |
| 126 | 5' | GAGAAAGGAUACUUCUGAA | 3' |
| 127 | 5' | CUUGUGUUAUCGUUUGUA | 3' |
| 128 | 5' | GCUUGUUUAUAUAGUGUCU | 3' |
| 129 | 5' | CAUUUGCUGAACGCAUUUA | 3' |
| 130 | 5' | CUGUAUGACAGAAUCAUGU | 3' |
| 131 | 5' | CAAGUCCUGAGUGGUAAGA | 3' |
| 132 | 5' | GGAGAUUAGAUCCUGAGGA | 3' |
| 133 | 5' | GCUCAUAGUAUAAUGAGGA | 3' |
| 134 | 5' | CAUGGAGUAUUUGUAAGGU | 3' |
| 135 | 5' | CCUUUGCCAUAUAAUCUAA | 3' |
| 136 | 5' | GUUCAGCAUAGUAGCUACA | 3' |
| 137 | 5' | CAUCCUCCAAAUGAAAGGA | 3' |
| 138 | 5' | GGAUUUGUUUAUGUUUGCU | 3' |
| 139 | 5' | CACUUCAGAUCACAGAUGU | 3' |
| 140 | 5' | GGAUACUUCUGAACAAGGA | 3' |
| 141 | 5' | CACACUGAGAAUCAACACA | 3' |
| 142 | 5' | GUUCUUCUAAAGAUAGUCU | 3' |
| 143 | 5' | CAUCCAAGAUACAAACUCA | 3' |
| 144 | 5' | GAGAUUAGAUCCUGAGGAA | 3' |
| 145 | 5' | GUCAAGUAUAAACUUCACU | 3' |
| 146 | 5' | CACAUGUCAAGGCUGAAGA | 3' |
| 147 | 5' | GUCUUCUUGUCAUGUGAGU | 3' |
| 148 | 5' | CAGUGUCAUAGCAUAAGGA | 3' |
| 149 | 5' | CUGUGCAGUAUCUGUUCCA | 3' |
| 150 | 5' | CAUGUGCAUUUGUACAGUA | 3' |
| 151 | 5' | CUCUGAACAUGAACUGACA | 3' |
| 152 | 5' | GAAGUCAUCUGGACAAGCA | 3' |
| 153 | 5' | CAGUGUACCUUGACUGCUA | 3' |
| 154 | 5' | CAUCUUAUUAUGCCUUGGU | 3' |
| 155 | 5' | GCUUAAUGAUUUGCUCACA | 3' |
| 156 | 5' | CUGAGUCAAUCUAGUCCUA | 3' |
| 157 | 5' | CUUCUAAAGAUAGUCUACA | 3' |
| 158 | 5' | CAAGGACCUAUAUGUGGUA | 3' |
| 159 | 5' | CACAUAGUCUACUCAGUCU | 3' |
| 160 | 5' | CACAUUUGGAGGAGACGUA | 3' |
| 161 | 5' | CUAUUCCUAAGUCCUAACU | 3' |
| 162 | 5' | CAUAGUAUAAUGAGGAGAU | 3' |
| 163 | 5' | CUCUAGGACAGAGUUUGGA | 3' |
| 164 | 5' | CUUCUUGUCAUGUGAGUGU | 3' |
| 165 | 5' | CUACAAGUAUACAUUGGAA | 3' |
| 166 | 5' | CUUGGCCAUAUUCUGGUGU | 3' |
| 167 | 5' | GUAUGACAGAAUCAUGUCU | 3' |
| 168 | 5' | GUUAUCUGUUUGUACAUGU | 3' |

TABLE 16-continued

Sense strand sequences of PDL1 siRNAs

| Sequence number | | siRNA sense strand | |
|---|---|---|---|
| 169 | 5' | GCUUUACAAUUAUGUGGUA | 3' |
| 170 | 5' | CCAAGGACCUAUAUGUGGU | 3' |
| 171 | 5' | CAAGUAUACAUUGGAAGCA | 3' |
| 172 | 5' | CCAAAUGAAAGGACUCACU | 3' |
| 173 | 5' | GAUUUGCUCACAUCUAGUA | 3' |
| 174 | 5' | CCAUUGCUCAUCCUAGGAA | 3' |
| 175 | 5' | GAUGAUACCUAAUUCUGCA | 3' |
| 176 | 5' | GUCUUUAUAUUCAUGACCU | 3' |
| 177 | 5' | CUUCAGAUCACAGAUGUGA | 3' |
| 178 | 5' | CCUUGCAAUAUCAAUCGCU | 3' |
| 179 | 5' | CUGAACGCAUUUACUGUCA | 3' |
| 180 | 5' | GUCACCUUUAUUUAACCCA | 3' |
| 181 | 5' | GUGAUACACAUUUGGAGGA | 3' |
| 182 | 5' | CACAUUGUAUGUCUGCUGU | 3' |
| 183 | 5' | GAAUUACUGUGAAAGUCAA | 3' |
| 184 | 5' | CUCUUGGCCAUAUUCUGGU | 3' |
| 185 | 5' | CUUAAUGAUUUGCUCACAU | 3' |
| 186 | 5' | CUUGUCAUGUGAGUGUGGU | 3' |
| 187 | 5' | GUGUUUCUUAUAUAGCAGA | 3' |
| 188 | 5' | CUGAUCUUCAAGCAGGGAU | 3' |
| 189 | 5' | CAUUGUAUGUCUGCUGUGU | 3' |
| 190 | 5' | CCAAACUAAACUUGCUGCU | 3' |
| 191 | 5' | CAUUCAAGUUUCCUUUCCA | 3' |
| 192 | 5' | CUAAUUGUCUAUUGGGAAA | 3' |
| 193 | 5' | GAUACUUUCAAAUGCCUGA | 3' |
| 194 | 5' | CAUAGUAGCUACAGACAGA | 3' |
| 195 | 5' | CAGAUGUGAAAUUGCAGGA | 3' |
| 196 | 5' | CUGAAUUGGUCAUCCCAGA | 3' |
| 197 | 5' | GUUUCAUCGUAAAUGGCAU | 3' |
| 198 | 5' | GAAUGAAGAAAGAUGGAGU | 3' |
| 199 | 5' | GAUACACAUUUGGAGGAGA | 3' |
| 200 | 5' | GUUACUUGGUACACCAGCA | 3' |
| 201 | 5' | CAAGAAUUGUGGCUGAGCA | 3' |
| 202 | 5' | CUUUGAUGCUGUACUUGCA | 3' |
| 203 | 5' | CCAAUUCCAAGAGAGGA | 3' |
| 204 | 5' | GUGUUGGAUUUGUAAGGCA | 3' |
| 205 | 5' | GUAAAUAGCAGACCUCAGA | 3' |
| 206 | 5' | CUUUCCAGAAGCAACUGCU | 3' |
| 207 | 5' | CAUUUGUACAGUAAUUGGU | 3' |
| 208 | 5' | CUAUUGGGAAAUGGAGGAU | 3' |
| 209 | 5' | CUAAGUCCUAACUCCUCCU | 3' |
| 210 | 5' | GAAUCCCUAAUUUGAGGGU | 3' |
| 211 | 5' | CACUAAUUGUCUAUUGGGA | 3' |
| 212 | 5' | GAUUAAGUAACUUGCCCAA | 3' |
| 213 | 5' | CUUGAACCCUUGAAUGCCA | 3' |
| 214 | 5' | CAUUCCAGAAAGAUGAGGA | 3' |
| 215 | 5' | CAAACCAGUAAAUAGCAGA | 3' |
| 216 | 5' | CUUUCUGGAAAUUCCGGCA | 3' |

The expression vector construction method in Example 1 was repeated to construct a PDL1 siRNA expression vector.

The PDL1 siRNA and PDCD1 siRNA overexpression vectors constructed were used to study the anti-tumour effect in vivo.

1. The Inhibitory Effect of PDL1 siRNAs and PDCD1 siRNAs on the Lung Cancer

For the specific experimental materials and methods, please refer to Example 2, except that the test compounds were PDL1 siRNA plasmid and PDCD1 siRNA plasmid provided by the College of Life Sciences, Nanjing University.

The expression levels of PDL1 and PDCD1 mRNAs and proteins in the lung were detected.

Figure 50:
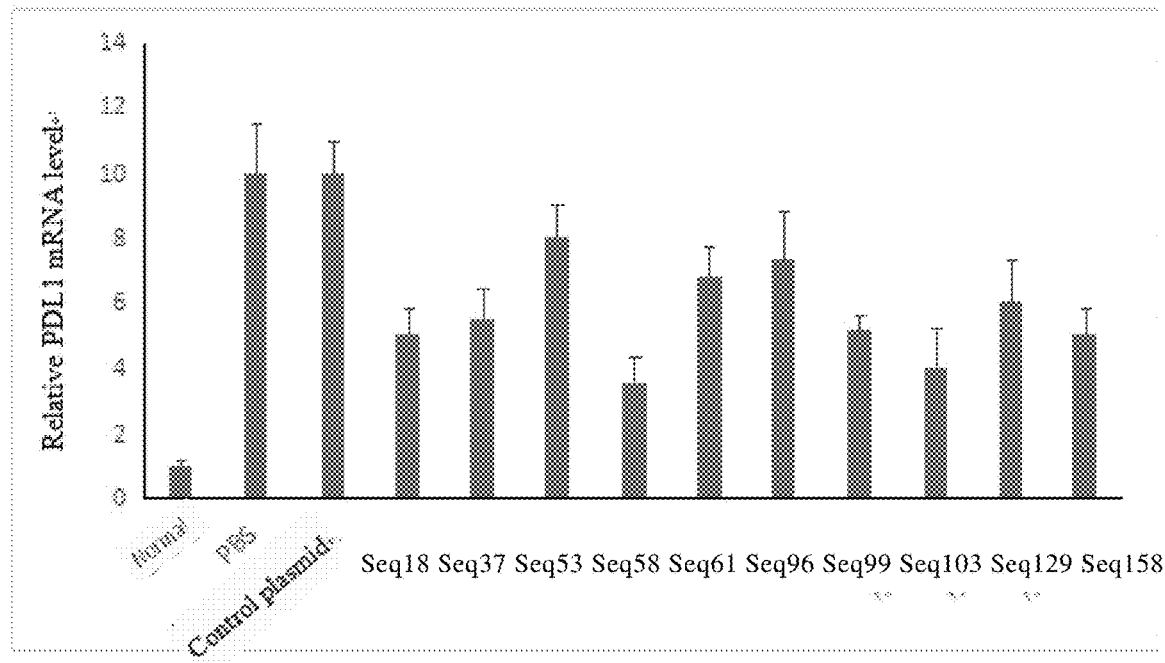
FIG. 50 shows the expression level of the PDL1 mRNA in the lung.

FIG. 50 shows the expression level of the PDL1 mRNA in the lung, and the results showed that all the plasmids constructed using the screened ten PDL1 siRNAs reduced the PDL1 mRNA level in the lung tissues and organs.

Figure 51:
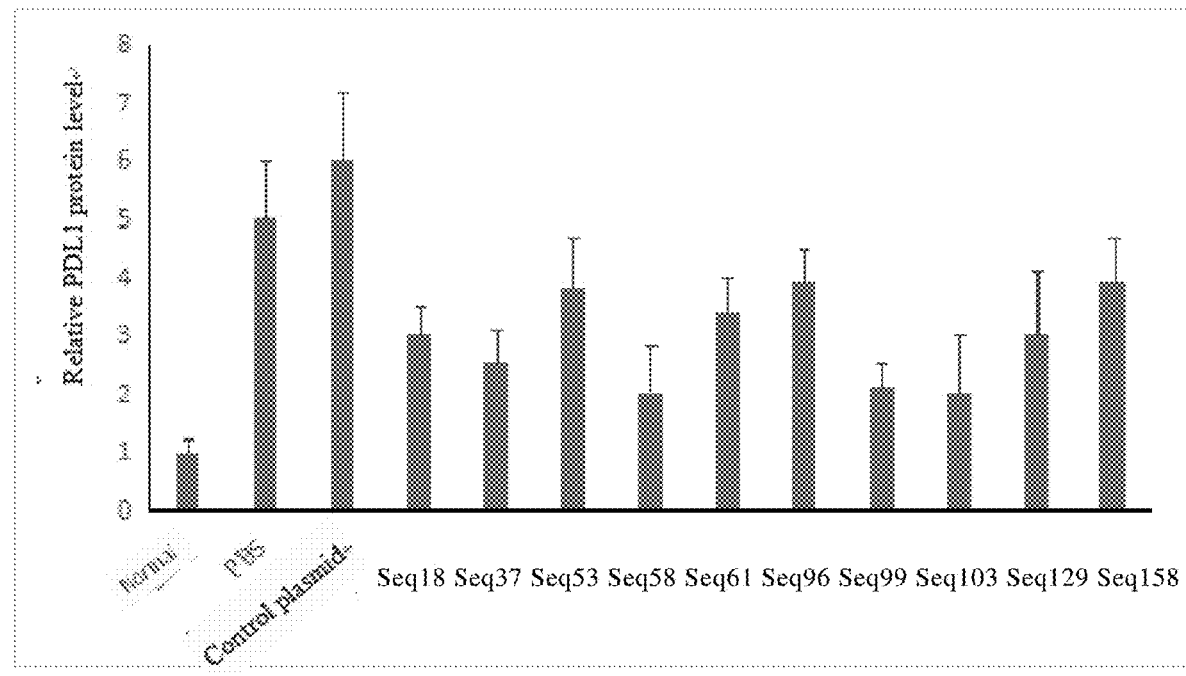
FIG. 51 shows the expression level of the PDL1 protein in the lung.

FIG. 51 shows the expression level of the PDL1 protein in the lung tissues detected using a western blotting experiment after the lung tissue proteins were extracted. The results above showed that the plasmids constructed using the screened ten PDL1 siRNAs can significantly reduce the expression level of the PDL1 protein in the lung tumour tissues.

Figure 52:
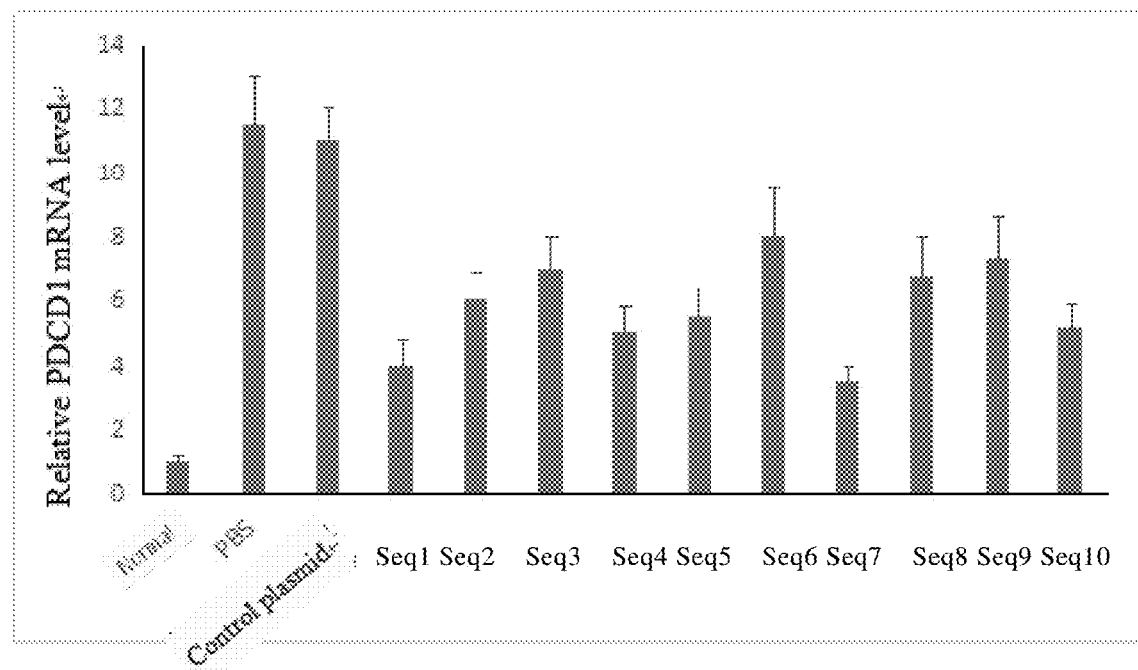
FIG. 52 shows the expression level of the PDCD1 mRNA in the lung.

FIG. 52 shows the expression level of the PDCD1 mRNA in the lung, and the results showed that all the plasmids constructed using the screened ten PDCD1 siRNAs reduced the PDCD1 mRNA level in the lung tissues and organs.

Figure 53:
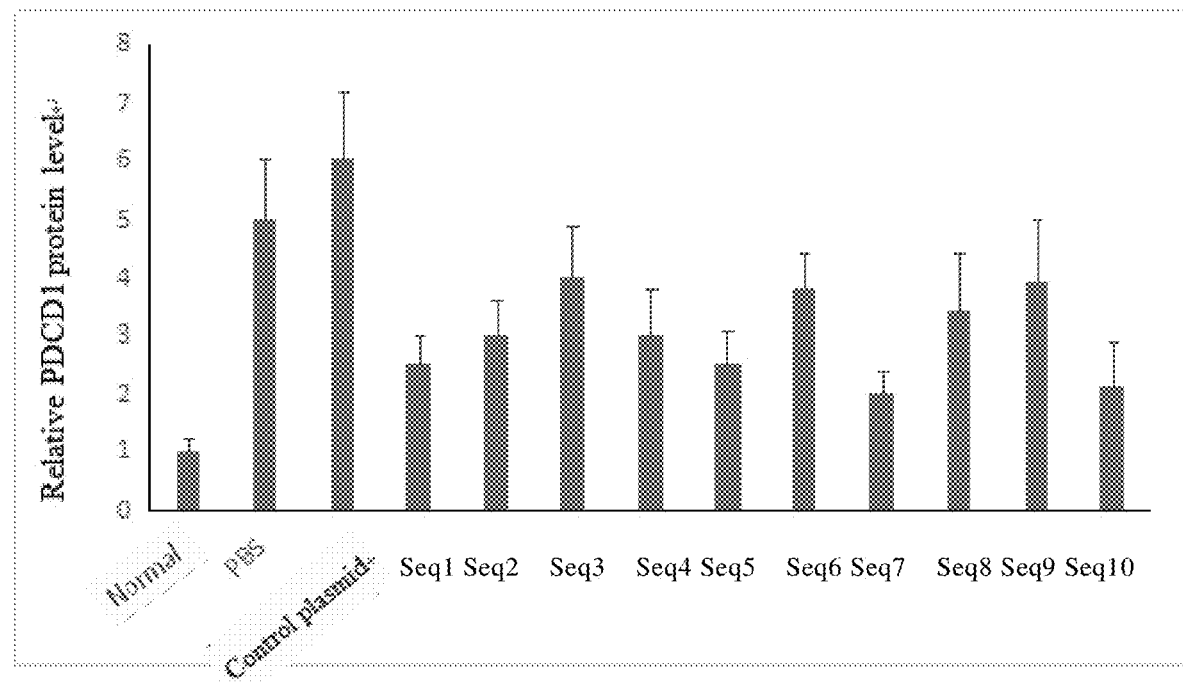
FIG. 53 shows the expression level of the PDCD1 protein in the lung.

FIG. 53 shows the expression level of the PDCD1 protein in the lung tissues detected using a western blotting experiment after the lung tissue proteins were extracted. The results above showed that the plasmids constructed using the screened ten PDCD1 siRNAs can significantly reduce the expression level of the PDCD1 protein in the lung tumour tissues.

The PDL1 siRNA plasmid and PDCD1 siRNA plasmid had a therapeutic effect on the lung cancer, and the abnormal responses related with the medication were not seen during administration.

2. The Inhibitory Effect of PDL1 siRNAs and PDCD1 siRNAs on the Melanoma

Test compounds: PDL1 siRNA plasmid and PDCD1 siRNA plasmid provided by the College of Life Sciences, Nanjing University. The compounds were diluted to desired concentrations with normal saline for injection in the experiments. The control plasmid was provided by the College of Life Sciences, Nanjing University. The compound was diluted to a desired concentration with normal saline for injection in the experiments.

Cell line: B16 mouse melanoma cell line provided by the College of Life Sciences, Nanjing University.

Experimental animals for model construction: 5-6 week-old male C57BL/6 mice provided by the Model Animal Institute, Nanjing University.

Animal model establishment: Cells in logarithmic growth phase were taken, followed by Versene digestion and resuspension with culture media to collect cells. The cell concentration was adjusted with normal saline for use. The mice were anesthetized with diethyl ether for 3-5 s, the forelimb armpit skin of mice was disinfected with 75% alcohol, and B16 mouse melanoma cells whose concentration had been adjusted were taken and inoculated subcutaneously at the forelimb armpit of mice. After inoculation at a dose of 0.2 ml/mouse, the mice were fed with a normal diet.

1 week later, tumour growth was seen in the axilla of all the tumour-bearing B16 mice, that is, the model construction was successful.

20 mice were selected, and the melanoma mice were randomly classified into four groups:

Group 1: mice injected with PBS on the left axilla subcutaneously (negative control group);

Group 2: mice injected with the control plasmid (5 mg/kg) on the left axilla subcutaneously;

Group 3: mice injected with the PDL1 siRNA plasmid (5 mg/kg) on the left axilla subcutaneously; and Group 4: mice injected with the PDCD1 siRNA plasmid (5 mg/kg) on the left axilla subcutaneously.

In addition, another group of normal mice was taken and used as a normal control. During model construction, the existing condition, tumour size and appearance of the tumour-bearing mice were observed periodically. Starting from day 14, the mice were administered with 0.1 ml/10 g body weight by intravenous tail injection, and the control group was administered with the corresponding amount of normal saline. During administration, the mice were administered with same once every 3 days, 7 times in total. On day 3 after the final administration, the mice were anaesthetized with diethyl ether, the skin was incised quickly at the site of tumour growth, and the tumour was completely excised.

The levels of PDL1 and PDCD1 mRNAs and proteins in the transplanted tumours were detected according to Example 2.

Figure 54:
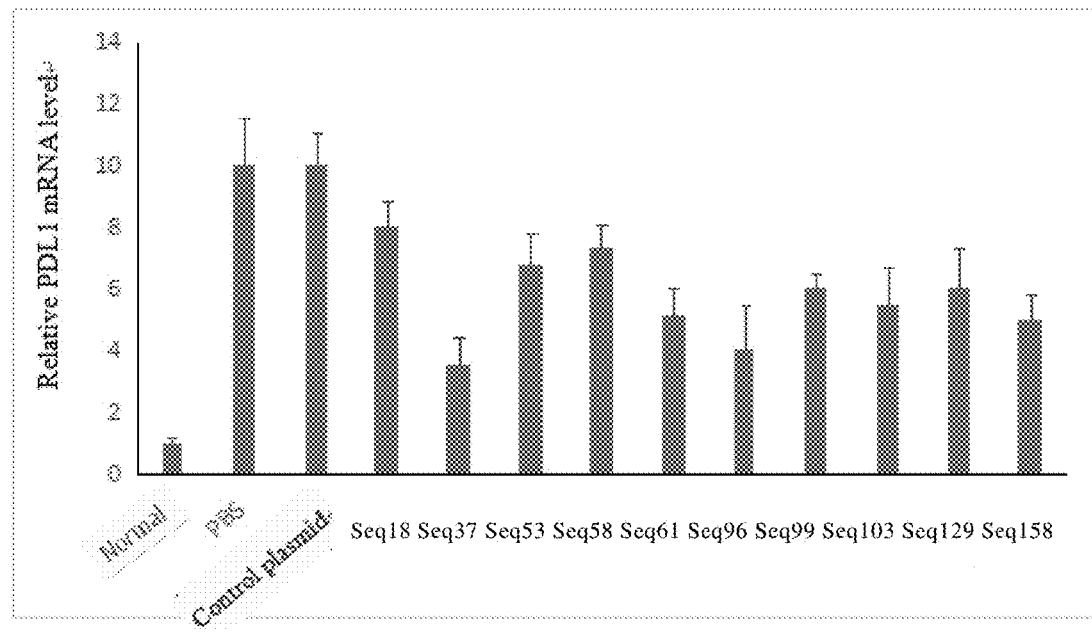
FIG. 54 shows the expression level of the PDL1 mRNA in melanoma transplanted tumours.

FIG. 54 shows the expression level of the PDL1 mRNA in the melanoma transplanted tumours, and the results showed that all the plasmids constructed using the screened ten PDL1 siRNAs reduced the PDL1 mRNA level in the melanoma transplanted tumours.

Figure 55:
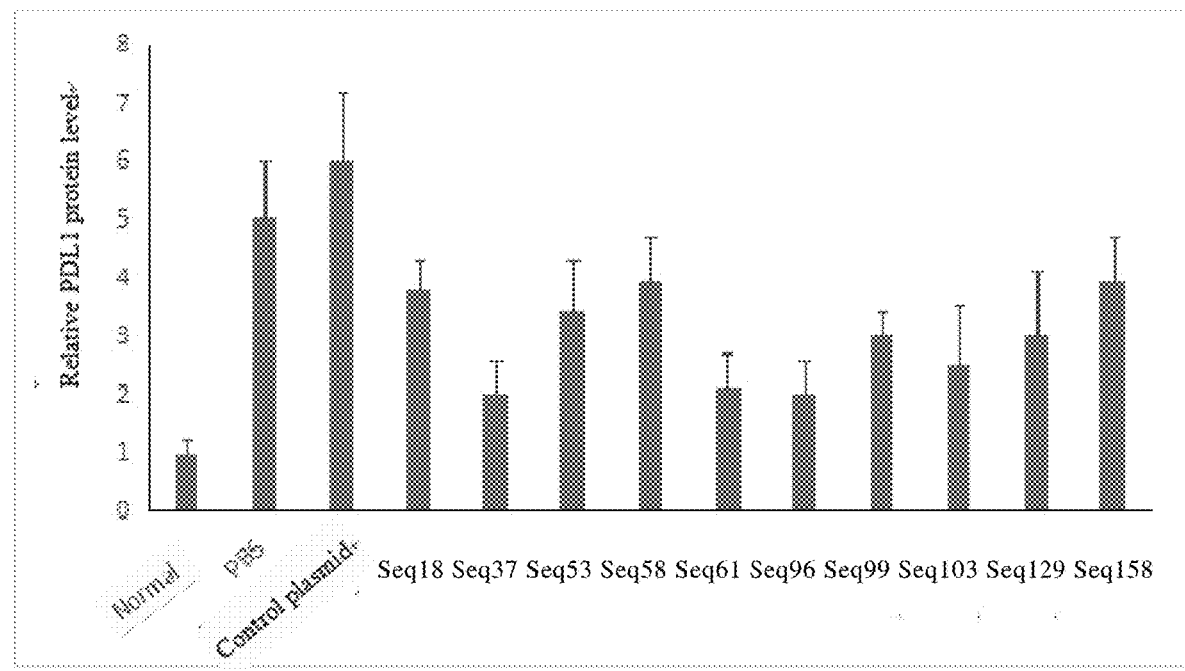
FIG. 55 shows the expression level of the PDL1 protein in melanoma transplanted tumours.

FIG. 55 shows the expression level of the PDL1 protein in the transplanted tumour tissues detected using a western blotting experiment after the transplanted tumour tissue proteins were extracted. The results above showed that the plasmids constructed using the screened ten PDL1 siRNAs can significantly reduce the expression level of the PDL1 protein in the melanoma transplanted tumours.

Figure 56:
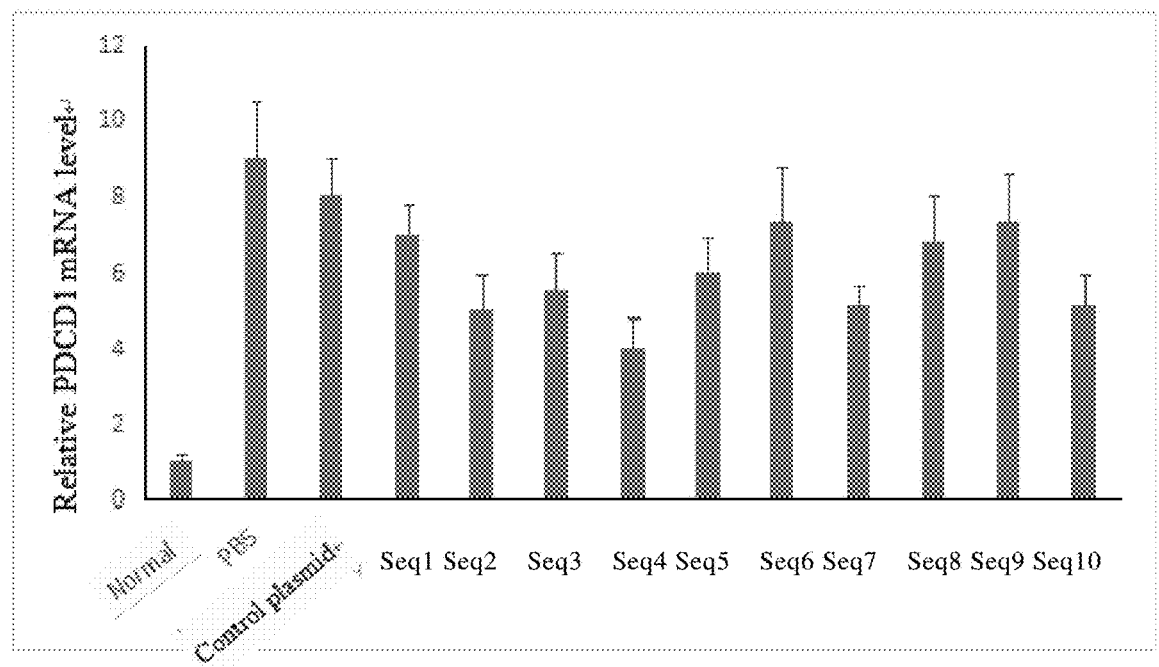
FIG. 56 shows the expression level of the PDCD1 mRNA in melanoma transplanted tumours.

FIG. 56 shows the expression level of the PDCD1 mRNA in the melanoma transplanted tumours, and the results showed that all the plasmids constructed using the screened ten PDCD1 siRNAs reduced the PDCD1 mRNA level in the melanoma transplanted tumours.

Figure 57:
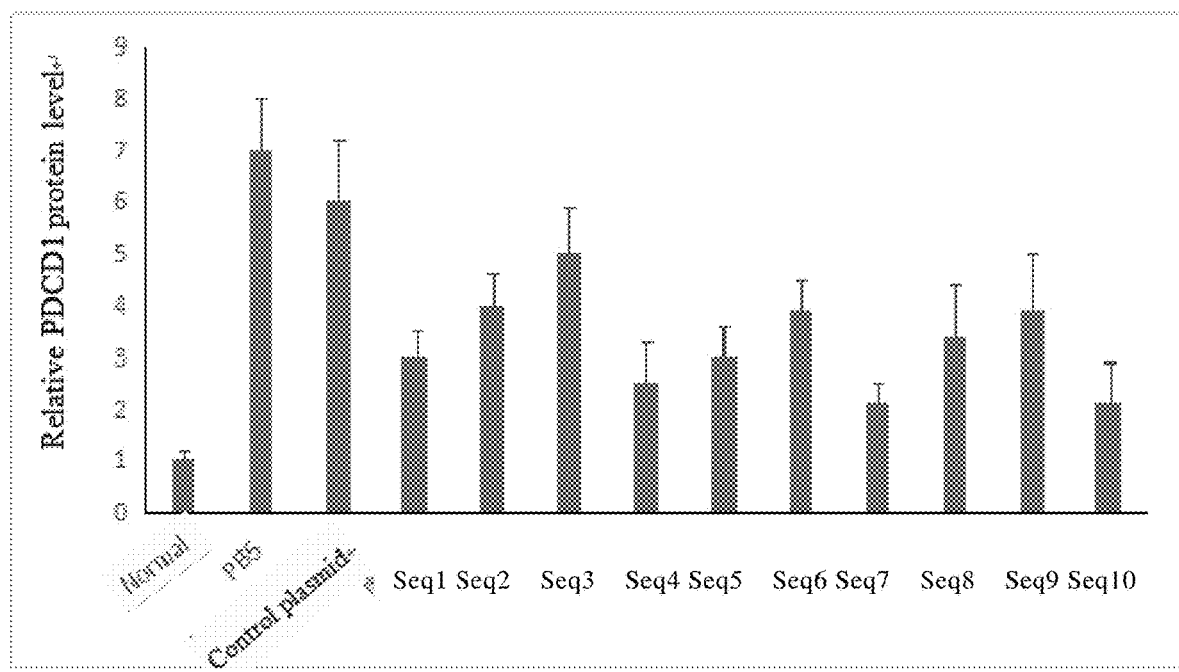
FIG. 57 shows the expression level of the PDCD1 protein in melanoma transplanted tumours.

FIG. 57 shows the expression level of the PDCD1 protein in the lung tissues detected using a western blotting experiment after the transplanted tumour tissue proteins were extracted. The results above showed that the plasmids constructed using the screened ten PDCD1 siRNAs can significantly reduce the expression level of the PDCD1 protein in the melanoma transplanted tumours.

The PDL1 siRNA plasmid and PDCD1 siRNA plasmid had a therapeutic effect on melanoma, and the abnormal responses related with the medication were not seen during administration.

The PDL1 siRNA and PDCD1 siRNA can effectively block the PDL1/PDCD1 pathway, and effectively inhibit the tumour growth. Accordingly, using the PDL1 siRNA and the PDCD1 siRNA in combination will have a better inhibitory effect on tumours, and can inhibit non-small cell lung cancer, melanoma, breast cancer, stomach cancer, intestinal cancer, esophageal cancer, ovarian cancer, cervical cancer, pancreatic cancer, renal cancer, bladder cancer, etc., and intervention of PD-1/PD-L1 signaling will become a new strategy for tumour immunotherapy.

Example 14: ALK siRNAs were Effectively Expressed by a Precursor Sequence and had a Therapeutic Effect on Cancer Furthermore, ALK siRNAs can be effectively expressed by a precursor sequence and have a therapeutic effect on cancer.

121 possible siRNA sequences were designed for the ALK gene locus in this example, and please refer to Table 17 for the sequences. Ten siRNA sequences with excellent stability and evident specific inhibitory effects were further screened from the siRNA sequences above for the expression verification. The sequence numbers of the ten siRNAs in Table 17 were 6, 11, 16, 19, 23, 27, 30, 32, 40 and 41, respectively.

TABLE 17

Sense strand sequences of ALK siRNAs

| Sequence number | | siRNA sense strand | |
|---|---|---|---|
| 1 | 5' | GGCCUGUAUACCGGAUAAU | 3' |
| 2 | 5' | GCCCUGAUCAUCAGCAAAU | 3' |
| 3 | 5' | GAGCCACCUACGUAUUUAA | 3' |
| 4 | 5' | GGAGCCACCUACGUAUUUA | 3' |
| 5 | 5' | GGGCGAGCUACUAUAGAAA | 3' |
| 6 | 5' | GGAGAGGGAACGGAAAUAA | 3' |
| 7 | 5' | CCAGUACAAACCAGUUAAU | 3' |
| 8 | 5' | CCCAGUACAAACCAGUUAA | 3' |
| 9 | 5' | GGUGGCUGGAAUGAUAACA | 3' |
| 10 | 5' | CCACCUACGUAUUUAAGAU | 3' |
| 11 | 5' | GCUGCUUCUAUGUUUCAUA | 3' |
| 12 | 5' | GAGUGCUGCUAUGGGAAAU | 3' |

TABLE 17-continued

Sense strand sequences of ALK siRNAs

| Sequence number | siRNA sense strand | |  |
|---|---|---|---|
| 13 | 5' | CCGGCAUCAUGAUUGUGUA | 3' |
| 14 | 5' | GUGCUGCUAUGGGAAAUCU | 3' |
| 15 | 5' | CAGAGAGACUGGAGAAUAA | 3' |
| 16 | 5' | GUGGACAUGAGCCAUUUGA | 3' |
| 17 | 5' | GCUCCUUUCUCCUUCUCAA | 3' |
| 18 | 5' | GCUCCUGGUUUACAGAGAA | 3' |
| 19 | 5' | CCUCCCUUCAACCAUAGUA | 3' |
| 20 | 5' | CUGCAUUGGAGAGAACAAU | 3' |
| 21 | 5' | CUCCUGGUUUACAGAGAAA | 3' |
| 22 | 5' | GCUGGUCAUUACGAGGAUA | 3' |
| 23 | 5' | GGUCAUAGCUCCUUGGAAU | 3' |
| 24 | 5' | GCUUCAAUGUAGUCAGAAU | 3' |
| 25 | 5' | CAGCACCCAAAUCAAGAAA | 3' |
| 26 | 5' | GCAGAAUACAGCACCCAAA | 3' |
| 27 | 5' | GCUUCCAGGUCUGUUUCAU | 3' |
| 28 | 5' | GAGCAUGGGUUCAUCCUAU | 3' |
| 29 | 5' | CUUGUGGGAAUGUCAAUUA | 3' |
| 30 | 5' | GCCUUGUUGAUGUGGACAU | 3' |
| 31 | 5' | GUGGCUGUCAGUAUUUGGA | 3' |
| 32 | 5' | CAGGUCUGUUUCAUUUAGA | 3' |
| 33 | 5' | CCUUAUGCUUCUUUCAAAU | 3' |
| 34 | 5' | CACGUGAAUAUGGCAUUCU | 3' |
| 35 | 5' | CUCCUUCACUUGUUGGAAU | 3' |
| 36 | 5' | CAUGGGUUCAUCCUAUUCU | 3' |
| 37 | 5' | CUGUGAGGUAGACGAAUGU | 3' |
| 38 | 5' | GAGAGAACAAUGUGAUAGA | 3' |
| 39 | 5' | GAAGGAAUAUUCACUUCUA | 3' |
| 40 | 5' | GUCAGAAUUAGCUGCUUCU | 3' |
| 41 | 5' | CUCCUUGGAAUCACCAACA | 3' |
| 42 | 5' | CCUACGUAUUUAAGAUGAA | 3' |
| 43 | 5' | GGAAGGAAUAUUCACUUCU | 3' |
| 44 | 5' | GCAUUGGAGAGAACAAUGU | 3' |
| 45 | 5' | GGAGUUAUUUGUAAUGACU | 3' |
| 46 | 5' | GCCGAUAGAAUAUGGUCCA | 3' |
| 47 | 5' | GGGAAGUGAAUAUUAAGCA | 3' |
| 48 | 5' | GCAUCUUCAACCUGGAGAA | 3' |
| 49 | 5' | CUGCCAAUAUGAAGGAGGU | 3' |
| 50 | 5' | GGACACGUGAAUAUGGCAU | 3' |
| 51 | 5' | GAGAAGAUGAGAGCCAGAU | 3' |
| 52 | 5' | CUGAUCAUCAGCAAAUUCA | 3' |
| 53 | 5' | GGAAGUGAAUAUUAAGCAU | 3' |
| 54 | 5' | GAAGAUGAGAGCCAGAUGU | 3' |
| 55 | 5' | CGCUUCUGAAAGUGCUACA | 3' |
| 56 | 5' | GAGGAUAUAUAGGCGGCAA | 3' |
| 57 | 5' | CAUGCUCUAUUGCUCAGUA | 3' |
| 58 | 5' | CUCCUUCACAAACCAGAGA | 3' |
| 59 | 5' | CUGCUCCAGUUCAAUCUCA | 3' |
| 60 | 5' | CUGCUUCAAUGUAGUCAGA | 3' |
| 61 | 5' | GUACCAAGGACUGUUCAGA | 3' |
| 62 | 5' | GAAACCUGUUUGAGAGAAA | 3' |
| 63 | 5' | GUGAGGUAGACGAAUGUCA | 3' |
| 64 | 5' | GAACUGCAGUGAAGGAACA | 3' |
| 65 | 5' | CCAUCUUUGACCCUACAGU | 3' |
| 66 | 5' | CACACUCACUUCUCUUCCU | 3' |
| 67 | 5' | CACAAGGUCAUCUGCUUCU | 3' |
| 68 | 5' | GCAAAUUCAACCACCAGAA | 3' |
| 69 | 5' | CCCAAAUCAAGAAACCUGU | 3' |
| 70 | 5' | CAAGAGAGAUCCUCCUGAU | 3' |
| 71 | 5' | GCUGUCAGUAUUUGGAGGA | 3' |
| 72 | 5' | CAUGGAAUCUCACCUGGAU | 3' |
| 73 | 5' | CAUGGAAGGAAUAUUCACU | 3' |
| 74 | 5' | CCAUGCUCUAUUGCUCAGU | 3' |
| 75 | 5' | CUGAAAGCCACAAGGUCAU | 3' |
| 76 | 5' | GUUCAUCCUAUUCUUUCGA | 3' |
| 77 | 5' | CUGUCAGUAUUUGGAGGAA | 3' |
| 78 | 5' | CAGAGACCAAAUGUCACGU | 3' |
| 79 | 5' | GUCAUUACGAGGAUACCAU | 3' |
| 80 | 5' | CUGAAAGGCAUCCAGAUCU | 3' |
| 81 | 5' | CUUUGACCCUACAGUUCAU | 3' |
| 82 | 5' | CUGAGUACAAGCUGAGCAA | 3' |
| 83 | 5' | CACCAGAACAUUGUUCGCU | 3' |
| 84 | 5' | CCAUAGUAGUUCCUCUGUA | 3' |
| 85 | 5' | GGAACGGAAAUAAAGGAGU | 3' |
| 86 | 5' | CAAUGUGAUAGAAGAAGAA | 3' |
| 87 | 5' | GGGAAUGUCAAUUACGGCU | 3' |

TABLE 17-continued

Sense strand sequences of ALK siRNAs

| Sequence number | siRNA sense strand | | |
|---|---|---|---|
| 88 | 5' | GAAAGCCACAAGGUCAUCU | 3' |
| 89 | 5' | GAAUACAGCACCCAAAUCA | 3' |
| 90 | 5' | CGGAUAAUGACUCAGUGCU | 3' |
| 91 | 5' | CUCUGCUUCAAUGUAGUCA | 3' |
| 92 | 5' | CACUUGUGGAAGAGGAAGA | 3' |
| 93 | 5' | GUACAAACCAGUUAAUCCA | 3' |
| 94 | 5' | CUCUUGGAUAUAUGCCAUA | 3' |
| 95 | 5' | GAGCUACUAUAGAAAGGGA | 3' |
| 96 | 5' | GAAGAAGAAAUCCGUGUGA | 3' |
| 97 | 5' | GUAGUCAGAAUUAGCUGCU | 3' |
| 98 | 5' | CAACCAUAGUAGUUCCUCU | 3' |
| 99 | 5' | CUUGUUGGAAUGGGACAGU | 3' |
| 100 | 5' | CUUCUUUCAAAUUGUGUGU | 3' |
| 101 | 5' | CAUUGGCUGUUCACCACAU | 3' |
| 102 | 5' | GCAUUAUCUAAACUGCAGU | 3' |
| 103 | 5' | CAAACCAGUUAAUCCAGAA | 3' |
| 104 | 5' | CUUGCCUUGUUGAUGUGGA | 3' |
| 105 | 5' | GUUCUGGAGUUUGUCACCA | 3' |
| 106 | 5' | GGAAUGUCAAUUACGGCUA | 3' |
| 107 | 5' | CUGUUUCAUUUAGACUCCU | 3' |
| 108 | 5' | CGAUAGAAUAUGGUCCACU | 3' |
| 109 | 5' | CACUUCUCUUCCUUGGGAU | 3' |
| 110 | 5' | GAUAGAAGAAGAAAUCCGU | 3' |
| 111 | 5' | CUGUUUGAGAGAAACCCAA | 3' |
| 112 | 5' | CUUUGAAGAUGGCUUCUGU | 3' |
| 113 | 5' | GAAACCCAAACAAGGAGCU | 3' |
| 114 | 5' | GAAUACAUCUCCAGUGGAA | 3' |
| 115 | 5' | GGAUUGAAUACUGCACCCA | 3' |
| 116 | 5' | CUUUCAAAUUGUGUGUGCU | 3' |
| 117 | 5' | GAAAGUGCUACAGUGACCA | 3' |
| 118 | 5' | GAUAACACUUCCUUGCUCU | 3' |
| 119 | 5' | GAUAAAUACAAGGCCCAGA | 3' |
| 120 | 5' | GUGAUAAAUACAAGGCCCA | 3' |
| 121 | 5' | CAUAGAUGUUUCCUUGCCU | 3' |

The expression vector construction method in Example 1 was repeated to construct an ALK siRNA expression vector.

The ALK siRNA overexpression vector constructed was used to study the anti-tumour effect in vivo.

For the specific experimental materials and methods, please refer to Example 2, except that the test compound was ALK siRNA plasmid provided by the College of Life Sciences, Nanjing University.

The expression levels of the ALK mRNA and the protein in the lung were detected.

Figure 58:
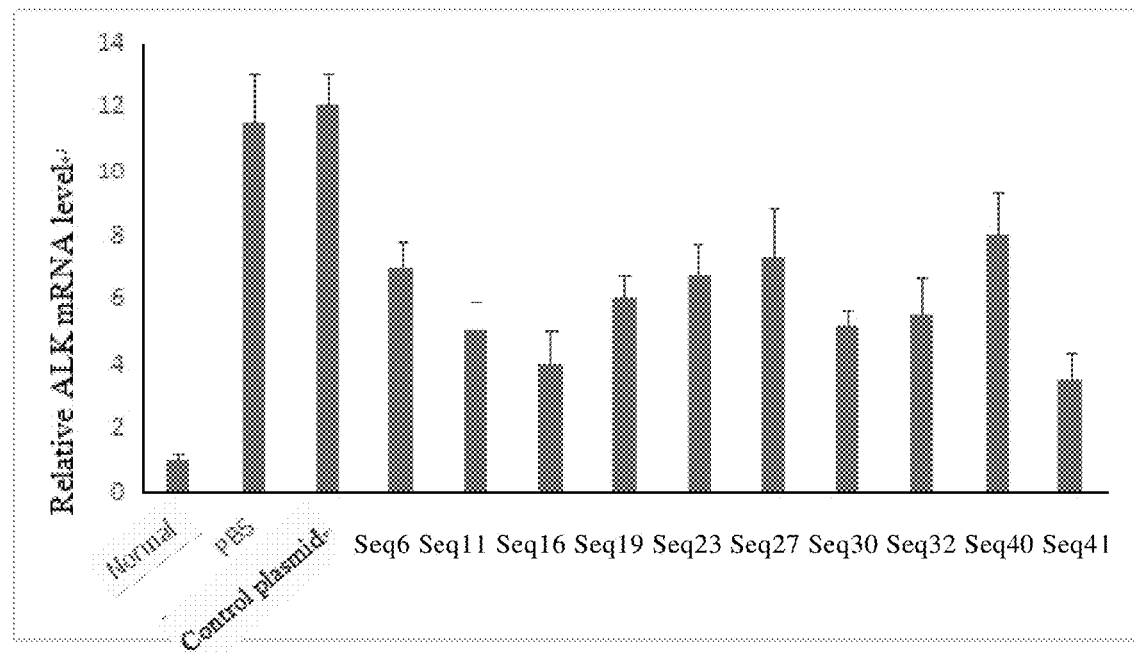
FIG. 58 shows the expression level of the ALK mRNA in the lung.

FIG. 58 shows the expression level of the ALK mRNA, and the results showed that all the plasmids constructed using the screened ten ALK siRNAs reduced the ALK mRNA level in the lung tissues and organs.

Figure 59:
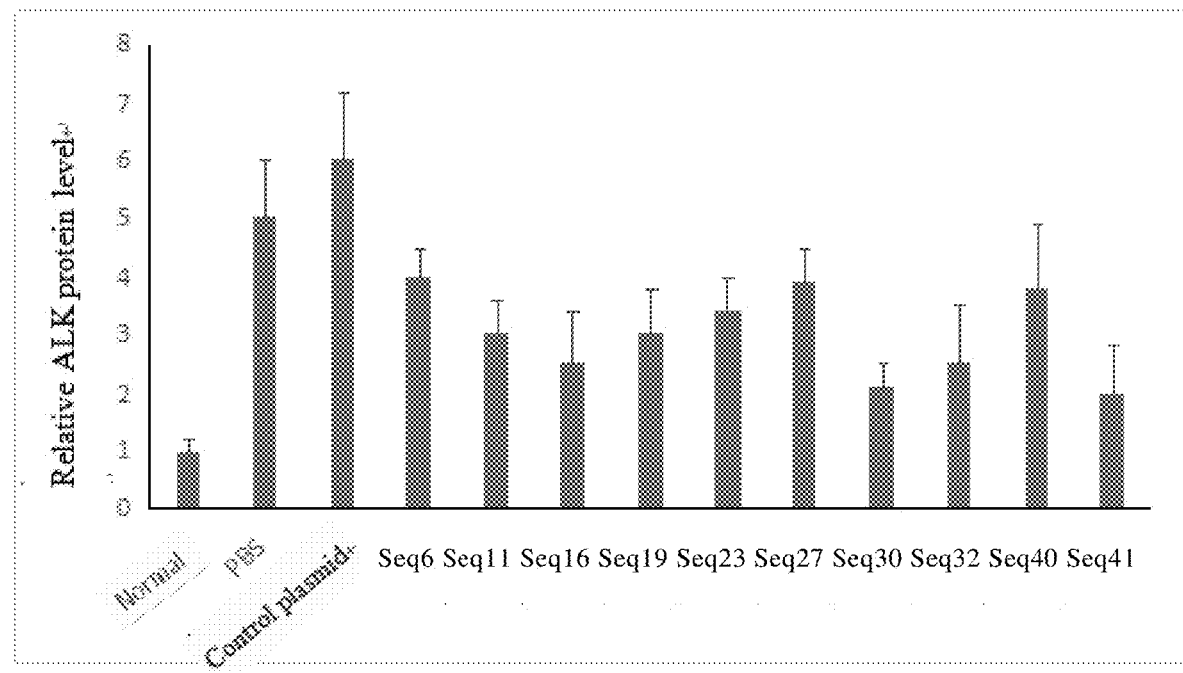
FIG. 59 shows the expression level of the ALK protein in the lung tissues detected using a western blotting experiment after the lung tissue proteins are extracted.

FIG. 59 shows the expression level of the ALK protein in the lung tissues detected using a western blotting experiment after the lung tissue proteins were extracted. The results above showed that the plasmids constructed using the screened ten ALK siRNAs can significantly reduce the expression level of the ALK protein in the lung tumour tissues.

The ALK siRNA plasmid had a therapeutic effect on the lung cancer, and the abnormal responses related with the medication were not seen during administration.

Example 15: IDO1 siRNAs were Effectively Expressed by a Precursor Sequence

Furthermore, IDO1 siRNAs can be effectively expressed by a precursor sequence and have a therapeutic effect on cancer.

107 possible siRNA sequences were designed for the IDO1 gene locus in this example, and please refer to Table 18 for the sequences. Ten siRNA sequences with excellent stability and evident specific inhibitory effects were further screened from the siRNA sequences above for the expression verification. The sequence numbers of the ten siRNAs in Table 18 were 2, 4, 8, 9, 11, 13, 26, 28, 29 and 47, respectively.

TABLE 18

Sense strand sequences of IDO1 siRNAs

| Sequence number | siRNA sense strand | | |
|---|---|---|---|
| 1 | 5' | GGAGCUACCAUCUGCAAAU | 3' |
| 2 | 5' | GUGGCAGCAACUAUUAUAA | 3' |
| 3 | 5' | GUGCUCAUUAGAGUCAAAU | 3' |
| 4 | 5' | GCAGCAACUAUUAUAAGAU | 3' |
| 5 | 5' | GAGGCACUGAUUUAAUGAA | 3' |
| 6 | 5' | CAGGACAUGAGAAGAUAUA | 3' |
| 7 | 5' | CCCUGACUUAUGAGAACAU | 3' |
| 8 | 5' | GGCAGCAACUAUUAUAAGA | 3' |
| 9 | 5' | GAGCCACAAACUAAUACUA | 3' |
| 10 | 5' | GCGUCUUUCAGUGCUUUGA | 3' |
| 11 | 5' | CUCCUGGACAAUCAGUAAA | 3' |
| 12 | 5' | CCUGGACAAUCAGUAAAGA | 3' |
| 13 | 5' | GAGGAGCAGACUACAAGAA | 3' |
| 14 | 5' | CAGUGUUCUUCGCAUAUAU | 3' |
| 15 | 5' | GGCAAUGCAAAUGCAAGAA | 3' |
| 16 | 5' | CAGCAGCCAAAGGAGAAUA | 3' |

TABLE 18-continued

Sense strand sequences of IDO1 siRNAs

| Sequence number | siRNA sense strand | |  |
|---|---|---|---|
| 17 | 5' | CUCCAGGACAUGAGAAGAU | 3' |
| 18 | 5' | CCGUGAGUUUGUCCUUUCA | 3' |
| 19 | 5' | GACUGUGUCUUGGCAAACU | 3' |
| 20 | 5' | CCUCUGAAGACCCUUCAAA | 3' |
| 21 | 5' | GCUGUUGGAAAUAGCUUCU | 3' |
| 22 | 5' | GACUGCAGUAAAGGAUUCU | 3' |
| 23 | 5' | GUACCAUAUUGAUGAAGAA | 3' |
| 24 | 5' | GCAUCACCAUGGCAUAUGU | 3' |
| 25 | 5' | GGAUGUUCAUUGCUAAACA | 3' |
| 26 | 5' | CCUGUCAUUACCCAUUGUA | 3' |
| 27 | 5' | GUGAGUUUGUCCUUUCAAA | 3' |
| 28 | 5' | GAGACCAUCUUGGCUAACA | 3' |
| 29 | 5' | GUGCAUUUCUUGUAGGAAA | 3' |
| 30 | 5' | GCUUCUGCAAUCAAAGUAA | 3' |
| 31 | 5' | CCUGAAGACUGUAAGAAGU | 3' |
| 32 | 5' | GUUCUUCGCAUAUAUUUGU | 3' |
| 33 | 5' | GAUGUUCAUUGCUAAACAU | 3' |
| 34 | 5' | GACUGUAAGAAGUACAACU | 3' |
| 35 | 5' | GGAGACUGCAGUAAAGGAU | 3' |
| 36 | 5' | GAGUUGAGAAGUUAAACAU | 3' |
| 37 | 5' | CUUCUGCAAUCAAAGUAAU | 3' |
| 38 | 5' | GGUUAAUGUAACCCAACAA | 3' |
| 39 | 5' | CUUGGAGAAAGCCCUUCAA | 3' |
| 40 | 5' | GUCUCUCUAUUGGUGGAAA | 3' |
| 41 | 5' | GCUACCAUCUGCAAAUCGU | 3' |
| 42 | 5' | GCAGAGACAUCUGUAUGCA | 3' |
| 43 | 5' | GGUCUCUCUAUUGGUGGAA | 3' |
| 44 | 5' | GUGAUGGAGACUGCAGUAA | 3' |
| 45 | 5' | GUCAUGGAGAUGUCCGUAA | 3' |
| 46 | 5' | CAGACUGUGUCUUGGCAAA | 3' |
| 47 | 5' | CCCUGUGAUAAACUGUGGU | 3' |
| 48 | 5' | GUUCCUUACUGCCAACUCU | 3' |
| 49 | 5' | GGAAAUAGCAGCUGCUUCU | 3' |
| 50 | 5' | GCAACUAUUAUAAGAUGCU | 3' |
| 51 | 5' | CUGUGCUCAUUAGAGUCAA | 3' |
| 52 | 5' | CCUGUGCUCAUUAGAGUCA | 3' |
| 53 | 5' | CAGCAUUGAUCAUCUCACA | 3' |
| 54 | 5' | GUAAGGUCUUGCCAAGAAA | 3' |
| 55 | 5' | GCAAAGGUCAUGGAGAUGU | 3' |
| 56 | 5' | GAACGGGACACUUUGCUAA | 3' |
| 57 | 5' | CGUAAGGUCUUGCCAAGAA | 3' |
| 58 | 5' | CUACUGUAUUCAAGGCAAU | 3' |
| 59 | 5' | CCAUCUGCAAAUCGUGACU | 3' |
| 60 | 5' | GUCUUGGCAAACUGGAAGA | 3' |
| 61 | 5' | CUGUUCCUUACUGCCAACU | 3' |
| 62 | 5' | CUUGCCAAGAAAUAUUGCU | 3' |
| 63 | 5' | CUGUAUGCAUUCCUGUCAU | 3' |
| 64 | 5' | GACUGGAUGUUCAUUGCUA | 3' |
| 65 | 5' | GUCUAGUUCUGGGAUGCAU | 3' |
| 66 | 5' | GAAGACUGUAAGAAGUACA | 3' |
| 67 | 5' | CUUCAAGUGUUUCACCAAA | 3' |
| 68 | 5' | GACAUCUGUAUGCAUUCCU | 3' |
| 69 | 5' | GUGAUAAACUGUGGUCACU | 3' |
| 70 | 5' | CCCUUCAAGUGUUUCACCA | 3' |
| 71 | 5' | GUGACUAAGUACAUCCUGA | 3' |
| 72 | 5' | GCAGACUACAAGAAUGGCA | 3' |
| 73 | 5' | GUAAUUCCUACUGUAUUCA | 3' |
| 74 | 5' | GUUUCACCAAAUCCACGAU | 3' |
| 75 | 5' | CAUCUGCAAAUCGUGACUA | 3' |
| 76 | 5' | GAAGGUUAAUGUAACCCAA | 3' |
| 77 | 5' | GUAAAGAGUACCAUAUUGA | 3' |
| 78 | 5' | CUGUGCAUUUCUUGUAGGA | 3' |
| 79 | 5' | GUUCUCAUUUCGUGAUGGA | 3' |
| 80 | 5' | GCAUUGAUCAUCUCACAGA | 3' |
| 81 | 5' | CUGUAUCUUAUCAUUGGAA | 3' |
| 82 | 5' | CCUACUGUAUUCAAGGCAA | 3' |
| 83 | 5' | CUGUAUUCAAGGCAAUGCA | 3' |
| 84 | 5' | GAUUCUUCCUGGUCUCUCU | 3' |
| 85 | 5' | CUUCGAGAAAGAGUUGAGA | 3' |
| 86 | 5' | CAUUGUAACAGAGCCACAA | 3' |
| 87 | 5' | GAUCAUCUCACAGACCACA | 3' |
| 88 | 5' | CACAAACUAAUACUAUGCA | 3' |
| 89 | 5' | CGCAUAUAUUUGUCUGGCU | 3' |
| 90 | 5' | GAGAAGAUAUAUGCCACCA | 3' |
| 91 | 5' | CUGUGAUAAACUGUGGUCA | 3' |

TABLE 18-continued

Sense strand sequences of IDO1 siRNAs

| Sequence number | | siRNA sense strand | |
|---|---|---|---|
| 92 | 5' | GGAAGGUUAAUGUAACCCA | 3' |
| 93 | 5' | GAGAAGUUAAACAUGCUCA | 3' |
| 94 | 5' | CAAAGUAAUUCCUACUGUA | 3' |
| 95 | 5' | GUAAGAAGUACAACUGAGA | 3' |
| 96 | 5' | GUACAACUGAGAAAUCCCU | 3' |
| 97 | 5' | CUUACUGCCAACUCUCCAA | 3' |
| 98 | 5' | CUAAACAUCUGCCUGAUCU | 3' |
| 99 | 5' | CCAAAGGAGAAUAAGACCU | 3' |
| 100 | 5' | CAAUCAGUAAAGAGUACCA | 3' |
| 101 | 5' | GCAUUCCUGUCAUUACCCA | 3' |
| 102 | 5' | CAAAUCGUGACUAAGUACA | 3' |
| 103 | 5' | CAUGAAGAUAUAUGCCA | 3' |
| 104 | 5' | GUAAAGGAUUCUUCCUGGU | 3' |
| 105 | 5' | CUUAUGAGAACAUGGACGU | 3' |
| 106 | 5' | CAUUACCCAUUGUAACAGA | 3' |
| 107 | 5' | CAUUGCUAAACAUCUGCCU | 3' |

The expression vector construction method in Example 1 was repeated to construct an IDO1 siRNA expression vector.

The IDO1 siRNA overexpression vector constructed was used to study the anti-tumour effect in vivo, and the inhibitory effect of such a vector on lung cancer, colorectal cancer and pancreatic cancer was observed.

1. IDO1 siRNAs have an Inhibitory Effect on the Lung Cancer.

For the specific experimental materials and methods, please refer to Example 2, except that the test compound was IDO1 siRNA plasmid provided by the College of Life Sciences, Nanjing University.

The expression levels of the IDO1 mRNA and the protein in the lung were detected.

Figure 60:
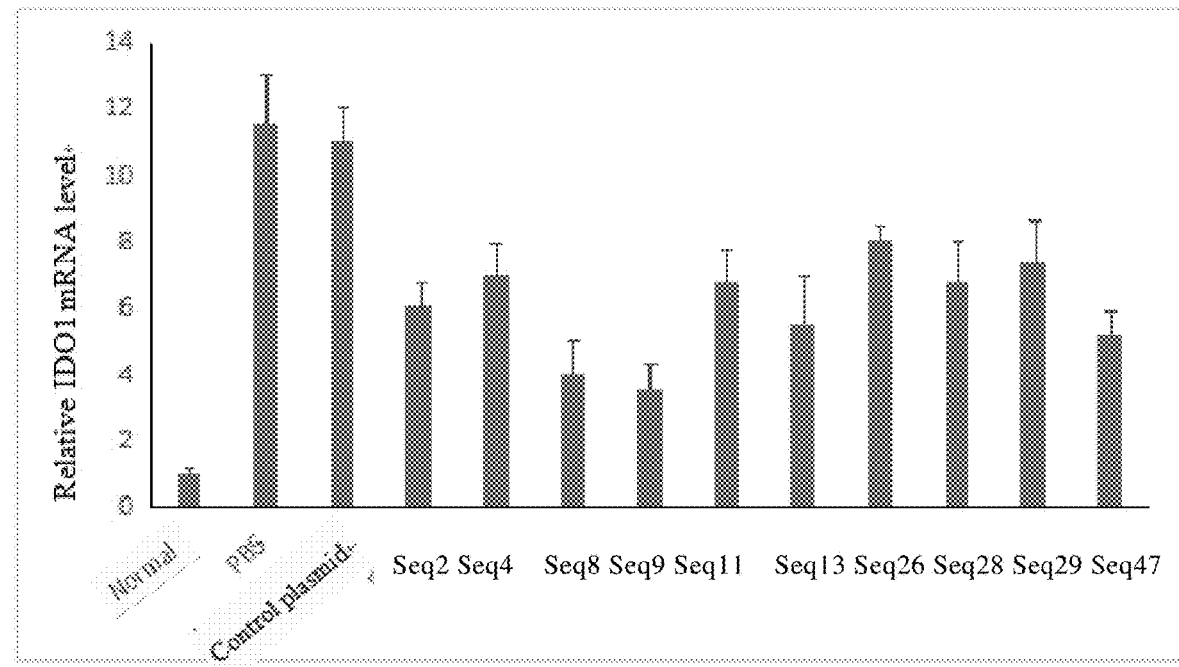
FIG. 60 shows the expression level of the IDO1 mRNA in the lung, and the results show that all the plasmids constructed using the screened ten IDO1 siRNAs reduce the mRNA level of IDO1 in the lung tissues and organs.

FIG. 60 shows the expression level of IDO1 mRNAs, and the results showed that all the plasmids constructed using the screened ten IDO1 siRNAs reduced the IDO1 mRNA level in the lung tissues and organs.

Figure 61:
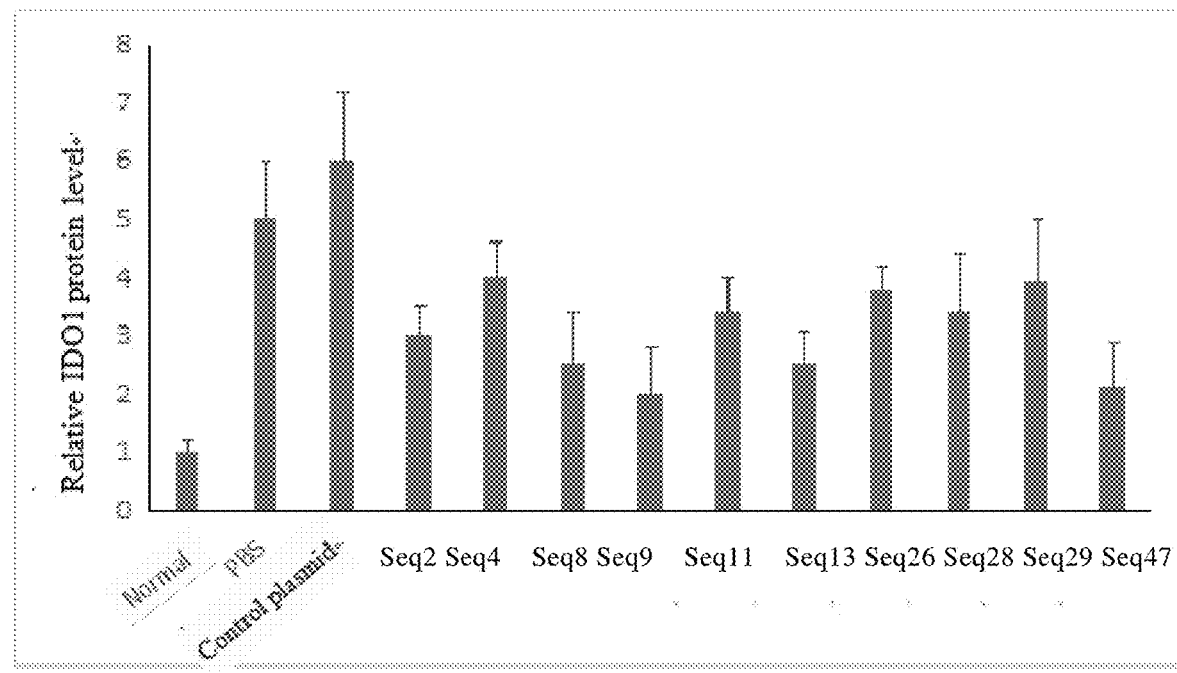
FIG. 61 shows the expression level of the IDO1 protein in the lung tissues detected using a western blotting experiment after the lung tissue proteins are extracted.

FIG. 61 shows the expression level of the IDO1 protein in the lung tissues detected using a western blotting experiment after the lung tissue proteins were extracted. The results above showed that the plasmids constructed using the screened ten IDO1 siRNAs can significantly reduce the expression level of the IDO1 protein in the lung tumour tissues.

The IDO1 siRNA plasmid had a therapeutic effect on the lung cancer, and the abnormal responses related with the medication were not seen during administration.

2. IDO1 siRNAs have an Inhibitory Effect on the Colorectal Cancer.

For the specific experimental materials and methods, please refer to Example 11, except that the test compound was IDO1 siRNA plasmid provided by the College of Life Sciences, Nanjing University.

The expression levels of the IDO1 mRNA and the protein in the transplanted tumours were detected.

Figure 62:
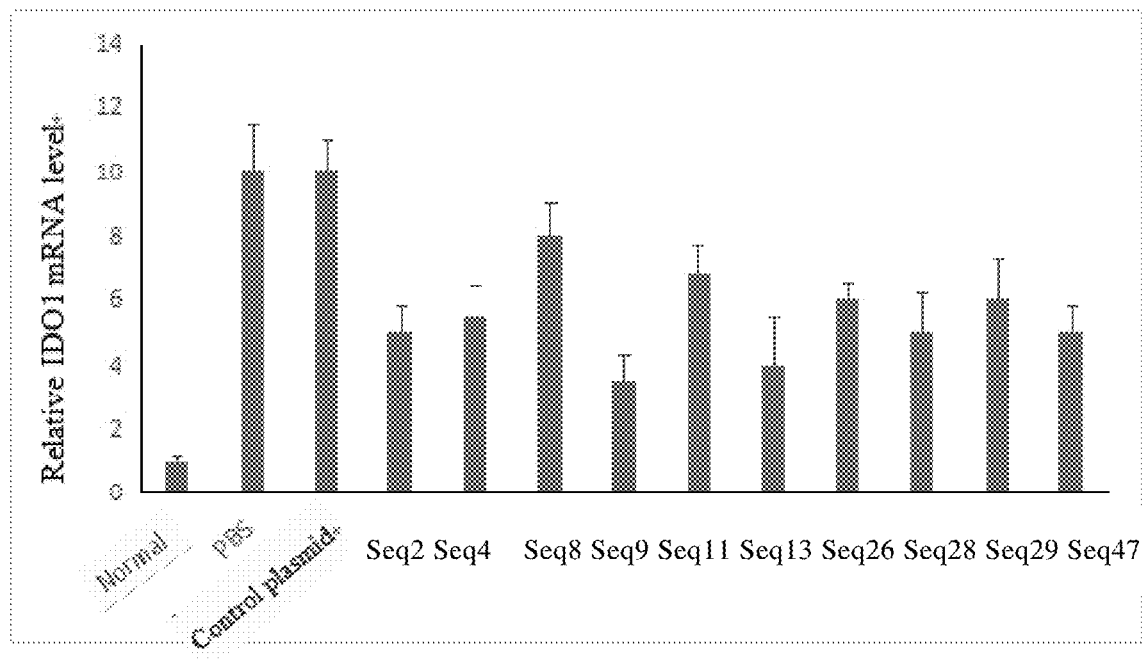
FIG. 62 shows the expression level of the IDO1 mRNA in colorectal cancer transplanted tumours.

FIG. 62 shows the expression level of IDO1 mRNAs in the colorectal cancer transplanted tumours, and the results showed that the IDO1 siRNA plasmid significantly reduced the IDO1 mRNA level in the transplanted tumours.

Figure 63:
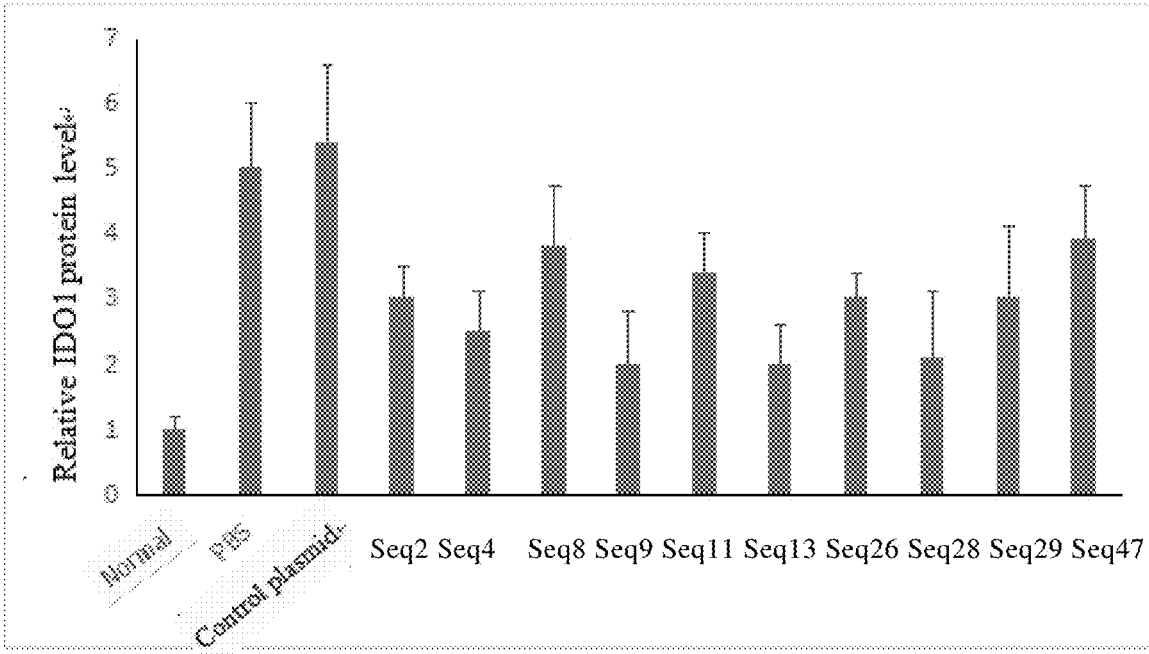
FIG. 63 shows the expression level of the IDO1 protein in the transplanted tumour tissues detected using a western blotting experiment after the colorectal cancer transplanted tumour tissue proteins are extracted.
Figure 64:
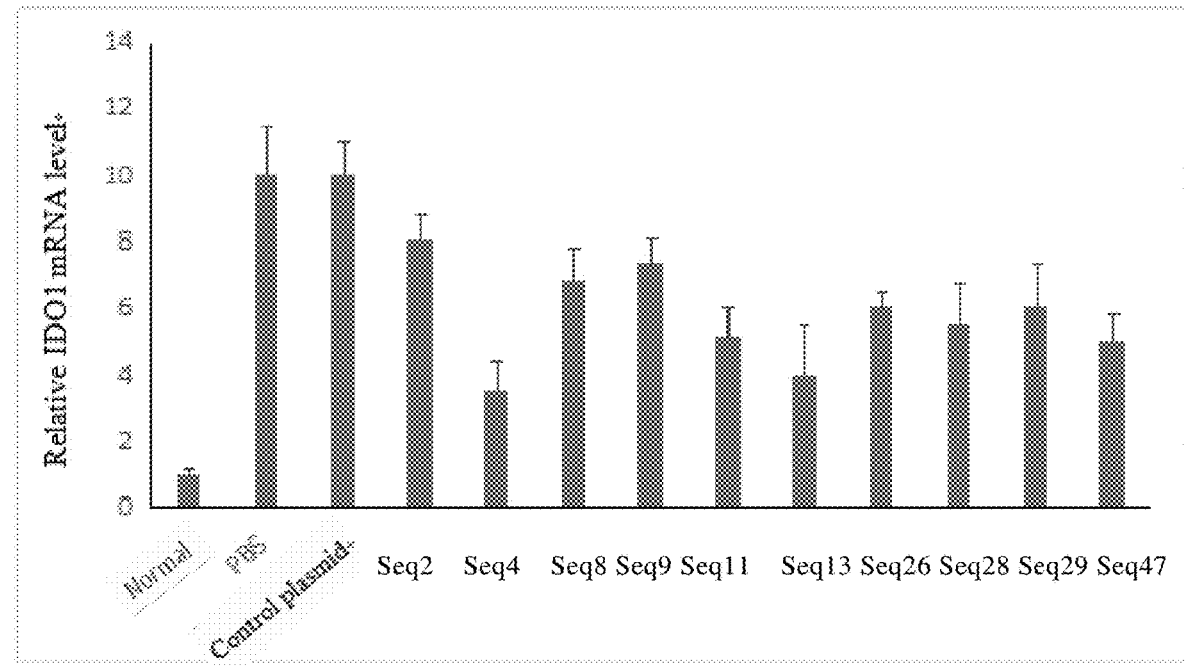
FIG. 64 shows the expression level of the IDO1 mRNA in the pancreas.

FIG. 63 shows the expression level of the IDO1 protein in the transplanted tumour tissues detected using a western blotting experiment after the colorectal cancer transplanted tumour tissue proteins were extracted. The results above showed that the IDO1 siRNA plasmid can significantly reduce the IDO1 protein in the transplanted tumour tissues.

The IDO1 siRNA plasmid had a therapeutic effect on the colon cancer, and the abnormal responses related with the medication were not seen during administration.

3. IDO1 siRNAs have an Inhibitory Effect on the Pancreatic Cancer.

For the specific experimental materials and methods, please refer to Example 11, except that the test compound was IDO1 siRNA plasmid provided by the College of Life Sciences, Nanjing University.

The expression levels of the IDO1 mRNA and the protein in the pancreas were detected.

FIG. 62 shows the expression level of IDO1 mRNAs in the pancreas, and the results showed that the IDO1 siRNA plasmid significantly reduced the IDO1 mRNA level in the pancreas.

Figure 65:
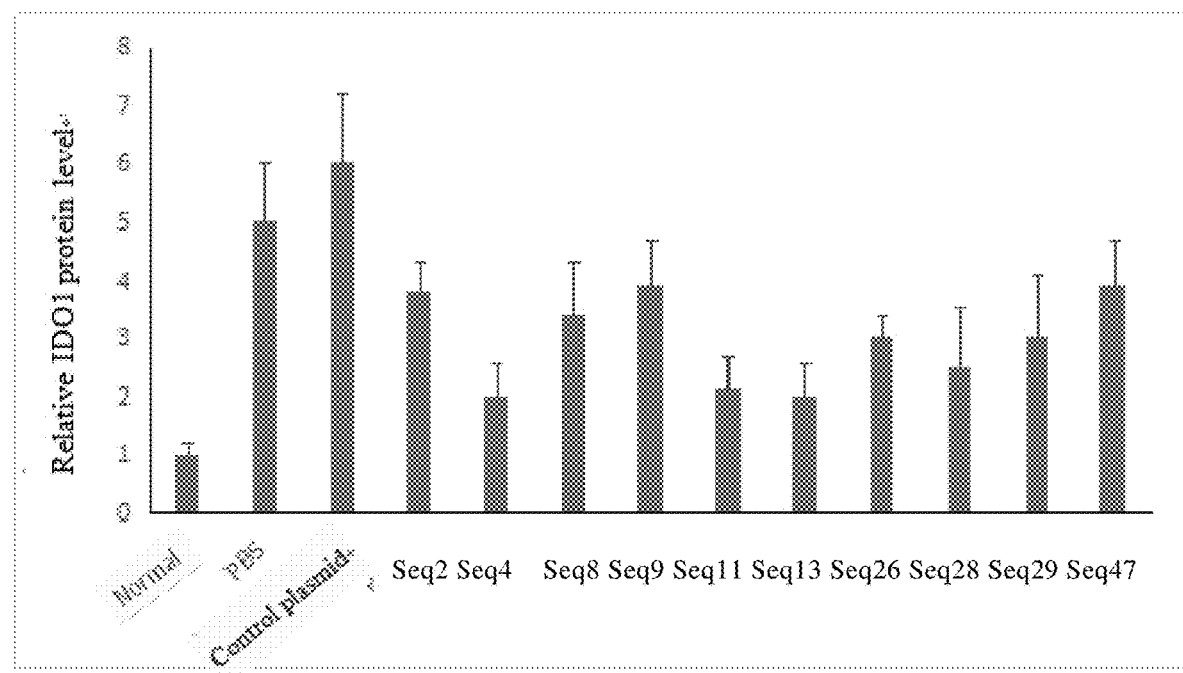
FIG. 65 shows the expression level of the IDO1 protein in the pancreatic tissue detected using a western blotting experiment after the pancreatic tissue proteins are extracted.

FIG. 65 shows the expression level of the IDO1 protein in the pancreatic tissues detected using a western blotting experiment after the pancreatic tissue proteins were extracted. The results above showed that the IDO1 siRNA plasmid can significantly reduce the IDO1 protein in the pancreatic tissues.

The IDO1 siRNA plasmid had a therapeutic effect on the pancreatic cancer, and the abnormal responses related with the medication were not seen during administration.

All the documents mentioned in the present invention are referred to by incorporation, as well as alone. In addition, it should be understood that after reading the teachings of the present invention as described above, a skilled person in the art can make various changes or modifications to the invention, and these equivalent forms shall also fall into the scope of the present application as defined by the appended claims.

The invention claimed is:

1. A pharmaceutical preparation, wherein the preparation comprises:
   (a) an expression vector for expressing anti-miRNAs and/or siRNAs; and
   (b) a pharmaceutically acceptable carrier;
   wherein the expression vector comprise precursor sequence having a structure from the 5' terminus to the 3' terminus as shown in formula I:

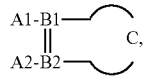

formula I wherein B1 is a first ribonucleic acid sequence, and comprises an anti-miRNA sequence form or an siRNA sequence form;
   B2 is a second ribonucleic acid sequence substantially or completely complementary to B1, and B2 is not complementary to C; wherein substantially complementary is that there are 2-8 non-complementary bases between B2 and B1;
   C is a stem-loop structure sequence; and
   A1 and A2 are null or are optionally RNA sequences consisting of 4-5 bases respectively;
   wherein the precursor can express the first ribonucleic acid sequence in a host, but cannot express the second ribonucleic acid sequence complementary to the first ribonucleic acid sequence.

2. The pharmaceutical preparation of claim 1, wherein the anti-miRNA and/or siRNA is a RNA selected from the group consisting of anti-miRNA-214, K-RAS siRNA, EGFR siRNA, PDL1 siRNA, PDCD1 siRNA, ALK siRNA and IDO1 siRNA;

the K-RAS siRNA has a sequence selected from the group consisting of SEQ ID NO: 12, SEQ ID NO: 35, SEQ ID NO: 50, SEQ ID NO: 56, SEQ ID NO: 61, SEQ ID NO: 82, SEQ ID NO: 97, SEQ ID NO: 107, SEQ ID NO: 110 and SEQ ID NO: 115 (or sequence numbers 3, 26, 41, 47, 52, 73, 88, 98, 101 and 106 in Table 11);

the EGFR siRNA has a sequence selected from the group consisting of SEQ ID NO: 294, SEQ ID NO: 297, SEQ ID NO: 312, SEQ ID NO: 319, SEQ ID NO: 324, SEQ ID NO: 329, SEQ ID NO: 336, SEQ ID NO: 340, SEQ ID NO: 345 and SEQ ID NO: 349 (or sequence numbers 17, 20, 35, 42, 47, 52, 59, 63, 68 and 72 in Table 14);

the PDL1 siRNA has a sequence selected from the group consisting of SEQ ID NO: 693, SEQ ID NO: 694, SEQ ID NO: 695, SEQ ID NO: 696, SEQ ID NO: 697, SEQ ID NO: 698, SEQ ID NO: 699, SEQ ID NO: 700, SEQ ID NO: 701 and SEQ ID NO: 702 (or sequence numbers 1, 2, 3, 4, 5, 6, 7, 8, 9 and 10 in Table 15);

the PDCD1 siRNA has a sequence selected from the group consisting of SEQ ID NO: 494, SEQ ID NO: 513, SEQ ID NO: 529, SEQ ID NO: 534, SEQ ID NO: 537, SEQ ID NO: 572, SEQ ID NO: 575, SEQ ID NO: 579, SEQ ID NO: 605 and SEQ ID NO: 634 (or sequence numbers 18, 37, 53, 58, 61, 96, 99, 103, 129 and 158 in Table 16);

the ALK siRNA has a sequence selected from the group consisting of SEQ ID NO: 708, SEQ ID NO: 713, SEQ ID NO: 718, SEQ ID NO: 721, SEQ ID NO: 725, SEQ ID NO: 729, SEQ ID NO: 732, SEQ ID NO: 734, SEQ ID NO: 742 and SEQ ID NO: 743 (or sequence numbers 6, 11, 16, 19, 23, 27, 30, 32, 40 and 41 in Table 17); and the IDO1 siRNA has a sequence selected from the group consisting of SEQ ID NO: 825, SEQ ID NO: 827, SEQ ID NO: 831, SEQ ID NO: 832, SEQ ID NO: 834, SEQ ID NO: 836, SEQ ID NO: 849, SEQ ID NO: 851, SEQ ID NO: 852 and SEQ ID NO: 870 (or sequence numbers 2, 4, 8, 9, 11, 13, 26, 28, 29 and 47 in Table 18).

3. A method for administering a medicament, wherein the method comprises the step of:
administering the pharmaceutical preparation of claim 1 at a first site on a mammal, so that the expression vector is processed to form a microvesicle in the mammal which is transported to a second site on the mammal where the anti-miRNAs and/or siRNAs are expressed.

4. The pharmaceutical preparation sequence of claim 1, wherein the sequence has a structure from the 5' terminus to the 3' terminus as shown in formula I:

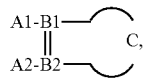

formula I wherein B1 is anti-miRNA-214-5p;
B2 is a sequence substantially or completely complementary to B1, and B2 is not complementary to C;
C is a stem-loop structure sequence, and
A1 and A2 are null or are optionally RNA sequences consisting of 4-5 bases respectively;
wherein the sequence of B1 as shown can be processed in the host to form anti-miRNA-214, and only the anti-miRNA-214-5p, rather than the anti-miRNA-214-3p, in the anti-miRNA-214 is expressed, wherein the precursor cannot express the ribonucleic acid of B2.

5. The pharmaceutical preparation of claim 4, wherein substantially complementary is that there are 2-8 non-complementary bases between the said B2 and B1.

6. The pharmaceutical preparation of claim 4, wherein A1 is UGCUG; and/or A2 is CAGG or CAGGA.

7. The pharmaceutical preparation of claim 1, wherein the dosage form of the pharmaceutical composition comprises a tablet, a capsule, a powder, a pill, a granule, a syrup, a solution, a suspension liquid, an emulsion, a suspension, an injection solution, or an injectable powder.

8. The pharmaceutical preparation of claim 1, wherein the administration mode of the pharmaceutical composition comprises oral, respiratory tract, injection, transdermal, mucosal, or cavity administration.

9. A method for inhibiting miRNA-214; and/or treating a malignant tumor highly expressing miRNA-214;
comprising administering to a subject in need thereof an effective amount of the pharmaceutical preparation of claim 4.

10. The pharmaceutical preparation of claim 1, wherein the sequence has a structure from the 5' terminus to the 3' terminus as shown in formula I:

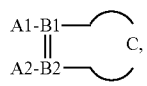

formula I wherein B1 is K-RAS siRNA;
B2 is a sequence substantially or completely complementary to B1, and B2 is not complementary to C;
C is a stem-loop structure sequence; and
A1 and A2 are null or are optionally RNA sequences consisting of 4-5 bases respectively;
wherein the precursor sequence as shown can be processed in the host to form the K-RAS siRNA; and
wherein the nucleotide sequence of the sense strand of the K-RAS siRNA is selected from the group consisting of sequences shown as SEQ ID NO: 12, SEQ ID NO: 35, SEQ ID NO: 50, SEQ ID NO: 56, SEQ ID NO: 61, SEQ ID NO: 82, SEQ ID NO: 97, SEQ ID NO: 107, SEQ ID NO: 110 and SEQ ID NO: 115 in the sequence listing, wherein the precursor cannot express the ribonucleic acid of B2.

11. The pharmaceutical preparation of claim 1, wherein the sequence has a structure from the 5' terminus to the 3' terminus as shown in formula I:

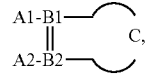

formula I

B1 is EGFR siRNA;
B2 is a sequence substantially or completely complementary to B1, and B2 is not complementary to C;
C is a stem-loop structure sequence; and
A1 and A2 are null or are optionally RNA sequences consisting of 4-5 bases respectively;
wherein the precursor sequence as shown can be processed in the host to form the EGFR siRNA; and
wherein the nucleotide sequence of the sense strand of the EGFR siRNA is selected from the group consisting of sequences shown as SEQ ID NO: 294, SEQ ID NO: 297, SEQ ID NO: 312, SEQ ID NO: 319, SEQ ID NO: 324, SEQ ID NO: 329, SEQ ID NO: 336, SEQ ID NO: 340, SEQ ID NO: 345 and SEQ ID NO: 349 in the sequence listing, wherein the precursor cannot express the ribonucleic acid of B2.

12. The pharmaceutical preparation of claim 1, wherein B1 is PDL1 siRNA, wherein the nucleotide sequence of the sense strand of the PDL1 siRNA is selected from the group consisting of sequences shown as SEQ ID NO: 693, SEQ ID NO: 694, SEQ ID NO: 695, SEQ ID NO: 696, SEQ ID NO: 697, SEQ ID NO: 698, SEQ ID NO: 699, SEQ ID NO: 700, SEQ ID NO: 701 and SEQ ID NO: 702 in the sequence listing.

13. The pharmaceutical preparation of claim 1, wherein B1 is PDCD1 siRNA, wherein the nucleotide sequence of the sense strand of the PDL1 siRNA is selected from the group consisting of sequences shown as SEQ ID NO: 494, SEQ ID NO: 513, SEQ ID NO: 529, SEQ ID NO: 534, SEQ ID NO: 537, SEQ ID NO: 572, SEQ ID NO: 575, SEQ ID NO: 579, SEQ ID NO: 605 and SEQ ID NO: 634 in the sequence listing.

14. The pharmaceutical preparation of claim 1, wherein B1 is ALK siRNA, wherein the nucleotide sequence of the sense strand of the ALK siRNA is selected from the group consisting of sequences shown as SEQ ID NO: 708, SEQ ID NO: 713, SEQ ID NO: 718, SEQ ID NO: 721, SEQ ID NO: 725, SEQ ID NO: 729, SEQ ID NO: 732, SEQ ID NO: 734, SEQ ID NO: 742 and SEQ ID NO: 743 in the sequence listing.

15. The pharmaceutical preparation of claim 1, wherein B1 is IDO1 siRNA, wherein the nucleotide sequence of the sense strand of the IDO1 siRNA is selected from the group consisting of sequences shown as SEQ ID NO: 825, SEQ ID NO: 827, SEQ ID NO: 831, SEQ ID NO: 832, SEQ ID NO: 834, SEQ ID NO: 836, SEQ ID NO: 849, SEQ ID NO: 851, SEQ ID NO: 852 and SEQ ID NO: 870 in the sequence listing.

16. The pharmaceutical preparation of claim 1, wherein A1 is UGCUG; and/or A2 is CAGG or CAGGA.

17. The pharmaceutical preparation of claim 2, wherein the anti-miRNA-214 has a sequence shown as SEQ ID NO: 2.

18. The pharmaceutical preparation of claim 10, wherein the C is a stem-loop structure sequence, is a sequence shown as SEQ ID NO.: 1.

19. The pharmaceutical preparation of claim 11, wherein the C is a stem-loop structure sequence, is a sequence shown as SEQ ID NO.: 1.

20. The method of claim 9 wherein the malignant tumor is selected from the group consisting of liver cancer, lung cancer, stomach cancer, oesophageal cancer, ovarian cancer, colorectal cancer, cervical cancer, pancreatic cancer, prostatic cancer, leukaemia and breast cancer.

* * * * *